(12) United States Patent
Danishefsky et al.

(10) Patent No.: US 6,544,952 B1
(45) Date of Patent: *Apr. 8, 2003

(54) SYNTHESIS OF GLYCOCONJUGATES OF THE GLOBO-H EPITOPE AND USES THEREOF

(75) Inventors: Samuel J. Danishefsky, Englewood, NJ (US); Philip O. Livingston, New York, NY (US); Govindaswami Ragupathi, New York, NY (US); In Jong Kim, New York, NY (US); Howard Scher, Tenafly, NJ (US); Susan Slovin, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/017,611

(22) Filed: Feb. 2, 1998

Related U.S. Application Data

(63) Continuation-in-part of application No. 08/506,251, filed on Jul. 24, 1995, now Pat. No. 6,303,120, which is a continuation-in-part of application No. 08/430,355, filed on Apr. 28, 1995, now Pat. No. 5,708,163, which is a continuation-in-part of application No. 08/213,053, filed on Mar. 15, 1994, now Pat. No. 5,543,505.

(51) Int. Cl.$^7$ ............................................. A01N 113/04
(52) U.S. Cl. ............................... 514/23; 514/42; 514/54; 514/62; 424/184.1; 424/277.1
(58) Field of Search ............................. 514/23, 42, 54, 514/62, 885; 424/184.1, 277.1

(56) References Cited

U.S. PATENT DOCUMENTS 5,622,929 A    4/1997   Willner et al.
5,708,163 A  * 1/1998   Danishefsky et al.
6,090,789 A  * 7/2000   Danishefsky et al.

OTHER PUBLICATIONS

Aspinall, G.O. et al. Synthesis of allyl glycosides for conversion into neoglycoproteins bearing epitopes of mycobacterial glycolipid antigens. *Carbohydrate Research*, 216: 337–355, 1991.*

Hakomori, S. et al. A new series of blood group A and H antigens expressed in human erythrocytes and the incompatible A antigens expressed in tumours of blood group O and B individuals. Biochem. Soc. Trans. 15(4): 593–596, 1987.*

Kudryashov, V. et al. Characterization of a mouse monoclonal IgG3 antibody to the tumor–associated globo H structure produced by immunization with a synthetic glycoconjugate. Glycoconjugate Journal, 15: 243–249, 1998.*

Alper, Joseph, New Bind for Ulcer Bacterium, *Science*, vol. 262, Dec. 17, 1993 (Exhibit 2).

Altman, Lawrence K., Stomach Microbe Offers Clues To Cancer as Well as Ulcers, The New York Times 1994 (Exhibit 3).

Behar, V. and Danishefsky, S.J., A Highly Convergent Synthesis of the Lewis–γ Blood Group Determinant In Conjugatable Form, *Angewandte Chem. Int. Ed. Eng.* (1994) 33(14): 1468–1470 (Exhibit 4).

Behar, V. and Danishefsky, S.J., *Angewandte Chem. Int. Ed. Eng.* (1994) 106: 1536–1538 (Exhibit 5).

Bernstein, M.A. and Hall, L.D., A General Synthesis of Model Glycoproteins: Coupling of Alkenyl Glycoside to Proteins, Using Reductive Ozonolysis Followed By Reductive Amination with Sodium Cyanoborohydride, *Carbohydrate Research* (1980) 78: C1–C3 (Exhibit 6).

Bilodeau, M.T., Total Synthesis of a Human Breast Tumor Associated Antigen, *J. Am. Chem. Soc.* May 1995, vol. 117, pp. 7840–7841 (Exhibit 7).

Boon, Thierry, Toward A Genetic Analysis of Tumor Rejection Antigens, *Advances In Cancer Research*, vol. 58, pp. 177–210, 1992. (Exhibit 8).

Borén, et al., Attachment of *Helicobacter pylori* to Human Gastric Epithelium Mediated by Blood Group Antigens, *Science*, vol. 262, Dec. 17, 1993 (Exhibit 9).

(List continued on next page.)

Primary Examiner—Sheela Huff
(74) Attorney, Agent, or Firm—John P. White; Cooper & Dunham LLP

(57) ABSTRACT

The present invention provides a method of synthesizing a compound having the structure:

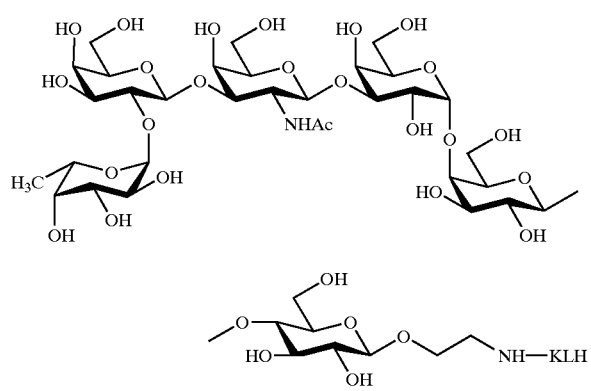

as well as other related glycoconjugates useful as vaccines for inducing antibodies to epithelial cancer cells in an adjuvant therapy therefore, and in a method for preventing recurrence of epithelial cancer. The present invention also provides a vaccine comprising an amount of the compound described above effective to prevent the recurrence of cancer in a subject.

11 Claims, 64 Drawing Sheets

OTHER PUBLICATIONS

Bremer, E.G., et al., "Characterization of a Glycosphingolipid Antigen Defined by the Monoclonal Antibody MBr1 Expressed in Normal and Neoplastic Epithelial Cells of Human Mammary Gland", *J. Biol. Chem.* (1984) 259(23): 14773–14777 (Exhibit 10).

Chemical Abstracts, vol. 109, No. 15, issued Oct. 10, 1988, Ogawa et al, "Glycosphingolipids Bearing a Lewis b Type Antigenic Determinant and a Process for Their Preparation", p. 752, column 2, abstract No. 129595w, *Jpn. Kokai Tokyo Koho* JP 63 51,396 (Exhibit 11).

Christiansen–Brams, Ida. et al., Protected–mode Synthesis of N–linked Glycopeptides: Single–step Preparation of Buliding Blocks as Peracetyl Glycosylated N Fmoc Asparagine Opfp Esters, *Journal of the Chemical Society*, perkin trans. 1, 1993 (Exhibit 12).

Chiu, Shuet–Hing Lee and Anderson, Laurens, Oligosaccharide Synthesis by the Thioglycoside Scheme on Soluble and Insoluble Polystyrene Supports, *Carbohydrate Research*, vol. 50, pp. 227–238, 1976 (Exhibit 13).

Danishefsky, S.J., Applications of Glycals to Problems in Organic Synthesis in the Synthesis of Oligosaccharides and Glycoconjugates, *Abstracts of American Chemical Society: Division of* Chemistry, 207 AC Organic Chemistry, 207 ACS National Meeting, San Diego, CA, Mar. 13–17, 1994 (Exhibit 14).

Danishefsky, S.J., et al., "Application of the Glycal Assembly Method to the Concise Synthesis of Neoglycoconjugates of Le$^y$ and Le$^b$ Blood Group Determinants and H–Type I and H–Type II Oligosaccharides", J. Am. Chem. Soc. (1995) 117: 5701–5711 (Exhibit 15).

Danishefsky, S., et al., "A Strategy For the Solid–Phase Synthesis of Oligosaccharides", Science (1993) 260: 1307–1309 (Exhibit 16).

Dennis, J., "N–linked Oligosaccharides processing and tumor cell biology", Oxford Glycosystems Glyconews Second 1992 (Exhibit 17).

Eby, Ronald and Schuerch, Conrad, Solid–phase synthesis of oligosaccharides V. Preparation of an inorganic support, Carbohydrate Research, vol. 39, pp. 151–155, 1975 (Exhibit 18).

Ezzell, Carol, Cancer "Vaccines": An Idea Whose Time Has Come?, Journal of NIH Research, vol. 7, pp. 46–49, Jan. 1995 (Exhibit 19).

Falk, Per et al., Strategies for Characterization of Microbial Host Receptors, Methods in Enzymology, vol. 236, 1994 (Exhibit 20).

Falk, Per et al., An in vitro adherence assay reveals that *Helicobacter pylori* exhibits cell lineage–specific tropism in the human gastric epithelium, Proc. Natl. Acad. Sci., vol. 90, pp. 2035–2039, Mar. 1993 (Exhibit 21).

Feizi, T., "Carbohydrate antigens in human cancer", Cancer Surveys (1985) 4(1): 245–269 (Exhibit 22).

Gordon, D.M. and Danishefsky, S.J., "Displacement reactions of a 1, 2–anhydro–α–D–hexopyranose: Installation of useful functionality at the anomeric carbon", Carbohydr. Res. (1990) 206(2): 361–366 (Exhibit 23).

Gray, G.R., "Antibodies to Carbohydrates: Preparation of Antigens By Coupling Carbohydrates to Proteins By Reductive Amination With Cyanoborohydride", Methods in Enzymology (1978) 50: 155–160 (Exhibit 24).

Hakomori, S., "Aberrant Glycosylation in Cancer Cell Membranes as Focused on Glycolipids: Overview and Perspectives", Cancer Res. (1985) 45: 2405–2414 (Exhibit 25).

Harlow and Lane (Antibodies? A Laboratory Manual. Ltd., Spring Harbor Laboratory, Cold Spring Harbor, p. 77, 1988)(Exhibit 26).

Helling et al., Cancer Res. 1994, 54: 197–203 (Exhibit 27).

Kim, I.J. Defining the Molecular Recognition of Globo H (Human Breast Cancer) Antigen through Probe Structures Prepared by Total Synthesis. J. Org. Chem. Aug. 1995, vol. 60, pp. 7716–7717 (Exhibit 29).

Kitamura, K et al. Specificity Analysis of Blood Group Lewis–γ Antibodies Generated Against Synthetic and Natural Lewis–γ Determinants, Proc. Natl. Acad. Sci. USA, Dec. 1994, vol. 91, pp. 12957–12961 (Exhibit 30).

Kobata, Akira, Glycobiology: An Expanding Research Area in Carbohydrate Chemistry, Acc. Chem. Res., vol. 26, pp. 319–324, 1993 (Exhibit 31).

Kong et al., Fucosylated Glycosphingolipids of Human Myeloid Cells Arch. Biochem. Biophys. 300: 677–683, 1993 (Exhibit 32).

Lay, L., et al., "Oligosaccharides Related to Tumor–Associated Antigens", Helv. Chim. Acta. (1994) 77: 509–514 (Exhibit 33).

Lay, L., et al., "Oligosaccharides Related to Tumor–Associated Antigens", Helv. Chim. Acta. (1995) 78: 533–538 (Exhibit 34).

Livingston, P.O. Augmenting the immunogenicity of carbohydrate tumor antigens, Seminars in Cancer Biology, Dec. 1995, vol. 6, pp. 357–366 (Exhibit 35).

Livingston, P.O. Construction of cancer vaccines with carbohydrate and protein (peptide) tumor antigens, Current Opinion in Immunology 1992, vol. 4, pp. 624–629 (Exhibit 36).

Livingston et al., Characterization of IgG and IgM ALH Antibodies Induced In Melanoma Patients by Immunization with Purified $G_{m2}$ Ganglioside Cancer Res. 1989, 49: 7045–7050 (Exhibit 37).

Lloyd, K.O., "Blood Group Antigens as Markers for Normal Differentiation and Malignant Change in Human Tissues", Am. J. Clin. Pathol. (1987) 87(1): 129–139 (Exhibit 38).

Lloyd, K.O., "Humoral immune responses to tumor–associated carbohydrate antigens", Cancer Biol. (1991) 2: 421–431 (Exhibit 39).

Lloyd, K.O., Tumor Antigens Known to be Immunogenic, Man. Ann. N.Y. Acad. Sci. 1993, vol. 690, pp. 50–58 (Exhibit 40).

McDonald, Frank E. and Danishefsky, Sameul J., A Stereoselective Route from Glycals to Asparagine–Linked N–Protected Glycopeptides, The Journal of Organic Chemistry, vol. 57, No. 26, Dec. 18, 1992 (Exhibit 41).

Mahajan, R., et al., Synthesis of Neoglycoproteins as Artificial Antigens. J. Carbohydrate Chemistry (1994) 13(1): 63–73 (Exhibit 42).

Menard, S., et al., "Generation of Monoclonal Antibodies Reacting with Normal and Cancer Cells of Human Breast", Cancer Res. (1983) 43: 1295–1300 (Exhibit 43).

Meldal, Morten, Glycopeptide Synthesis, Neoglycoconjugates: Preparation and Applications, chapter 4, 1994 (Exhibit 44).

Merrifield, R.B., Solid Phase Peptide Synthesis I. The synthesis of a Tetrapeptide, Journal of the American Chemical Society, vol. 85 pp. 2149–2154 Jul. 20, 1963 (Exhibit 45).

Otvos, Laszlo Jr., et al., Automated solid–phase of glycopeptides. Incorporation of unprotected mono–and disaccharide unites of N–glycoprotein antennae into T cell epitopic peptides, Tetrahedron Letters, vol. 33, pp. 5889–5892, 1990 (Exhibit 46).

Pastan, I. et al. Characterization of Monoclonal Antibodies B1 and B3 That React with Mucinous Adenocarcinomas, Cancer Res. Jul. 15, 1991, vol. 51, pp. 3781–3787 (Exhibit 47).

Ragupathi, Govindaswami, et al., Immunization of Mice with a Fully Synthetic Globo H Antigen Results in Antibodies against Human Cancer Cells: A combined Chemical–Immunological Approach to the Fashioning of an Anticancer Vaccine, Angewandte Chemie, vol. 36, No. 1/2, pp. 125–128, Feb. 3, 1997 (Exhibit 48).

Randolph, J.T. and Danishefsky, S.J., An Interactive Strategy for the Assembly of Complex, Branched Oligosaccharides Domains on a Solid Support: "A Concise Synthesis of the Lewis$^b$ Domain in Bioconjugatable Form", Angewandte Chem. Int. Ed. Eng. (1994) 33(14): 1470–1473 (Exhibit 49).

Salyan, M.E.K. et al. Differentiation of Type 1 and Type 2 Chain Linkages of Native Glycosphingolipids by Positive–ion Fast–atom Bombardment Mass Spectrometry with Collision–induced Dissociation and Linked Scanning, Rapid Communication in Mass Spectrometry, 1991, vol. 5, pp. 456–462 (Exhibit 50).

Schuster, Matthias, et al., Solid–phase chemical–enzymatic synthesis of glycopeptides and oligosaccharides, *J. Am. Chem. Soc.*, vol. 116, pp. 1135–1136, 1994 (Exhibit 51).

Spitler, Lynn E., M.D., Cancer Vaccines: The Interferon Analogy, *Cancer Biotheraphy*, vol. 10, No. 1, 1995 (Exhibit 52).

Tao, M. et al., Idiotype/Granulocyte–Macrophage–Colony–Stimulating Factor Fusion Protein as a Vaccine to B–Cell Lymphoma, *Nature* Apr. 22, 1993, vol. 362, pp. 755–758 (Exhibit 53).

Tompkins, Lucy S. et al., The New Path to Preventing Ulcers, *Science*, vol. 267, Mar. 17, 1995 (Exhibit 54).

Williams, Paul Lloyd, et al., Tetrahedron report No. 347, Convergent Solid–phase peptide Synthesis, *Tetrahedron*, vol. 49, No. 48, pp. 11065–11092, 1993 (Exhibit 55).

Wong, Chi–Huey, et al., Enzymatic Synthesis of N– and O–linked Glycopeptides, *Journal of the American Chemical Society*, vol. 115, No. 14, Jul. 14, 1993 (Exhibit 56).

* cited by examiner

FIGURE 7B
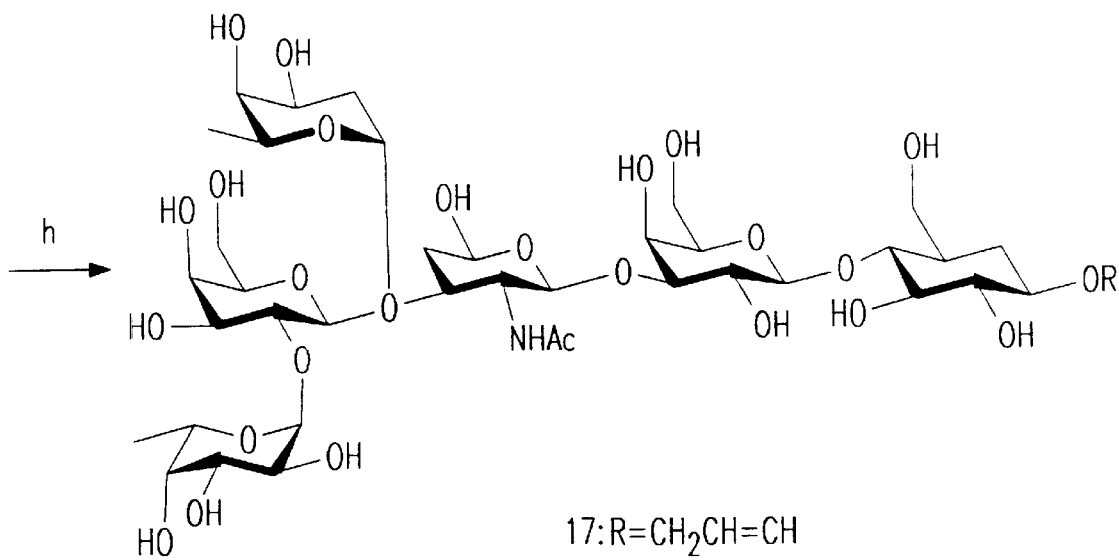
17: R=CH₂CH=CH
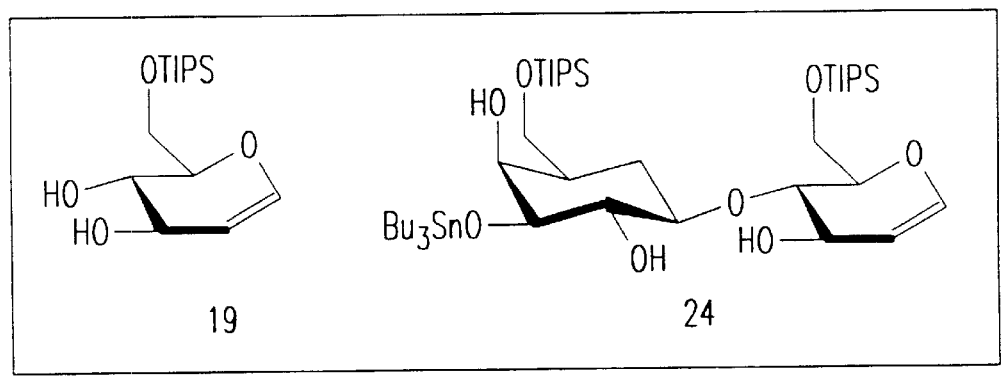
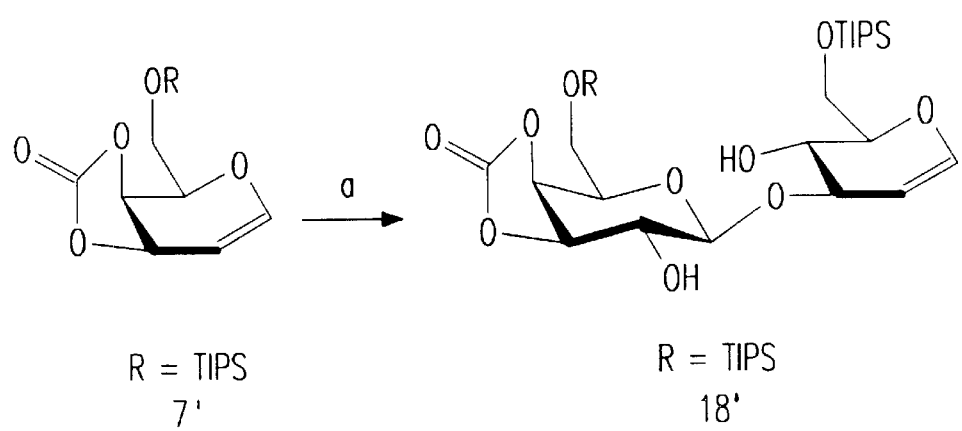

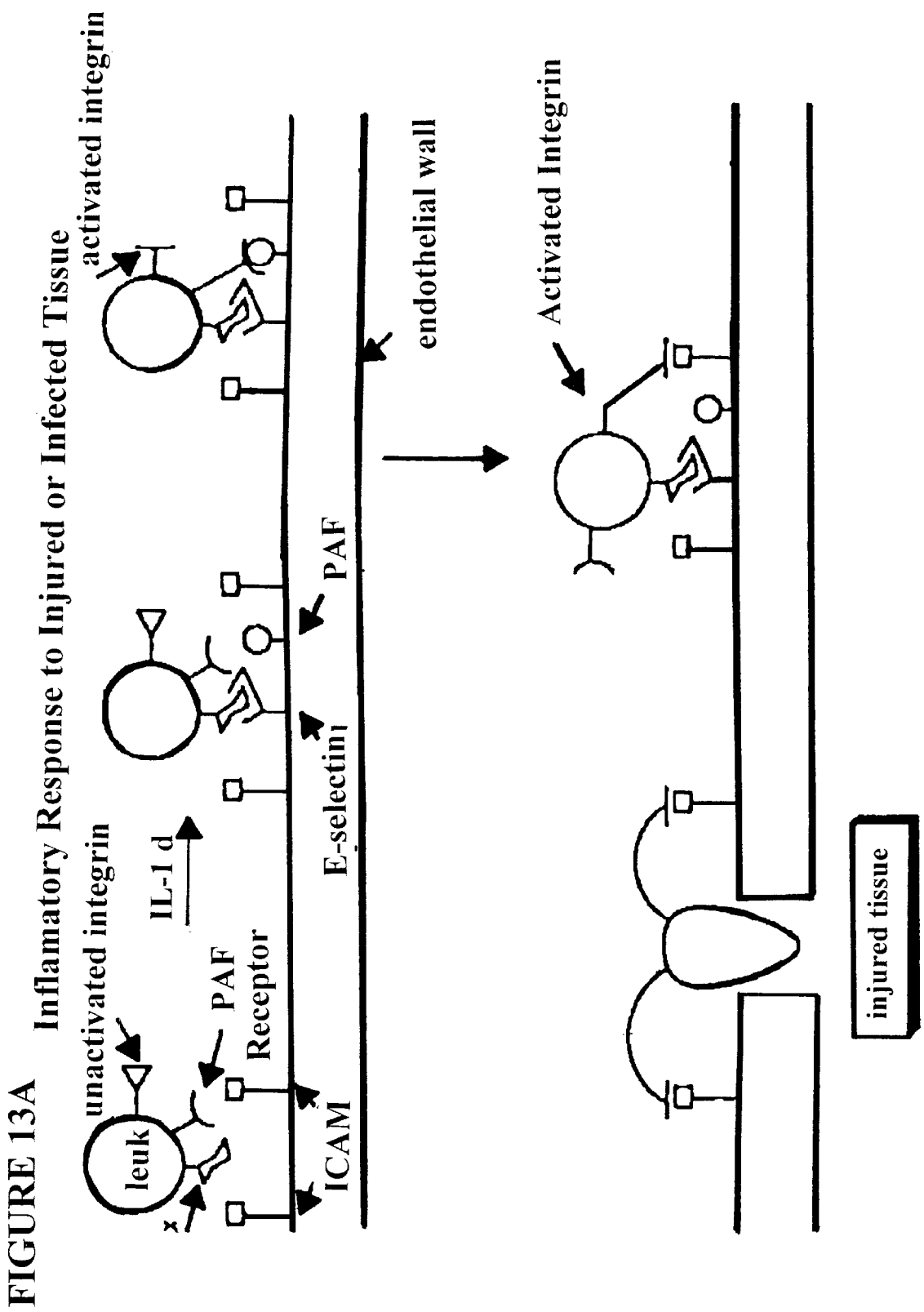

SLe$^x$
1 d

- Expressed as glycolipid on cell membrane leukocytes
- Implicated as the ligand for E- Selectin in inflammatory response
- High levels of SLe$^x$ are found in cell surface of a variety of metastatic tumor cells

FIGURE 13C
Feizi's Discovery of Sulfated E-Selectin Ligands
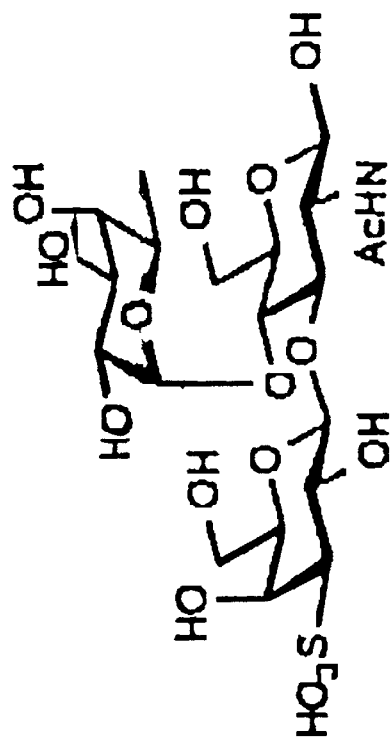
3 d
Sulfated Le$^x$
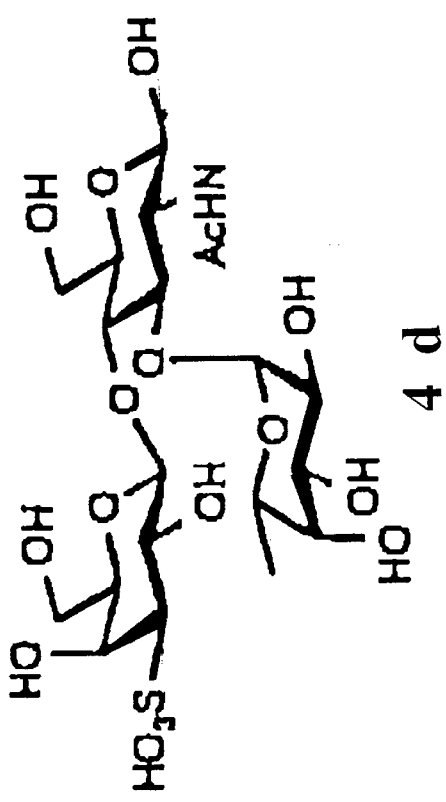
4 d
Sulfated Le$^x$

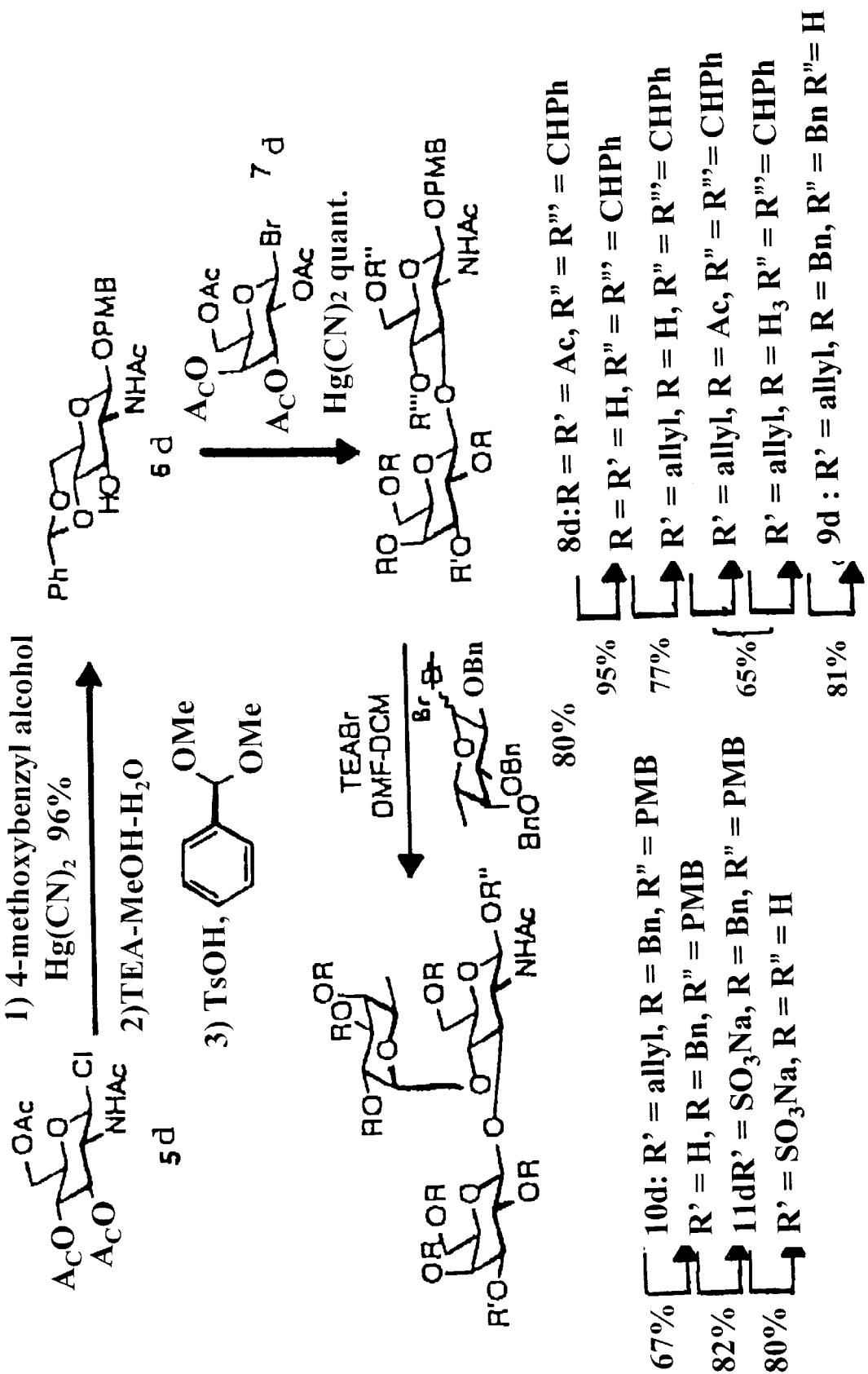
FIGURE 14A    Lubineau Sulfated Le

FIGURE 21A FIGURE 21B FIGURE 21C

Ig IgM IgG

Ig

IgM

IgG

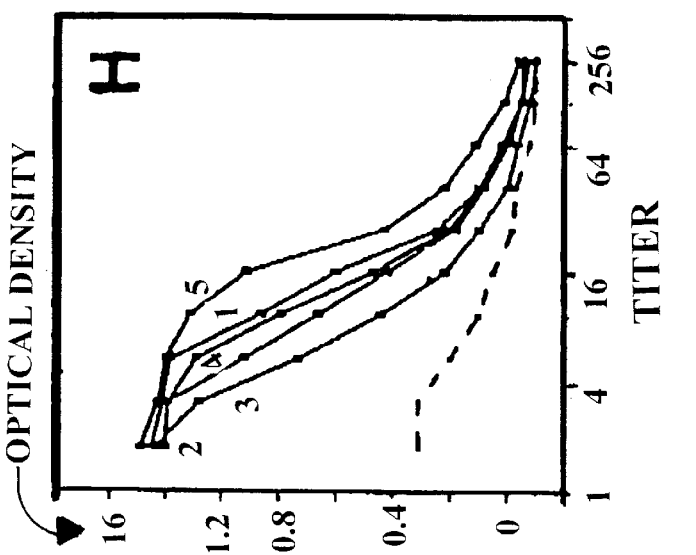
FIGURE 21G  FIGURE 21H  FIGURE 21I
Ig         IgM         IgG
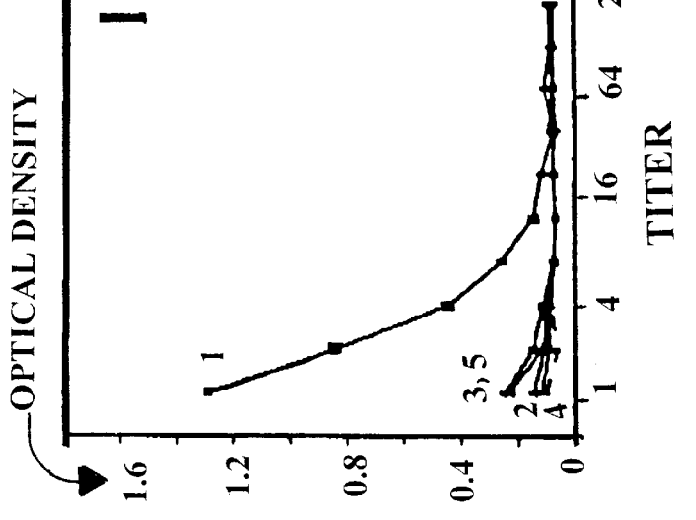
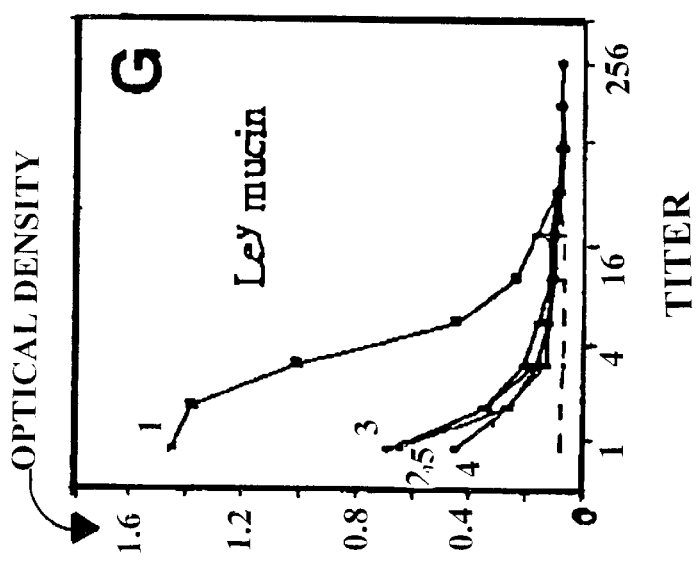

Ig         IgM         IgG

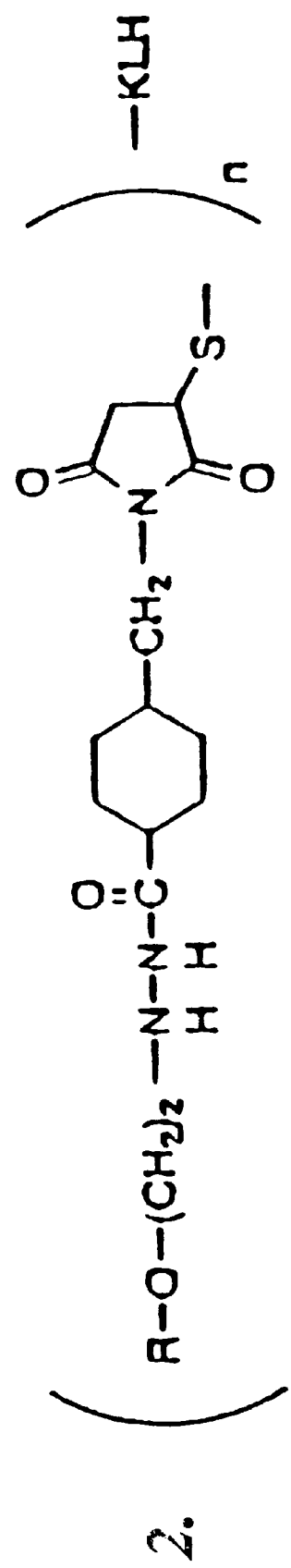
FIGURE 30B  Structure of Le^y - protein conjugates
1. $(R-O-(CH_2)_2-NH)_n$ - KLM or BSA
2. (structure shown)
$R = Le^y$ pentasaccharide

FIGURE 30C

*Structures of $Le^a$, $Le^b$, $Le^x$, and $Le^y$ blood group epitopes*

$Le^a$     Galβ1- 3 [Fucα1-4]GlcNAcβ1 - 3Gal-
$Le^b$   Fucα 1- 2 Galβ1- 3 [Fucα1-4]GlcNAcβ1 - 3Gal-
$Le^x$     Galβ1- 4 [Fucα1-4]GlcNAcβ1 - 3Gal-
$Le^y$   Fucα 1- 2 Galβ1- 4 [Fucα1-3]GlcNAcβ1- 3Gal-

FIGURE 33 Summary of Reactivity of Antisera of Mice Immunized with Le$^Y$-KLH or Le$^Y$-BSA Conjugates Tested on Various Glycoconjugates

| Antibody used in ELISA | Le$^Y$-KLH Immunized Mice | | Le$^Y$-M$_2$C$_2$H-KLH Immunized Mice | | Le$^Y$-BSA Immunized Mice | |
|---|---|---|---|---|---|---|
| | High Reactivity [1] | Medium Reactivity [2] | High Reactivity [1] | Medium Reactivity [2] | High Reactivity [1] | Medium Reactivity [2] |
| | | | Le$^Y$/Le$^b$ Mucin Test Antigen | | | |
| Anti - m Ig (H+L) | 2/5 | 5/5 | 1/5 | 5/5 | 0/5 | 1/5 |
| Anti - m IgG | 3/5 | 4/5 | 2/5 | 2/5 | 0/5 | 1/5 |
| Anti - m IgM | 5/5 | 5/5 | 5/5 | 5/5 | 5/5 | 5/5 |
| | | | Le$^Y$ - Ceramide Test Antigen | | | |
| Anti - m Ig (H + L) | 2/5 | 5/5 | 0/5 | 3/5 | 0/5 | 0/5 |
| Anti - m IgG | 3/5 | 5/5 | 0/5 | 3/5 | 0/5 | 0/5 |
| Anti - m IgM | 5/5 | 5/5 | 5/5 | 5/5 | 0/5 | 3/5 |
| | | | Le$^Y$ - BSA or KLH Test Antigen [3] | | | |
| Anti - m Ig (H + L) | 5/5 | 5/5 | 5/5 | 5/5 | 0/5 | 0/5 |
| Anti - m IgG | 5/5 | 5/5 | 5/5 | 5/5 | 0/5 | 0/5 |
| Anti - m IgM | 5/5 | 5/5 | 5/5 | 5/5 | 5/5 | 5/5 |
| | | | Le$^x$ / Le$^a$ Mucin Test Antigen [4] | | | |
| Anti - m Ig (H + L) | 0/5 | 3/5 | 0/5 | 1/5 | 0/5 | 1/5 |
| Anti - m IgG | 0/5 | 0/5 | 0/5 | 0/5 | 0/5 | 0/5 |
| Anti - m IgM | 5/5 | 5/5 | 5/5 | 5/5 | 0/5 | 5/5 |

[1] Proportion of mice with antisera giving OD > 1.0 in ELISA at 1:20 dilution (60 min)

[2] Proportion of mice with antisera giving OD > 0.5 in ELISA at 1:20 dilution (60 min)

[3] Le$^Y$-BSA was used as the test antigen for Le$^Y$-KLH immunized mice and Le$^Y$-KLH for Le$^Y$-BSA immunized mice.

[4] The positive reactions to this Le$^x$/Le$^a$ mucin were shown to be directed against Le$^x$ by testing separately with Le$^x$-polyacrylamide and Le$^a$-polyacrylamide (GlycoTech, Rockville, MD).

FIGURE 35

Cytotoxicity Assay of Antisera on Cultured Cells

| Antibody or antiserum | MCF-7 (Le$^y$ +) | SK-MEL-28 (Le$^y$ -) |
|---|---|---|
| Mouse No. 1 (Le$^y$-KLH) | 1:80 [1] | >1:1280 [1] |
| Mouse No. 4 (Le$^y$-KLH) | 1:40 | >1:1280 |
| Mouse No. 3 (Le$^y$-M$_2$C$_2$H-KLH) | 1:40 | >1:1280 |
| Mouse No. 4 (Le$^y$-M$_2$C$_2$H-KLH) | 1:40 | >1:1280 |
| 3S193 (anti-Le$^y$) | 0.5 µg/ml | >10 µg/ml |
| R24 (anti-GD3) | >10 µg/ml | 0.62 µg/ml |

[1] Greatest dilution giving detectable lysis; no lysis (>1:1280) was observed in pre-immune sera.

X = carrier protein, KLH, lipopeptide

FIGURE 38B
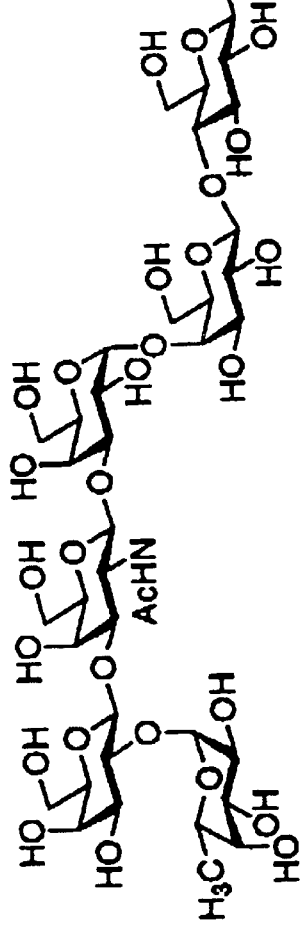
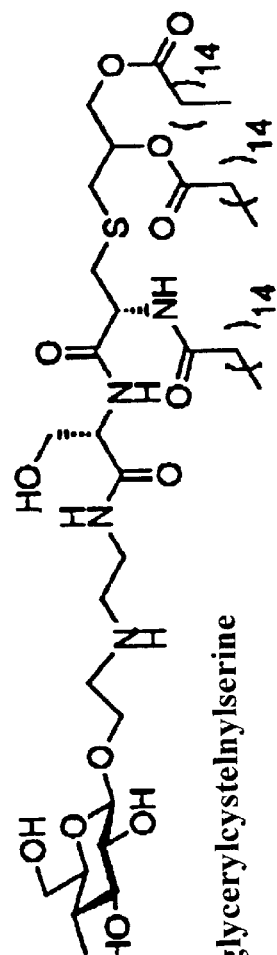
One specific example of X = lipopeptide
X = tripalmitoyl-S-glycerylcystelnylserine

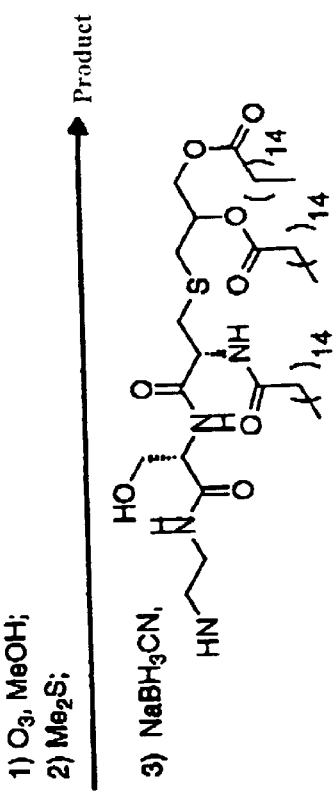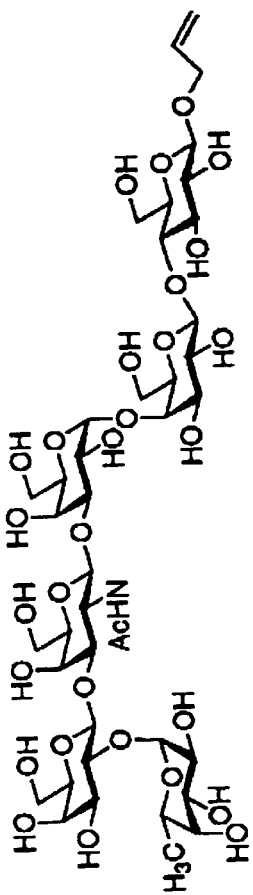
FIGURE 38C
Possible synthetic scheme

SYNTHESIS OF GLYCOCONJUGATES OF THE GLOBO-H EPITOPE AND USES THEREOF

This application is a continuation-in-part of U.S. Ser. No. 08/506,251, filed Jul. 24, 1995, now U.S. Pat. No. 6,303,120 which is a continuation-in-part of U.S. Ser. No. 08/430,355, filed Apr. 28, 1995, now U.S. Pat. No. 5,708,163 which is a continuation-in-part of U.S. Ser. No. 08/213,053, filed Mar. 15, 1994, now U.S. Pat. No. 5,543,505 the contents of which are hereby incorporated by reference into this application.

This invention was made with government support under grants GM-15240-02, GM-16291-01, HL-25848-14 and AI-16943 from the National Institutes of Health. Accordingly, the U.S. Government has certain rights in the invention.

BACKGROUND OF THE INVENTION

Throughout this application, citations for various publications are provided within parentheses in the text. The disclosures of these publications are hereby incorporated in their entirety by reference into this application in order to more fully describe the state of the art to which this invention pertains.

The function of carbohydrates as structural materials and as energy storage units in biological systems is well recognized. By contrast, the role of carbohydrates as signaling molecules in the context of biological processes has only recently been appreciated. (M. L. Phillips, E. Nudelman, F. C. A. Gaeta, M. Perez, A. K. Singhal, S. Hakomori, J. C. Paulson, *Science*, 1990, 250, 1130; M. J. Polley, M. L. Phillips, E. Wagner, E. Nudelman, A. K. Singhal, S. Hakomori, J.C. Paulson, *Proc. Natl. Acad. Sci. USA*, 1991, 88, 6224: T. Taki, Y. Hirabayashi, H. Ishikawa, S. Kon, Y. Tanaka, M. Matsumoto, *J. Biol. Chem.*, 1986, 261, 3075; Y. Hirabayashi, A. Hyogo, T. Nakao, K. Tsuchiya, Y. Suzuki, M. Matsumoto, K. Kon, S. Ando, ibid., 1990, 265, 8144; O. Hindsgaul, T. Norberg, J. Le Pendu, R. U. Lemieux, *Carbohydr. Res.*, 1982, 109, 109; U. Spohr, R. U. Lemieux, ibid., 1988, 174, 211) The elucidation of the scope of carbohydrate involvement in mediating cellular interaction is an important area of inquiry in contemporary biomedical research. The carbohydrate molecules, carrying detailed structural information, tend to exist as glycoconjugates (cf. glycoproteins and glycolipids) rather than as free entities. Given the complexities often associated with isolating the conjugates in homogeneous form and the difficulties in retrieving intact carbohydrates from these naturally occurring conjugates, the applicability of synthetic approaches is apparent. (For recent reviews of glycosylation see: Paulsen, H., *Angew. Chem. Int. Ed. Engl.*, 1982, 21, 155; Schmidt, R. R., *Angew. Chem. Int. Ed. Engl.*, 1986, 25, 212; Schmidt, R. R., *Comprehensive Organic Synthesis*, Vol. 6, Chapter 1(2), Pergamon Press, Oxford, 1991; Schmidt, R. R., *Carbohydrates, Synthetic Methods and Applications in Medicinal Chemistry*, Part I, Chapter 4, VCH Publishers, Weinheim, N.Y., 1992. For the use of glycals as glycosyl donors in glycoside synthesis, see Lemieux, R. U., *Can. J. Chem.*, 1964, 42, 1417; Lemieux, R. U., Faser-Reid, B., *Can. J. Chem.*, 1965, 43, 1460; Lemieux, R. U., Morgan, A. R., *Can. J. Chem.*, 1965, 43, 2190; Thiem, J., Karl, H., Schwentner, J., *Synthesis*, 1978, 696; Thiem. J. Ossowski, P., *Carbohydr. Chem.*, 1984, 3, 287; Thiem, J., Prahst, A., Wendt, T. *Liebigs Ann. Chem.*, 1986, 1044; Thiem, J. in *Trends in Synthetic Carbohydrate Chemistry*, Horton, D., Hawkins, L. D., McGarvvey, G. L., eds., ACS Symposium Series #386, American Chemical Society, Washington, D.C., 1989, Chapter 8.)

The carbohydrate domains of the blood group substances contained in both glycoproteins and glycolipids are distributed in erythrocytes, epithelial cells and various secretions. The early focus on these systems centered on their central role in determining blood group specificities. (R. R. Race and R. Sanger, *Blood Groups in Man*, 6th ed., Blackwell, Oxford, 1975) However, it is recognized that such determinants are broadly implicated in cell adhesion and binding phenomena. (For example, see M. L. Phillips, E. Nudelman, F. C. A. Gaeta, M. Perez, A. K. Singhal, S. Hakomori, J. C. Paulson, *Science*, 1990, 250, 1130.) Moreover, ensembles related to the blood group substances in conjugated form are encountered as markers for the onset of various tumors. (K. O. Lloyd, *Am. J. Clinical Path.*, 1987, 87, 129; K. O. Lloyd, *Cancer Biol.*, 1991, 2, 421) Carbohydrate-based tumor antigenic factors might find applications at the diagnostic level, as resources in drug delivery or ideally in immunotherapy. (Toyokuni, T., Dean, B., Cai, S., Boivin, D., Hakomori, S., and Singhal, A. K., *J. Am. Chem Soc.*, 1994, 116, 395; Dranoff, G., Jaffee, E., Lazenby, A., Golumbek, P., Levitsky, H., Brose, K., Jackson, V., Hamada, H., Paardoll, D., Mulligan, R., *Proc. Natl. Acad. Sci. USA*, 1993, 90, 3539; Tao, M-H., Levy, R., *Nature*, 1993, 362, 755; Boon, T., *Int. J. Cancer*, 1993, 54, 177; Livingston, P. O., *Curr. Opin. Immunol.*, 1992, 4, 624; Hakomori, S., *Annu. Rev. Immunol.*, 1984, 2, 103; K. Shigeta, et al., *J. Biol. Chem.*, 1987, 262, 1358)

The use of synthetic carbohydrate conjugates to elicit antibodies was first demonstrated by Gobel and Avery in 1929. (Goebel, W. F., and Avery, O. T., *J. Exp. Med.*, 1929, 50, 521; Avery, O. T., and Goebel, W. F., *J. Exp. Med.*, 1929, 50, 533.) Carbohydrates were linked to carrier proteins via the benzenediazonium glycosides. Immunization of rabbits with the synthetic antigens generated polyclonal antibodies. Other workers (Allen, P. Z., and Goldstein, I. J., *Biochemistry*, 1967, 6, 3029; Rüde, E., and Delius, M. M., *Carbohydr. Res.*, 1968, 8, 219; Himmelspach, K., et al., *Eur. J. Immunol.*, 1971, 1, 106; Fielder, R. J., et al., *J. Immunol.*, 1970, 105, 265) developed similar techniques for conjugation of carbohydrates to protein carriers. Most of them suffered by introducing an antigenic determinant in the linker itself, resulting in generation of polyclonal antibodies. Kabat (Arakatsu, Y., et al., *J. Immunol.*, 1966, 97, 858), and Gray (Gray, G. R., *Arch. Biochem. Biophys.* 1974, 163, 426) developed conjugation methods that relied on oxidative or reductive coupling, respectively, of free reducing oligosaccharides. The main disadvantage of these techniques, however, is that the integrity of the reducing end of the oligosaccharide was compromised. In 1975 Lemieux described the use an 8-carbomethoxy-1-octanol linker (Lemieux, R. U., et al., *J. Am. Chem. Soc.*, 1975, 97, 4076) which alleviated the problem of linker antigenicity and left the entire oligosaccharide intact. Equally effective in producing glycoconjugates was the allyl glycoside method described by Bernstein and Hall. (Bernstein, M. A., and Hall, L. D., *Carbohydr. Res.*, 1980, 78, C1.) In this technique the allyl glycoside of the deblocked sugar is ozonized followed by a reductive workup. The resultant aldehyde is then reductively coupled to a protein carrier with sodium cyanoborohydride.

In the mid-70's and early 80's Lemieux and his collaborators made contributions to antibody production stimulated by synthetic glycoconjugates (Lemieux, R. U., et al., *J. Am. Chem. Soc.*, 1975, 97, 4076) and to conformational issues (Lemieux, R. U., et al., *Can. J. Chem.*, 1979, 58, 631; Spohr, U., et al., *Can. J. Chem.*, 1985, 64, 2644; Vandonselaar, M., et al., *J. Biol. Chem.*, 1987, 262, 10848) important in the interactions of the blood group determinants (and analogues thereof) with the carbohydrate binding proteins known as lectins. More recently, workers at Bristol-Meyers Squibb reported the X-ray crystal structure of the Lewis$^y$ epitope complexed with the antibody BR96. (Jeffrey, P. D., et al., *Nature Structural Biol.*, 1995, 2, 466.) Two main components appear to govern recognition between carbohydrates and most antibodies. The first is multiple hydrogen bonding between the sugar hydroxyls and the amino acid residues of Asp, Asn, Glu, Gln, and Arg. The second major interaction is stacking between the sugar-ring faces and aromatic side chains, which occurs most frequently with tryptophan. In the complex with BR96 the most significant interactions involve the latter; additional hydrogen bonding occurs between the sugar hydroxyls and the indole nitrogens. Most antibody binding sites can support about 6 linear carbohydrate residues in a groove or cavity shaped binding site.

Glycoconjugates would be used, ideally, in direct immunotherapy or the monoclonal antibodies generated from vaccinations could be used to specifically target known chemotherapeutic agents to tumor sites. The immune response to carbohydrates is generally not strong, resulting mainly in production of IgM type antibodies. IgM antibodies are capable of complement fixation. Complement is a family of enzymes that can lyse cells to which antibodies are bound. The response to carbohydrate antigens normally does not enlist the use of T-cells which would aid in the body's rejection of the tumor. While the probability of complete tumor rejection as a result of vaccination with a conjugate is unlikely, such treatments will boost immune surveillance and recurrence of new tumor colonies can be reduced. (Dennis, J., *Oxford Glycosystems Glyconews Second*, 1992; Lloyd, K. O., in *Specific Immunotherapy of Cancer with Vaccines*, 1993, New York Academy of Sciences, 50–58.) Toyokuni and Singhal have described a synthetic glycoconjugate (Toyokuni, T., et al., *J. Am. Chem. Soc.*, 1994, 116, 395) that stimulated a measurable IgG titer, a result which is significant since an IgG response is generally associated with enlistment of helper T cells.

The use of immunoconjugates has shown promise in the reduction of large tumor masses. The workers at Bristol-Meyers Squibb (Trail, P. A., et al., *Science*, 1993, 261, 212) have described the attachment of the known chemotherapeutic drug doxorubicin to the antibody BR96. BR96 is an anti-Lewis$^y$ antibody which has been shown to bind to human breast, lung and colon carcinomas. Athymic mice that have had human cancers (L2987-lung, RCA-colon, and MCF7-breast carcinomas) xenografted subcutaneously were treated with the drug-antibody conjugate (BR96-DOX). The result was complete regression of the tumor mass in 78% of the mice treated. BR96 is efficiently internalized by cellular lysosomes and endosomes following attachment to the cell surface. The change in pH upon internalization results in cleavage of the labile hydrazone thereby targeting the drug specifically to the desired site.

Many of the blood group determinant structures can also occur in normal tissues. Antigen expression in normal cells and cancer cells can have subtle distributional differences. In the case of Le$^y$, (which does appear in normal tissues) the expression of the determinant in tumor cells tends to be in the form of mucins which are secreted. Mucins are glycoproteins with a high content of the amino acids serine and threonine. It is through the hydroxyl functionality of these amino acids that Lewis$^y$ is linked. Thus, in terms of generating competent antibodies against tumor cells expressing the Le$^y$ antigen it is important that the antibody recognize the mucin structure.

Structurally, the blood group determinants fall into two basic categories known as type I and type II. Type I is characterized by a backbone comprised of a galactose 1-3b linked to N-acetyl glucosamine while type II contains, instead, a 1-4b linkage between the same building blocks (cf. N-acetyl lactosamine). The position and extent of a-fucosylation of these backbone structures gives rise to the Lewis-type and H-type specificities. Thus, monofucosylation at the $C_4$-hydroxyl of the N-acetyl glucosamine (Type I series) constitutes the Le$^a$ type, whereas fucosylation of the $C_3$-hydroxyl of this sugar (Type II series) constitutes the Le$^x$ determinant. Additional fucosylation of Le$^a$ and Le$^x$ types at the $C_2$,-hydroxyl of the galactose sector specifies the Le$^b$ and Le$^y$ types, respectively. The Le$^y$ determinant is expressed in human colonic and liver adenocarcinomas. (Levery, S. B., et al., *Carbohydr. Res.*, 1986, 151, 311; Kim, Y. S., *J. Cellular Biochem. Suppl.*, 16G 1992, 96; Kaizu, T., et al., *J. Biol. Chem.*, 1986, 261, 11254; Levery, S. B., et al., *Carbohydr. Res.* 1986, 151, 311; Hakomori, S., et al., *J. Biol. Chem.*, 1984, 259, 4672; Fukushi, Y., et al., ibid., 1984, 259, 4681; Fukushi, Y., et al., ibid., 1984, 259, 10511.)

The presence of an a-monofucosyl branch, solely at the $C_2$,-hydroxyl in the galactose moiety in the backbone, constitutes the H-type specificity (Types I and II). Further permutation of the H-types by substitution of a-linked galactose or a-linked N-acetylgalactosamine at its $C_3$,-hydroxyl group provides the molecular basis of the familiar serological blood group classifications A, B, and O. (Lowe, J. B., *The Molecular Basis of Blood Diseases*, Stamatoyannopoulos, et. al., eds., W. B. Saunders Co., Philadelphia, Pa, 1994, 293.)

Several issues merit consideration in contemplating the synthesis of such blood group substances and their neoglycoconjugates. For purposes of synthetic economy it would be helpful to gain relief from elaborate protecting group manipulations common to traditional syntheses of complex branched carbohydrates. Another issue involves fashioning a determinant linked to a protein carrier. It is only in the context of such conjugates that the determinants are able to galvanize B-cell response and complement fixation. In crafting such constructs, it is beneficial to incorporate appropriate spacer units between the carbohydrate determinant and the carrier. (Stroud, M. R., et al., *Biochemistry*, 1994, 33, 10672; Yuen, C.-T., et al., *J. Biochem.*, 1994, 269, 1595; Stroud, M. R., et al., *J. Biol. Chem.*, 1991, 266, 8439.)

The present invention provides new strategies and protocols for oligosaccharide synthesis. The object is to simplify such constructions such that relatively complex domains can be assembled with high stereo-specificity. Major advances in glycoconjugate synthesis require the attainment of a high degree of convergence and relief from the burdens associated with the manipulation of blocking groups. Another requirement is that of delivering the carbohydrate determinant with appropriate provision for conjugation to carrier proteins or lipids. (Bernstein, M. A., and Hall, L. D., *Carbohydr. Res.*, 1980, 78, Cl; Lemieux, R. U., *Chem. Soc. Rev.*, 1978, 7, 423; R. U. Lemieux, et al., *J. Am. Chem. Soc.*, 1975, 97, 4076) This is a critical condition if the synthetically derived carbohydrates are to be incorporated into carriers suitable for biological application.

Antigens which are selective or ideally specific for cancer cells could prove useful in fostering active immunity. (Hakomori, S., *Cancer Res.*, 1985, 45, 2405–2414; Feizi, T., *Cancer Surveys*, 1985, 4, 245–269) Novel carbohydrate patterns are often presented by transformed cells as either cell surface glycoproteins or as membrane-anchored glycolipids. In principle, well chosen synthetic glycoconjugates which stimulate antibody production could confer active immunity against cancers which present equivalent structure types on their cell surfaces. (Dennis, J., *Oxford Glycosystems Glyconews Second*, 1992; Lloyd, K. O., in *Specific Immunotherapy of Cancer with Vaccines*, 1993, New York Academy of Sciences pp. 50–58) Chances for successful therapy improve with increasing restriction of the antigen to the target cell. A glycosphingolipid was isolated by Hakomori and collaborators from the breast cancer cell line MCF-7 and immunocharacterized by monoclonal antibody MBr1-(Bremer, E. G., et al., *J. Biol. Chem.*, 1984, 259, 14773–14777; Menard, S., et al., Cancer Res., 1983, 43, 1295–1300) The novel glycosphingolipid structure 1b (FIG. 8) was proposed for this breast tumor-associated antigen on the basis of methylation and enzymatic degradation protocols. A $^1$H NMR spectrum consistent with but not definitive for the proposed structure was obtained from trace amounts of isolated antigen. While individual sectors of the proposed structure were not unknown, the full structure was first described based on studies on the breast cancer line. It should be noted that MBr1 also binds to normal human mammary gland tissue and ovarian cancer cell lines. Therefore, 1b as a total entity is likely not restricted to the transformed breast cells. Alternatively, smaller subsections of 1b are adequate for antibody recognition and binding. (The synthesis of the DEF fragment of 1b has been reported, and has been shown to bind to MBr1: Lay, L., et al., *Helv. Chim. Acta*, 1994, 77, 509–514.)

The compounds prepared by processes described herein are antigens useful in adjuvant therapies as vaccines capable of inducing antibodies immunoreactive with epithelial carcinomas, for example, human colon, lung and ovarian tumors. Such adjuvant therapies have potential to reduce the rate of recurrence of cancer and increase survival rates after surgery. Clinical trials on 122 patents surgically treated for AJCC stage III melanoma who were trated with vaccines prepared from melanoma differentiation antigen GM2 (another tumor antigen which like MBr1 is a cell surface carbohydrate) demonstrated in patients (lacking the antibody prior to immunization) a highly significant increase in disease-free interval (P. O. Livingston, et al., *J. Clin Oncol.*, 12, 1036 (1994))

The present invention provides a method of synthesizing Le$^y$-related antigens as well as artificial protein-conjugates of the oligosaccharide which might be more immunogenic than the smaller glycolipid. The antigen contains a novel array of features including the α-linkage between the B and the C entities, as well as the β-linked ring D gal-NAc residue. (For the synthesis of a related structure (SSEA-3) which lacks the fucose residue see: Nunomura, S.; Ogawa, T., *Tetrahedron Lett.*, 1988, 29, 5681–5684.) The present invention also provides a total synthesis of 1b, rigorous proof that the Hakomori antigen does, in fact, correspond to 1b and the synthesis of a bioconjugatable version of 1b. The conciseness of the synthesis reflects the efficiency of glycal assembly methods augmented by a powerful method for sulfonamidoglycosylation (see, e.g., the transformation of 14b –15b, FIG. 10).

BRIEF DESCRIPTION OF THE FIGURES

FIGS. 7a and 7b show the synthesis of a Le$^b$ hexasaccharide in bioconjugatable form. Reagents: (a) 1. 3,3-dimethyldioxirane, CH$_2$Cl$_2$; 2. 19, ZnCl$_2$, THF; (b) 10, Sn(OTf)$_2$ di-tert-butylpyridine, THF; (c) TBAF, AcOH, THF; (d) TIPSCl, imidazole, DMF; (e) I(coll)$_2$ClO$_4$, PhSO$_2$NH$_2$, CH$_2$Cl$_2$; (f) 24, AgBF$_4$, 4A M.S., THF; (g) 1. TBAF, AcOH, THF; 2. Na/NH$_3$; 3. Ac$_2$O, pyridine; (h) 1. 3,3-dimethyl-dioxirane, CH$_2$Cl$_2$; 2. allyl alcohol, ZnCl$_2$; 3. NaOMe, MeOH.

FIG. 13(a) shows the proposed mode of action for inflammatory response.

FIG. 13(c) shows the structure of sulfated E-selectin ligands.

FIG. 14(a) shows a reaction pathway to prepare the Lubineau sulfated Le$^a$.

FIG. 21(g–l) shows in panels G, H and I the measured titer of Ig, IgM and IgG type antibodies with the Le$^y$ mucin structure as the test antigen, respectively, mice immunized with conjugate 17c; in panels J, K and L show results of immunization with ceramide conjugate 32b.

FIG. 35. Cytotoxicity assay of antisera on cultured cells.

SUMMARY OF THE INVENTION

Figure 1:
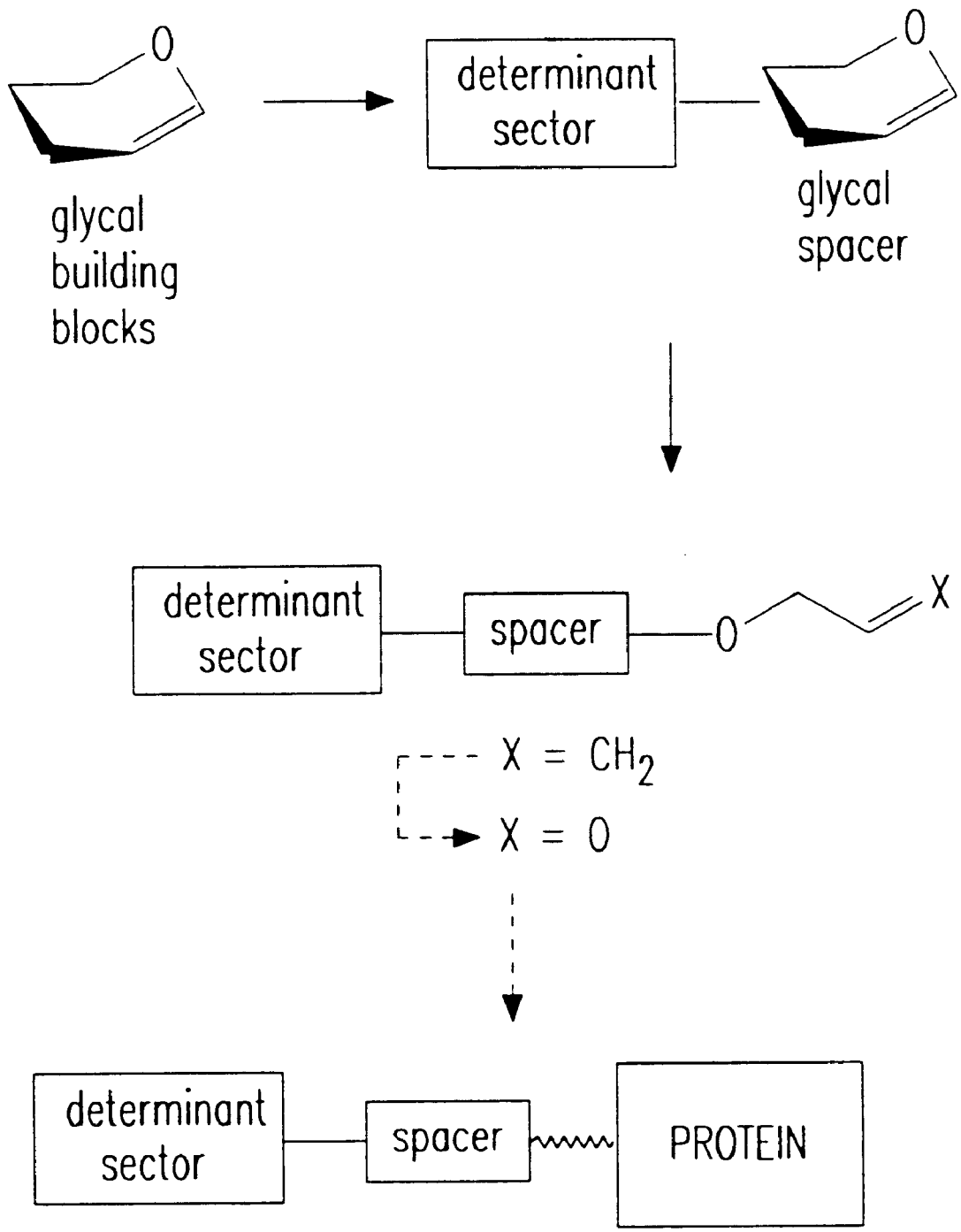
FIG. 1 shows glycal assembly leading to neoglycoproteins.

This invention provides a compound having the structure:

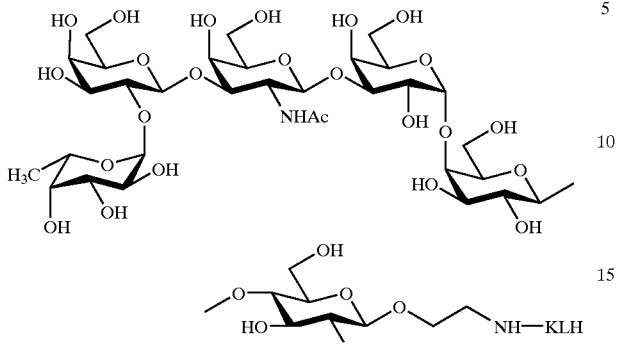

This invention further provides a method of inducing in a subject, antibodies capable of specifically bending with tumor cells selected from the group consisting of epithelial, colon, ovarian, lung, breast and prostate tumor cells which comprises administering to the subject an amount of the compound described above effective to induce antibodies capable of specifically binding with the tumor cells.

This invention also provides a method of preventing recurrence of cancer in a subject which comprises administering to the subject an amount of the compound described above effective to prevent the recurrence of cancer.

This invention also provides a vaccine comprising an amount of the compound described above effective to prevent the recurrence of cancer in a subject.

This invention provides a process of synthesizing a compound having the structure:

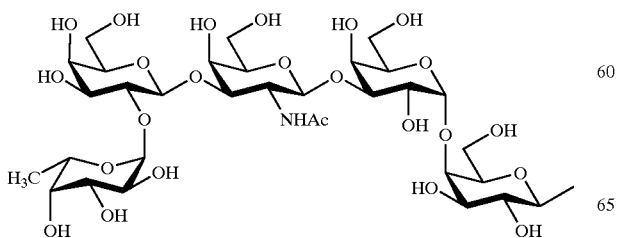

-continued

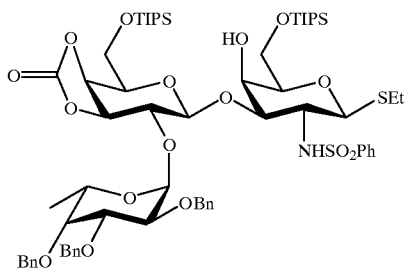

which comprises:

(a) coupling a compound having the structure:

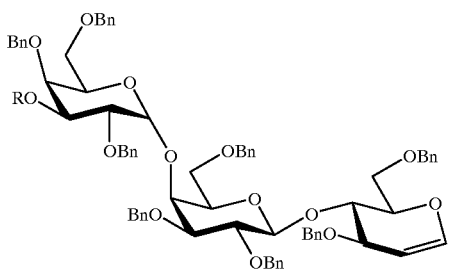

with a compound having the structure:

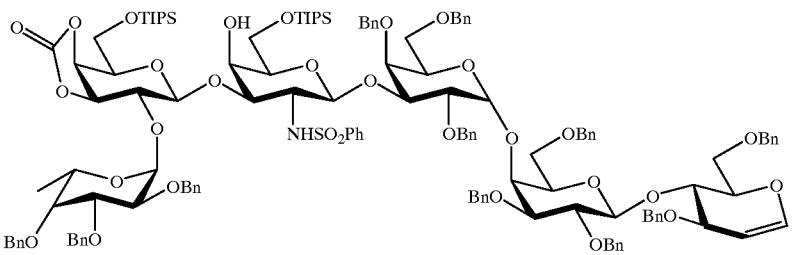

wherein R is H under suitable conditions to form a hexasaccharide having the structure:

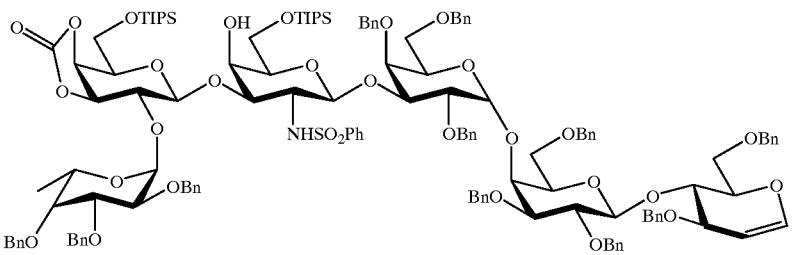

(b) (i) desilylating the compound formed in step (a) with $R_4NF$ wherein each R is independently the same or different and is a linear or branched chain alkyl, aralkyl or aryl group under suitable conditions to form a partially deprotected hexasaccharide;

(ii) de-protecting the hexasaccharide formed in step (b)(1) under suitable conditions to form a deprotected hexasaccharide; and (iii) peracylating the compound formed in step (b) (ii) under suitable conditions to form a hexasaccharide peracetate having the structure:

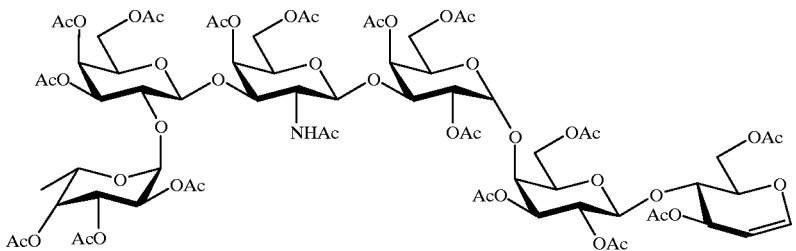

(c) (i) reacting the hexasaccharide peracetate formed in step (b) (iii) with an epoxidizing agent under suitable conditions to form a hexasaccharide epoxide peracetate;
(ii) treating the hexasaccharide epoxide peracetate formed in step (c) (i) with an allyl alcohol under suitable conditions to form an allyl hexasaccharide peracetate;
(iii) saponifying the allyl hexasaccharide peracetate under suitable conditions to form an ally hexasaccharide having the structure:

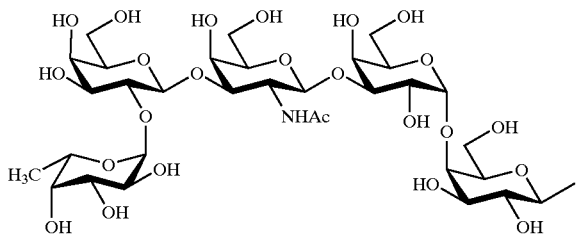

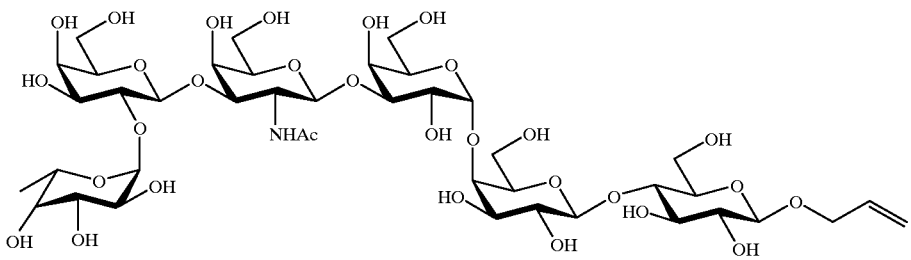

(d) (i) ozonolyzing the allyl hexasaccharide formed in step (c) (iii) in MeOH under suitable conditions and then treating the resulting product with dimethylsulfide to yield an aldehyde;

(ii) treating the aldehyde formed in step (d) (i) with keyhole limpet hemocyanin (KLH) in pH 7 phosphate buffer and excess sodium cyanoborohydride to yield:

-continued purifying the product of step (d) (ii) by exhaustive dialysis.

This invention also provides a process of synthesizing a compound having the structure:

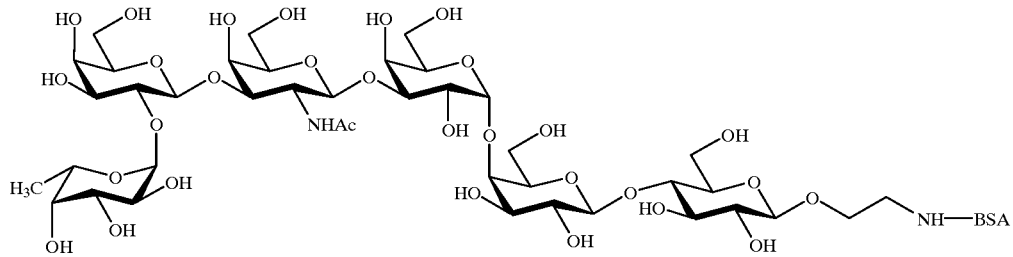

which comprises:

(a) coupling a compound having the structure:

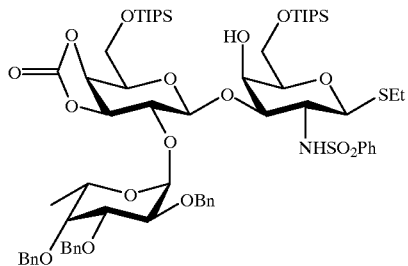

with a compound having the structure:

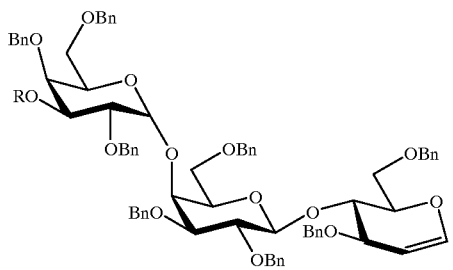

wherein R is B under suitable conditions to form a hexasaccharide having the structure:

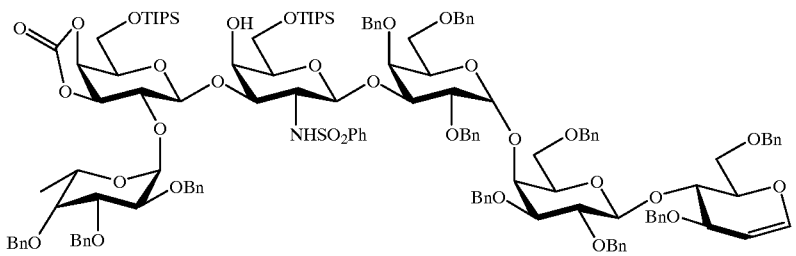

(b) (i) desilylating the compound formed in step (a) with R4NF wherein each R is independently the same or different and is a linear or branched chain alkyl, aralkyl or aryl group under suitable conditions to form a partially deprotected hexasaccharide;

(ii) de-protecting the hexasaccharide formed in step (b)(1) under suitable conditions to form a deprotected hexasaccharide; and (iii) peracylating the compound formed in step (b) (ii) under suitable conditions to form a hexasaccharide peracetate having the structure:

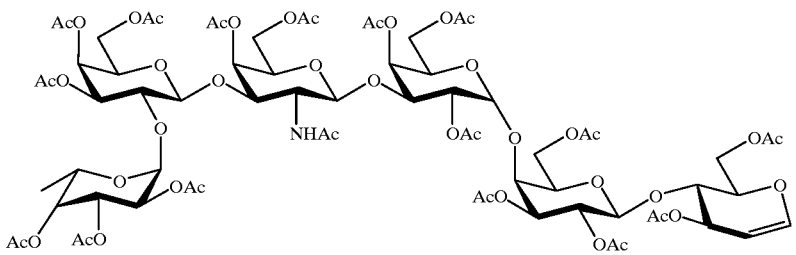

(c) (i) reacting the hexasaccharide peracetate formed in step (b) (iii) with an epoxidizing agent under suitable conditions to form a hexasaccharide epoxide peracetate;

(ii) treating the hexasaccharide epoxide peracetate formed in step (c) (i) with an allyl alcohol under suitable conditions to form an allyl hexasaccharide peracetate;

(iii) saponifying the allyl hexasaccharide peracetate under suitable conditions to form an ally hexasaccharide having the structure:

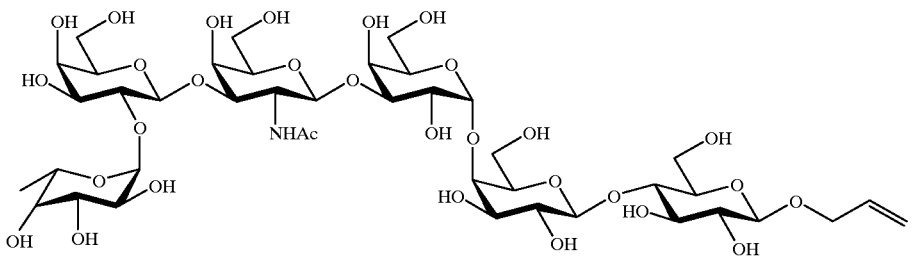

(d) (i) ozonolyzing the allyl hexasaccharide formed in step (c) (iii) in MeOH under suitable conditions and then treating the resulting product with dimethylsulfide to yield an aldehyde;

(ii) treating the aldehyde formed in step (d)(i) with bovine serum albumin (BSA) in pH 7 buffer solution and excess sodium cyanoborohydride to yield:

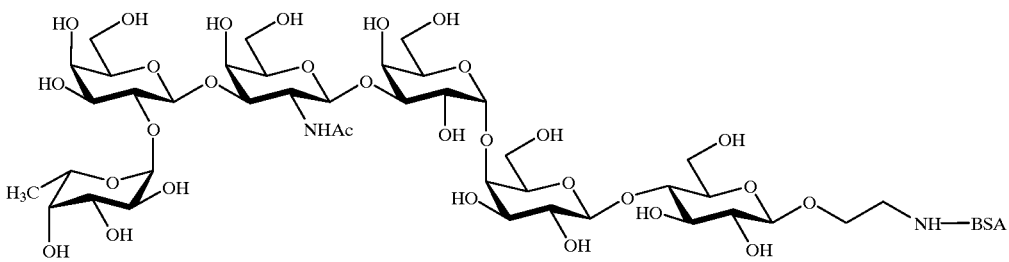

purifying the product of step (d) (ii) by exhaustive dialysis.

DETAILED DESCRIPTION OF THE INVENTION

This invention provides a compound having the structure:

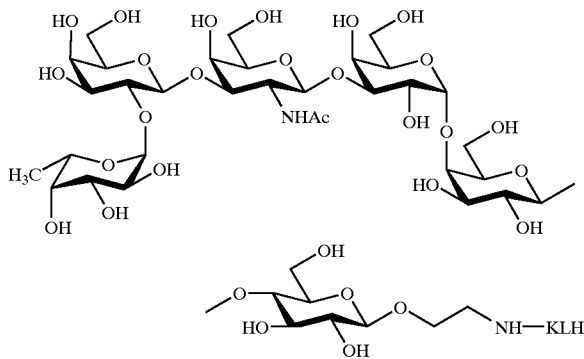

This invention further provides a pharmaceutical composition comprising an amount of the compound described above effective to induce antibodies capable of specifically binding with tumor cells and a pharmaceutically acceptable carrier.

This invention also provides a vaccine comprising an amount of the compound described above effective to prevent the recurrence of cancer in a subject. In an embodiment of the present invention the compound described above is a component in a polyvalent vaccine. In a further embodiment of the present invention the polyvalent vaccine contains one or more of the compounds disclosed in the subject application. In a further embodiment of the present invention the polyvalent vaccine contains an immunological adjuvant such as QS21.

This invention also provides a method of inducing in a subject, antibodies capable of specifically binding with tumor cells selected from the group consisting of epithelial, colon, ovarian, lung, breast and prostate tumor cells which comprises administering to the subject an amount of the compound described above effective to induce antibodies capable of specifically binding with the tumor cells.

In an embodiment, the tumor cells are breast tumor cells and the antibodies induced are MBr1 antibodies.

This invention further provides a method of preventing recurrence of cancer in a subject which comprises administering to the subject an amount of the compound of described above effective to prevent the recurrence of cancer.

In an embodiment of the present invention the cancer is selected from the group consisting of epithelial, colon, breast, prostate, ovarian or lung.

In a further embodiment of the present invention the compound described above is administered in conjunction with an immunological adjuvant. Examples of immunological adjuvants which may be used in the subject invention include, but are not limited to, bacteria, liposomes, pluronic block copolymers, QS21, lipid formulations containing endotoxins, bacteria such as bacille Calmette-Guerin, and Salmonella Minnesota R595 mutant cells. In an embodiment of the present invention the compound described above is administered in conjunction with QS21.

In a further embodiment, the subject is in clinical remisssion or, where the subject has been treated by surgery, or where the subject has limited unresected disease.

This invention also provides a process of synthesizing a compound having the structure:

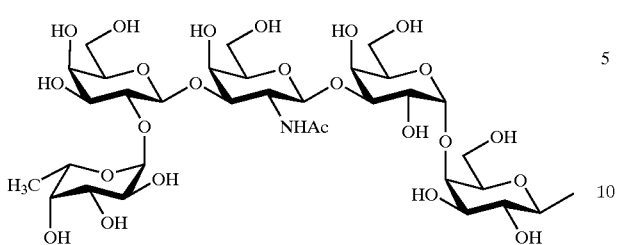
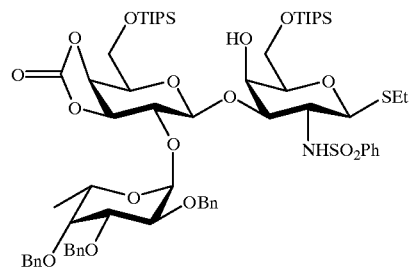

(a) coupling a compound having the structure:

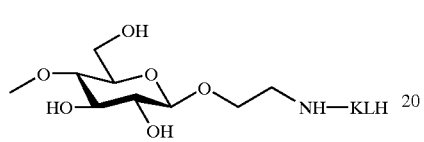

with a compound having the structure:

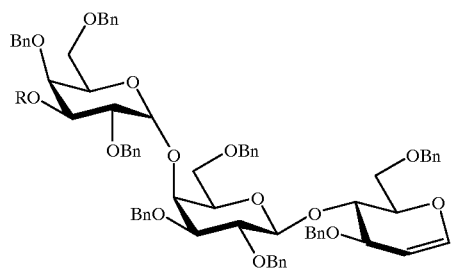

which comprises:

wherein R is H under suitable conditions to form a hexasaccharide having the structure:

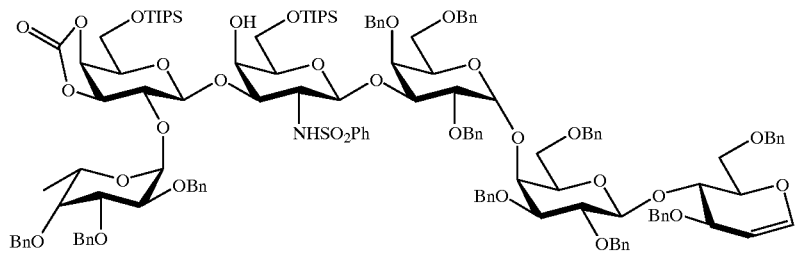

(b) (i) desilylating the compound formed in step (a) with $R_4NF$ wherein each R is independently the same or different and is a linear or branched chain alkyl, aralkyl or aryl group under suitable conditions to form a partially deprotected hexasaccharide;

(ii) de-protecting the hexasaccharide formed in step (b) (1) under suitable conditions to form a deprotected hexasaccharide; and (iii) peracylating the compound formed in step (b) (ii) under suitable conditions to form a hexasaccharide peracetate having the structure:

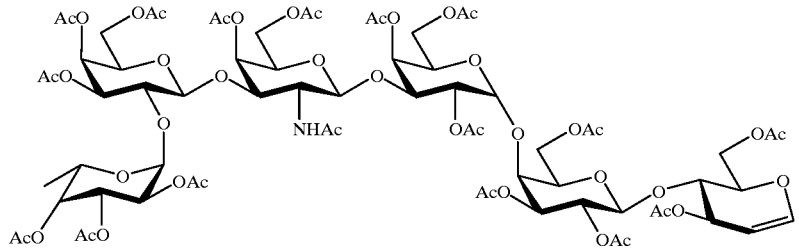

(c) (i) reacting the hexasaccharide peracetate formed in step (b) (iii) with an epoxidizing agent under suitable conditions to form a hexasaccharide epoxide peracetate;

(ii) treating the hexasaccharide epoxide peracetate formed in step (c) (i) with an allyl alcohol under suitable conditions to form an allyl hexasaccharide peracetate;

(iii) saponifying the allyl hexasaccharide peracetate under suitable conditions to form an ally hexasaccharide having the structure:

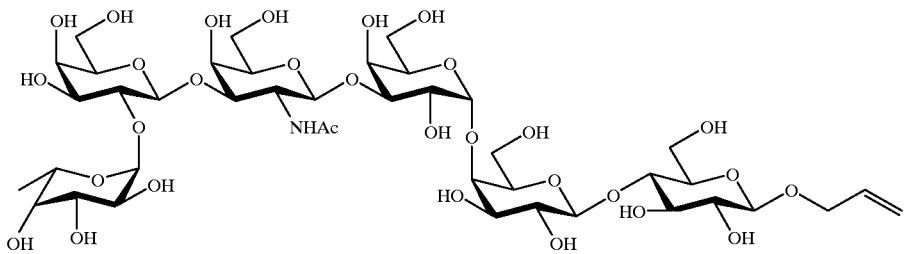

(d) (i) ozonolyzing the allyl hexasaccharide formed in step (c) (iii) in MeOH under suitable conditions and then treating the resulting product with dimethylsulfide to yield an aldehyde;

(ii) treating the aldehyde formed in step (d) (i) with keyhole limpet hemocyanin (KLH) in pH 7 phosphate buffer and excess sodium cyanoborohydride to yield:

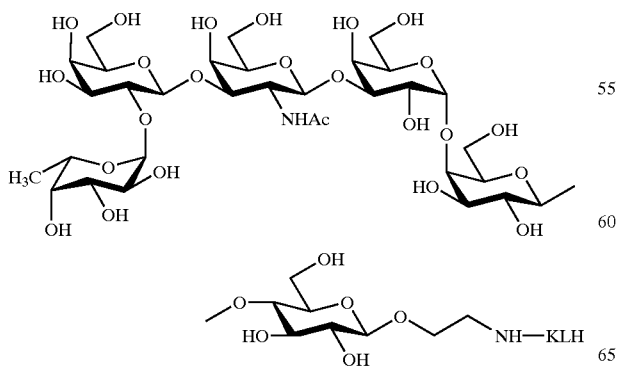

purifying the product of step (d) (ii) by exhaustive dialysis. This invention also provides a process of synthesizing a compound having the structure:

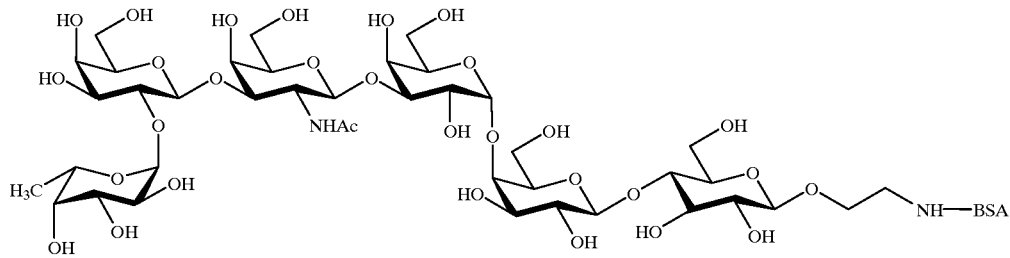

which comprises:

(a) coupling a compound having the structure:

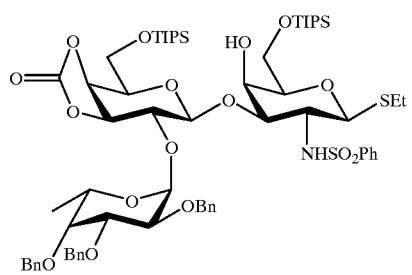

with a compound having the structure:

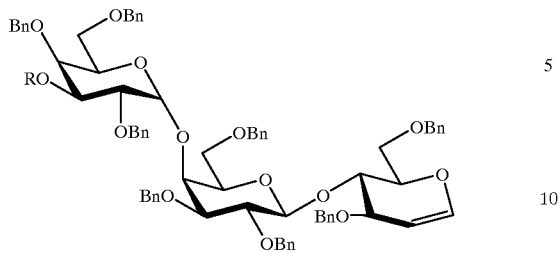

wherein R is H under suitable conditions to form a hexasaccharide having the structure:

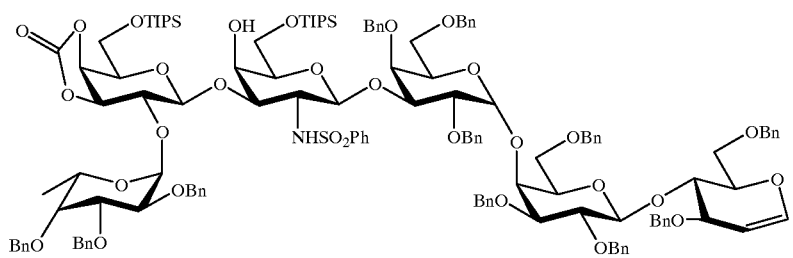

(b) (i) desilylating the compound formed in step (a) with $R_4NF$ wherein each R is independently the same or different and is a linear or branched chain alkyl, aralkyl or aryl group under suitable conditions to form a partially deprotected hexasaccharide;
(ii) de-protecting the hexasaccharide formed in step (b)(1) under suitable conditions to form a deprotected hexasaccharide; and
(iii) peracylating the compound formed in step (b) (ii) under suitable conditions to form a hexasaccharide peracetate having the structure:

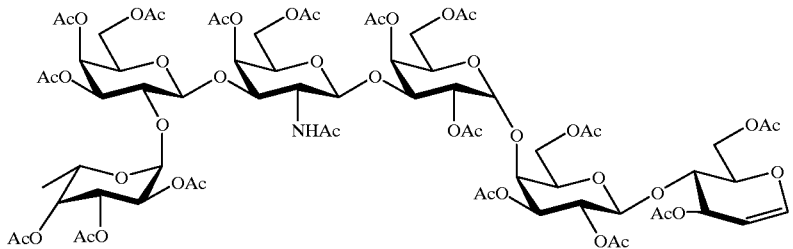

(c) (i) reacting the hexasaccharide peracetate formed in step (b) (iii) with an epoxidizing agent under suitable conditions to form a hexasaccharide epoxide peracetate;
(ii) treating the hexasaccharide epoxide peracetate formed in step (c) (i) with an allyl alcohol under suitable conditions to form an allyl hexasaccharide peracetate;
(iii) saponifying the allyl hexasaccharide peracetate under suitable conditions to form an ally hexasaccharide having the structure:

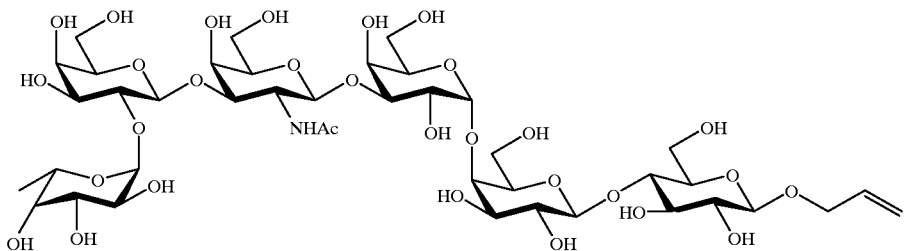

(d) (i) ozonolyzing the allyl hexasaccharide formed in step (c) (iii) in MeOH under suitable conditions and then treating the resulting product with dimethylsulfide to yield an aldehyde;

(ii) treating the aldehyde formed in step (d) (i) with bovine serum albumin (BSA) in pH 7 buffer solution and excess sodium cyanoborohydride to yield:

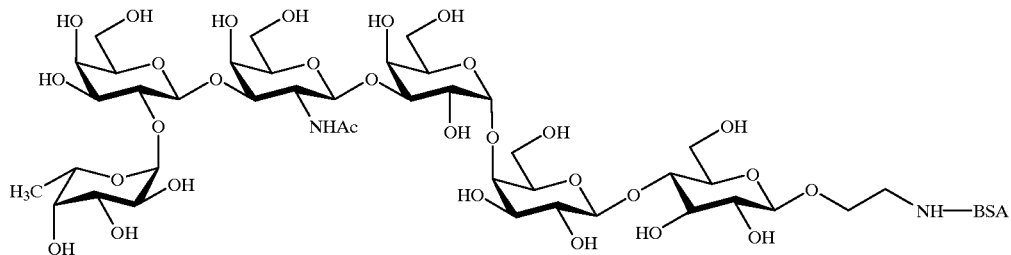

purifying the product of step (d) (ii) by exhaustive dialysis.

The present invention provides a method of synthesizing an allyl pentasaccharide having the structure:

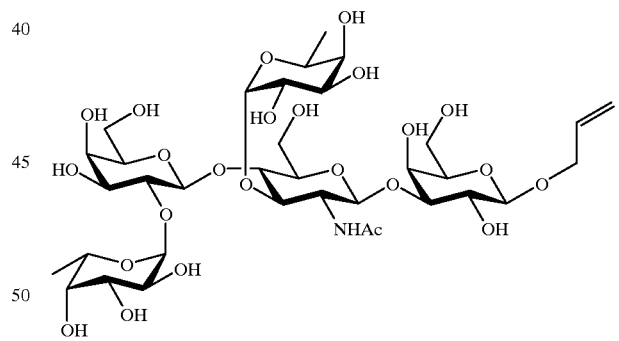

which comprises:

(a) (i) de-silylating a compound having the structure:

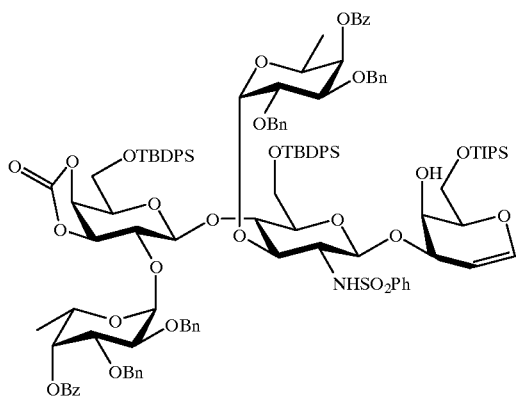

with $R^1R^2R^3R^4NF$ wherein $R^1$, $R^2$, $R^3$, and $R^4$ are independently a linear or branched chain alkyl, aralkyl or aryl, to form an N-sulfonamide pentasaccharide; (ii) cleaving the N-sulfonamide pentasaccharide formed in step (a) (i) to form a deprotected pentasaccharide; and (iii) acetylating the deprotected pentasaccharide formed in step (b) (ii) to form a peracetate having the structure:

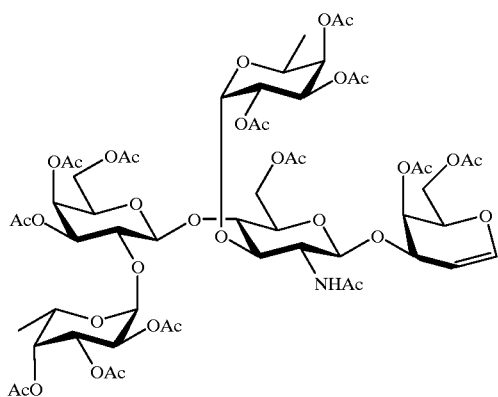

(b) (i) treating the peracetate formed in step (a) (iii) with an epoxidizing agent to form an epoxide peracetate; (ii) reacting the epoxide peracetate formed in step (b) (i) with allyl alcohol to form an allylglycoside peracetate; and (iii) cleaving the allylglycoside peracetate with an alkoxide salt to form the allyl pentasaccharide. In one embodiment, the present invention provides the method wherein $R^1$, $R^2$, $R^3$, and $R^4$ in step (a) (i) are n-butyl. In another embodiment, the present invention provides a method wherein the cleaving step (a) (ii) is performed with $Na/NH_3$. In another embodiment, the present invention provides a method wherein the epoxidizing agent of step (b) (i) is 3,3-dimethyl-dioxirane. In another embodiment, the present invention provides a method wherein the alkoxide salt of step (b) (iii) is NaOMe.

Step (a) (i) may be carried out using a fluoride salt such as tetra-n-butylammonium fluoride in a suitable nonaqueous dipolar solvent, such as THF. Cleaving step (a) (ii) may be effected using a reducing metal in liquid ammonia with a proton donor such as methanol or ethanol. Peracetylation step (a) (iii) is performed using acetyl chloride or acetic anydride in the presence of an organic base such as pyridine. Epoxidation step (b) (i) is effected using an epoxidizing agent such as peracetic acid, m-chloroperbenzoic acid or trifluoroacetic acid, but preferably with 3,3-dimethyldioxirane. Ring-opening step (b) (ii) is carried out with allyl alcohol in the presence of a Lewis acid catalyst such as $ZnCl_2$. Saponification step (b) (iii) is effected using a metal alkoxide such as sodium, lithium or potassium methoxide or ethoxide in the presence of the corresponding alcohol.

The present invention also provides a method of synthesizing a ceramide having the structure:

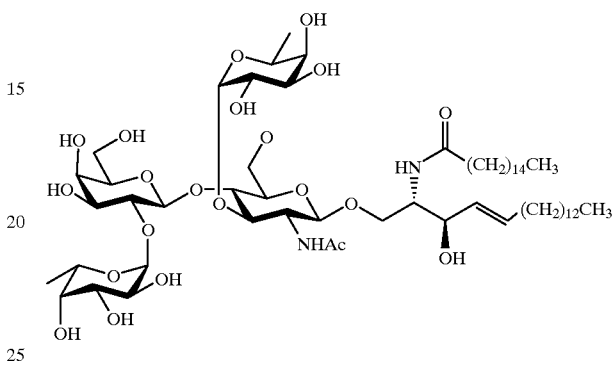

which comprises:

(a) treating a compound having the structure:

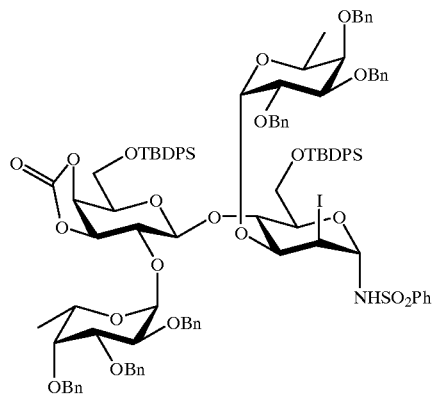

with aqueous silver(I) followed by reacting with diethylaminosulfur trifluoride to form a compound having the structure:

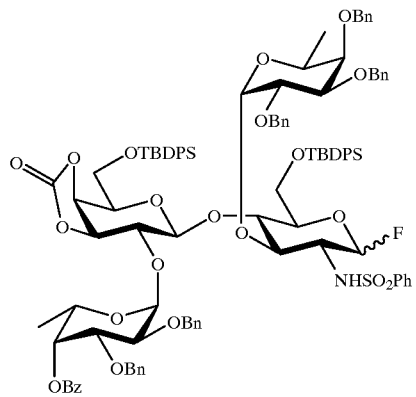

(b) treating the compound formed in step (a) with azidosphingosine to form a compound having the structure:

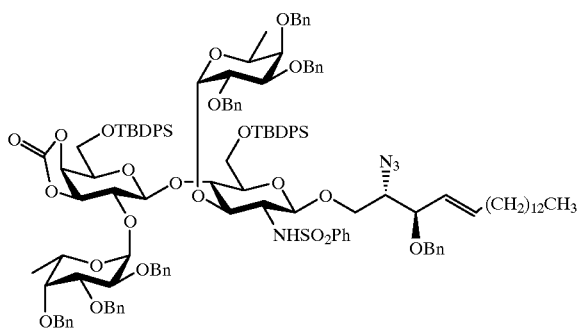

(c) reducing the compound formed in step (b) to form a compound having the structure:

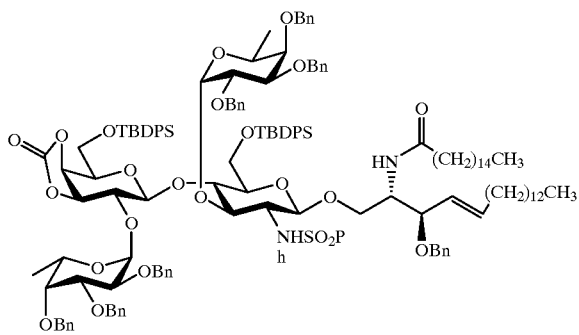

and (d) (i) de-silylating the compound formed in step (c) with $R^1R^2R^3R^4NF$ wherein $R^1$, $R^2$ $R^3$, and $R^4$ are independently a linear or branched chain alkyl, aralkyl or aryl; (ii) reductively cleaving the compound formed in step (d) (i) to form a polyalcohol tetrasaccharide; (iii) peracetylating the polyalcohol tetrasaccharide to form a peracetate tetrasaccharide; and (iv) saponifying the peracetate tetrasaccharide with a metal alkoxide to form the ceramide. In one embodiment, the present invention provides a method wherein silver(I) in step (a) is silver carbonate. In another embodiment, the present invention provides a method wherein step (b) is performed in the presence of zirconocene dichloride and silver triflate. In another embodiment, the present invention provides a is method wherein the reducing step (c) is performed using hydrogen gas and palmitic anhydride in the presence of Lindlar's catalyst. In yet another embodiment, the present invention provides a method wherein $R^1$, $R^2$, $R^3$, and $R^4$ in step (d) (i) are n-butyl and step (d) (ii) is performed using $Na/NH_3$.

Treating step (a) is effected using a silver salt, such as silver carbonate, in the presence of a nonnucleophilic base, such as triethylamine, in a mixed aqueous and dipolar solvent such as THF. After aqueous solvents are removed, the mixture is treated in situ at low temperatures, between $-60°$ and $0°$, preferably at about $-30°$, with diethylaminosulfur trifluoride (DAST) under suitable conditions. Coupling step (b) is carried out using a mixed metal system such as $Cp_2ZrCl_2$ and silver triflate in an organic solvent such as dichloromethane. Reducing step (c) is effected using a noble metal catalyst such as Lindlar's catalyst and a hydrogen atmosphere at ambient to 100 psi. De-silylating step (d) (i) may be carried out using a fluoride salt such as tetra-n-butylammonium fluoride in a suitable nonaqueous dipolar solvent, such as THF. Cleaving step (d) (ii) may be effected using a reducing metal in liquid ammonia with a proton donor such as methanol or ethanol. Peracetylation step (d) (iii) is performed using acetyl chloride or acetic anydride in the presence of an organic base such as pyridine. Saponification step (d) (iv) is effected using a metal alkoxide such as sodium, lithium or potassium methoxide or ethoxide in the presence of the corresponding alcohol.

The present invention provides a compound having the structure:

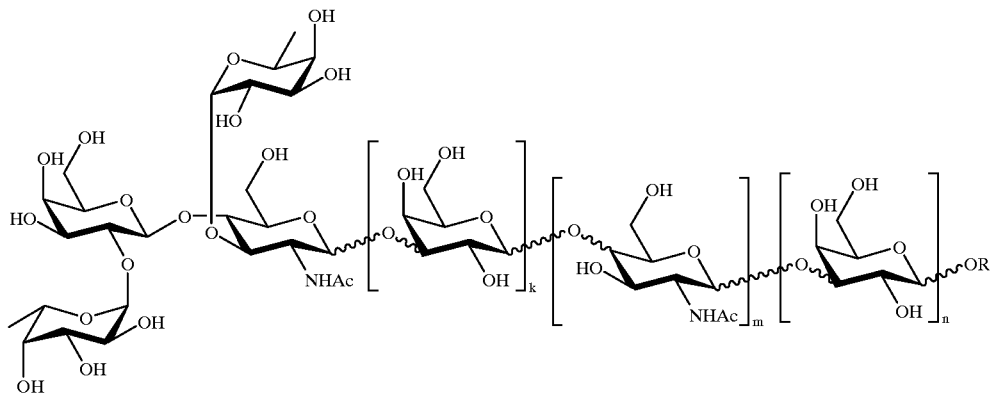

wherein R is H, substituted or unsubstituted alkyl, aryl or allyl, or an amino acyl moiety, an amino acyl residue of a peptide, an amino acyl residue of a protein, which amino acyl moiety or residue bears an ω-amino group or an ω-(C=O)— group, which group is linked to O via a polymethylene chain having the structure —(CH$_2$)$_r$—, where r is an integer between about 1 and 9, or a moiety having the structure:

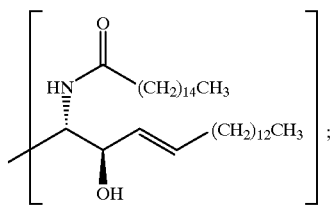

and wherein k, m and n are independently 0, 1, 2 or 3.

In one embodiment, the present invention further provides a compound having the structure:

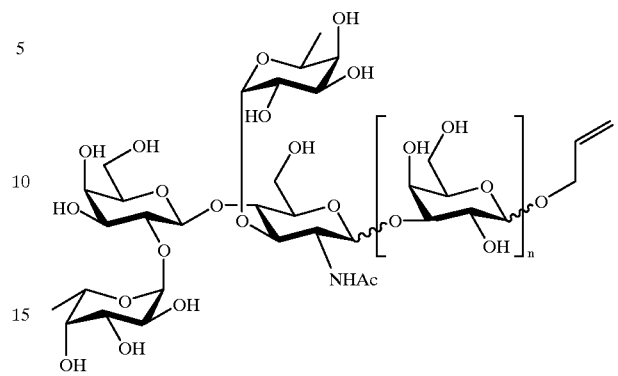

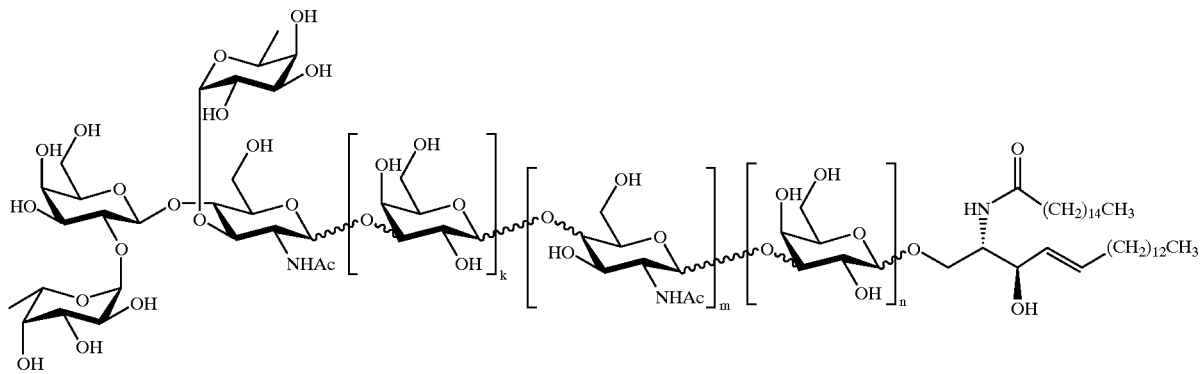

wherein k, m and n are independently 0, 1, 2 or 3. In another embodiment, the present invention provides a compound having the structure:

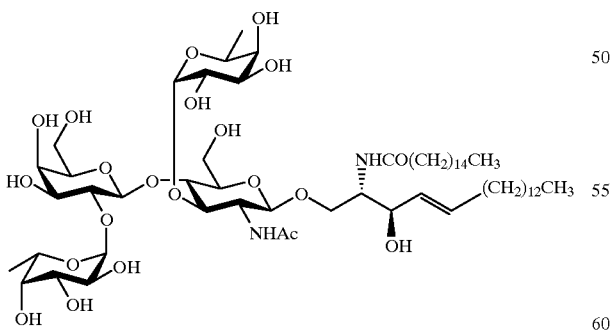

The present invention also provides a compound having the structure:

wherein n is 0, 1, 2, 3 or 4. In one embodiment, the present invention provides a compound wherein n is 1.

In another embodiment, the present invention provides a compound wherein n is 2.

In general, each O-allyl Le$^y$ containing oligosaccharide may be linked to a carrier protein by a two-step process. Ozonolysis affords an aldehyde which is then reductively aminated by the free surface ε-amines of the carrier protein, using a reducing agent such as sodium cyanoborohydride. The product is a Le$^y$-carrier protein adduct useful for inducing antibodies as disclosed herein.

The present invention also provides a compound having the structure:

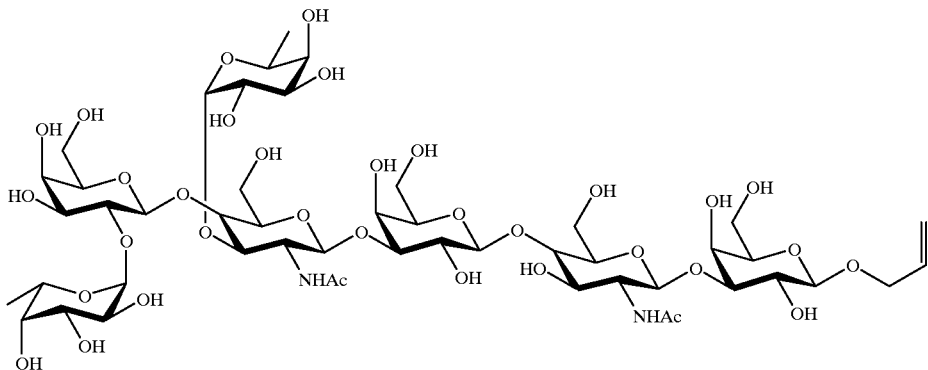

The present invention provides several therapeutic uses for the compounds disclosed herein. Accordingly, the present invention provides a method of inducing antibodies in a subject, wherein the antibodies are capable of specifically binding with epithelial tumor cells, which comprises administering to the subject an amount of a compound which contains a Le$^y$ tetrasaccharide determinant having the structure:

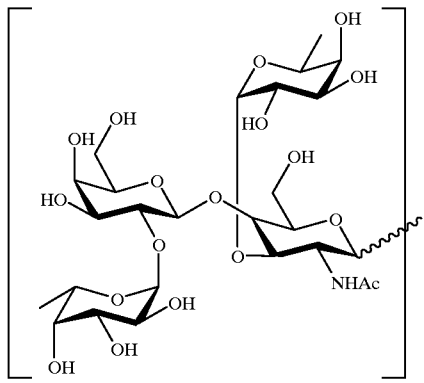

effective to induce the antibodies. In one embodiment, the present invention provides a method wherein the compound is bound to a suitable carrier protein. In a certain embodiment, the present invention provides a method wherein the carrier protein is bovine serum albumin, polylysine, or KLH. In another certain embodiment, the present invention provides a method which further comprises coadministering an immunological adjuvant. In another embodiment, the present invention provides a method wherein the adjuvant is bacteria or liposomes. Specifically, the invention provides a method wherein the adjuvant is *Salmonella minnesota* cells, bacille Calmette-Guerin, or QS21. In various embodiments, the present invention may be practiced using any of the compounds disclosed hereinabove. In a further embodiment, the present invention provides a method wherein the subject is in clinical remission or, where the subject has been treated by surgery, has limited unresected disease.

The present invention also provides a method of inducing antibodies in a subject, wherein the antibodies are capable of specifically binding with colon tumor cells, which comprises administering to the subject an amount of a compound which contains a Le$^y$ tetrasaccharide determinant having the structure:

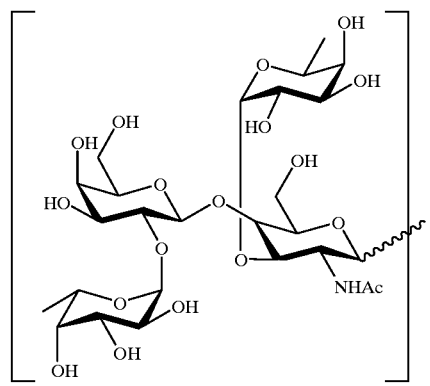

effective to induce the antibodies. In one embodiment, the present invention provides a method wherein the compound is bound to a suitable carrier protein. In a certain embodiment, the present invention provides a method wherein the carrier protein is bovine serum albumin, polylysine, or KLH. In another certain embodiment, the present invention provides a method which further comprises coadministering an immunological adjuvant. In another embodiment, the present invention provides a method wherein the adjuvant is bacteria or liposomes. Specifically, the invention provides a method wherein the adjuvant is *Salmonella Minnesota* cells, bacille Calmette-Guerin, or QS21. In various embodiments, the present invention may be practiced using any of the compounds disclosed hereinabove. In a further embodiment, the present invention provides a method wherein the subject is in clinical remission or, where the subject has been treated by surgery, has limited unresected disease.

The present further provides a method of inducing antibodies in a subject, wherein the antibodies are capable of specifically binding with ovarian tumor cells, which comprises administering to the subject an amount of a compound which contains a Le$^y$ tetrasaccharide determinant having the structure:

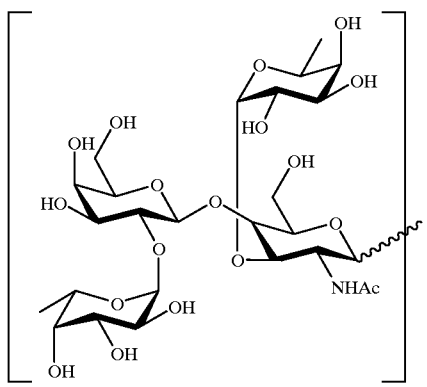

effective to induce the antibodies. In one embodiment, the present invention provides a method wherein the compound is bound to a suitable carrier protein. In a certain embodiment, the present invention provides a method wherein the carrier protein is bovine serum albumin, polylysine, or KLH. In another certain embodiment, the present invention provides a method which further comprises coadministering an immunological adjuvant. In another embodiment, the present invention provides a method wherein the adjuvant is bacteria or liposomes. Specifically, the invention provides a method wherein the adjuvant is *Salmonella minnesota* cells, bacille Calmette-Guerin, or QS21. In various embodiments, the present invention may be practiced using any of the compounds disclosed hereinabove. In a further embodiment, the present invention provides a method wherein the subject is in clinical remission or, where the subject has been treated by surgery, has limited unresected disease.

The present invention provides a method of preventing recurrence of epithelial cancer in a subject which comprises vaccinating the subject with a compound which contains a Le$^y$ tetrasaccharide determinant having the structure:

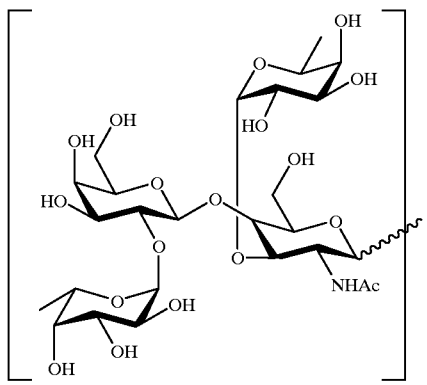

effective to induce the antibodies.

In particular, the present invention provides a method of preventing recurrence of colon cancer in a subject which comprises vaccinating the subject with a compound which contains a Le$^y$ tetrasaccharide determinant having the structure:

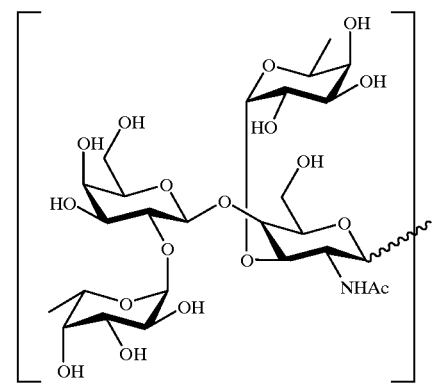

effective to induce the antibodies. In various embodiments, the present invention may be practiced using any of the compounds disclosed hereinabove.

The present invention also provides a method of preventing recurrence of ovarian cancer in a subject which comprises vaccinating the subject with a compound which contains a Le$^y$ tetrasaccharide determinant having the structure:

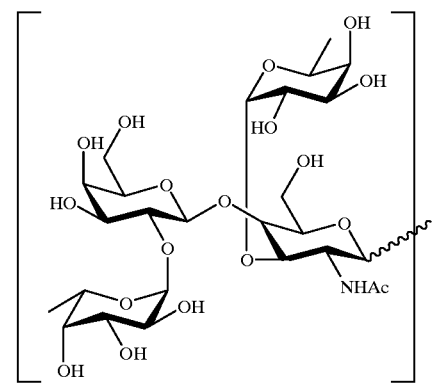

effective to induce the antibodies. In various embodiments, the present invention provides a method of treating epithelial tumors, including colon, lung, ovarian, and prostate, wherein the compound is bound to a suitable carrier protein. In various embodiments, the present invention provides a method wherein the carrier protein is bovine serum albumin,

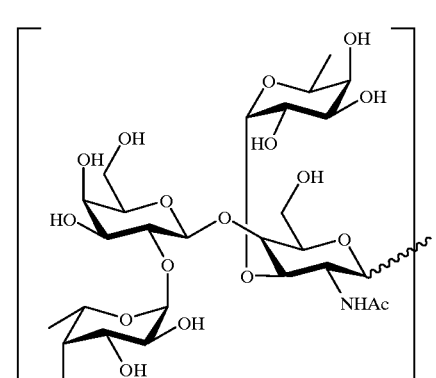

polylysine, or KLH. In other embodiments, the present invention provides a method which further comprises coadministering an immunological adjuvant. In certain embodiments, the present invention provides a method wherein the adjuvant is bacteria or liposomes. In specific embodiments, the present invention provides a method wherein the adjuvant is *Salmonella minnesota* cells, bacille Calmette-Guerin, or QS21. In certain embodiments, the present invention may be practiced using any of the compounds disclosed hereinabove.

The present invention provides a compound having the structure:

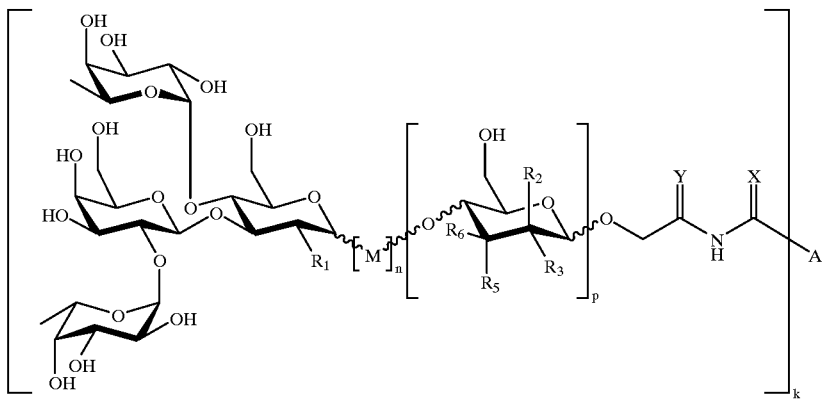

wherein A is selected from the group consisting of (i) an amino acid bearing an ω-amino group or an ω-(C=O)— group, (ii) an amino acid residue of a peptide, which residue bears an ω-amino group or an ω-(C=O)— group, and (iii) an amino acid residue of a protein, which residue bears an ω-amino group or an ω-(C=O)— group; wherein $R_1$ is H, OH, $NH_2$ or $NHR_4$, where $R_4$ is $SO_2Ph$, a linear or branched chain alkyl or acyl group, or an aryl group; wherein M has the structure:

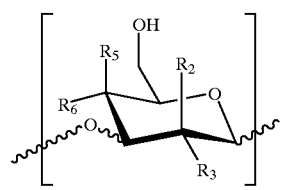

wherein n is an integer from 0 to 18, and where n is greater than 1, each M is independently the same or different; wherein p is either 0 or 1; wherein $R_2$, $R_3$, $R_5$ and $R_6$ are independently the same or different and are H or OH, with the proviso that geminal $R_2$ and $R_3$ are not both OH, and geminal $R_5$ and $R_6$ are not both OH; wherein each wavy line between a carbon atom and an oxygen atom denotes an R or S configuration at the carbon atom; wherein X and Y are independently the same or different and are $H_2$ or O; and wherein k is an integer greater than or equal to 1, with the proviso that when A is an amino acid bearing an ω-amino group or an ω-(C=O)— group, k is equal to 1.

In one embodiment, the present invention provides the compound disclosed hereinabove wherein A is lysine or a lysine residue.

In another embodiment, the present invention provides the compound disclosed hereinabove wherein A is glutamic acid or a glutamic acid residue.

In another embodiment, the present invention provides the compound disclosed hereinabove wherein A is aspartic acid or an aspartic acid residue.

The invention also provides the compound disclosed hereinabove wherein A is an amino acid residue of a globular protein. In one embodiment, the invention provides the compound wherein the globular protein is selected from the group consisting of bovine serum albumin and human serum albumin.

In one embodiment, the invention provides the compound disclosed hereinabove wherein k is 1.

In another embodiment, the invention provides the compound disclosed hereinabove wherein n and p are both equal to 0.

The invention provides a compound having the structure:

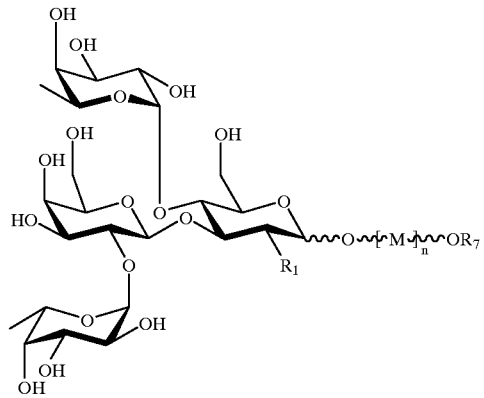

wherein $R_1$ is H, OH, $NH_2$ or $NHR_4$, where $R_4$ is $SO_2Ph$, a linear or branched chain alkyl or acyl group, or an aryl group; wherein M has the structure:

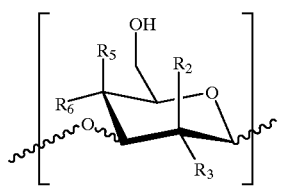

wherein n is an integer from 0 to 18, and where n is greater than 1, each M is independently the same or different;

wherein $R_2$, $R_3$, $R_5$ and $R_6$ are independently the same or different and are H or OH, with the proviso that geminal $R_2$ and $R_3$ are not both OH, and geminal $R_5$ and $R_6$ are not both OH; wherein each wavy line between a carbon atom and an oxygen atom denotes an R or S configuration at the carbon atom; and wherein $R_7$ is a substituted or unsubstituted allyl group.

The invention also provides a compound having the structure:

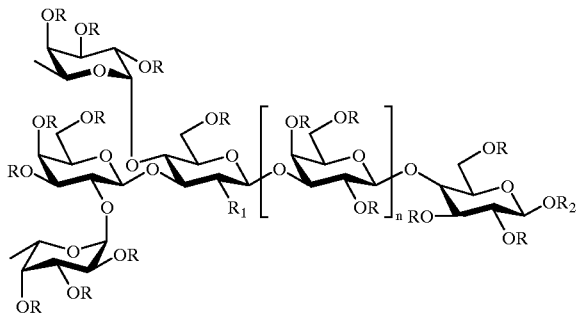

wherein n is an integer from 1 to 18; wherein R is H or a linear or branched chain acyl group; wherein $R_1$ is H, OH, $NH_2$ or $NHR_4$, where $R_4$ is $SO_2Ph$, a linear or branched chain alkyl or acyl group, or an aryl group; and wherein $R_2$ is a substituted or unsubstituted allyl group. In one embodiment, the invention provides the compound wherein n is 1.

The invention further provides a compound having the structure:

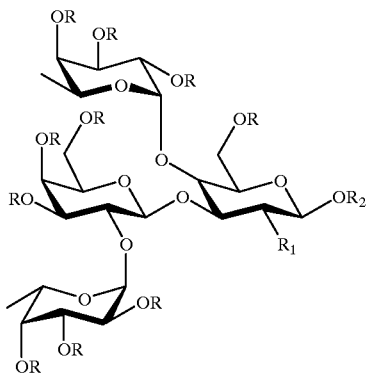

wherein R is H or a linear or branched chain acyl group; wherein $R_1$ is H, OH, $NH_2$ or $NHR_4$, where $R_4$ is $SO_2Ph$, a linear or branched chain alkyl or acyl group, or an aryl group; and wherein $R_2$ is a substituted or unsubstituted allyl group.

The invention also provides a compound having the structure:

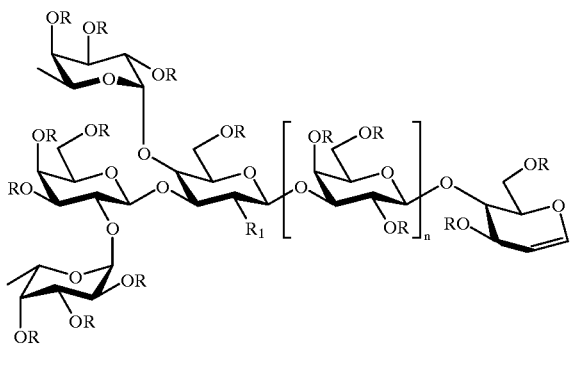

wherein R is H or a linear or branched chain acyl group; wherein $R_1$ is H, OH, NH2 or $NHR_4$, where $R_4$ is $SO_2Ph$, a linear or branched chain alkyl or acyl group, or an aryl group; wherein $R_2$ is a substituted or unsubstituted allyl group; and wherein n is an integer from 1 to 18. In one embodiment, the invention provides the compound wherein n is 1.

The invention also provides a compound having the structure:

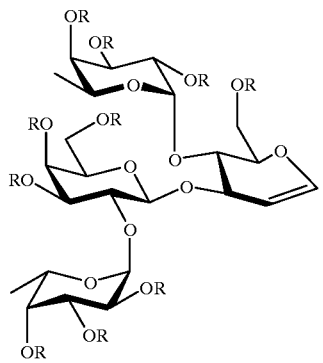

wherein R is H or a linear or branched chain acyl group.

The invention also provides a process for synthesizing a compound having the structure:

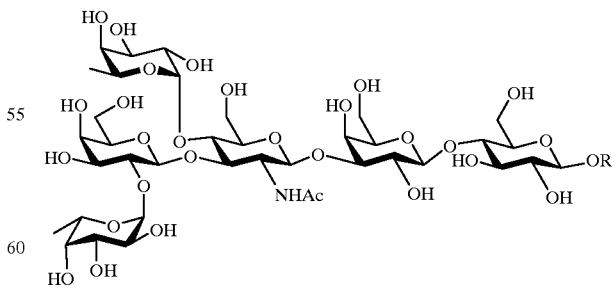

wherein R is a substituted or substituted allyl group, which comprises the steps of (a) synthesizing a compound having the structure:

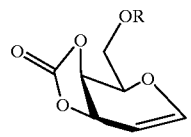

wherein R is a trialkylsilyl, aryldialkylsilyl, alkyldiarylsilyl or triarylsilyl group; (b) reacting the compound of step (a) with a compound having structure:

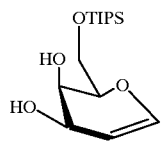

under suitable conditions to form a compound having the structure:

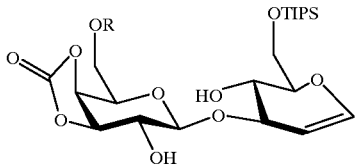

wherein R is a trialkylsilyl, aryldialkylsilyl, alkyldiarylsilyl or triaarylsilyl group; (c) reacting the compound formed in step (b) with a compound having the structure:

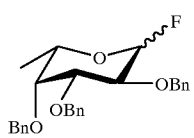

under suitable conditions to form a compound having the structure:

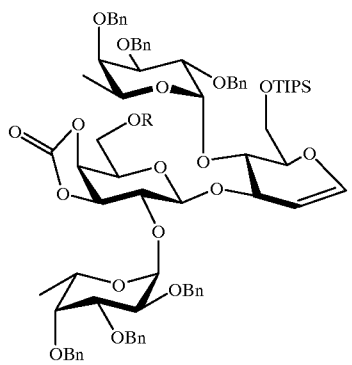

wherein R is a trialkylsilyl, aryldialkylsilyl, alkyldiarylsilyl or triaarylsilyl group; (d) deprotecting and re-protecting the compound formed in step (c) under suitable conditions to form a compound having the structure:

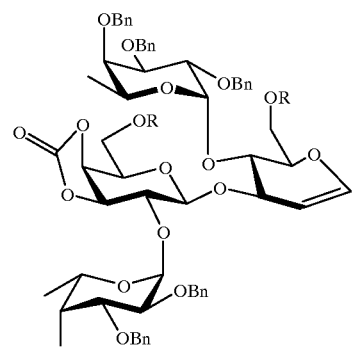

wherein R is TIPS; (e) iodosulfonamidating the compound formed in step (d) under suitable conditions to form a compound having the structure:

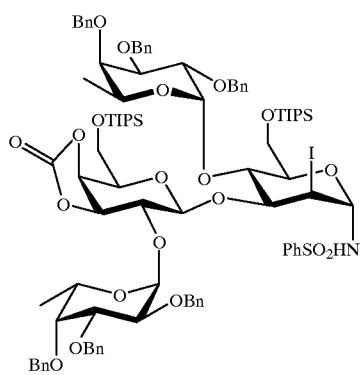

(f) reacting the compound formed in step (e) with a compound having the structure:

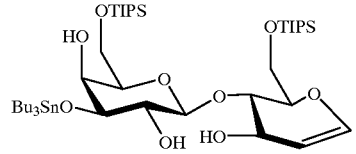

under suitable conditions to form a compound having the structure:

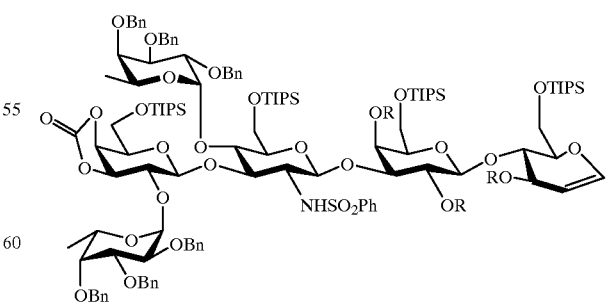

wherein R is H; (g) deprotecting and peracetylating the compound formed in step (f) under suitable conditions to form a compound having the structure:

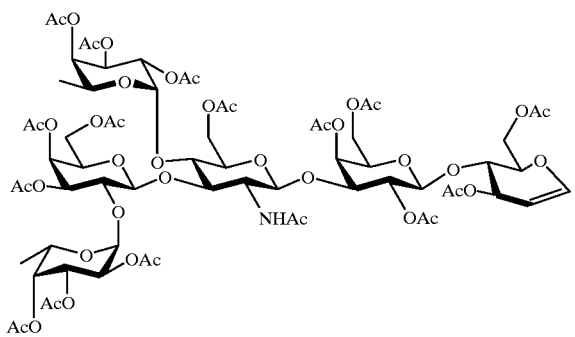

(h) epoxidizing the compound formed in step (g) under suitable conditions to form an epoxide thereof and reacting the epoxide under suitable conditions to form a compound having the structure:

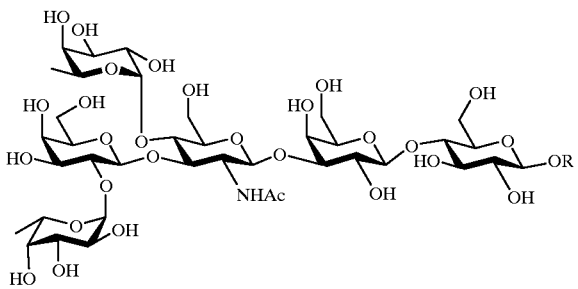

wherein R is a substituted or unsubstituted allyl group; and (i) treating the compound formed in step (h) under suitable conditions to form a compound having the structure:

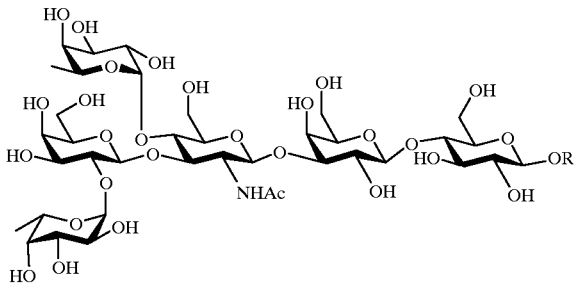

wherein R is a substituted or unsubstituted allyl group. In the above process the suitable conditions necessary for the various reactions and treatments may be found in the Experimental Details section which follows hereinafter. However, it is within the confines of the present invention that the specific reagents and solvents provided as well as the specific conditions necessary for reaction or treatment may be substituted with other suitable reactants, solvents and conditions well known to those skilled in the art.

The allyl compound may be conjugated to a peptide or protein via amine or carboxylic acid side chain. In practicing the invention, a bioconjugate is prepared according to the protocol of Bernstein and Hall (Carbohydr. Res. 1980, 78, C1). The allyl group is ozonolyzed to form either an aldehyde or carboxylic acid, which is condensed to a terminal amine to form, respectively, an imine or an amide. The imine is reduced with sodium borohydride to the amine. Alternatively, the aldehyde is reductively aminated using procedures known in the art to form an amine which is reacted with a side-chain terminal carboxylic acid to form an amide conjugate.

The invention provides a pharmaceutical composition which comprises a therapeutically effective amount of the compound disclosed hereinabove and a pharmaceutically acceptable carrier.

Pharmaceutically acceptable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

The invention further provides a method for treating a subject afflicted with a disorder caused by *Helicobacter pylori* which comprises administering to the subject a therapeutically effective amount of the pharmaceutical composition disclosed hereinabove so as to treat the subject afflicted with the disorder.

In one embodiment, the invention provides a method of treating a subject afflicted with gastric or duodenal ulcer. In another embodiment, the invention provides a method of treating a subject afflicted with gastric adenocarcinoma.

In addition, the invention provides a method for inhibiting the adhesion of *Helicobacter pylori* to gastric epithelium in a subject which comprises administering to the subject an amount of the compound disclosed hereinabove effective to inhibit the adhesion of *Helicobacter pylori* to gastric epithelium in the subject.

The present invention also provides a process for synthesizing a compound having the structure:

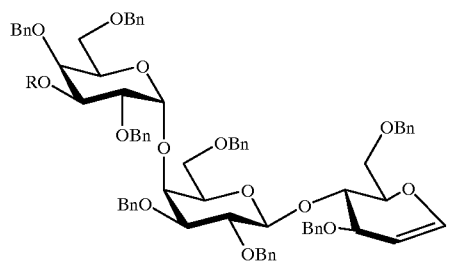

wherein R is H which comprises: (a) (i) reacting a compound having the structure:

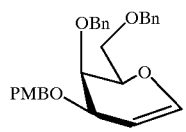

with an epoxidizing agent under suitable conditions to form an epoxide; (ii) cleaving the epoxide formed in step (a) (i) under suitable conditions with R$_4$NF wherein each R is independently the same or different and is a linear or branched chain alkyl, aralkyl or aryl group to form a fluoroalcohol; and (iii) alkylating the fluoroalcohol formed in step (b)(ii) under suitable conditions with a non-nucleophilic base and an organic halide having the formula C$_6$H$_5$CH$_2$X wherein X is Br, Cl, I or F to form a compound having the structure:

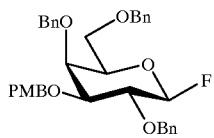

(b) (i) synthesizing a compound having the structure:

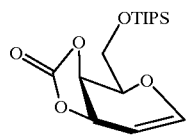

(c) (i) treating the compound formed in step (b) with an epoxidizing agent under suitable conditions to form an epoxide; and (ii) coupling the epoxide formed in step (c)(i) with a compound having the structure:

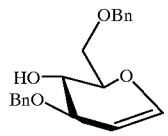

under suitable conditions to form a compound having the structure:

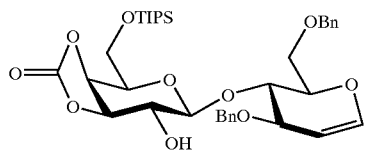

(d) (i) alkylating the compound formed in step (c) (ii) under suitable conditions with a non-nucleophilic base and an organic halide having the formula C$_6$H$_5$CH$_2$X wherein X is Br, Cl, I or F; and (ii) de-silylating the compound formed in step (d) (i) under suitable conditions with R$_4$NF wherein each R is independently the same or different and is a linear or branched chain alkyl, aralkyl or aryl group; (iii) treating the compound formed in step (d) (ii) under suitable conditions with a metal alkoxide to form a deprotected disaccharide; and (iv) alkylating the disaccharide formed in step (d) (iii) under suitable conditions to form a selectively deprotected disaccharide having the structure:

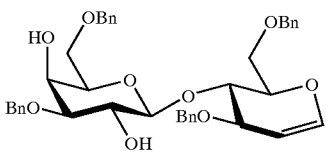

(e) (i) coupling the selectively deprotected disaccharide formed in step (d)(iv) with the compound formed in step (a) (iii) under suitable conditions to form a protected trisaccharide; and (ii) de-protecting the protected trisaccharide formed in step (e)(i) under suitable conditions to form a trisaccharide having the structure:

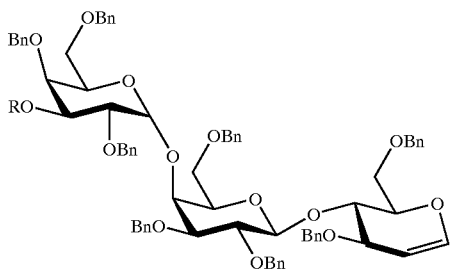

wherein R is H. In step (a) reaction (i) may be carried out using a variety of epoxidizing agents including peracetic acid, m-chlorobenzoic acid, trifluoroacetic acid, and hydrogen peroxide. A preferred agent is 3,3-dimethyldioxirane. Non-nucleophilic, inert solvents may be used, such as dichloromethane. Reaction (a)(ii) may be performed using organic ammonium fluoride salts, including tetrabutylammonium fluoride, in a range of solvents, including ethereal solvents, preferably in tetrahydrofuran. Step (iii) may be performed using a non-nucleophilic base such as sodium hydride in a non-nucleophilic solvent such as DMF. In step (b) the compound shown may be prepared as described herein. Step (c)(i) may be carried out using a variety of epoxidizing agents including peracetic acid, m-chlorobenzoic acid, trifluoroacetic acid, and hydrogen peroxide, 3,3-dimethyldioxirane being preferred, in non-nucleophilic, inert solvents, such as dichloromethane. Coupling step (c)(ii) may be carried out using a metal catalyst, such as zinc chloride, in an inert solvent, such as THF. Step (d)(i) is carried out using a non-nucleophilic base such as sodium hydride in a non-nucleophilic solvent such as DMF. In step (d) (ii) de-silylation is effected using an organic ammonium fluoride salt, including tetrabutylammonium fluoride, in a range of solvents, including ethereal solvents, preferably in tetrahydrofuran. The carbonate ester is cleaved using a metal alkoxide, such as sodium methoxide, in an alcoholic medium such as methanol. Step (d) (iv) is selectively performed using a metal oxide, such as (n-Bu$_3$Sn)$_2$O, in the presence of an organic ammonium bromide, such as tetra-n-butylammonium bromide, in an inert solvent such as benzene. Step (e) is a coupling performed in the presence of a metal halide salt, such as SnCl$_2$, in the presence of silver perchlorate and 2,6-di-t-butylpyridine, in a solvent, such as ether, containing molecular sieves. Oxidative removal of PMB is performed with an oxidizing agent such as DDQ in an inert solvent system, which may preferably be heterogeneous, for example, using water/dichloromethane.

The present invention also provides a process for synthesizing a trisaccharide ceramide having the structure:

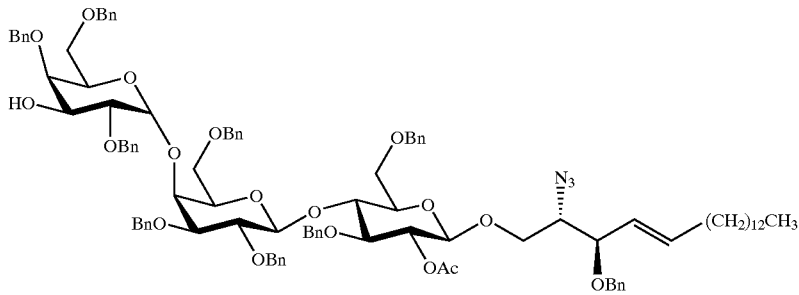

which comprises: (a) synthesizing a trisaccharide having the structure:

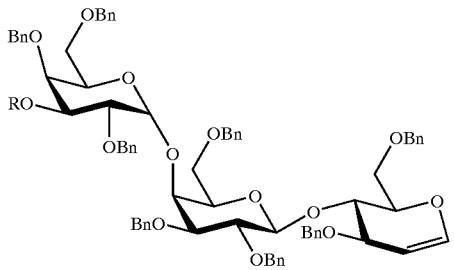

wherein R is PMB; (b) (i) reacting the trisaccharide formed in step (a) with an epoxidizing agent under suitable conditions to form a trisaccharide epoxide; and (ii) reacting the trisaccharide epoxide formed in step (b)(i) with a compound having the structure:

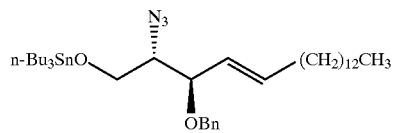

under suitable conditions to form a protected trisaccharide ceramide having the structure:

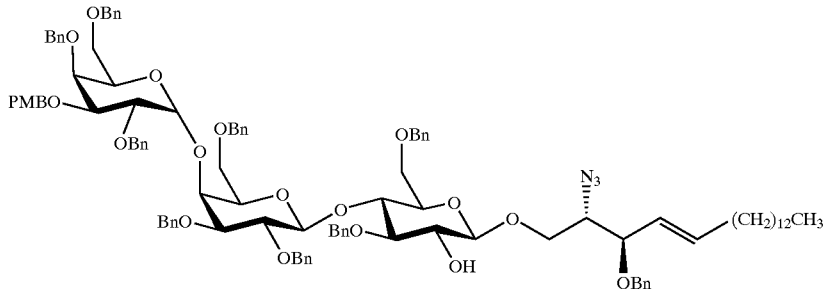

(c) (i) acylating the ceramide formed in step (b) (ii) under suitable conditions; and (ii) selectively de-protecting the compound formed in step (c) (i) under suitable conditions to form the trisaccharide ceramide.

In step (a) the trisaccharide may be synthesized as described herein. Step (b)(i) is performed using using a variety of epoxidizing agents including peracetic acid, m-chlorobenzoic acid, trifluoroacetic acid, and hydrogen peroxide, 3,3-dimethyldioxirane being preferred, in non-nucleophilic, inert solvents, such as dichloromethane. Coupling step (b)(ii) may be carried out using a tributyltin ether of the ceramide precursor and a metal catalyst, such as zinc chloride, in an inert solvent, such as THF. In step (c) (i) acylation is performed using a linear or branched chain alkyl anhydride preferably acetic anhydride or halide in the presence of triethylamine and DMAP in an inert organic solvent such as dichloromethane. The PMB protecting group is removed oxidatively, preferably as described above.

The present invention further provides a process for synthesizing a mercaptotrisaccharide having the structure:

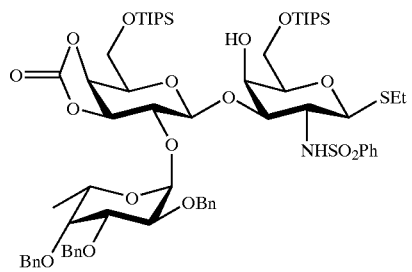

which comprises: (a) (i) synthesizing a compound having the structure:

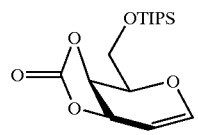

(ii) coupling the compound of step (a) (i) with a compound having structure:

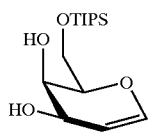

under suitable conditions to form a disaccharide having the structure:

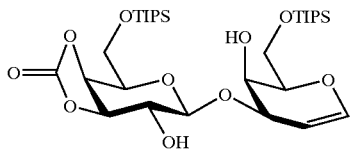

(b) coupling the disaccharide formed in step (a) (ii) with a compound having the structure:

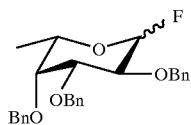

under suitable conditions to form a trisaccharide having the structure:

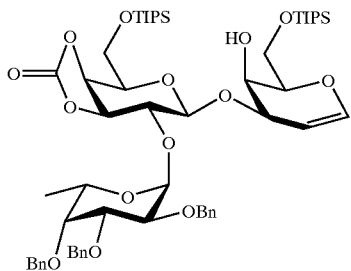

(c) iodosulfonamidating the trisaccharide formed in step (b) under suitable conditions to form a iodosulfonamide having the structure:

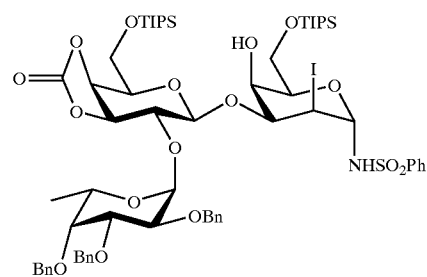

and (d) reacting the iodosulfonamide formed in step (c) under suitable conditions with a thiolate to form the mercaptotrisaccharide.

Step (a)(ii) is performed by reacting the compound of step (a) (i), which may be obtained as described herein or otherwise, with a variety of epoxidizing agents including peracetic acid, m-chlorobenzoic acid, trifluordacetic acid, and hydrogen peroxide, 3,3-dimethyldioxirane being preferred, in non-nucleophilic, inert solvents, such as dichloromethane, followed by coupling with the diol monosaccharide of step (a)(ii) which may be carried out using a metal catalyst, such as zinc chloride, in an inert solvent, such as THF. Coupling with the fluorosugar is carried out in step (b) in the presence of a metal halide salt, such as SnCl$_2$, in the presence of silver perchlorate and 2,6-di-t-butylpyridine, in a solvent, such as ether, containing molecular sieves. Step (c) is performed using I(coll)$_2$ perchlorate and PhSO$_2$NH$_2$ in the presence of molecular sieves. Step (d) is carried out using alkyl thiol and a base such as LiHMDS in an inert solvent as DMF.

The present invention also provides a process of synthesizing a hexasaccharide ceramide having the structure:

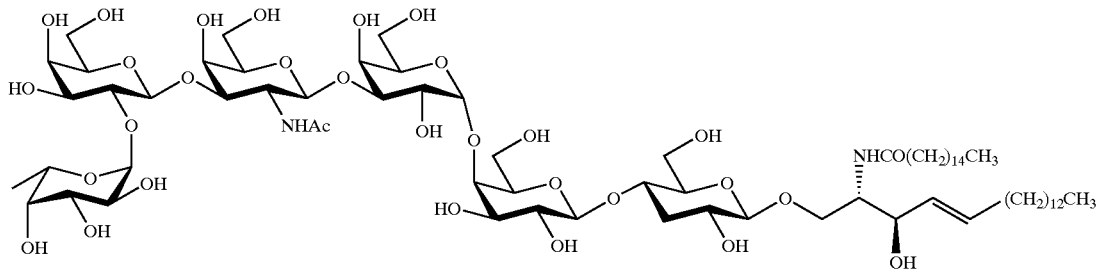

which comprises:

(a) coupling a compound having the structure:

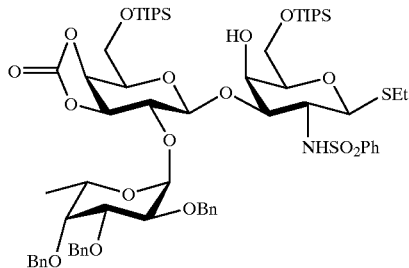

with a compound having the structure:

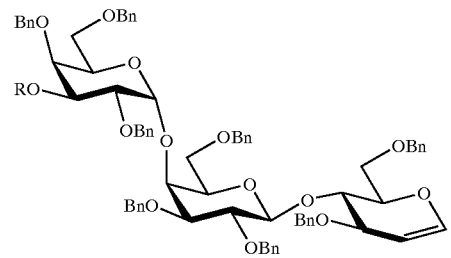

under suitable conditions to form a compound having the structure:

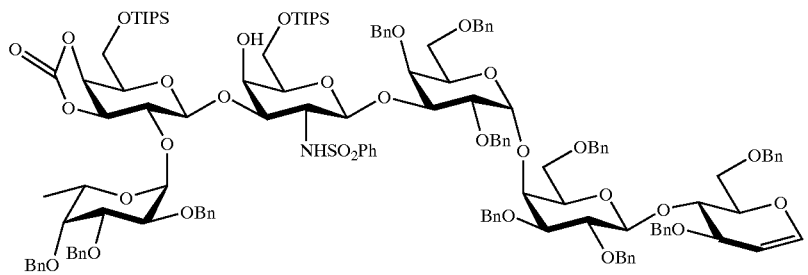

(b) (i) reacting the compound formed in step (a) with an epoxidizing agent under suitable conditions to form a hexasaccharide epoxide; and (ii) reacting the hexasaccharide epoxide with a stannyl ether having the structure:

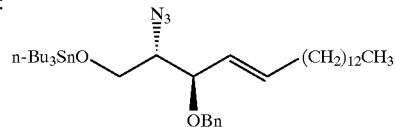

under suitable conditions to form a hexasaccharide alcohol; (c) acylating the hexasaccharide alcohol formed in step (b)(ii) under suitable conditions to form a hexasaccharide acetate having the structure:

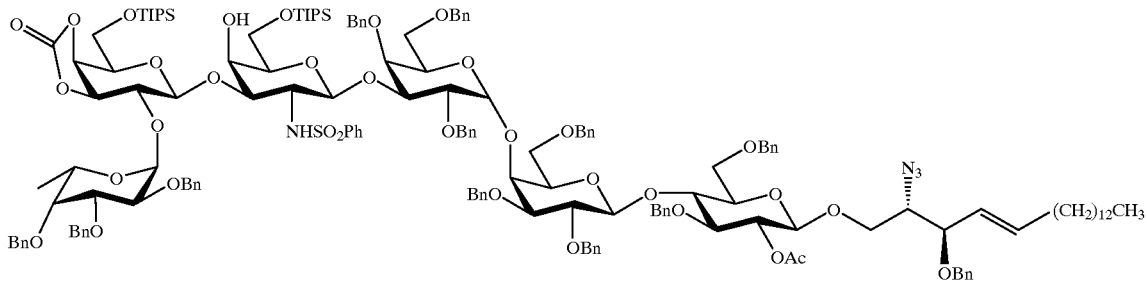

(d) reductively acylating the hexasaccharide acetate formed in step (c) under suitable conditions in the presence of palmitic anhydride to form a hexasaccharide ceramide; (e) desilylating and partially deprotecting the hexasacchararide ceramide under suitable conditions to form a partially deprotected hexasaccharide ceramide; (f) (i) reducing the partially deprotected hexasaccharide ceramide under suitable conditions to form a deprotected hexasaccharide ceramide acetate; and (ii) acylating the deprotected hexasaccharide ceramide acetate under suitable conditions to form a hexasaccharide ceramide peracetate; and (g) saponifying the hexasaccharide ceramide peracetate under suitable conditions to form the hexasaccharide ceramide.

Step (a) is performed using triflate esters, such as methyl triflate, in the presence of molecular sieves in an inert solvent. Step (b) (i) is carried out using a variety of epoxidizing agents including peracetic acid, m-chlorobenzoic acid, trifluoroacetic acid, and hydrogen peroxide, 3,3-dimethyldioxirane being preferred, in non-nucleophilic, inert solvents, such as dichloromethane. Step (b) (ii) is performed using a stannyl ether of the ceramide precursor, preferably the tri-n-butyl stannylether, in the presence of a metal salt, such as Zn triflate, in an inert solvent, such as THF. Step (c) is carried out using acetic anhydride in the presence of a base such as triethylamine and DMAP. Step (d) is carried out using a noble metal catalyst such as Lindlar's catalyst and hydrogen gas in the presence of palmitic anhydride in an inert solvent such as ethyl acetate. Desilylation step (e) is effected using organic ammonium fluoride salts, such as tetra-n-butylammonium fluoride in THF. The carbonate ester is cleaved using a metal alkoxide such as NaOMe in an alcohol such as methanol. In step (f)(i) reduction is performed using a metal such as lithium or sodium in liquid ammonia and an inert solvent such as THF. Step (f)(ii) is carried out using acetic anhydride in the presence of a base such as $Et_3N$ and DMAP in an inert solvent such as dichloromethane. The peracetate is saponified using a metal alkoxide such as sodium methoxide in an alcohol such as methanol.

The present invention also provides a process of synthesizing a hexasaccharide ceramide having the structure:

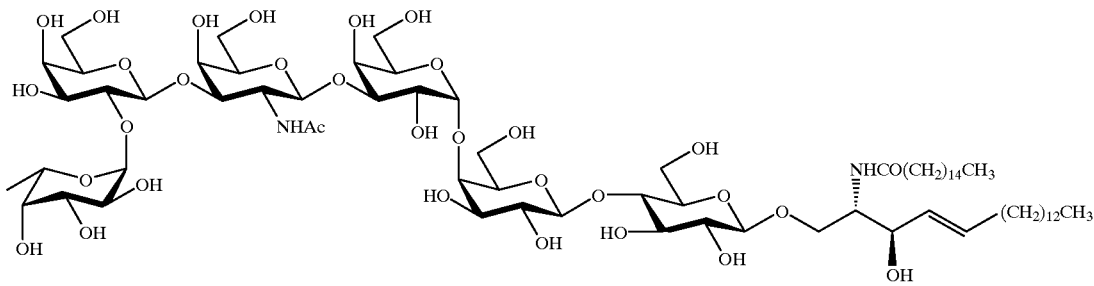

which comprises: (a) coupling a compound having the structure:

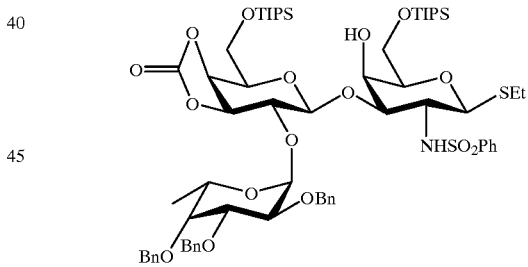

with a compound having the structure:

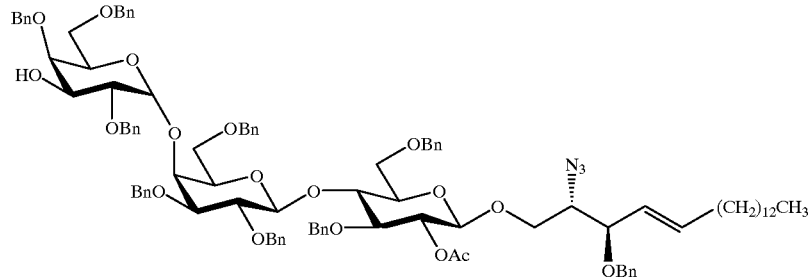

under suitable conditions to form a hexasaccharide having the structure:

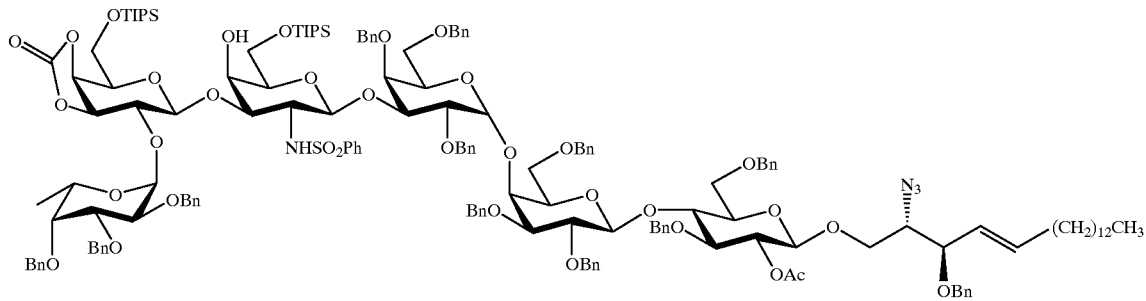

and (b) (i) reducing the hexasaccharide formed in step (a) under suitable conditions in the presence of palmitic anhydride to form a palmitoyl amide; (ii) desilylating the palmitoyl amide with $R_4NF$ wherein each R is independently the same or different and is a linear or branched chain alkyl, aralkyl or aryl group under suitable conditions to form a partially deprotected hexasaccharide; (iii) de-protecting the hexasaccharide formed in step (b) (ii) under suitable conditions to form a deprotected hexasaccharide; (iv) acylating the hexasaccharide formed in step (b) (iii) under suitable conditions to form a hexasaccharide ceramide peracetate; and (v) saponifying the hexasaccharide ceramide peracetate under suitable conditions to form the hexasaccharide ceramide.

Step (a) is performed using triflate esters, such as methyl triflate, in the presence of molecular sieves in an inert solvent. Step (b) (i) is carried out using using a noble metal catalyst such as Lindlar's catalyst and hydrogen gas in the presence of palmitic anhydride in an inert solvent such as ethyl acetate. Step (b) (ii) is performed using organic ammonium fluoride salts, such as tetra-n-butylammonium fluoride in THF. In step (b) (iii) reduction is performed using a metal such as lithium or sodium in liquid ammonia and an inert solvent such as THF. Step (b) (iv) is carried out using acetic anhydride in the presence of a base such as $Et_3N$ and DMAP in an inert solvent such as dichloromethane. In step (v) the peracetate carbonate is saponified using a metal alkoxide such as sodium methoxide in an alcohol such as methanol.

The present invention also provides a process of synthesizing an allyl hexasaccharide having the structure:

which comprises: (a) coupling a compound having the structure:

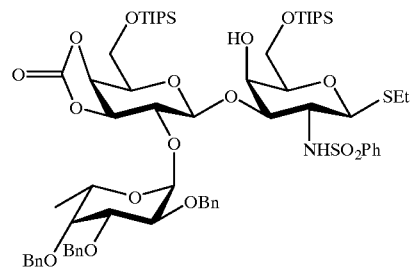

with a compound having the structure:

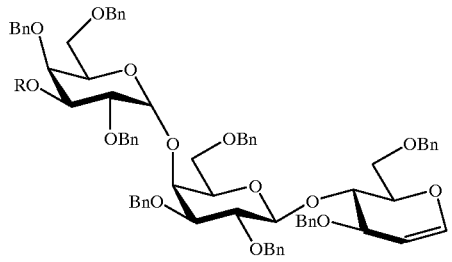

wherein R is H under suitable conditions to form a hexasaccharide having the structure:

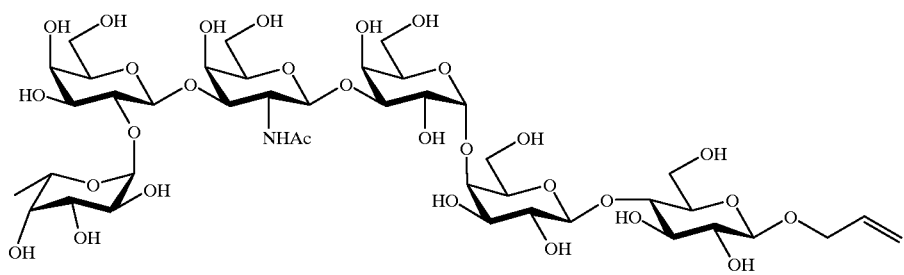

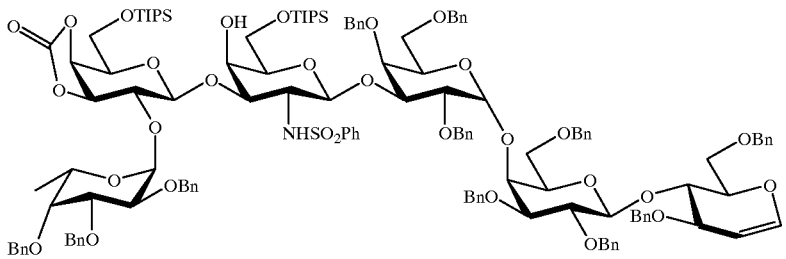

(b) (i) desilylating the compound formed in step (a) with $R_4NF$ wherein each R is independently the same or different and is a linear or branched chain alkyl, aralkyl or aryl group under suitable conditions to form a partially deprotected hexasaccharide; (ii) de-protecting the hexasaccharide formed in step (b) (i) under suitable conditions to form a deprotected hexasaccharide; and (iii) peracylating the compound formed in step (b) (ii) under suitable conditions to form a hexasaccharide peracetate having the structure:

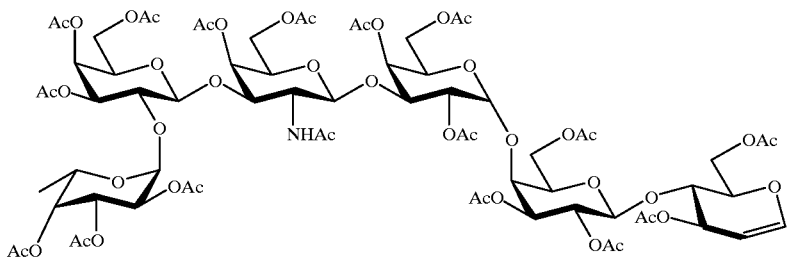

(c) (i) reacting the hexasaccharide peracetate formed in step (b) (iii) with an epoxidizing agent under suitable conditions to form an hexasaccharide epoxide peracetate; (ii) treating the hexasaccharide epoxide peracetate formed in step (c)(i) with allyl alcohol under suitable conditions to form an allyl hexasaccharide peracetate; and (iii) saponifying the allyl hexasaccharide peracetate under suitable conditions to form the allyl hexasaccharide.

Step (a) is performed using triflate esters, such as methyl triflate, in the presence of molecular sieves in an inert solvent. Step (b)(i) is carried out using organic ammonium fluoride salts, such as tetra-n-butylammonium fluoride in THF. Step (b) (ii) is performed using a metal alkoxide such as sodium methoxide in an alcohol such as methanol, followed by reduction performed using a metal such as lithium or preferably sodium in liquid ammonia and an inert solvent such as THF. Step (b) (iii) is carried out using acetic anhydride in the presence of a base such as $Et_3N$ and DMAP in an inert solvent such as dichloromethane. In step (c) (i) is carried out using a variety of epoxidizing agents including peracetic acid, m-chlorobenzoic acid, trifluoroacetic acid, and hydrogen peroxide, 3,3-dimethyldioxirane being preferred, in non-nucleophilic, inert solvents, such as dichloromethane. Step (c)(ii) is carried out using allyl alcohol in an inert solvent. Step (c) (iii) the peracetate carbonate is saponified using a metal alkoxide such as sodium methoxide in an alcohol such as methanol.

The present invention provides a process of synthesizing a hexasaccharide having the structure:

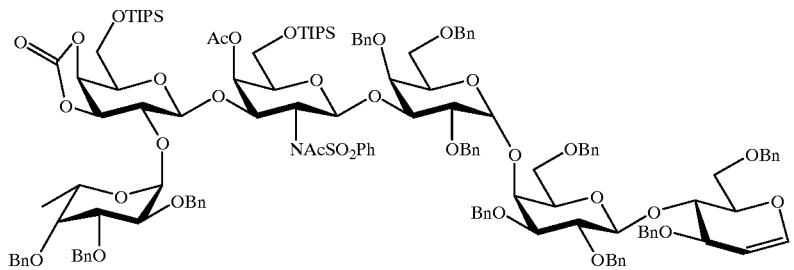

which comprises:

which comprises: (a) coupling a compound having the structure:

with a compound having the structure:

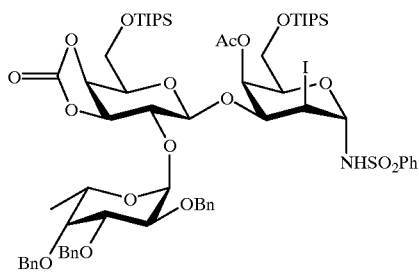

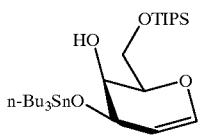

under suitable conditions to form a compound having the structure:

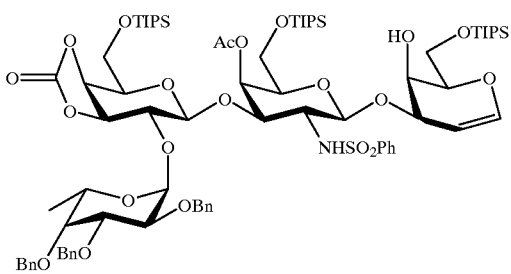

(b) (i) acylating the compound formed in step (a) under suitable conditions; and (ii) reacting the compound formed in step (b) (i) with an epoxidizing agent under suitable conditions to form an epoxide having the structure:

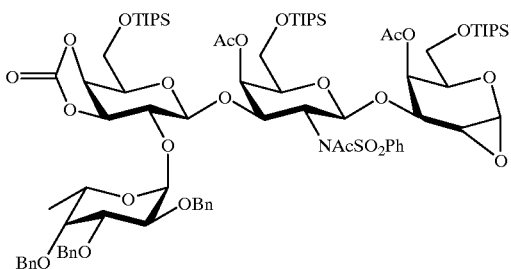

(c) (i) treating the epoxide with R₄NF wherein each R is independently the same or different and is a linear or branched chain alkyl, aralkyl or aryl group under suitable conditions; and (ii) alkylating the compound formed in step (c)(i) under suitable conditions to form a compound having the structure:

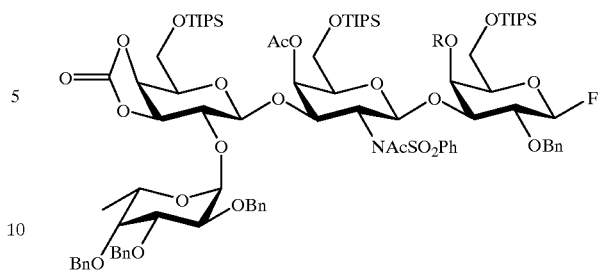

wherein R is H or acyl; (d) coupling the compound formed in step (c)(ii) with a compound having the structure:

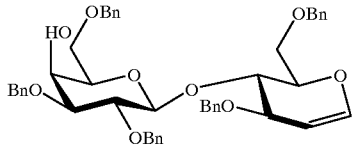

under suitable conditions to form the hexasaccharide.

Step (a) is performed using a metal catalyst such as silver tetrafluoroborate in an inert solvent. Step (b) (i) is carried out using acetic anhydride in the presence of a base such as Et₃N and DMAP in an inert solvent such as dichloromethane. Step (b) (ii) is carried out using a variety of epoxidizing agents including peracetic acid, m-chlorobenzoic acid, trifluoroacetic acid, and hydrogen peroxide, 3,3-dimethyldioxirane being preferred, in non-nucleophilic, inert solvents, such as dichloromethane. Step (c) (i) is effected with organic ammonium fluoride salts, such as tetra-n-butylammonium fluoride in THF. Step (c)(ii) is performed using a non-nucleophilic base such as sodium hydride in an inert solve. Step (d) is performed using a metal salt catalyst such as tin dichloride in the presence of silver perchlorate in an inert solvent such as di-t-butylpyridine. Further transformations provide deprotected products or conjugates with proteins or other carriers.

The present invention further provides a compound having the structure:

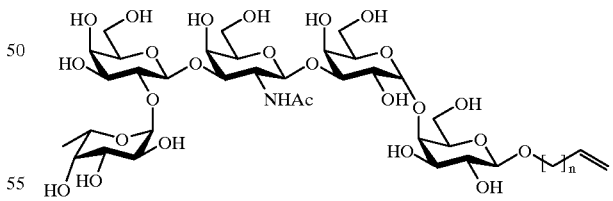

wherein n is an integer between about 0 and about 9.

The allyl glycoside shown is prepared using the glycal coupling methods taught herein, and may be bound to protein carriers using general reactions described herein or by standard methods in the art For example, the allyl glycoside may be prepared by coupling compound 9b disclosed herein with a suitably protected 8b, followed by coupling with 12b, then coupling with allyl alcohol and an appropriate deprotection sequence.

The present invention also provides a compound having the structure:

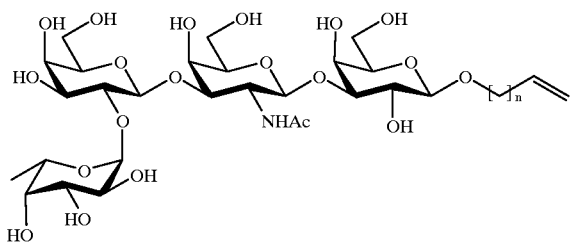

wherein n is an integer between about 0 and about 9.

Figure 12:
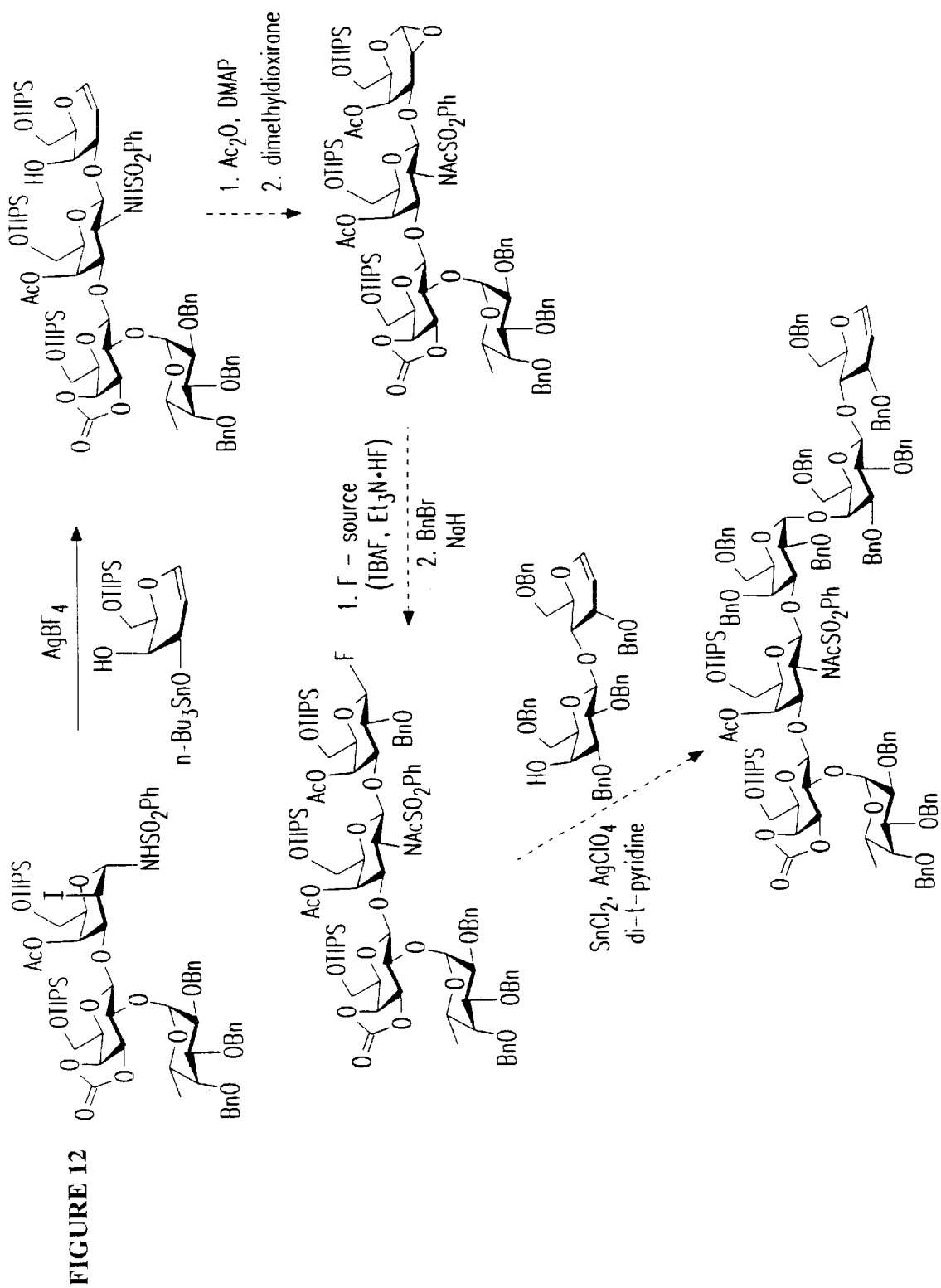
FIG. 12 shows a reaction pathway to the hexasaccharide antigen MBr1 by a 4+2 synthetic approach.
Figure 13B:
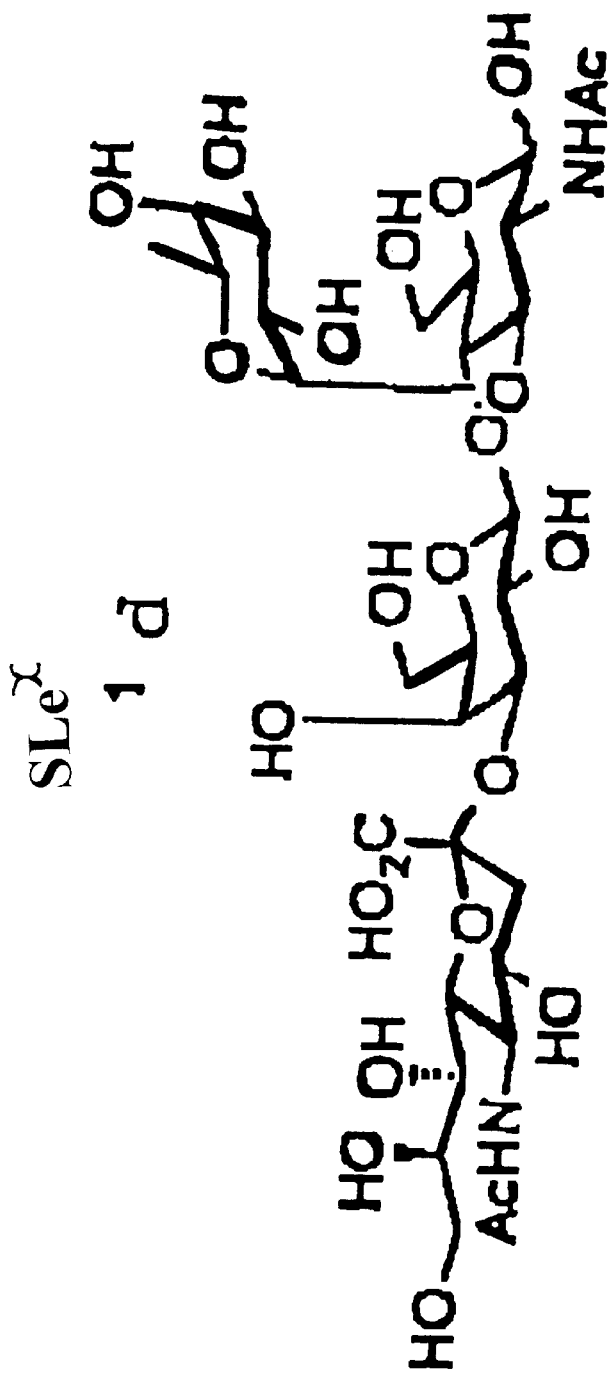
FIG. 13(b) shows the structure of SLe$^x$.
Figure 14B:
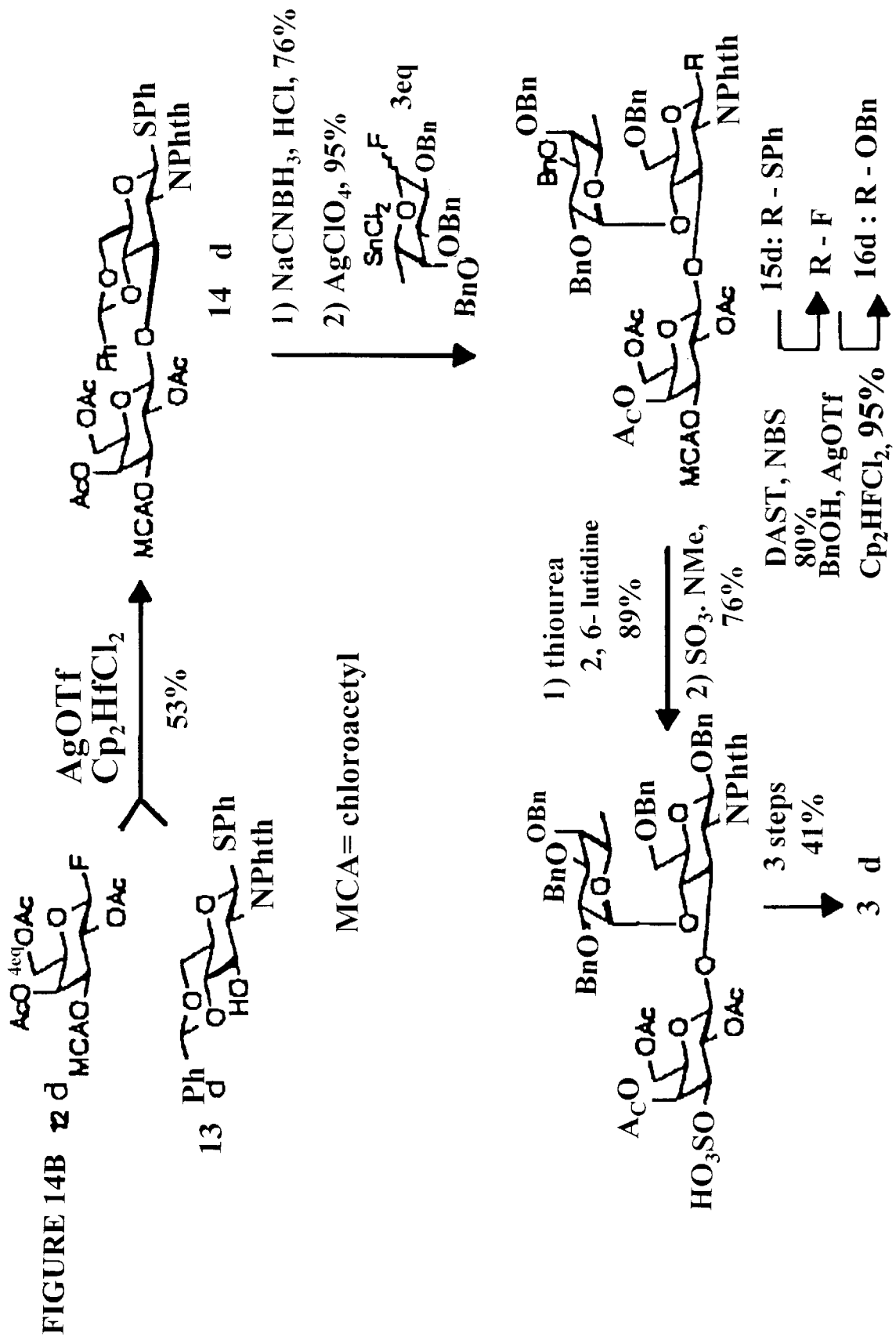
FIG. 14(b) shows a reaction pathway to prepare the Nicolau sulfated Le$^a$.
Figure 15A:
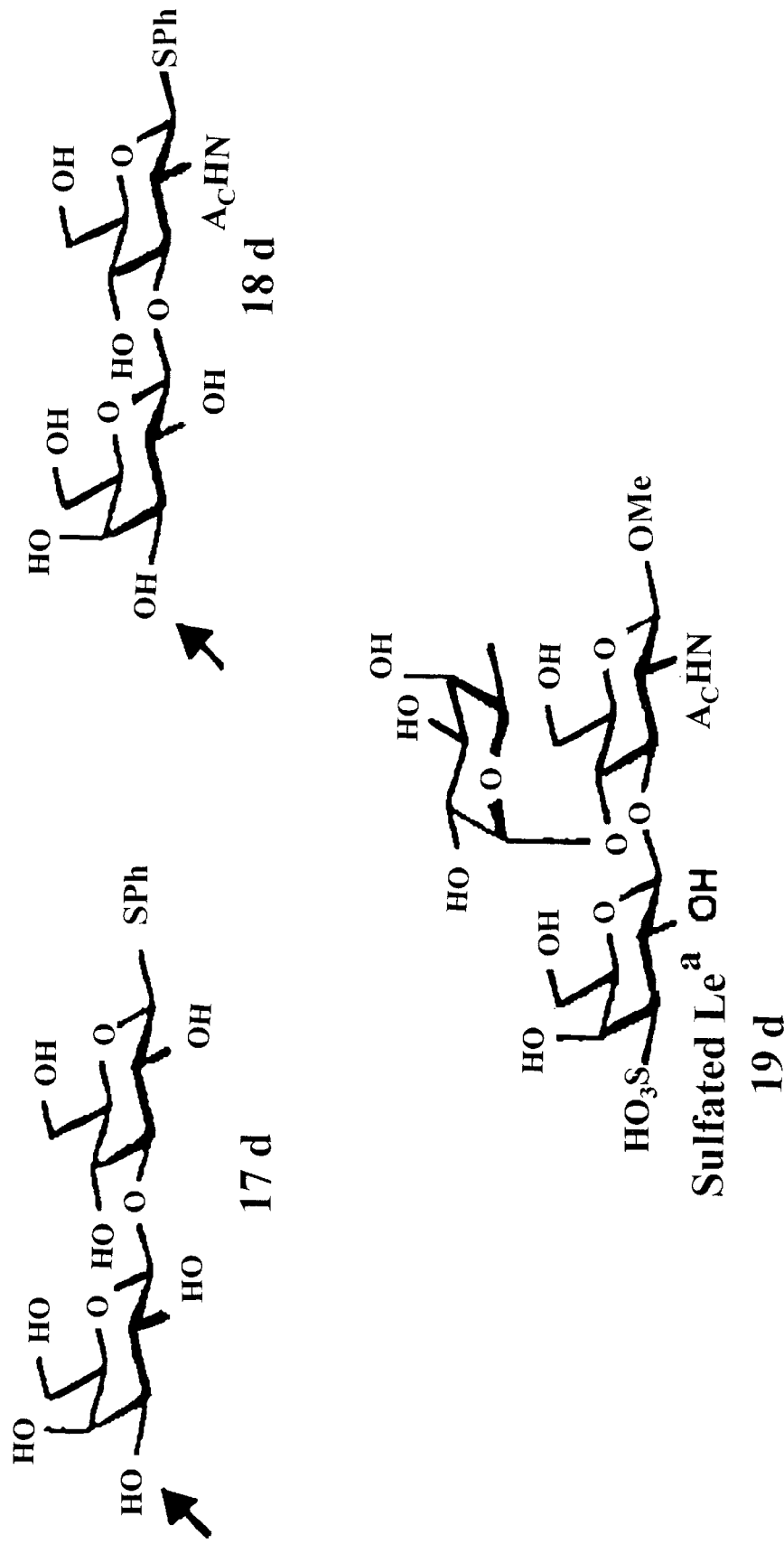
FIG. 15(a) shows compounds 17d, 18d and sulfated Lea 19d.
Figure 15B:
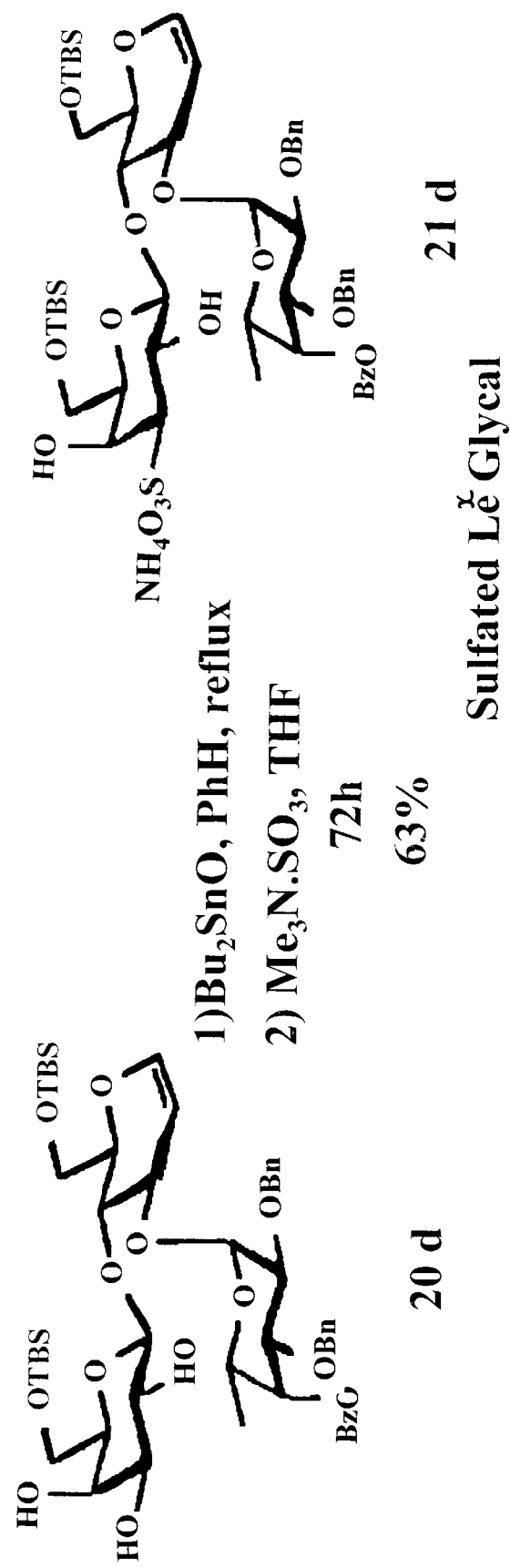
FIG. 15(b) shows the preparation of sulfated Le$^x$ glycal 21d.
Figure 15C:
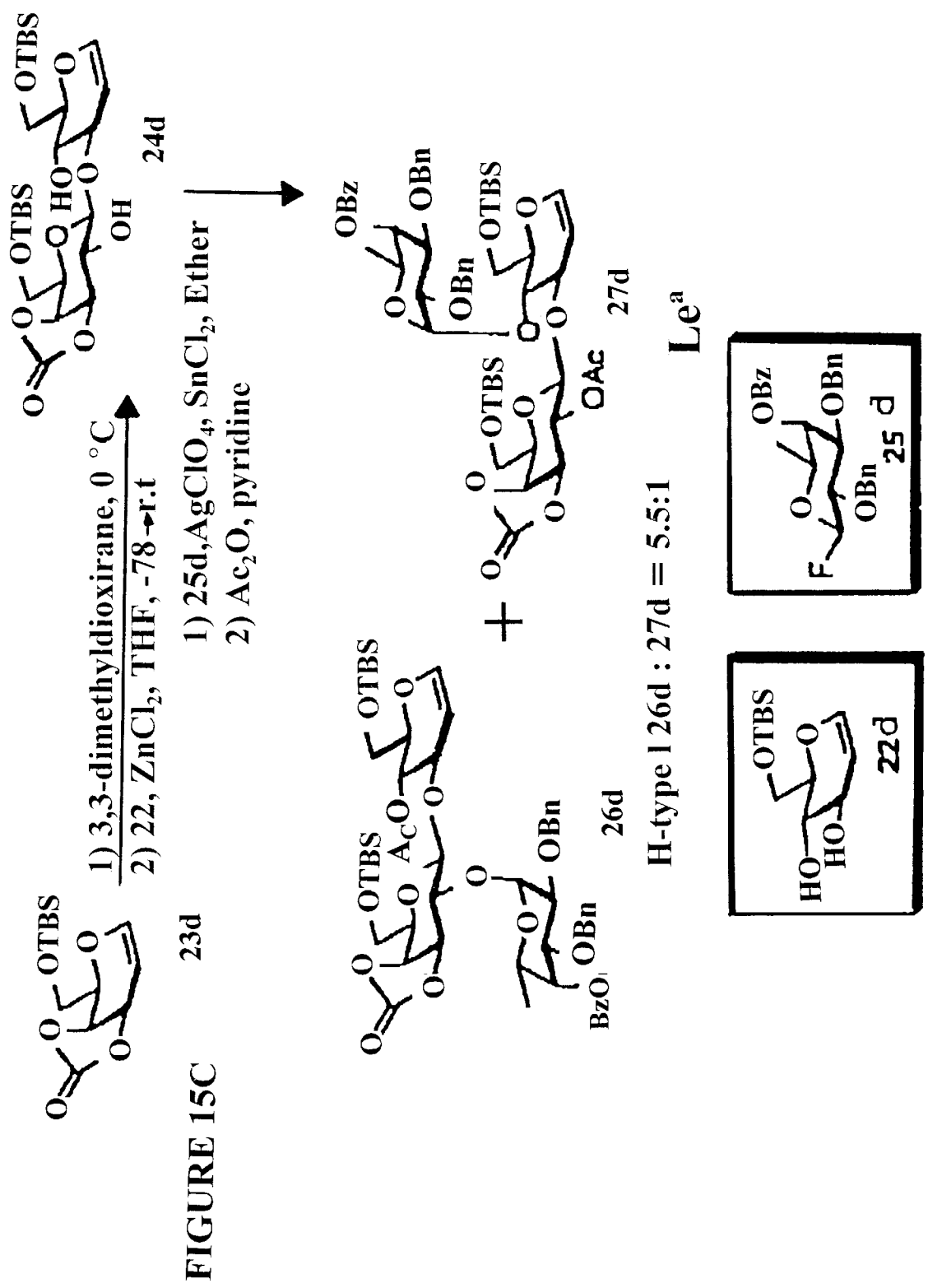
FIG. 15(c) shows the preparation of trisaccharide intermediates 26d and 27d.
Figure 16A:
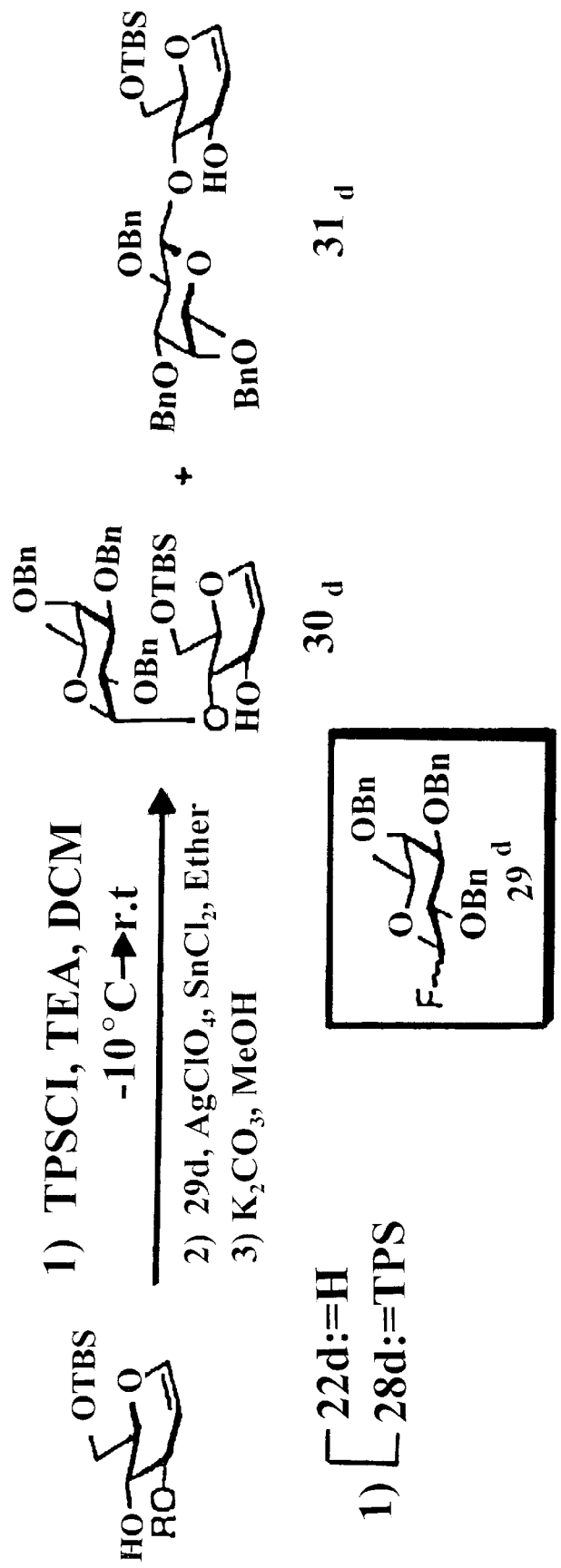
FIG. 16(a) shows the preparation of disaccharide intermediates 30d and 31d.
Figure 16B:
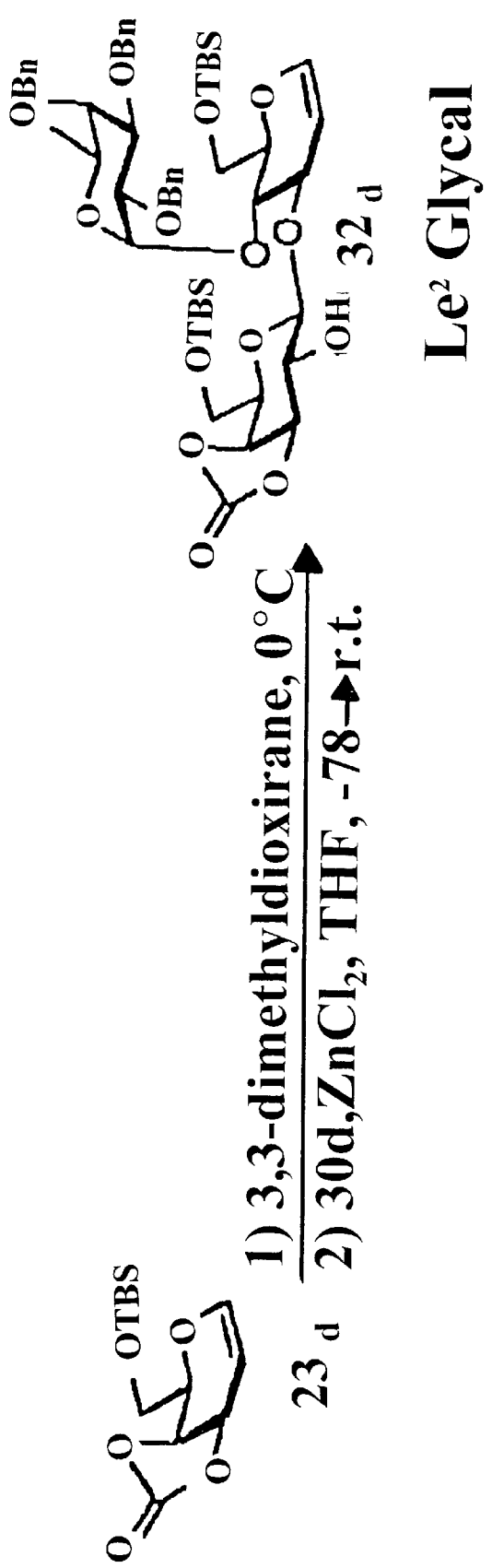
FIG. 16(b) shows the preparation of trisaccharide Le$^a$ glycal 32d.
Figure 16C:
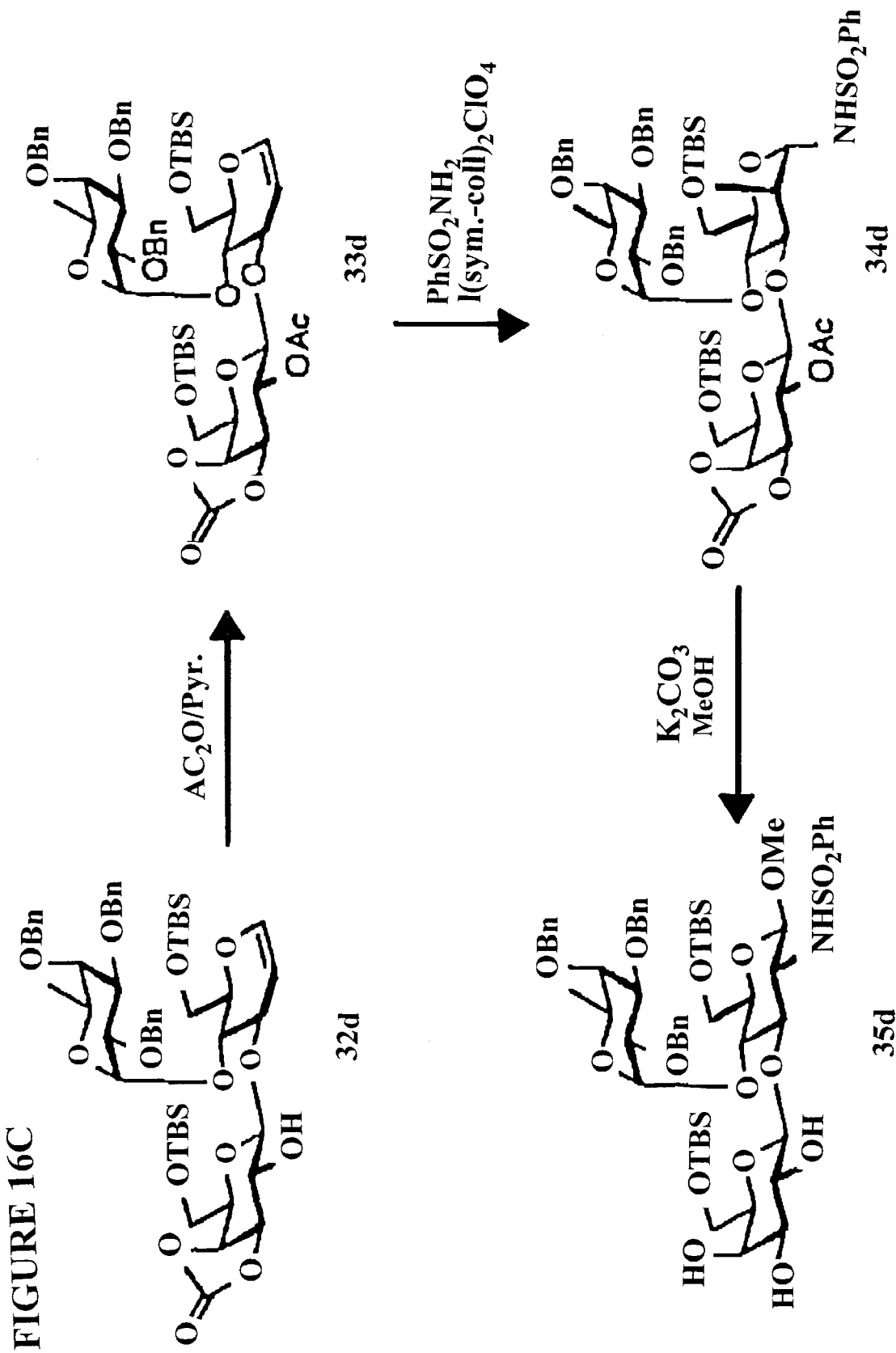
FIG. 16(c) shows the preparation of trisaccharide intermediate 35d.
Figure 17:
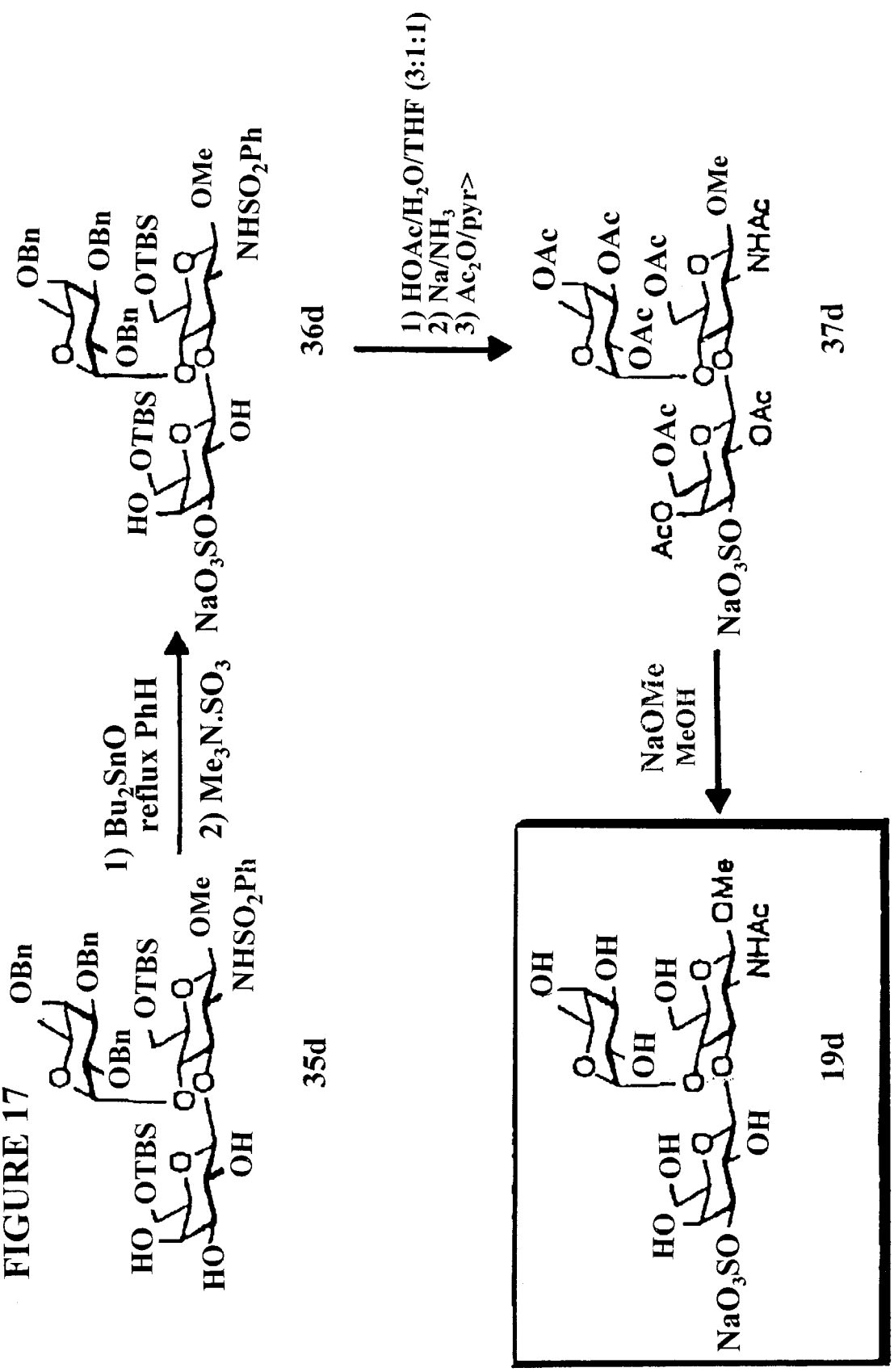
FIG. 17 shows the preparation of sulfated trisaccharide 19d.

The allyl glycoside shown is prepared using the glycal coupling methods, allylation and a deprotection sequence as taught herein (see FIG. 12), and may be bound to protein carriers using general reactions described herein or by standard methods in the art.

The present invention also provides a compound having the structure:

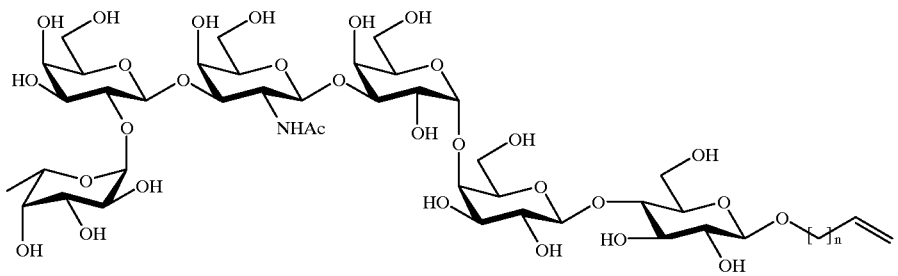

wherein n is an integer between about 0 and about 9.

The allyl glycosides shown are prepared using the glycal coupling methods taught herein, and may be bound to protein carriers using general reactions described herein or by standard methods in the art.

It is within the scope of the present invention to vary the combination of protecting groups for the various sugar hydroxyl groups in accord with ordinary skill in the art.

The present invention provides a method of inducing antibodies in a human subject, wherein the antibodies are immunoreactive with human breast tumor cells, which comprises administering to the subject an amount of a compound having the structure:

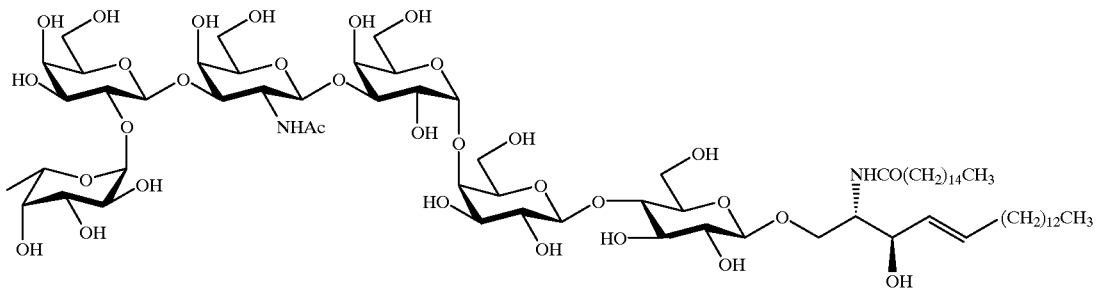

alone or bound to a suitable immunological adjuvant effective to induce the antibodies. In one embodiment, the present invention provides a method wherein the antibodies induced are MBr1 antibodies. In another embodiment, the present invention provides a method wherein the subject is in clinical remission or, where the subject has been treated by surgery, has limited unresected disease. In another embodiment, the present invention provides a method wherein the adjuvant is a protein carrier, bacteria or liposomes. In yet another embodiment, the present invention provides wherein the adjuvant is bacille Calmette-Guerin (BCG).

The present invention provides a method of preventing recurrence of breast cancer in a subject which comprises vaccinating the subject with the compound shown hereinabove either alone or bound to a suitable immunological carrier, adjuvant or vehicle.

The present invention also provides a method of inducing antibodies in a subject, wherein the antibodies are immunoreactive with human breast tumor cells, which comprises administering to the subject an amount of the compound having the structure:

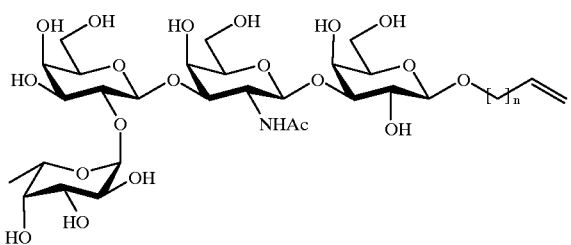

wherein n is an integer between about 0 and about 9 either alone or bound to a suitable immunological adjuvant effective to induce the antibodies. In one embodiment, the present invention provides a method wherein the antibodies induced are MBr1 antibodies. In another embodiment, the present invention provides a method wherein the subject is in clinical remission or, where the subject has been treated by surgery, has limited unresected disease. In another embodiment, the present invention provides a method wherein the adjuvant is a protein carrier, bacteria or liposomes. In yet another embodiment, the present invention provides wherein the adjuvant is bacille Calmette-Guerin.

The present invention provides a method of preventing recurrence of breast cancer in a subject which comprises vaccinating the subject with the compound shown hereinabove either alone or bound to a suitable immunological carrier, adjuvant or vehicle.

The present invention also provides a method of inducing antibodies in a subject, wherein the antibodies are immunoreactive with human breast tumor cells, which comprises administering to the subject an amount of the compound having the structure:

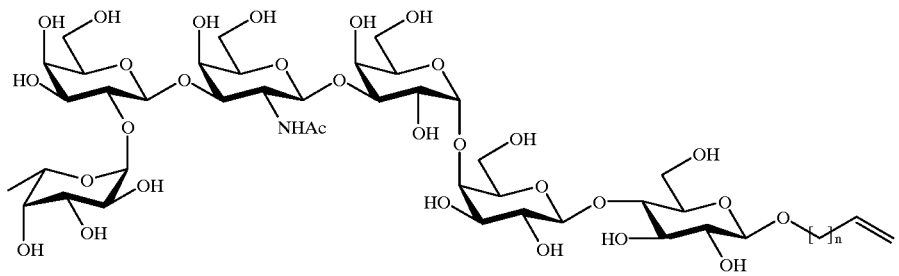

wherein n is an integer between about 0 and about 9 either alone or bound to a suitable immunological adjuvant effective to induce the antibodies. In one embodiment, the present invention provides a method wherein the antibodies induced are MBr1 antibodies. In another embodiment, the present invention provides a method wherein the subject is in clinical remission or, where the subject has been treated by surgery, has limited unresected disease. In another embodiment, the present invention provides a method wherein the adjuvant is a protein carrier, bacteria or liposomes. In yet another embodiment, the present invention provides wherein the adjuvant is bacille Calmette-Guerin.

The present invention also provides a method of preventing recurrence of breast cancer in a subject which comprises vaccinating the subject with the compound shown hereinabove either alone or bound to a suitable immunological carrier, adjuvant or vehicle.

The present invention additionally provides a method of inducing antibodies in a subject, wherein the antibodies are immunoreactive with human breast tumor cells, which comprises administering to the subject an amount of the compound having the structure:

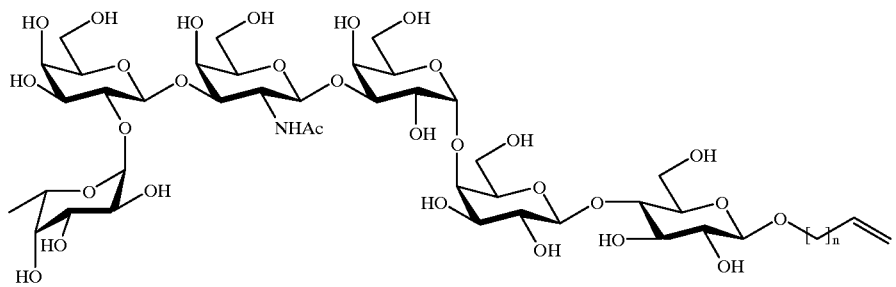

wherein n is an integer between about 0 and about 9 either alone or bound to a suitable immunological adjuvant effective to induce the antibodies. In one embodiment, the present invention provides a method wherein the antibodies induced are MBr1 antibodies. In another embodiment, the present invention provides a method wherein the subject is in clinical remission or, where the subject has been treated by surgery, has limited unresected disease. In another embodiment, the present invention provides a method wherein the adjuvant is a protein carrier, bacteria or liposomes. In yet another embodiment, the present invention provides wherein the adjuvant is bacille Calmette-Guerin.

The present invention also provides a method of preventing recurrence of breast cancer in a subject which comprises vaccinating the subject with the compound shown hereinabove either alone or bound to a suitable immunological carrier, adjuvant or vehicle.

EXPERIMENTAL DETAILS

General Procedures

All air- and moisture-sensitive reactions were performed in a flame-dried apparatus under an argon atmosphere unless otherwise noted. Air-sensitive liquids and solutions were transferred via syringe or canula. Wherever possible, reactions were monitored by thin-layer chromatography (TLC). Gross solvent removal was performed in vacuum under aspirator vacuum on a Buchi rotary evaporator, and trace solvent was removed on a high vacuum pump at 0.1–0.5 mmHg.

Melting points (mp) were uncorrected and performed in soft glass capillary tubes using an Electrothermal series IA9100 digital melting point apparatus.

Infrared spectra (IR) were recorded using a Perkin-Elmer 1600 series Fourier-Transform instrument. Samples were prepared as neat films on NaCl plates unless otherwise noted. Absorption bands are reported in wavenumbers (cm$^{-1}$).

Only relevant, assignable bands are reported.

Proton nuclear magnetic resonance ($^1$H NMR) spectra were determined using a Bruker AMX-400 spectrometer at 400 MHz. Chemical shifts are reported in parts per million (ppm) downfield from tetramethylsilane (TMS; $\delta$=0 ppm) using residual CHCl$_3$ as a lock reference ($\delta$=7.25 ppm). Multiplicities are abbreviated in the usual fashion: s=singlet; d=doublet; t=triplet; q=quartet; m=multiplet; br=broad.

Carbon nuclear magnetic resonance ($^{13}$C NMR) spectra were performed on a Bruker AMX-400 spectrometer at 100 MHz with composite pulse decoupling. Samples were prepared as with $^1$H NMR spectra, and chemical shifts are reported relative to TMS (0 ppm); residual CHCl$_3$ was used as an internal reference ($\delta$=77.0 ppm).

All high resolution mass spectral (HRMS) analyses were determined by electron impact ionization (EI) on a JEOL JMS-DX 303HF mass spectrometer with perfluorokerosene (PFK) as an internal standard. Low resolution mass spectra (MS) were determined by either electron impact ionization (EI) or chemical ionization (CI) using the indicated carrier gas (ammonia or methane) on a Delsi-Nermag R-10-10 mass spectrometer. For gas chromatography/mass spectra (GCMS), a DB-5 fused capillary column (30 m, 0.25 mm thickness) was used with helium as the carrier gas. Typical conditions used a temperature program from 60–250° C. at 40° C./min Thin layer chromatography (TLC) was performed using precoated glass plates (silica gel 60, 0.25 mm thickness).

Visualization was done by illumination with a 254 nm UV lamp, or by immersion in anisaldehyde stain (9.2 mL p-anisaldehyde in 3.5 mL acetic acid, 12.5 mL conc. sulfuric acid and 338 mL 95% ethanol (EtOH)) and heating to colorization.

Flash silica gel chromatography was carried out according to the standard protocol.

Unless otherwise noted, all solvents and reagents were commercial grade and were used as received, except as indicated hereinbelow, where solvents were distilled under argon using the drying methods listed in paretheses: CH$_2$Cl$_2$ (CaH$_2$); benzene (CaH$_2$); THF (Na/ketyl); Et$_2$O (Na/ketyl); diisopropylamine (CaH$_2$).

ABBREVIATIONS

OTf triflate
TLC thin layer chromatography
EtOAc ethyl acetate
TIPS triisopropylsilyl
PMB p-methoxybenzyl
Bn benzyl
Ac acetate
hex hexane
THF tetrahydrofuran
coil collidine
LiHMDS lithium hexamethyldisilazide
DAST diethylaminosulfur trifluoride
DMF N,N-dimethylformamide
DMAP 2-dimethylaminopyridine
DDQ 2,3-dichloro-5,6-dicyano-1,4-benzoquinone
TBAF tetra-n-butylammonium fluoride
M.S. molecular sieves
r.t. room temperature
r.b. round bottom flask

EXAMPLE 1

Figure 7A:
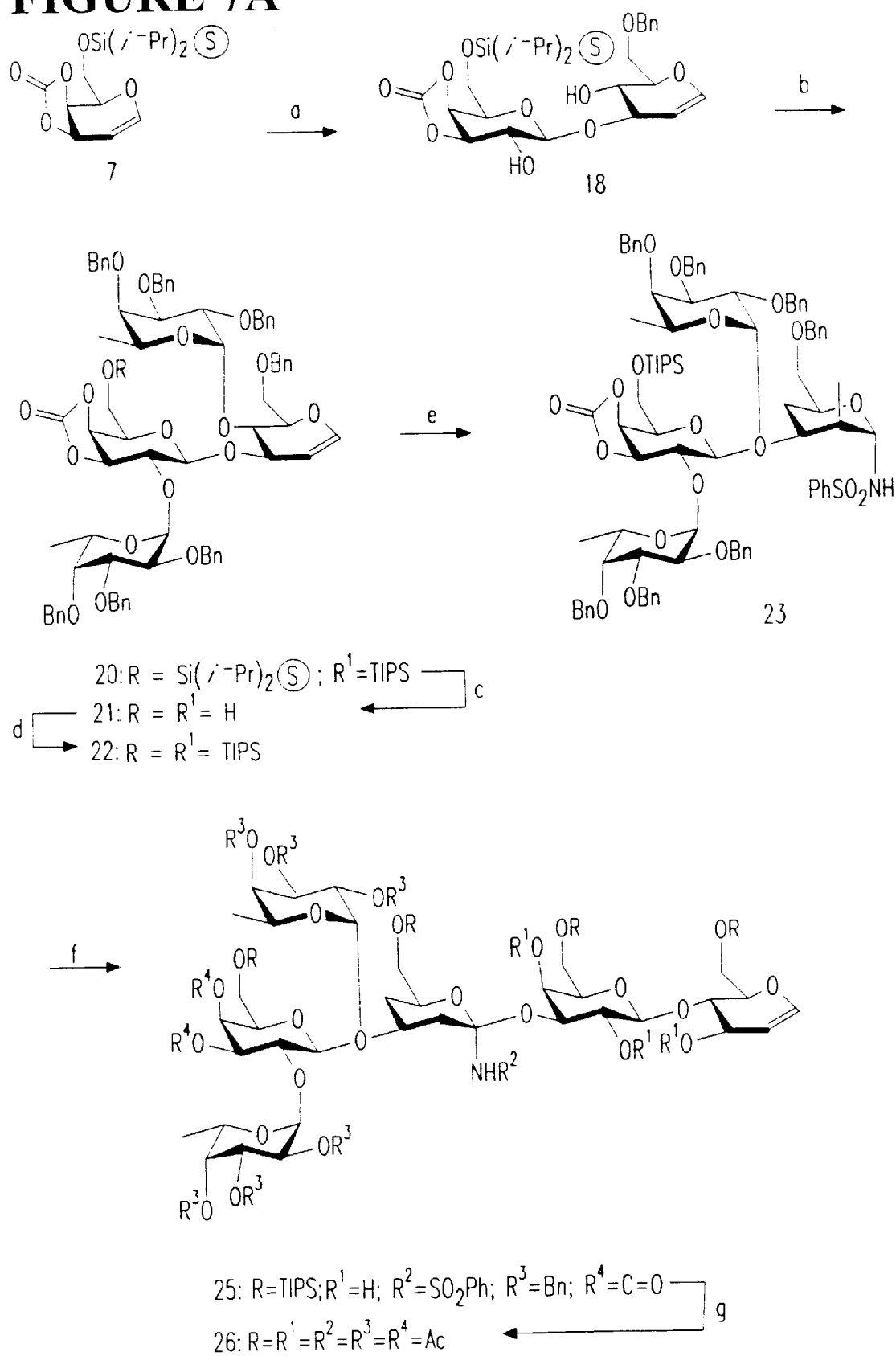

Preparation of Polymer-Bound Glucal 18 (See FIG. 7(a))

Polymer-bound galactal 7 (500 mg; S. J. Danishefsky, et al., J. Am. Chem. Soc. 1992, 8331) was placed in a 100 mL polymer flask and dried in vacuo. On cooling to 0° C. under N$_2$, dry CH$_2$Cl$_2$ (20 mL) and freshly prepared Murray solution (30 mL; R. W. Murray and R. Jeyaraman, J. Org Chem. 1985, 2847) was added. After stirring at 0° C. for ~90 min., solubles were filtered using N$_2$ pressure. The oxidation procedure was repeated. The resulting epoxide of 7 kept on a vacuum line for ~3 h to dry. A solution of glucal 19 (FIG. 7(b)) (1.0 g in 8 mL dry THF) was added, and the mixture was cooled to −23° C. (dry ice-CCl$_4$). A solution of ZnCl$_2$ in THF (0.8 mL 1.0 M) was added. The mixture was slowly allowed to warm to r.t. (over ~2 h), and then stirred at r.t. overnight. The polymer-bound glucal 18 was rinsed with 3×20 mL THF, and dried on a vacuum line.

Preparation of Polymer-Bound Tetrasaccharide 20 (See FIG. 7(a))

Polymer-bound glucal 18 and Sn(OTf)$_2$ (0.80 g, 1.92 mmol) were combined and dried in vacuo. On cooling to 0° C. under N$_2$, a solution of fucosyl donor 10 (FIG. 6) (1.8 g, 4.1 mmol) in 20 mL dry THF with di-t-butylpyridine (1.7 mL, 7.57 mmol) was added. The mixture was allowed to warm slowly to r.t., and stirred overnight. The polymer was washed with 2×20 mL dry THF, 2×20 mL dry dioxane, 20 mL DMSO, and 2×20 mL THF. The resulting polymer-bound tetrasaccharide 20 was kept on a vacuum line to dry.

Preparation of Tetrasaccharide Glycal 21 (See FIG. 7(a))

The polymer-bound tetrasaccharide 20 (50 mg) was stirred in 2 mL THF, and treated with 0.2 mL each of 1.0 M solutions of TBAF and AcOH in THF. The mixture was stirred at 40° C. overnight. The polymer was washed with 3×5 mL THF. The combined rinsings were concentrated and column-chromatographed on silica (2:1 EtOAc:hex) providing tetrasaccharide glycal 21 as a colorless gum. Yield: 9.0 mg.

EXAMPLE 2

Preparation of Diol 18' (See FIG. 7(b))

Galactal 7' (0.100 g, 0.304 mmol) in 5 mL dry $CH_2Cl_2$ at 0° C. under a $N_2$ atmosphere was treated with 10 mL Murray solution (freshly prepared) and stirred at 0° C. for 40 min. TLC (1:1 EtOAc:hex) showed no trace of 7'. Solvents were evaporated using a dry $N_2$ stream. The residual epoxide of 7' was kept on a vac. line ~2 h. To the epoxide under a $N_2$ atmosphere was added a solution of glucal derivative 3' (0.150 g, 0.496 mmol) in 3 mL dry THF. On cooling to −78° C., 1.0 M $ZnCl_2$ in $Et_2O$ (0.50 mL, 0.50 mmol) was added. The mixture was allowed to slowly warm to r.t. (over ~2 h) and stirred overnight. TLC (1:1 EtOAc:hex) showed that the reaction was complete. Saturated aq. $NaHCO_3$ (20 mL) was added, and the mixture was then extracted with EtOAc (3×20 mL). The organic layer was dried over $MgSO_4$. Column chromatography on silica (1:3 EtOAc:hex) afforded diol 18' as a colorless solid. Yield: 173 mg (89%). $[\alpha]_D^{23}$ −9.8° (c 1.0, $CH_2Cl_2$).

Preparation of Tetrasaccharide 22

Diol 18' (86 mg, 0.133 mmol) and fucosyl donor 10 (0.290 g, 0.665 mmol) were azeotropically dried using benzene. The mixture was dissolved in 3 mL dry THF together with 0.65 mL di-t-butylpyridine and then added via canula to a flask containing $Sn(OTf)_2$ (0.30 g, 0.72 mmol) and 4 Å MS (500 mg) at. 0° C. under $N_2$ atm. The mixture was stirred at 0° C. ~7 h. TLC (1:3 EtOAc:hex) shows no trace of diol 18'. The mixture was partitioned between saturated aq. $NaHCO_3$ (100 mL) and EtOAc (2×100 mL). The organic layer was dried over $MgSO_4$. The organic layer was filtered through silica using EtOAc to obtain crude material, which was then purified by chromatography on silica (1:9 EtOAc:hex) affording tetrasaccharide 22. Yield: 170 mg (86%).

Preparation of Iodosulfonamide 23 (See FIG. 7(a))
Procedure 1.

Tetrasaccharide glycal 22 (120 mg, 81.1 mmol) and $PhSO_2NH_2$ (20 mg, 0.13 mmol) were azeotropically dried using benzene. Added (glove bag) 4 Å MS (0.2 g). After cooling to 0° C. under $N_2$, dry $CH_2Cl_2$ (1.0 mL) was added. The mixture was treated with a solution of $I(coll)_2ClO_4$ (prepared from 100 mg $Ag(coll)_2ClO_4$, 5 mL collidine, and 60 mg $I_2$ in 1 mL dry $CH_2Cl_2$) via canula through a plug of flame-dried celite and 4 Å MS. The mixture was stirred at 0° C. for 40 min. TLC (1:4 EtOAc:hex) showed iodosulfonamide 23 as the major component. The mixture was filtered through celite, which was rinsed with $Et_2O$. The organic layer was extracted with saturated aq. $Na_2S_2O_3$, saturated aq. $CuSO_4$, brine, and then dried over $MgSo_4$. Column chromatography on silica (1:4 EtOAc:hex) gave iodosulfonamide 23 as a colorless solid.

Yield: 115 mg (80%).
Procedure 2.

Tetrasaccharide glycal 22 (200 mg, 0.135 mmol), $PhSO_2NH_2$ (42 mg, 0.27 mmol), and 200 mg powdered 4 Å MS in 2.0 mL dry $CH_2Cl_2$ at 0° C. under a $N_2$ atmosphere was treated with $I(coll)_2ClO_4$ (prepared from 120 mg $Ag(coll)_2ClO_4$ and 67 mg $I_2$ in 1 mL dry $CH_2Cl_2$). The mixture was stirred at 0° C. (protected from light using foil) for 30 min. TLC (1:2 EtOAc:hex) showed mainly iodosulfonamide with some glycal.

After ~1 h more at 0° C., TLC showed no noticeable improvement. The mixture was filtered through celite, which was washed with $Et_2O$. After extracting with saturated aq. $Na_2S_2O_3$, saturated aq. $CuSO_4$, brine, the organics were dried over $MgSO_4$. Column chromatography on silica (1:3 EtOAc:hex) gave 23 as a colorless solid.

Yield: 165 mg (69%). $[\alpha]_D^{23}$=−85.7° (c 1.0; $CH_2Cl_2$).

Preparation of Hexasaccharide 25 (See FIG. 7(a))

Iodosulfonamide 23 (60 mg, 34 mmol) in a 35 mL r.b. was treated with 200 mg powdered 4 Å MS (glove bag). To this flask under $N_2$ was added a solution of protected lactal 24 (FIG. 7(b)) in THF (1.5 mL). On cooling the mixture to −78° C., a solution of $AgBF_4$ (40 mg, 0.206 mmol) was added in 0.25 mL dry THF. The mixture was stirred and slowly warmed to r.t. overnight. The mixture was warmed to 45° C. and stirred ~36 h. TLC showed only a trace of iodosulfonamide. Saturated aq. $NH_4Cl$ (5 mL) was added, and the mixture was extracted with 3×10 mL EtOAc. The organic layer was dried over $MgSO_4$. Column chromatography on silica (1:3 EtOAc:hex) afforded 25 as a colorless oil. Yield: 42 mg (55%).

$[\alpha]_D^{23}$=−33.8° (c 2.0, $CH_2Cl_2$)

Preparation of Hexasaccharide 25a

Hexasaccharide 25 (55 mg, 24.4 mmol) in ~1.5 mL THF was treated at 0° C. with TBAF (0.25 mL, 1.0 M solution in THF, 0.25 mmol), and stirred at r.t. overnight. TLC (1:9 MeOH:$CH_2Cl_2$) showed a 3:1 mixture of 25a vs. a less polar substance. Additional 1.0 M TBAF (0.10 mL) was added, and the mixture was stirred overnight at r.t. TLC showed that the reaction was complete. Solvents were removed using a $N_2$ stream. Column chromatography on silica (1:19 MeOH:$CH_2Cl_2$) afforded a ~1:2 mixture corresponding to two compounds which differ only in the presence or absence of a 3,4-cyclic carbonate group. Crude yield: 35 mg total weight for two products. The crude mixture was used as such for the next reaction.

Preparation of Peracetylated Hexasaccharide 26 (See FIG. 7(a))

Hexasaccharide 25a (36 mg) in 0.25 mL dry THF was added via canula to ~8 mL bright blue $Na/NH_3$ solution at −78° C. (dry ice bath) under $N_2$ atm. After removing the dry ice bath, the mixture was stirred in refluxing $NH_3$ (dry ice condenser) for 15 min. After adding 2 mL dry MeOH (slowly!), the resulting mixture was stirred while blowing off $NH_3$ with a $N_2$ stream. The MeOH solution was treated with Dowex 50×8 [$H^+$] until pH ~8–9, and then filtered. The resin was washed with MeOH. The residue was concentrated and kept on a vacuum line to dry. Under a $N_2$ atmosphere, the residue was treated with 1 mL dry pyridine and 0.5 mL Ac$_2$O, and stirred at r.t. overnight. TLC (EtOAc) showed that hexasaccharide 26 is major component. Upon concentration, the residue was purified by column chromatography on silica (1:4 hex:EtOAc).

Preparation of Hexasaccharide 17 (See FIG. 7(b))

Hexasaccharide 26 (FIG. 7(a)) (10.0 mg, 6.3 mmol) under N$_2$ at 0° C. was treated with 0.5 mL dry CH$_2$Cl$_2$. Dioxirane solution (0.20 mL) was added, and the mixture was stirred at 0° C. ~40 min. TLC (EtOAc) showed no trace of 26. Solvents were evaporated with a N$_2$ stream. The epoxide was dried on a vacuum line for ~2 h. The epoxide was treated under a N$_2$ atmosphere with 0.5 mL allyl alcohol (passed through basic alumina to dry) and 0.5 mL dry THF. On cooling to −78° C., 1.0 M ZnCl$_2$ (10 mL) in dry Et$_2$O was added. After warming slowly to r.t., the mixture was stirred overnight. Saturated aq. NaHCO$_3$ (5 mL) was added, and the mixture was extracted with 3×5 mL EtOAc. The combined organic layers were dried over MgSO$_4$, filtered and concentrated to an oil, which was dried on a vacuum line for ~2 h. The residue was treated to pyridine:Ac$_2$O (2:1, 1.5 mL) while stirring overnight. Solvents were removed, and the residue was purifed by column chromatography on silica (1:4 hex:EtOAc), affording hexasaccharide 17 as a colorless solid. Yield: 5.5 mg.

RESULTS AND DISCUSSION

Figure 2:
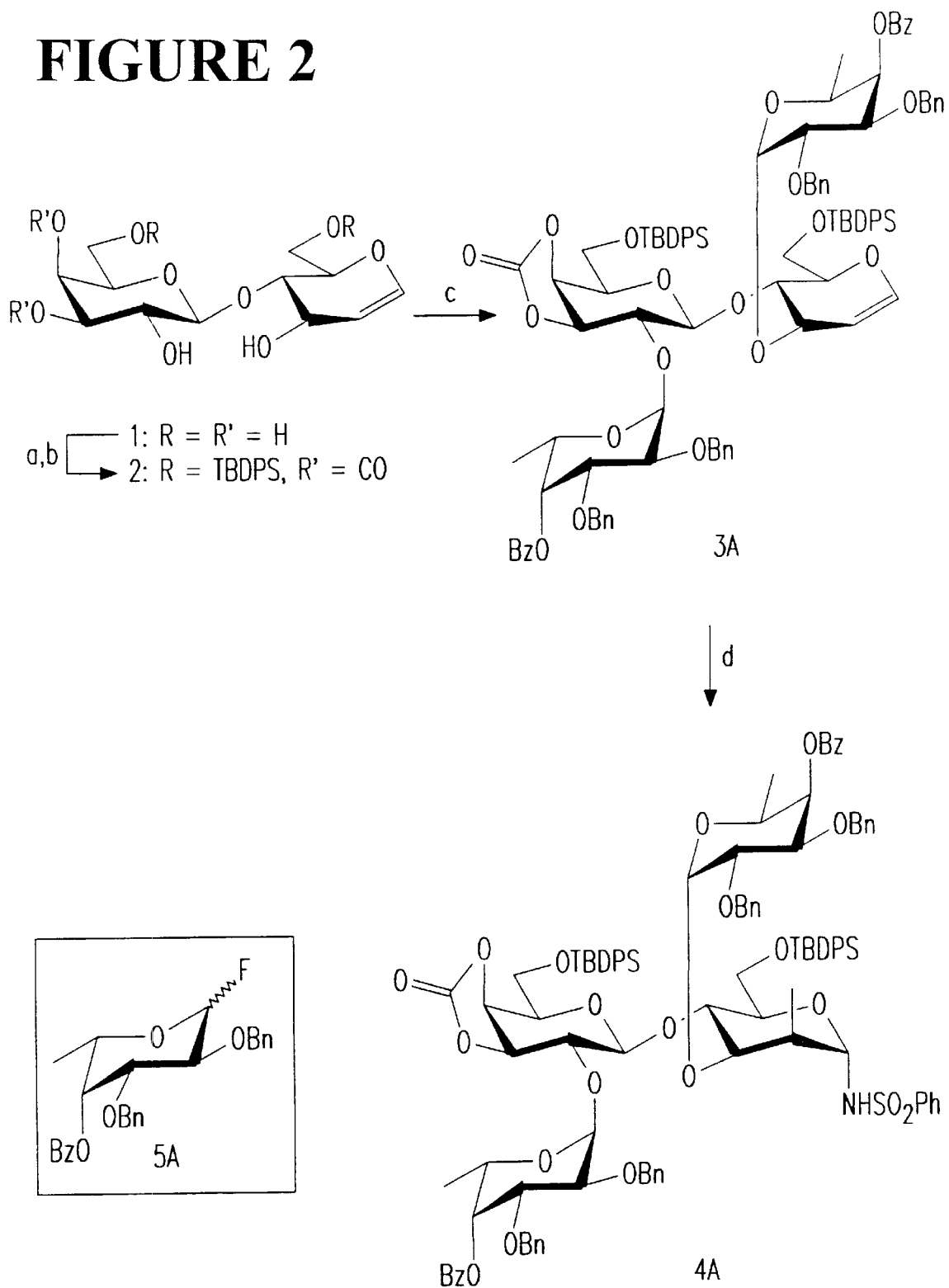
FIG. 2 shows the synthesis of 4a. Reagents: a) TBDPSCL, imidazole/DMF 84%; b) carbonyldiimidazole, cat. imidazole, THF (65%) c) 5a, di-tert-butylpyridine, AgClO$_4$, SnCl$_2$, ether (51%); PhSO$_2$NH$_2$, 1(sym-coll)$_2$ClO$_4$ (94%).
Figure 3:
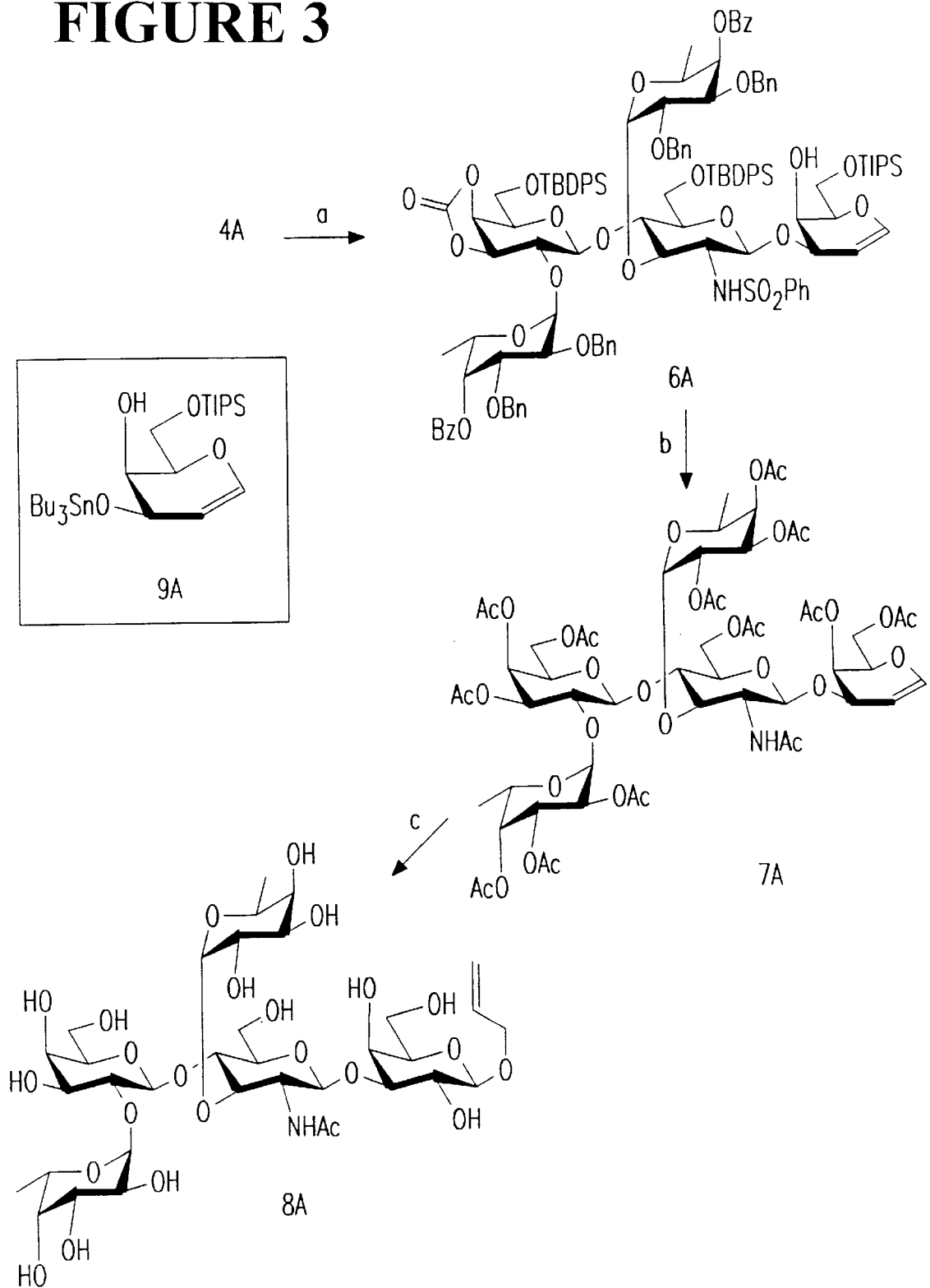
FIG. 3 shows the synthesis of 8a. Reagents: a) 9a, AgBF$_4$, 4A mol. sieves, THF (75%); b) i. TBAF, THF; ii. Na/NH$_3$; iii Ac$_2$O, pyr. c) i. 3,3-dimethioxirane; allyl alcohol, ZnCl$_2$ (72%); ii. NaOMe, MeOH (quant.).

A Highly Convergent Synthesis of the Lewis Y Blood Group Determinant in Conjugatable Form (See FIGS. 2 and 3)

Construction of the Le$^y$ determinant commences with lactal (1a) (W. N. Haworth, E. L. Hirst, M. M. T. Plant, R. J. W. Reynolds, *J. Chem. Soc.* 1930, 2644) as shown in FIG. 2. Capping both primary hydroxyl groups as their TBDPS ethers under standard conditions was followed by simple engagement of the 3' and 4' hydroxyl functions as a cyclic carbonate 2a. The stereospecific introduction of two α-linked fucose residues gave tetrasaccharide glycal 3a in 51% yield in a single step. The donor used was the known fluorosugar 5a (S. J. Danishefsky, J. Gervay, J. M. Peterson, F. E. McDonald, K. Koseki, T. Oriyama, D. A. Griffith, C-H. Wong, D. P. Dumas, *J. Am. Chem. Soc.* 1992, 114, 8329) following a modification of the original Mukaiyama conditions. (T. Mukaiyama, Y. Murai, S. Shoda, *Chem. Lett.* 1981, 431) Glycal 3a corresponds to the Le$^y$ hapten, lacking the N-acetyl function in the glucose residue. The problem was then to introduce this group as well as a galactose spacer module.

Methodology developed previously (D. A. Griffith, S. J. Danishefsky, "On the Sulfonamidoglycosylation of Glycals. A Route to Oligosaccharides With 2-Aminohexose Subunits+", *J. Am. Chem. Soc.* 1990 112, 5811) proved appropriate to attain these goals. Glycal 3a was treated with iodonium dicollidine perchlorate and benzene-sulfonamide to afford iodosulfonamide 4a (See FIG. 2). Azaglycosylation using the 3-stannyl ether of galactal (9a) (S. J. Danishefsky, K. Koseki, D. A. Griffith, J. Gervay, J. M. Peterson, F. E. McDonald, T. Oriyama, *J. Am. Chem. Soc.* 1992, 114, 8331) in the presence of silver tetrafluoroborate gave pentasaccharide glycal 6a in 75% yield as shown in FIG. 3. Having 6a in hand, one can iterate the azaglycosylation sequence or activate the glycal as its epoxide and continue with further glycosylations. To demonstrate the ability to fashion a conjugatable form of Le$^y$ hapten, formation of the allyl glycoside was important. The feasibility of converting the sulfonamido group into the target acetamide was demonstrated. Glycal 6a was deprotected in two steps as shown. Peracetylation afforded acetamido glycal 7a. Activation of the glycal as its epoxide with dimethyldioxirane (R. L. Halcomb, S. J. Danishefsky, *J. Am. Chem. Soc.* 1989, 111, 6661), followed by epoxide opening with allyl alcohol in the presence of zinc chloride gave the desired peracetylated β-allyl pentasaccharide which was deacetylated by action of methoxide to provide the target Le$^y$ hapten as its β-allyl glycoside 8a. (8a [α]$_D$ −72.7° (c. 1 MeOH); IR (thin film) 3350, 2940, 2900, 2830, 1650, 1550, 1365, 1300, 1155, 1070, 1030; $^1$H NMR (400 MHz, CD$_3$OD) δ 5.95 (m, 1H), 5.32 (d, J=17.25 Hz, 1H), 5.14–5.19 (m, 2H), 5.04 (d, J=3.83 Hz, 1H), 5.02 (d, J=3.50 Hz, 1H). 4.68 (d, J=8.15 Hz, 2H), 4.51 (d, J=5.70 Hz, 1H) 3.40–4.38 (m, 27H). 1.96 (s, 3H), 1.23 (m, 6H); HRMS (FAB) calcd for C$_{35}$H$_{56}$NO$_{24}$Na 900.3325 found 900.3310) The aldehyde, derived by ozonolysis of 8a, could be conjugated to a carrier protein by the method of Bernstein and Hall.

This synthesis is the most direct route to the Le$^y$ determinant known. (O. Hindsgaul, T. Norberg, J. Le Pendu, R. U. Lemieux, *Carbohydr Res.* 1982, 109, 109; U. Spohr, R. U. Lemieux ibid, 1988, 174, 211; for previous syntheses, see: J. C. Jacquinet, P. Sinay, *J. Org. Chem.* 1977, 42, 720; S. Nilsson, H. Lohn, T. Norberg, *Glycoconjugate J.* 1989, 6, 21; R. R. Schmidt, A. Topfer, *Tetrahedron Lett.* 1991, 32, 3353; W. Kinzy, A. Low, *Carbohydrate. Res.* 1993, 245, 193) The method is stereospecific at each step, and it illustrates the versatility of glycals both as donors and acceptors and takes advantage of 1,2-glycal epoxides and their presumed N-sulfonylaziridine counterparts. The method also makes possible extensive analog preparation and variation of conjugation strategies.

The synthesis of 3a and 6a are shown below:

3a (See FIG. 2): To 2.00 g (2.47 mmol) of lactal carbonate 2a was added 4.44 g (9.86 mmol) of fucosyl fluoride 5a. The mixture was azeotroped 5 times with benzene and placed under high vacuum for two hours. Under an argon atmosphere 2.77 ml (12.33 mmol) of di-tert-butyl pyridine and 16ml of dry ether were added. 2.0 g of freshly activated 4 A molecular sieves were added and the mixture stirred one hour at room temperature. In an argon glove bag, 2.34 g (12.33 mmol) of stannous chloride (SnCl$_2$) and 2.56 g (12.33 mmol) of silver perchlorate (AgClO$_4$) were added. The flask was equipped with a reflux condensor and the reaction brought to reflux for 72 hours. The reaction was quenched with 5 ml of saturated bicarbonate and filtered through a pad of celite. Diluted with 50 ml ethyl acetate and washed 2 times with sat. bicarbonate, 2 times with sat. copper sulfate and 2 times with sat. brine. The organics were dried over MgSO$_4$ and concentrated. Flash chromatography in 20% ethyl acetate/hexanes afforded 2.10 g (51%) of a white foam 3a: [α]$_D$31 78.9 (c.555, CHCl$_3$); IR (thin film) 3040, 3000, 2905, 2860, 2830, 1820, 1800, 1710, 1635, 1585, 1570, 1480, 1460, 1440, 1415, 1370, 1350, 1300, 1260, 1205, 1145, 1100, 950, 735, 695, $^1$ H NMR (400 MHz, CDCl$_3$) δ 8.09 (d, J=8.12 Hz, 2H), 8.00 (d, J=8.26 Hz, 2H) 7.66 (m, 4H), 7.59 (d, J=6.74 Hz, 4H), 7.56 (t, J=7.27 Hz, 1H), 7.30–7.50 (m, 22H), 7.16–7.26 (m, 10H) 7.09 (m, 2H), 6.99 (t, J=7.59 Hz, 2H) 6.89 (t, J=7.97 Hz, 1H), 6.43 (d, J=6.08 Hz, 1H), 5.46 (bs, 1H), 5.38 (bs, iH), 5.35 (d, J=3.42 Hz, 1H), 4.89 (d, J=11.35 Hz, 1H), 4.75–4.80 (m, 4H), 4.72 (d, J=5.88 Hz, 2H), 4.69 (d, J=4.27 Hz, 2H), 4.36–4.55 (m, 5H), 4.28 (q, J=6.51 Hz, 1H), 4.17 (bd, J=5.46 Hz, 1H), 3.90–4.00 (m, 6H), 3.85 (d, J=2.99 Hz, 1H), 3.82 (d, J=2.89 Hz, 1H), 3.56–3.78 (m, 4H), 1.07 (m, 24H); HRMS (FAB): calcd for C$_{99}$H$_{106}$O$_{20}$Si$_2$Na 1694.6740 found 1694.6787.

6a (See FIG. 3): 230 mg (0.12 mmol) of iodosulfonamide 4a (FIG. 2) was azeotroped 5 times with dry benzene and placed under high vacuum for two hours. Added 2.4 ml of THF solution of 15eq. of tin ether 9a (generated by azeotrophic removal of water overnight with a Dean-Stark trap equipped with freshly activated 4 A mol. sieves from 561 mg (1.80 mmol) of 6a-TIPS-galactal and 673 μl (1.32 mmol) bis(tributylin) oxide in 80 ml of benzene). To this solution stirring under an argon atmosphere was added 200 mg of freshly activated 4 A powdered molecular sieves. Stirred one hour at room temperature. Cooled solution to −78° C. and added, via cannula, a solution of 187 mg (0.96 mmol) of silver tetrafluroborate in 2.4 ml of THF. Warmed to room temperature over 15 hours and quenched the reaction, which had turned bright yellow, with 2 ml. of sat. bicarbonate. The reaction mixture was filtered through a pad of celite into a separatory funnel. The celite pad was washed thoroughly with ethyl acetate. The organics were washed twice with sat. bicarbonate and twice with sat. brine. The organics were dried over $MgSO_4$. Concentration and chromatography in 25% ethyl acetate/hexanes gave 193 mg (75%) as a white foam 6a: $[\alpha]_D$−126.4° (c,505, $CHCl_3$), IR (thin film) 3500, 3040, 3000, 2905, 2840, 1820, 1800, 1705,1635, 1590, 1440, 1410, 1255, 1195, 1100, 1080, 1035, 815, 730, 695; $^1$H NMR (400 MHz, $CDCl_3$) δ 8.09 (app t, 4H), 7.08–7.65 (m, 46H), 6.90 (t, J=7.65 Hz, 3H), 6.76 (d, J=6.91 Hz, 2H), 6.12 (d, J=6.59 Hz, 1H), 5.50 (bs 1H), 5.45 (bs 1H), 5.28 (app t, 2H), 3.03–4.91 (m, 36H), 1.09 (m, 45H); LRMS (FAB): cald for $C_{120}H_{141}NO_{26}SSi_3Na$ 2153 found 2153.

Figure 4:
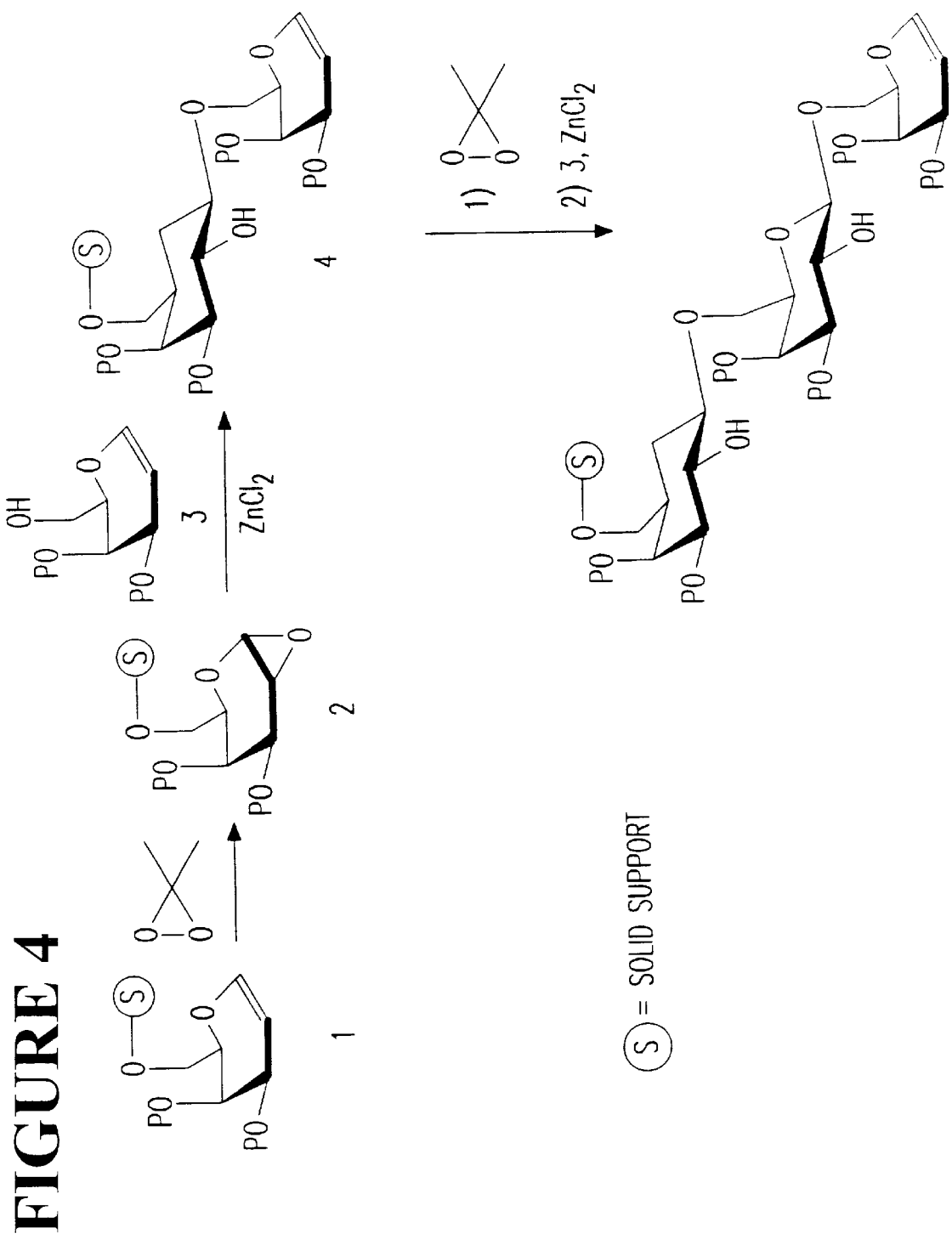
FIG. 4 shows a strategy for the solid-phase of oligosaccharides using the glycal assembly method.

A Strategy for the Assembly of Complex, Branched Oligosaccharide Domains on a Solid Support: An Application to a Concise Synthesis of the Lewis$^b$ Domain in Bioconjugatable Form The assembly of the Le$^b$ (type 1) domain is a relatively more difficult undertaking than was the Le$^y$ (type 2) target, wherein lactal was used as a convenient starting material. In the case of the type 1 determinant, lactal is not a useful starting material. The synthesis of the Le$^b$ system offered an opportunity to apply the polymer-based oligosaccharide construction method. (S. J. Danishefsky, K. F. McCLure, J. T. Randolph, R. B. Ruggeri, Science 1993, 260, 1307) The strategy is summarized in FIG. 4, wherein polymer-bound glycal 1 is activated for glycosyl donation via direct formation of a 1,2-anhydro derivative 2. Reaction of 2 with acceptor glycal 3 furnishes 4. Reiteration is achieved by means of direct epoxidation and reaction with acceptor 3. The self-policing nature of the method and the simple "one time" purification at the end of the synthesis are useful features.

Figure 5:
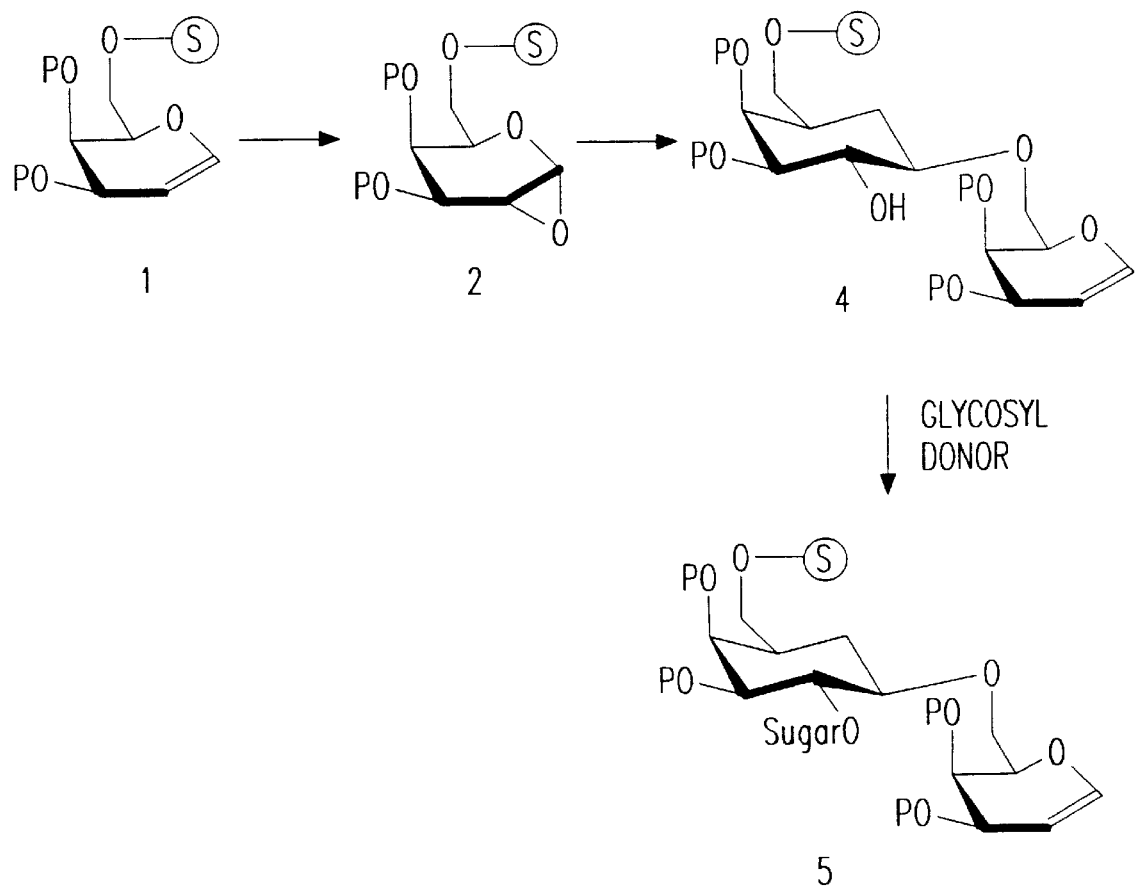
FIG. 5 shows the application of the solid-support method to the assembly of 1,2-branching patterns of complex carbohydrates.

The present invention discloses an important additional dimension of the polymer-bound method. The logic is captured by inspection of FIG. 5. Each glycosylation event generates a unique $C_2$ hydroxyl. In principle (and in fact, see infra) this hydroxyl can function as a glycosyl acceptor upon reaction with a solution based donor. The glycal linkage of 5, still housed on the support, can be further elongated. In this way, branching at $C_2$ is accomplished while minimizing the requirement for protecting group machinations. (For an application of this strategy in the synthesis of a complex saponin, see: J. T. Randolph, S. J. Danishefsky, J. Am Chem Soc. 1993, 115, 8473)

In principle, this branching can be implemented at any site in a growing chain. For such an extension, it would be necessary to cap all previously generated hydroxyl groups generated on the "polymer side" (non-reducing end) of the growing domain. Thus, the polymer-bound oligosaccharide can serve as either donor or acceptor, wherever appropriate.

Figure 6:
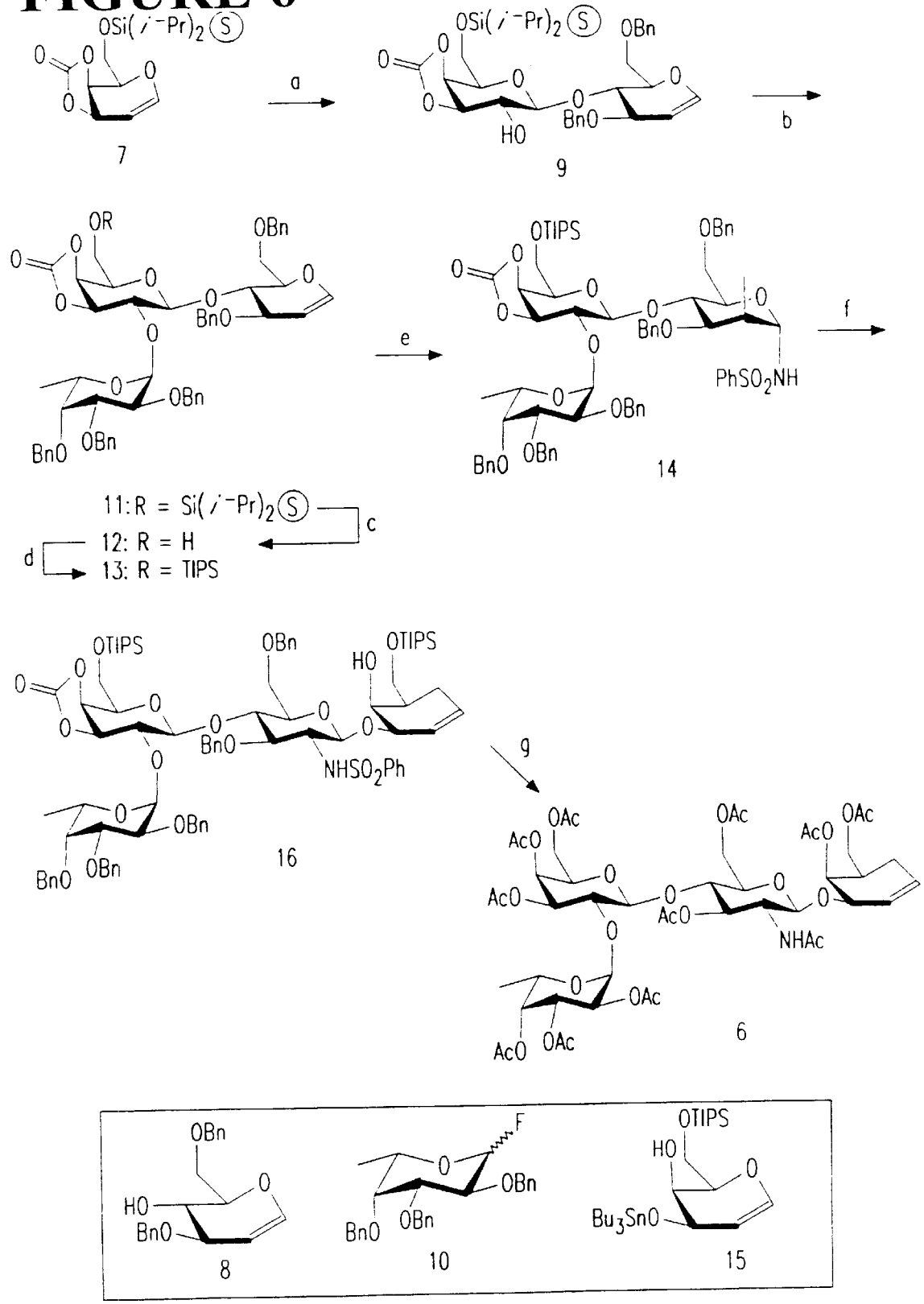
FIG. 6 shows the synthesis of a tetrasaccharide having H-type 2 blood group specificity. Reagents: (a) 1. 3,3-dimethyldioxirane, CH$_2$Cl$_2$; 2. 8, ZnCl$_2$, THF; (b) 10, Sn(OTf)$_2$, di-tert-butylpyridine, THF; (c) TBAF, AcOH, THF; (d) TIPSCl, imidazole, DMF; (e) I(coll)$_2$ClO$_4$, PhSO$_2$NH$_2$, CH$_2$Cl$_2$; (f) 15, AgBF$_4$, 4A M.S., THF; (g) 1. TBAF, AcOH, THF; 2. Na/NH$_3$; 3. Ac$_2$O, pyridine.

Initial efforts at reduction to practice identified tetrasaccharide glycal 6, bearing H-type 2 blood group specificity, as a goal (See FIG. 6). Polymer-supported galactal 7 (using as polymer support polystyrene crosslinked with 1% divinylbenzene functionalized using published procedures: T-H. Chan, W.-Q. Huang, J. Chem. Soc., Chem. Commun. 1985, 909; M. J. Farrall. J. M. J. Frechet, J. Org. Chem 1976, 41, 3877) reacted with a solution of 3,3-dimethyldioxirane (R. W. Murray, R. Jeyaraman, J. Org. Chem. 1985, 50, 2847), to provide the corresponding 1,2-anhydrosugar glycosyl donor, which was treated with a solution of glucal derivative 8 in the presence of $ZnCl_2$ to provide 9 (R. L. Halcomb, S. J. Danishefsky, J. Am. Chem Soc. 1989, 111, 6661) This polymer-bound disaccharide acted as a glycosyl acceptor upon treatment with a solution of fucosyl fluoride 10 (K. C. Nicoloau, C. W. Hummel, Y. Iwabuchi, J. Am. Chem. Soc. 1992, 114, 3126) in the presence of $Sn(OTf)_2$ thereby giving 11. Retrieval of the trisaccharide glycal from the support was accomplished using tetrabutylammonium fluoride (TBAF) to afford 12 in 50% overall yield from 7.

The trisaccharide, retrieved from the polymer, could then be further elaborated. Toward this end, compound 12 was converted to silyl ether 13 by reaction with TIPSCl. The latter was converted to the iodosulfonamide derivative 14 by the action of $I(coll)_2ClO_4$ in the presence of $PhSO_2NH_2$ Reaction of 14 with galactal stannyl ether derivative 15 in the presence of $AgBF_4$ gave 16 77% yield. (D. A. Griffith, S. J. Danishefsky, J. Am. Chem Soc. 1990, 112, 5811) Tetrasaccharide glycal 16 was deprotected and peracetylated to afford 6. (S. J. Danishefsky, K. Koseki, D. A. Griffith, J. Gervay, J. M. Peterson, F. E. MsDonald, T. Oriyama, J. Am. Chem Soc. 1992, 114, 8331)

Thus, the synthesis of the full H-type determinant was achieved by sequential polymer- and solution-based maneuvers. The next target was the more complex Le$^b$ hexasaccharide 17 (FIG. 7(b)). The campaign proceeded as shown in FIG. 7(a). Polymer-bound galactal 7 was converted to 18 upon epoxidation with 3,3-dimethyldioxirane followed by reaction with glucal derivative 19 (FIG. 7(b)). This disaccharide diol was then bisfucosylated using fucosyl donor 10 in the presence of $Sn(OTf)_2$ to afford 20. Retrieval from the support with TBAF provided 21, which was obtained in 40% overall yield from 7. Compound 21 reacted with TIPSCl to give 22.

Iodosulfonamide 23, obtained from 22 using $I(coll)_2ClO_4$ and $PhSO_2NH_2$, reacted with lactal derivative 24 (FIG. 7(b)) in the presence of $AgBF_4$ to provide hexasaccharide glycal 25 in 55% yield (See FIG. 7(a)). Deprotection of 25 was accomplished in two stages (TBAF to remove the silyl ethers, followed by $Na/NH_3$ reduction to remove the aromatic protecting groups), and the crude product was peracetylated to give 26 in a 51% overall yield. Compound 26 was converted, via the 1,2-anhydrosugar derivative, to allyl glycoside 17 (FIG. 7(b)), which can be activated by ozonolysis to the aldehyde (R=$CH_2CHO$) for subsequent coupling to a protein by the method of Bernstein and Hall.

In sum, the present invention extends the solid-support glycal assembly method for complex carbohydrate domain synthesis to include the branching patterns critical for biorecognition. Specifically, the determinant for the binding of H. pylori to human gastric epithelium has been stereospecifically fashioned, with simplicity, in a way which provides significant relief from some of the complexities of protecting group manipulations.

Experimental Procedure:

6 (See FIG. 6): $^1$H NMR (400 MHz, CDCl$_3$); δ 6.39 (d, 1H, J=6.2 Hz, H$_1$ galactal), 5.65 (d, 1H, J=8.9 Hz, NHAc), 5.35 (d, 1H, J=3.8 Hz), 5.33 (m, 1H), 5.29 (d, 1H, J=2.6 Hz), 5.27 (d, 1H, J=3.1 Hz), 5.17–5.09 (m, 2H), 4.97–4.90(m, 2H), 4.81 (dd, 1H, J=3 Hz, J=6.1 Hz, H$_2$ galactal), 4.75 (d, 1H, J=8.0 Hz), 4.52 (m, 1H), 4.48 (dd, 1H, J=12.0 Hz), 4.44–4.06 (m, 8H), 3.88–3.77 (m, 4H). 3.61 (m, 1H), 2.18–1.97 (m, 33 H, COCH$_3$), 1.18 (d, 3H, J=6.5 Hz, CH$_3$ fucose); $^{13}$C NMR (CDCl$_3$): δ 170.80, 170.77, 170.72, 170.67, 170.62, 170.34, 170.21, 170.09, 170.01, 169.99, 169.65, 144.92 (C$_1$ galactal), 100.22, 98.83, 98.58, 95.55, 74.48, 73.38, 73.13, 73.06, 71.48, 71.01, 70.68, 67.97, 67.42, 67.18, 67.05, 65.94, 64.83, 62.35, 62.22, 60.88, 60.37, 54.21, 23.23, 22.15, 20.85, 20.82, 20.79, 20.76, 20.65, 20.61, 20.57, 15.51, (C$_6$ fucose); IR (thin film): 3368.7 (NH),2965.6, 2934.6, 1746.5 (C=O), 1537.5, 1435.9, 1371.3, 1228.5, 1065.0, 1046.0; [α]$_D^{23}$=–51.1° (c 1.8, CH$_2$Cl$_2$); HRMS (FAB); calcd. for C$_{46}$H$_{63}$NNaO$_{28}$; m/z=1100.3434, found 1100.3436.

21 (See FIG. 7(a)): Polymer-bound galactal 7 (loading= 0.85 mmol glycal/g), which had been placed in a round-bottom flask equipped with a fritted outlet, was suspended in CH$_2$Cl$_2$ under N$_2$, cooled to 0° C., and then treated with a solution of 3,3-dimethyldioxirane. The mixture was stirred (teflon-coated magnetic stir bar) for 40 min. at 0° C., after which time solubles were removed by filtration through the fritted outlet (N$_2$ pressure). The polymer bound 1,2 anhydrosugar was evacuated (ca. 0.1 torr) for several hours in order to dry the material for the next step. This material was once again placed under N$_2$ before being treated with 19 (~10 molar equivalents as a 0.5 M solution in THF). The suspension was cooled to –40° C., and treated with ZnCl$_2$ (~2 molar equivalents as a 1.0 M solution in THF). The reaction mixture was allowed to slowly warm to rt (over ca. 2 h), and then stirred an additional 3–4 h. Solubles were removed by filtration, and polymer 18 was washed several times with THF and then dried in vacuo. To compound 18 was added, in a glove bag, solid Sn(OTf)$_2$ (~molar equivalents), and the mixture was placed under N$_2$ and cooled to 0° C. before being treated with 10 (FIG. 6) (~5 molar equivalents as a 0.2 M solution in THF and di-tert-butylpyridine (~8 molar equivalents). The suspension was allowed to warm to rt and stirred 8–10 h. The mixture was rinsed with anhydrous THF (2 times), 1,4-dioxane (2 times), again with THF, and then dried in vacuo. Compound 20 (100 mg) was suspended in THF, treated with a 1:3 mixture of AcOH and TBAF (~0.2 M in TBAF, ~10 molar equivalents), and the mixture was stirred for 18 h at 40° C. The polymer was rinsed with THF (3 times), and the combined rinsings were concentrated and purified by column chromatography on silica gel (1:1 EtOAc: hexanes). Compound 21 (18 mg) was obtained as a colorless solid (40% overall yield from 7): $^1$H NMR (400 MHz, CDCl$_3$): δ 7.40–7.25 (m, 30H, Ar H), 6.18 (d, 1H, J=6.0 Hz, H$_1$ glucal), 5.26 (d, 1H, J=3.5 Hz, H$_1$ fucose), 5.09 (d, 1 H, J=3.7 Hz, H$_1$ fucose), 4.96 (t, 2 H, J=10.8 Hz, PhCH$_2$), (4.90–4.56 (m, 13 H), 4.43 (m, 1H), 4.15–4.06 (m, 4 H), 3.97 (dt, 1 H, J=8.3 Hz, J=2.4 Hz), 3.87–3.65 (m, 10H), 3.64 (d, 1 H), 3.57 (d, 1 H), 2.69 (br, 1 H, OH), 2.52 (br, 1 H, OH), 1.11 (d, 3 H, J=7.0 Hz, CH$_3$ fucose), 1.09 (d, 3H, J=7.0 Hz, CH$_3$ fucose); $^{13}$C NMR (CDCl$_3$); δ 153.37 (C=O), 145.75 (C$_1$ glucal), 138.60, 138.52, 138.19, 137.61, 128.55, 128.52, 128.44, 128.24, 128.16, 128.07, 127.62, 127.56, 127.45, 98.71, 98.38, 97.65, 97.34, 79.26, 78.87, 78.67, 78.01, 77.79, 77.65, 76.37, 76.10, 74.92, 74.40, 74.16, 73.95, 72.86, 72.64, 72.53, 67.43, 67.29, 61.31, 60.90, 16.65 (C$_6$ fucose), 16.53 (C$_6$ fucose); IR (thin film): 3467.0 (OH), 3029.6, 2923.6, 1807.2 (C=O), 1647.3, 1496.0, 1453.5, 1358.1, 1240.2, 1095.6, 1049.2, 738.5, 697.2; [α]$_{D23}$=–82.5° (c 0.4, CH$_2$Cl$_2$); HRMS (FAB); calcd. for C$_{67}$H$_{74}$NaO$_{18}$: m/z=1189.4772, found 1189.4757.

25 (See FIG. 7(a)): To a mixture of 23 (60 mg, 34 μmol) and powdered 4 Å molecular sieves (200 mg) under N$_2$ was added, via canula, a solution of 24 (FIG. 7(b)) (0.21 mmol) in anhydrous THF (1.5 mL). The stirred suspension was cooled to –78° C. before being treated with a solution of AgBF$_4$ (0.21 mmol) in 0.25 mL of anhydrous THF. The mixture was stirred and allowed to slowly warm to rt overnight. The suspension, which had developed a bright-yellow color, was heated, with stirring, at 45° C. for an additional 36 h, until the TLC (2.5 EtOAc:hexanes) showed no trace of 23. The mixture was treated with saturated aqueous NH$_4$Cl (5 mL) and then extracted with EtOAc (3×10 mL), and the organics were dried over MgSO$_4$. The crude product was purified by silica gel chromatography (1:3 EtOAc:hexanes) to give 25 as a colorless oil (42 mg, 55%): $^1$H NMR (400 MHz, acetone-d$_6$): δ 8.17(d, 2 H, J=7.3 Hz, PhSO$_2$), 7.50–7.20 (m, 33H, ArH), 6.52 (d, 1 H, J=10.5 Hz, NH), 6.30 (dd, 1 H, J=6.0 Hz, H$_1$ glucal), 5.35–5.32 (m, 2H), 5.25 (d, 1H, J=7.9 Hz), 5.15 (m, 2 H), 4.99–4.92 (m, 3H), 4.86–4.52 (m, 14 H), 4.45 (dd, 1H, J=7.91 Hz, J=2.4 Hz), 4.32–4.23 (m, 3H), 4.22 (dd, 1 H), 4.17 (d, 1 H, J=10.1 Hz), 4.08–3.84 (m, 18 H), 3.79–3.73 (m, 2H), 3.66 (m, 1H), 3.55 (t, 1 H, J=6 Hz), 3.50 (dd, 1 H, J=9.7 Hz), 1.33 (d, 3 H, J=6.5 Hz, CH$_3$ fucose), 1.31 (d, 3H, J=6.4 Hz, CH$_3$ fucose), 1.20–0.98 (m, 84 H, 3×Si(i-Pr)$_3$); $^{13}$C NMR (acetone-d$_6$): 145.66 (C=O), 132.72, 131.48, 131.45, 131.28, 131.16, 130.77, 130.48, 121.31, 120.11, 119.86, 119.78, 119.25, 95.63, 94.70, 91.37, 89.64, 89.31, 86.52, 73.38, 72.24, 71.00, 70.71, 70.37, 69.80, 69.59, 69.06, 68.23, 67.92, 67.38, 67.10, 66.49, 65.67, 65.33, 64.60, 64.34, 64.03, 63.45, 63.30, 59.46, 58.83, 58.37, 54.45, 53.32, 49.86, 19.67 (C$_6$ fucose), 18.42 (C$_6$ fucose), 9.55, 9.48, 9.45, 9.31, 9.23, 3.82, 3.70, 3.64; IR (thin film): 3491.9 (OH), 3030.1, 2941.2, 2865.5, 1835.8, 1819.5, 1649.8, 1496.2, 1462.3, 1349.9, 1245.5, 1155.2, 1095.1, 1049.4, 882.2, 734.8, 692.0; [α]$_{D23}$=–33.8° (c 2.0, CH$_2$Cl$_2$); HRMS (FAB): calcd for $^{12}$C$_{120}$$^{13}$CH$_{179}$NNaO$_{29}$SSi$_4$: m/z= 2278.1292, found 2278.1296. 17 (See FIG. 7(b)): $^1$H NMR (400 MHz, CD$_3$OD): δ 6.00 (m, 1H, J=5.6 Hz, CH$_2$CH=CH$_2$), 5.37 (dd, 1 H, J=1.6 Hz, J=7.3 Hz, CH$_2$CH=CH$_2$), 5.20 (dd, 1 H, J=1.6 Hz, J=9.5 Hz, CH$_2$CH=CH$_2$), 5.18 (d, 1 H, J=3.9 Hz, H$_1$ fucose), 5.10 (d, 1H, J=3.8 Hz, H$_1$ fucose), 4.64 (d, 1 H, J=6.9 Hz), 4.45 (d, 1H, J=7.4 Hz), 4.43–4.23 (m, 2H), 4.27 (dd, 1H, J=9.3 Hz, J=10.6 Hz), 4.23–4.11 (m, 2H), 4.02–3.29 (m, 31 H), 2.06 (s, 3H, NAc), 1.31 (d, 3H, J=6.6 Hz, CH$_3$ fucose, 1.29 (d, 3 H, J=6.6 Hz, CH$_3$ fucose); $^{13}$C NMR (CD$_3$OD): δ 173.20 (C=O), 135.73 (CH C$_2$H=CH)$_2$ 105.13, 103.30, 102.49, 101.62, 99.63, 96.86, 80.79, 80.67, 78.44, 76.67, 76.49, 75.89, 74.80, 74.59, 73.94, 73.61, 73.40, 71.55, 71.38, 71.16, 70.42, 70.26, 70.14, 67.77, 67.30, 67.21, 62.79, 62.34, 61.99, 55.54, 22.97 (NAc), 16.65 (2 C's, C$_6$ fucose); IR (thin film): 3376.6 (OH), 2924.2, 1652.5 (C=O), 1383.1, 1032.4; [α]$_{D23}$=–12.8° (c 0.25, MeOH); HRMS (FAB): calcd. for C$_{41}$H$_{69}$NNaO$_{29}$: m/z=1062.3853, found 1062.3837.

Glycal Assembly Method Applied to the Synthesis of Human Breast Tumor-Associated Antigen The present invention provides a convergent synthesis of the hexasaccharide wherein the two trisaccharide domains have been efficiently assembled in forms readily ammenable for coupling. The synthesis of the ABC trisaccharide is presented in FIG. 8. The α-linkage of this trisaccharide might be formed by employing a fluoro-sugar donor 4b, using established conditions. (Gordon, D. M.; Danishefsky, S. J., *Carbohydr. Res.*, 1990, 206, 361–366.) Preparation of the appropriate disaccharide acceptor commenced with 5b (Danishefsky, S. J.; Behar, V.; Randolph, J. T.; Lloyd, K. O., *J. Am. Chem. Soc.* 1995, 0000), itself obtained from a glycal coupling. Benzylation followed by desilylation, carbonate removal and selective dibenzylation afforded the disaccharride 6b. The acceptor thus obtained was reacted with the fluorosugar 4b using modified Mukaiyama conditions (Mukaiyama, T.; Murai, Y.; Shoda, S., *Chem. Lett.*, 1981, 431–433) to provide the trisaccharide glycal 7b. Deprotection of the PMB ether provided the ABC trisaccharide 8b, which was poised for coupling with a suitable DEF trisaccharide donor.

Figure 9:
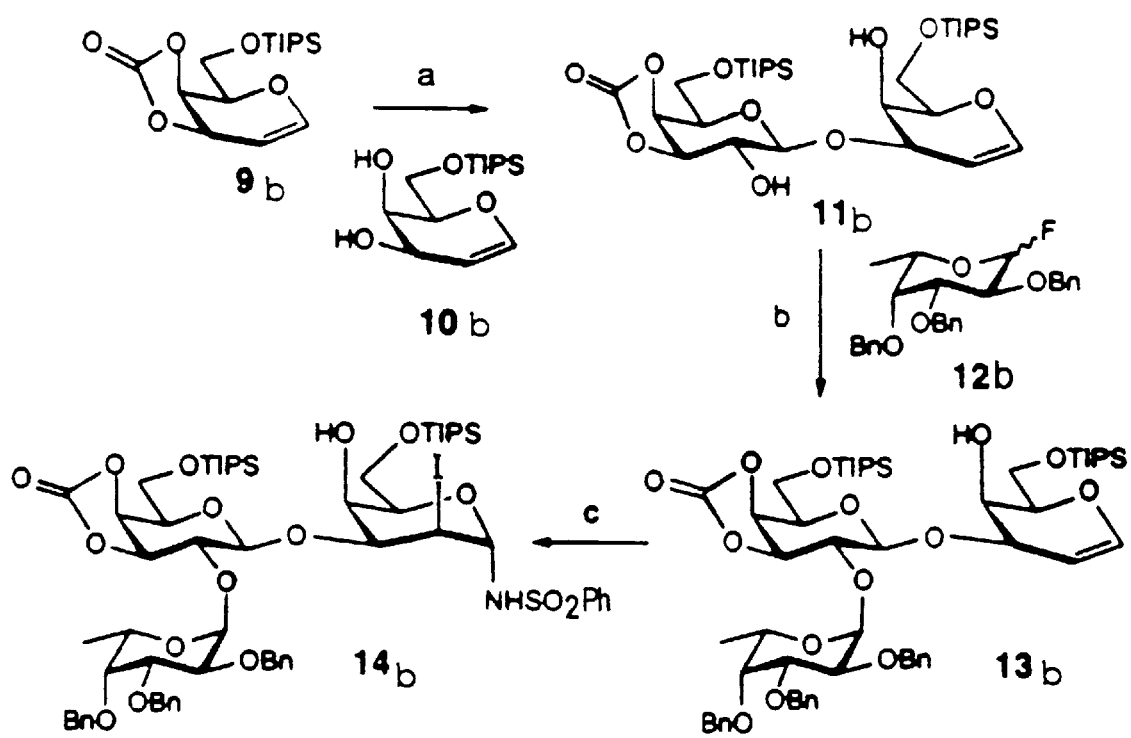
FIG. 9 shows a reaction pathway to the hexasaccharide MBr1 antigen. Reagents: a. EtSH, LiHMDS, DMF, 75%. B. 8b (0.5 equiv), MeOTf, 4 Å Mol. sieves, 70–85% B, (10:1 B α); c. (i) 3,3-dimethyldioxirane, CH$_2$Cl$_2$ (ii) 17b (5 equiv), Zn(OTf)$_2$20%; d. Ac$_2$O, Et$_3$N, DMAP, CH$_2$Cl$_2$ 95%; e. Lindlar's cat., H$_2$ palmitic anhydride, EtOAc, 90%; f. (i) TBAF, THF; (ii) NaOMe, MeOH, 94%; g. (i) Na, NH$_3$, THF; (ii) Ac$_2$O, Et$_3$N, DMAP, CH$_2$Cl$_2$, 80% h. NaOMe, MeOH, quant.

The synthesis of the DEF trisaccharide is described in FIG. 9. Epoxidation of the galactal 9b and standard coupling (Halcomb, R. L.; Danishefsky, S. J., *J. Am. Chem. Soc.*, 1989, 111, 6661–6666.) with acceptor 10b afforded, regioselectively, the disaccharide 11b. Fucosylation employing the fluoro-fucose 12b (Dejter-Juszynski, M.; Flowers, H. M., *Carbohydr. Res.*, 973, 28, 61) provided a 5:1 ratio of monoglycosylation regioisomers, the major isomer being the desired trisaccharide 13b. This material was treated under standard conditions to afford the trans-diaxial odosulfonamide 14b.

Direct coupling reactions (Griffith, D. A.; Danshefsky, S. J., *J. Am. Chem. Soc.*, 1990, 112, 5811–5819; Danishefsky, S. J.; Koseki, K.; Griffith, D. A.; Gervay, J.; Peterson, J. M.; McDonald, F. E.; oriyama, T., *J. Am. Chem. Soc.*, 1992, 114, 8331–8333) employing iodosulfonamides such as 14b with ABC trisaccharide acceptors failed, leading to a different donor functionality in the trisaccharide. In practice, the iodosulfonamide 14b was treated with excess lithium ethanethiolate to afford the ethyl thioglycoside 15b (FIG. 10). Precedent established by the present inventors lead to the prediction of sulfonamide participation to provide the desired β-linked product from 15b. (Griffith, D. A.; Ph.D. Thesis, Yale University, 1992) When donor 15b was treated with MeOTf in the presence of acceptor 8b (FIG. 8), a 10:1 mixture of hexasaccharide isomers was obtained. The major product 16b was obtained in 70–85% yield.

Ceramide attachment and elaboration commenced with epoxidation of 16b, followed by reaction with the stannyl ether 17b promoted by $Zn(OTf)_2$ (See FIG. 9). (Liu, K.K.-C.; Danishefsky, S. J., *J. Am. Chem. Soc.*, 1993, 115, 4933–4934) Although the yield of this ceramide coupling is low, when this reaction was performed on trisaccharide 7b (FIG. 8), the corresponding product was obtained in 66% yield. This material can then be used to obtain 18b. Following acetylation, the ceramide side-chain was elaborated by reduction of the azide functionality using Lindlar's catalyst under an atmosphere of $H_2$ in the presence of palmitic anhydride to provide 18b. Desilylation and saponification was followed by dissolving metal deprotection and MeOH quench. Peracetylation of the crude mixture, followed by saponification provided the glycosphingolipid 1b (See FIG. 8). Only the chemical shifts and coupling constants of the anomeric protons have been reported for the natural material. The spectrum of synthetic 1b is in complete agreement with this data. Furthermore, the product was characterized by exact mass, and $^1H$ and $^{13}C$ NMR. The synthetic material has also been shown to bind to the monoclonal antibody MBr1.

Figure 11A:
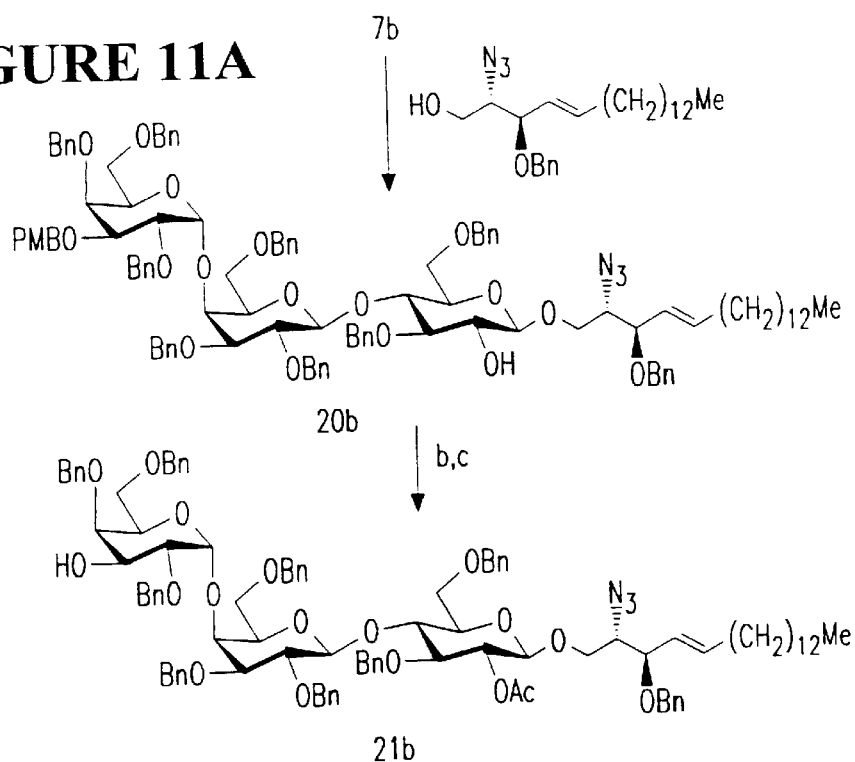
FIG. 11 (a–b) shows a reaction pathway to intermediates for preparing the hexasaccharide antigen MBr1.
Figure 11B:
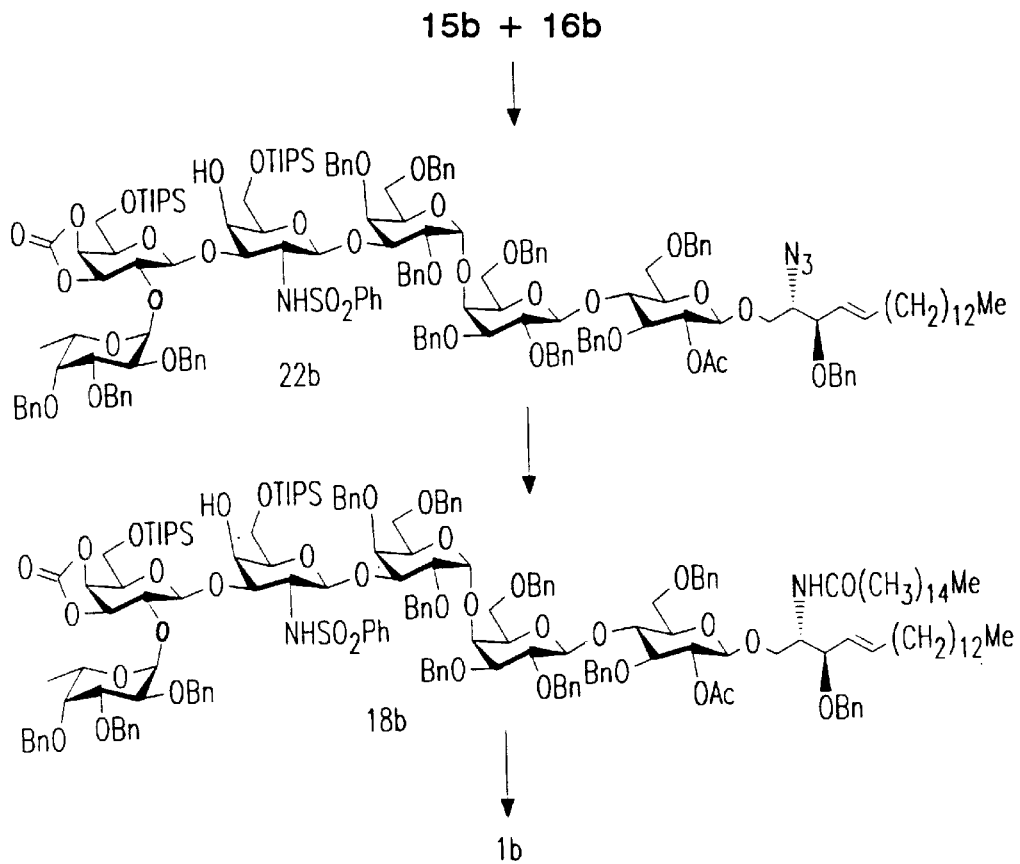

In addition, the present invention provides the corresponding allyl glycoside (FIG. 11). Deprotection of 16b, as above, and acetylation afforded the peracetate of the hexasaccharide glycal. Epoxidation, reaction with allyl alxohol, and saponification provided the allyl glycoside 19b.

As in the case of the Le determinant, ozonolysis of the allyl group of 19b will set the stage for reductive coupling to lysine residues of proteins.

Figure 8A:
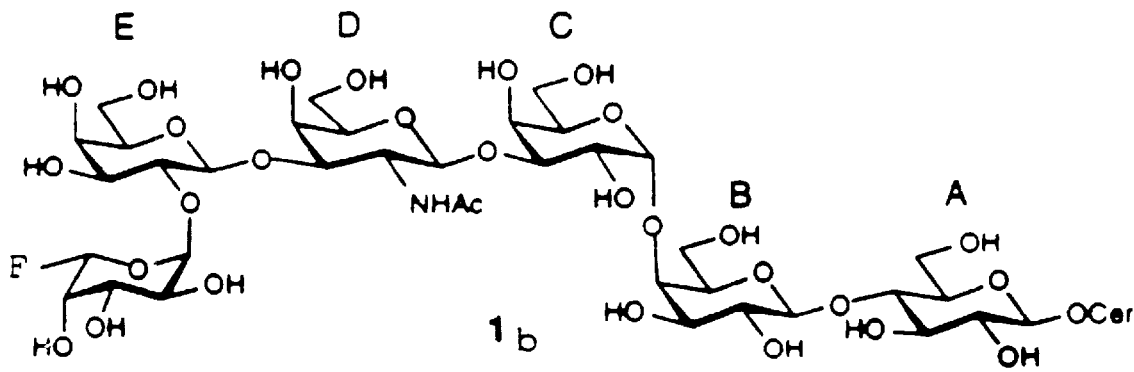
FIG. 8(a–b) shows the structure of the MBr1 antigen and a reaction pathway to a trisaccharide intermediate. Reagents: a. n-Bu$_2$SnO, PMBCl, TBABr, PhH, 70%; b. NaH, BnBr, DMF, 95%; c. (i) 3.3-dimethyldioxirane, CH$_2$Cl$_2$; (ii) TBAF, THF; (iii) NaH, BnBr, DMF, 40% (three steps); d. NaH, BnBr, DMF, 80%; e. (i) TBAF, THF; (ii) NaOMe, MeOH, 93% (two steps); f. (n-Bu$_3$Sn) $_2$O, BnBr, TBABr, PhH, 90%;g. SnCl$_2$, AgClO$_4$, 2,6-di-butylpyridine, 4 Å mol. sieves, Et$_2$O, 40% α (4.5:1 α:B); h. DDQ, CH$_2$Cl$_2$, H$_2$O, 84%.
Figure 8B:
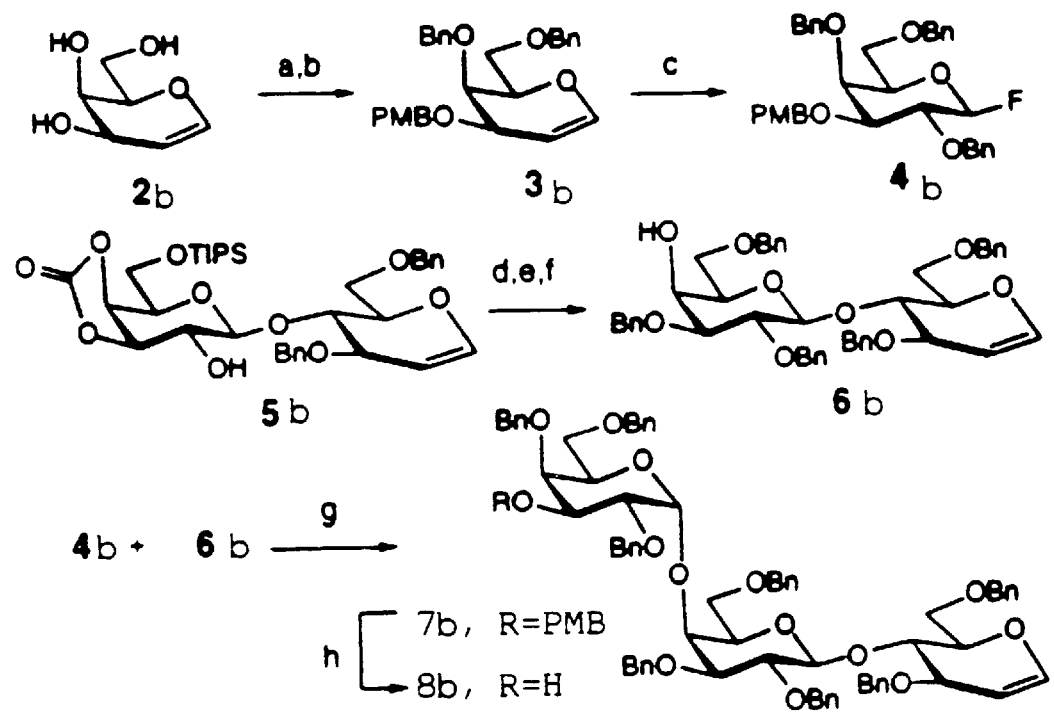

Synthesis of 3b (See FIG. 8)

3-0-(4-Methoxybenzyl)-D-galactal

A suspension of D-galactal (2b) (3.70 g, 25.3 mmol) and dibutyltin oxide (6.30 g, 1.0 equiv) in dry benzene (150 mL) was heated to reflux for 2 h with azeotropic removal of water. The reaction was cooled and treated with PMBCl (3.80 mL, 1.1 equiv) and tetrabutylammonium bromide (910 g, 1.1 equiv) and refluxed for 4 h. The reaction was filtered through silica column and eluted with EtOAc/hexanes (4:1). Fractions containing product were, concentrated and the residue triturated in hexanes to give 4.50 g (67%) of product as white crystalline solid.

mp (hexanes) 117–118° C.; $(a)^{23}$=–23.0° ($CHCl_3$, c=1.1); IR (KBr) 3313 (br), 1645, 1513, 1228, 1082, 821 $cm^{-1}$ $^1$H-NMR (400 MHz, $CDCl_3$) δ 7.28 (2H, d, J=8.4 Hz), 6.89 (2H, d, J=8.4 Hz), 6.44 (1H, dd, J=6.4 Hz), 4.70 (1H, dt, J=6.3, 1.9 Hz), 4.59–4.52 (2H, ABq, J=11.4 Hz), 4.20–4.18 (1H, m), 4.04–3.97 (1H, m), 3.90–3.82 (2H, m), 3.81 (3H, s), 2.73 (1H, d, J=3.1 Hz, C4-OH), 2.54 (1H, dd, J=8.2, 4.2 Hz, C6-OH); $^{13}$C-NMR (100 MHz, $CDCl_3$) δ 6 159.46, 145.02, 142.05, 129.46, 113.95, 99.36, 76.12, 70.17, 70.14, 63.65, 62.74, 55.26; $LRMS(NH_3)$ 284 $(M+NH_4)^+$, 266 $(M)^+$, 249.

4,6-di-O-benzyl-3-0-(4-methoxybenzyl)-D-galactal (3b). A solution of 3-0-(4-methoxybenzyl)-D-galactal (2.28 g, 8.56 mmol) and benzyl bromide (3.75 mL, 3.68 mol equiv; freshly passed through basic alumina) in DMF (30 mL) under $N^2$ at 0° C. was treated with NaH (1.37 g, 4.0 mol equiv) in two portions. The reaction was stirred 0.5 h at 0° C. and 1 h at rt. The reaction was carefully poured into 50 g of crushed ice, diluted to 100 mL with water, then extracted with EtOAc-hexanes (1:1, 100 mL×3). Organic extracts were washed with water (100 mL×2), dried ($Na^2SO^4$) and concentrated. Flash chromatography with 15% EtOAc-hexanes gave 3.58 g (94s) of the title compound as a clear liquid.

$[α]^{23}{}_D$=–48.2° ($CHCl_3$, c=0.85); IR (neat) 3030, 2867, 1645, 1613, 1513 1247, 1092, 821, 736 $cm^{-1}$; $^1$H-NMR (400 MHz, $CDCl_3$) δ7.34–7.23(12H, m), 4.62 (1H, d, J=12.0 Hz), 4.59–4.51 (2H, ABq, J=11.7 Hz), 4.50–4.39 (2H, ABq, J=11.9 Hz) $^{13}$C-NMR (100 MHz, $CDCl^3$) δ159.04, 143.99, 138.30, 137.90, 130.43, 128.26, 128.20, 128.03, 127.77, 127.57, 127.56, 113.67, 100.00, 75.58, 73.28, 73.17, 71.13, 70.42, 70.28, 68.35, 55.15; LRMS ($NH_3$) 464 (M+ $NH^{4+}$, 100), 326 (18), 309 (48), 253 (17).

Synthesis of 4b (See FIG. 8)

A solution of galactal 3b (3.20 g, 7.17 mmol) in dry $CH_2Cl_2$ under $N_2$ at 0° C. was treated with dimethyldioxirane (0.09M, 80 mL) and stirred until all of the glycal was consumed (0.5–1 h; TLC 30% EtOAc in hexanes). Volatiles were removed at 0° C. with stream of dry $N_2$. The residue was dissolved in 30 mL of dry THF under $N_2$ at 0° C. and treated TBAF (36 mL, stored over molecular sieves) then stirred at ambient temperature for 20 h. The dark brown solution was filtered through a pad of silica (~4 cm depth) and washed with EtOAc (200 mL). The filtrate was washed with water (200 mL×3) and dried ($MgSO_4$) and concentrated. The residue was redissolved in 30% EtOAc-hexanes (50 mL) and filtered through short silica column (10 cm d×4 cm h) and washed with the same solvent system (1 L). The filtrate was concentrated to give 2.59 g of fluorohydrin with >90% purity. The residue was dissolved in dry DMF (30 mL) under $N_2$ at 0° C. and treated with benzyl bromide (958 μL, 1.5 equiv, freshly filtered through basic alumina), finally with NaH (322 mg, 60% dispersion, 1.5 equiv) and stirred for 30 min at 0° C. and 30 min at rt. The reaction was quenched by pouring into 100 g of ice, and extracted with 1:1 EtOAc-hexanes (150 mL×2.). The organic extracts were washed with water (150 mL×2), dried ($MgSO_4$) and concentrated in vacuo. Flash chromatography with 10% EtOAc-hexanes gave 2.00 g (49%) of the title compound as a yellowish liquid.

$[\alpha]^{23}_D$=+15.3° ($CHCl_3$, c=0.85); IR ($CHCl_3$ film) 2916, 1612, 1513, 1248, 1103, 1056, 734 $cm^{-1}$; $^1$H-NMR (400 MHz, $CDCl_3$) δ 7.35–7.24 (17H, m), 6.84 (2H, d, J=8.4 Hz), 5.15 (1H, dd, J=53.2, 7.0 Hz), 4.92 (1 Hz, d, J=11.6 Hz), 4.48–4.74 (2H, ABq, J=11.8 Hz), 3.96–3.89 (1H, m), 3.86 (1H, br s), (3H, s), 3.65–3.56 (3H, m), 3.51 (1H, dd, J=9.8, 2.8 Hz); $^{13}$C-NMR (100 MHz, $CDCl_3$) δ 159.22, 138.33, 138.11, 137.62, 130.16, 129.19, 128.40, 128.29, 128.21, 128.04 (2C), 127.90, 127.81, 127.69, 127.59, 113.77, 110.20 (d, J=214 Hz), 80.60 (d, J=11.3 Hz), 79.00 (d, J=20.5 Hz), 74.92, 74.52, 73.59 (d, J=5.0 Hz), 73.54, 72.99, 72.70, 68.34, 55.20; LRMS ($NH_3$) 454 ($M+NH_4^+$, 100).

Synthesis of 6b (See FIG. 8)

A solution of TIPS-carbonate galactal 5b (Danishefsky, S. J.; Behar, V.; RAndolph, J. T.; Lloyd, K., *J. Am. Chem. Soc.*, 1995, 0000) (4.28 g, 5.62 mmol) in THF (25 mL)-MeOH (5 mL) was treated with TBAF solution (1.0M, 6.75 mL, 1.2 equiv). After 6 h, additional TBAF (4mL) was added and stirred additional 3 h. The reaction was concentrated and directly chromatographed with 4:1 EtOAc-hexanes to obtain 2.20 g of the triol. Remaining mixtures of cyclic carbonate and mixed carbonate was hydrolysed in MeOH with MeONa (1.0 mL, 25 wt %) and purified chromatographically. Total yield was 3.02 g (93%). This material was directly used for the dibenzylation step.

$^1$H-NMR (400 MHz, $CDCl_3$) δ7.35–7.24 (15H, m), 6.43 (1H, d, J=6.3 Hz), 4.87 (1H, dd, J=6.3, 3.4 Hz), 4.84 (1H, d, J=11.4 Hz), 4.63 (2H, apparent s), 4.61 (1H, d, J=11.4 Hz), 4.53–4.47 (3H, m), 4.19–4.16 (3H, m),3.87–3.84 (2H,m), 3.78–3.66 (3H, m), 3.46 (2H, apparent d, J=4.6 Hz), 3.29 (1H, t, J=5.5 Hz), 3.08 (1H, br), 2.73 (2H, br); $^{13}$C-NMR (100 MHz, $CDCl_3$) δ144.70, 138.41, 138.22, 137.83, 128.45, 128.33 (2C), 128.12, 127.84, 127.73, 127.64, 127.57, 102.28, 99.74, 78.99, 76.03, 74.64, 74.07, 73.24 (2C), 73.17, 72.64, 70.20, 69.10, 67.79, 62.15.

A mixture of triol glycal from above (2.95 g, 5.1 mmol), dibutyltin oxide (1.33 g, 1.05 equiv) and bistributyltin oxide (1.69 mL, 0.65 equiv) in dry benzene (50 mL) under $N_2$ was refluxed for 5 h with azeotropic removal of water. The reaction was cooled below boiling and treated with benzyl bromide (2.43 mL, 4.0 mol equiv) and tetrabutyl-ammonium bromide (3.29 g, 2.0 equiv). 10 mL of benzene was distilled off and the reaction refluxed for 16 h. The reaction was directly loaded on silica column and eluted with 15–20% EtOAc-hexanes to give 3.48 g (90 t) of product 6b as a clear oil.

$[\alpha]^{23}_D$=−3.3° ($CHCl_3$, c=0.87); IR ($CHCl_3$ film) 2867, 1652 1454, 1364, 1097, 736 $cm^{-1}$; $^1$H-MNR (400 MHz, $CDCl_3$) δ7.35–7.21 (25H, m), 6.45 (1H, d, J=6.2 Hz), 4.88 (1H, dd, J=6.2, 3.9 Hz), 4.83 (1H, d, J=10.9 Hz), 4.69 (2H, apparent s), 4.68 (1H, d, J=10.9 Hz), 4.59 (2H, apparent s), 4.55 (1H, d, J=7.8 Hz), 4.49 (2H, apparent s), 4.47 (2H, apparent s), 4.29 (1H, dd, J=9.6, 5.8 Hz), 4.18 (1H, t, J=4.4 Hz), 4.13 (1H, m), 3.99 (1H, br s), 3.85 (1H, dd, J=10.6, 6.4 Hz), 3.75–3.60 (4H, m), 3.47–3.41 (2H, m); $^{13}$C-NMR (100 MHz, $CDCl_3$) δ144.43, 138.64, 138.42, 137.99, 137.84, 137.80, 128.40, 128.34, 128.26, 128.23, 128.18, 128.15, 127.82, 127.75, 127.69, 127.67, 127.65, 127.55, 127.51, 127.46, 127.31102.56, 99.56, 80.57, 78.69, 75.72, 75.10, 73.57, 73.32, 72.94, 72.28, 71.94, 70.12, 68.90, 67.85, 66.62; LRMS ($NH_3$) 776 ($M+NH_4^+$, 100).

Synthesis of 7b (See FIG. 8)

Lactal 6b (1.32 g, 1.74 mmol, 1.0 equiv) and fluoro sugar 4b (1.49 g, 2.60 mmol, 1.5 equiv) were combined in ether and concentrated. The mixture were dried by evaporation in dry benzene (25 mL×2), in vacuum for 2 h then treated with di-t-butylpyridine (389 μL, 1.0 equiv) in glove bag and dissolved in dry ether (18 mL) under nitrogen atmosphere. In a separate 50 mL flask was placed 4 Å M.S. (4.0 g) then flame-dried under vacuum, cooled to room temperature. Anhydrous silver perchlorate (360 mg, 1.0 equiv) and $SnCl_2$ (329 mg, 1.0 equiv) were added in glove bag and flushed with nitrogen. The salt mixture was placed in water bath and sugar solution was introduced via double tipped needle and the mixture sonicated for 2 min. The reaction was wrapped with aluminum foil and stirred for 45 h at rt. The filtrate (200 mL) was washed with dil NaHCO3 (100 mL×2), dried ($MgSO_4$) and concentrated. Flash chromatography with 15–20% EtOAc/hexanes yielded trisaccharides (1.107 g, 49%) and impure lactal. The trisaccharide portion was rechromatographed with 2% ether-methylene chloride to give 879 mg (39%) of the desired α-product and 195 mg (8.6%) of β-product. The impure lactal fraction was rechromatographed with 3–4% ether-methylene chloride to give 479 mg (36%) of clean lactal. 77% of coupling (61% α-product) yield based on recovered starting material.

$[\alpha]^{23}_D$=+41.80 ($CHCl_3$, c=1.8); IR ($CHCl^3$film) 2867, 1648, 1513, 1496, 1453, 1364, 1248, 1097, 735 $cm^{-1}$; $^1$H-NMR (400 MHz, $CDCl_3$) δ 7.33–7.12 (42H, m) 6.83 (2H, d, J=8.4 Hz), 6.45 (1H, d, J=6.0 Hz), 5.03 (1H, d, J=2.3 Hz), 4.91–4.76 (6H, m), 4.68–4.40 (12H, m), 4.23–3.97 (11H, m), 3.86–3.82 (1H, dd, J=2.3 Hz), 3.76 (3H, s), 3.69–3.64 (2H, m)r, 3.53 (1H, t, J=8.7 Hz), 3.47–3.43 (1H, m), 3.40–3.36 (1H, m), 3.34–3.31 (1H, dd, J=9.9, 2.8 Hz), 3.22 (1H, dd, J=8.3, 4.8 Hz); $^{13}$C-NMR (100 MHz, $CDCl_3$) δ 158.93, 144.59, 138.98, 138.84, 138.78, 138.64, 138.58, 138.06, 138.02 (2C), 130.82, 129.04, 128.33, 128.24, 128.21, 128.15, 128.08, 128.05, 127.83, 127.81, 127.72, 127.64, 127.58, 127.55, 127.50, 127.44, 127.41, 127.36, 127.33, 127.31, 113.65, 103.02, 100.39, 100.01, 80.93, 78.93, 78.70, 76.53, 76.11, 75.14, 74.84, 74.79, 74.35, 73.91, 73.59, 73.36, 73.15, 73.10, 72.98, 72.15, 72.10, 71.99, 70.55, 69.25, 67.92 (2C), 67.69, 55.19.

Synthesis of 8b (See FIG. 8)

A solution of PMB-trisaccharide (37 mg, 0.028 mmol) in $CH_2Cl_2$ (1 mL) at 0° C. The reaction was directly loaded on silica column and eluted with 20% EtOAc-hexanes to give 28 mg (84%) of desired product.

$[\alpha]^{23}_D$=+45.6° ($CHCl_3$, c=1.78); IR ($CHCl_3$ film) 2866, 1648, 1496, 1453, 1248, 1097, 735 $cm^{-1}$; $^1$H-NMR (400 MHz; $CDCl_3$) δ 7.36–7.15 (40H, M), 6.43 (1H, d, J=6.2 Hz), 5.09 (1H, d, J=3.3 Hz), 4.85 (1H, dd, J=6.2, 3.6 Hz), 4.83–4.65 (5H, m), 4.61–4.41 (9H, m), 4.29–4.08 (8H, m), 4.02 (1H, d, J=2.6 Hz), 3.97 (1H, d, J=2.2 Hz), 3.93 (1H, t, J=8.4 Hz), 3.86–3.78 (2H, m), 3.67–3.61 (2H, m), 3.53 (1H, dd, J=8.5, 4.8 Hz); $^{13}$C-NMR (100 MHz, CDCl$_3$) δ 144.38, 138.78, 138.62, 138.47, (2C), 138.20, 138.00, 137.88, (2-C, 128.31, 128.29, 128.23, 128.19, 128.16, 128.05, 127.88, 127.83, 127.62, 127.57, 127.49, 127.45, 127.43, 127.41, 127.37, 127.32, 127.23, 102.68, 99.89, 99.34, 80.82, 78.72, 77.49, 77.10, 75.88, 75.13, 75.03, 74.23, 73.62, 73.05, 73.01, (3C), 72.62, 72.19 (2C), 70.46, 69.66, 68.92, 67.85, 67.74, 67.54.

Synthesis of 11b (See FIG. 10A) Glycal 9b (4.32 g, 3.14 mmol) was dissolved in CH$_2$Cl$_2$ (20 ml) and cooled to 0° C. It was then treated with dimethyldioxarane (219 ml, ~3.14 mmol) at 0° C. The epoxidation finished within 1 h and then the reaction mixture was concentrated to dryness using dry N$_2$ stream. The residue was further azeotroped once with benzene (20 ml) and put on a vacuum line for 30 min at 0° C. before being dissolved in THF (60 ml) and cooled to –78° C. Into the above solution was added, via canula, azeotropically dried galactal 10b (3.32 g, 10.95 mmol, 20 ml THF) and followed by ZnCl$_2$ (26.3 ml, 1.0 M in ether). The reaction mixture was warmed up to room temperature and stirred overnight. After treatment with sat'd aq. Na$_2$CO$_3$ (40 ml), the reaction mixture was concentrated and extracted with ether (500 ml). The organic phase was washed with sat'd aq. NaCl, dried (MgSO$_4$) and concentrated. The crude product was purified by silica gel chromatography (1:4 EtOAc-hexanes) to give 6.20 g of 11 b as a white foam (87.4%).

IR (CHl$_3$ film) xyz cm$^{-1}$; $^1$H-NMR (400 MHz, CDCl$_3$) δ 6.45 (1H, dd, J=6.4, 1.6 Hz), 4,85 (1H, dd, J=6.4, 2.0 Hz), 4.72–4.68 (2H, m), 4.65 (1H, d, J=7.2 Hz), 4.55 (1H, m), 4.21 (1H, m), 4.08 (1H, dd, J=9.6, 5.6 Hz), 3.96–3.82(6H, m), 3.33 (1H, d, J=3.2Hz, OH), 3.27 (1H, d, J=2.8 Hz, OH), 1.16–1.04 (42H, m); $^{13}$C-NMR (100 MHz, CDCl$_3$) δ 154.45, 145.75, 99.14, 98.27, 77.83, 76.59, 74.27, 72.04, 71.62, 70.86, 64.52, 62.57, 61.60, 17.84, 11.78, 11.77; LRMS (NH$_3$) 664 (M+NH$_4^+$, 100), 647 (M+1$^+$, 5), 422 (21), 380 (25).

Figure 10A:
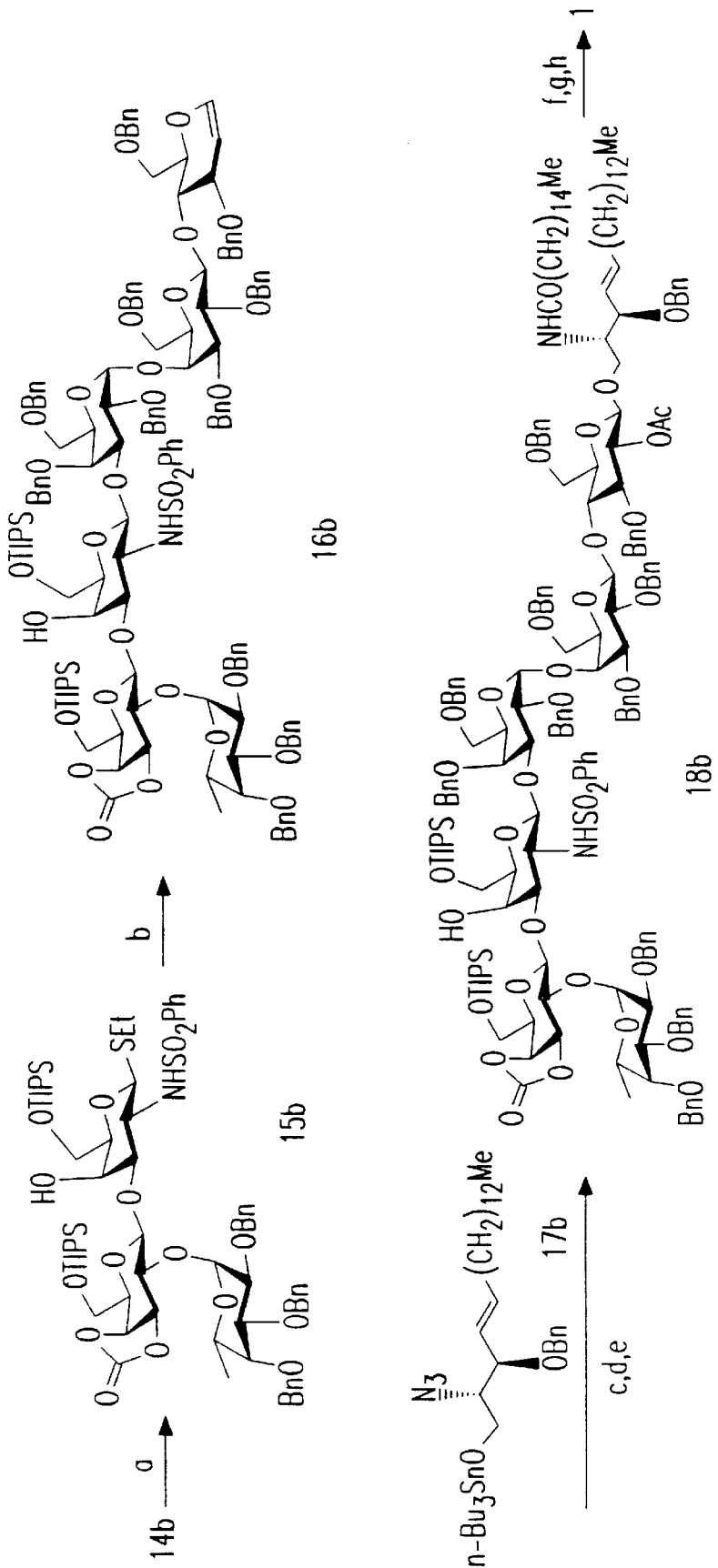
FIG. 10(a) shows a reaction pathway to a trisaccharide intermediate. Reagents: a. (i) 3,3-dimethyldioxirane, CH$_2$Cl$_2$; (ii) 10a, ZnCl$_2$, THF, 87%; b. SnCl$_2$, AgClO$_4$, Et$_2$O, 47%; c. I(coll)$_2$ClO$_4$, PhSO$_2$NH$_2$, 4 Å mol. sieves, 47%.

Synthesis of 13b (See FIG. 10A)

Disaccharide 11 b (2.64 g, 4.08 mmol) was azeotropically dried three times (3×10 ml) together with fluoro-fucose 12b (1.64 g, 3.77 mmol) and molecular sieves (4 A, 4.0 g) in THF (20 ml) with 2,6-di-tert-butypyridine. The solution was added via canula to a flask containing AgClO$_4$ (1.56 g, 7.54 mmol), SnCl$_2$ (1.43 g, 7.54 mmol) and molecular sieves (4 A, 4.0 g) in THF (15 ml) at –40° C. The reaction mixture was stirred 30 min at –40° C. and then 34 h at 5° C. until the disappearance of fluoro-fucose. After treatment with sat'd aq. NaHCO$_3$ (40 ml) at 5° C., the mixture was extracted with EtOAc (700 ml). The organic phase was washed with sat'd NaCl, dried (MgSO$_4$) and concentrated. The crude product was purified by silica gel chromatography to give 1.93 g of the desired trisaccharide glycal 13b (48%, based on fluoro-fucose used) and 500 mg of the recovered disaccharide with only a trace of the other monofucosyl product.

Synthesis of 15b (See FIG. 9)

An azeotropically dried mixture of the trisaccharide glycal 13b (1.11 g, 1.05 mmol) and benzensulphonamide (0.82 g, 5.24 mmol) was dissolved in the THF (20 ml) together with molecular shieves (4 A, 2.6 g). The mixture was cooled to –40° C. and then was added, via canula, a solution of I(sym-coll)$_2$COl$_4$ prepared in situ by stirring I$_2$ (0.54 g, 2.09 mmol) with Ag(symn-coll) (C$_2$Ol$_4$ (0.986 g, 2.29 mmol) in THF (20 ml) at room temperature for about 30 min until the disappearance of the brown color of I$_2$. The mixture was warmed up to 0° C. within 1 h and stirred for another 1 h. After quenching with sat'd aq. Na$_2$S$_2$O$_3$, the mixture was filtrate and extracted with EtOAc (3×100 ml). The combined organic phase was washed with sat'd aq. CuSO4 (100 ml), sat'd NaCl (100 ml×2) and dried (Na$_2$SO$_4$). After concentration, the crude product was purified by silica gel chromatography (1:4 EtOAc-hexanes) to give 981 mg of a colorless oil as a 21 mixture of the desired α-trans-diaxial iodosulphonamide and its cis isomer. The iodosulphonamide mixture was then added with stirring into a flask containing ethanthiol (226.3 mg, 3.64 mmol) and lithium hexamethy-disilylazide (1.46 ml, 1.46 mmol) in DMF (10 ml) at –40° C. The reaction mixture was stirred at –40° C. overnight, and then quenched with sat'd aq. NaHCO$_3$ and extracted with ether (3×100 ml). The combined organic phase was washed with sat'd aq. NaCl and dried (Na$_2$SO$_4$). After concentration, the crude product was purified by silica gel chromatography (3:97 EtOAc-CHC12) to yield 438 img of 15b (33%) and 333 mg of the intact cis iodosulphonamide.

Synthesis of 16b (See FIG. 9)

A mixture of acceptor trisaccharide 8b (92 mg, 0.077 mmol, 1.0 equiv), thiogycoside 15b (198 mg, 2.0 equiv) and freshly activated 4 Å-MS (560 mg) under N$_2$ at rt was suspended in CH$_2$Cl$_2$-Et$_2$O (1:2, 3.9 mL) and stirred for 10 min. The reaction was cooled to 0° C., then treated with methyl triflate (52.4 uL, 6.0 equiv). The reaction was stirred for 4.5 h at 0° C. and 1.5 h while warming to 15° C. The reaction was quenched with TEA(1.0 mL), filtered through a pad of silica and rinsed with Et$_2$O. The filtrate (70 mL) was washed with sat'd NaHCO$_3$ (50 mL×2), dried (Na$_2$SO4) and concentrated. The crude product was purified by HPLC (17% EtOAc in hexanes, 15 mL/min, 260 nm UV dection) to give 158 mg (85%) of the desired product and 27.7 mg of α-linked byproduct (ca 55% purity).

Retention time=22 min; $[\alpha]^{23}{}_D$=–13.3° (CHCl$_3$, c=1.4); IR (CHCl$_3$ film) 2940, 2865, 1792, 1652, 1454, 1161, 1101, 734 cm$^{-1}$; $^1$H-NMR (400 MHz, CDCl$_3$) δ7.8 (2H, m), 7.38–7.06 (58H, m), 6.43 (1H, d, J=6.1 Hz), 5.15 (1H, br s), 5.07 (1H, d, J=3.6 Hz), 5.03 (1H, d, J=3.6 Hz), 4.99 (1H, d, J=11.6 Hz), 4.89–4.61 (12H, m), 4.54–4.46 (4H, m)), 4.42 (2H, app s), 4.38 (1H, d, J=11.9 Hz), 4.34–4.26 (3H, m), 4.21–4.18 (4H, m), 4.13–4.03 (7H, m), 3.98–3.76 (14H, m), 3.70–3.61 (4H, m), 3.46–3.27 (7H, m), 2.84 (1H, OH), 1.16 (3H, d, J=6.4 Hz), 1.13–1.02 (42H, m); $^{13}$C-NMR (100 MHz, CDCl$_3$) δ155.35, 144.55, 140.78, 138.99, 138.75, 138.68, xxx, 138.54, 138.43, 138.13, 138.03, 137.94, 137.82, 132.31, 128.81, 128.52,128.38, 128.36, 128.27, 128.24, 128.20, 128.16, 128.02, 127.93, 127.72, 127.66, 127.58, 127.48, 127.43, 127.37, 127.20, 103.41, 102.75, 99.79, 99.55, 98.29, 97.76, 80.49, 80.39, 79.09, 78.91, 78.25, 77.68, xxx, 76.51, 75.88, 75.09, 74.99, 74.91, 74.73, 74.15, 74.02, 73.92, 73.52, 73.19, 73.10, 72.94, 72.67, 72.25, 72.07, 71.76, 71.56, 71.33, 70.33, 69.45, 69.32, 68.48, 68.08, 67.86, 67.75, 61.97, 61.60, 56.14, 17.99, 17.96, 17.95, 17.92, 16.75, 11.86; HRMS (FAB) calcd for C$_{138}$H$_{169}$NO$_{30}$SSi$_2$Na (M+Na) 2432.0920, found 2432.0970.

Figure 10B:
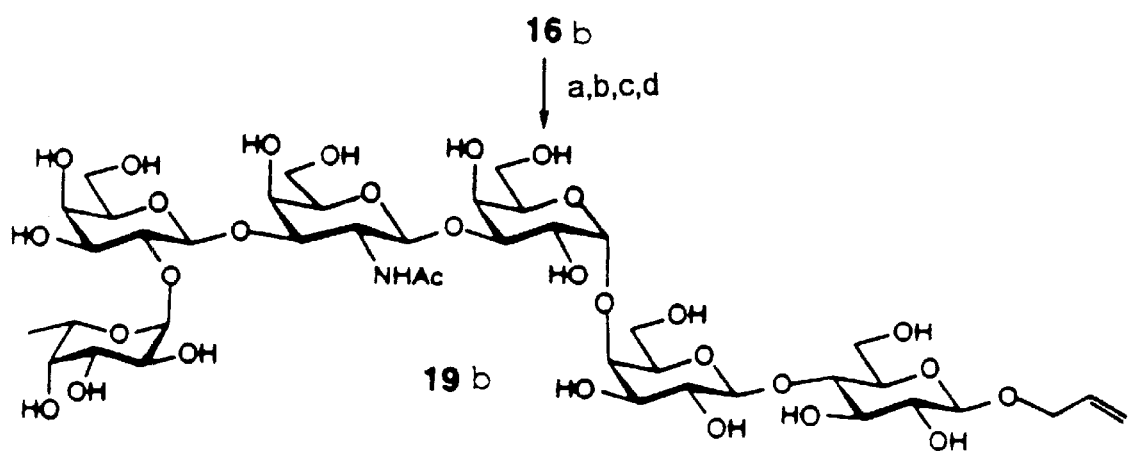
FIG. 10(b) shows a reaction pathway to the allyl glycoside. Reagents: a. TBAF, THF, 94%; b. (i) Na, NH$_3$, THF; (ii) Ac$_2$O, Et$_3$N, DMAP, THF, DMF, 85%; c. (i) 3,3-dimethyldioxirane, CH$_2$Cl$_2$, (ii) allyl alcohol, 65% (+29% of α-manno isomer); d. NaOMe, MeOH, quant.

Synthesis of 19b (See FIG. 10(b))

A solution of hexasaccharide glycal 16b (85 mg, 0.035 mmol) in THF (6 mL) under N$_2$ at rt was treated with TBAF (1.0 M, 353 uL, 10 equiv). After 38 h at rt, the reaction was concentrated to ca 1 mL, then dissolved in EtOAc (60 mL), washed with water (30 mL×2), dried ($Na_2SO_4$) and concentrated. Flash chromatography with 4% MeOH in $CH_2Cl_2$ gave 70.0 mg (98%) of the desilyl-decarbonated product.

$[\alpha]^{23}_D$=1.8° ($CHCl_3$ film) 2868, 1652, 1455, 1157, 1094, 735 $cm^{-1}$; $^1$H-NMR (400 MHz, $CDCl_3$) δ 7.80 (2H, d, J=7.4 Hz), 7.47 (2H, d, J=7.2 Hz), 7.37–6.95 (56H, m), 6.45 (1H, d, J=6.3 Hz), 5.86 (1H, br s), 5.35 (1H, d, J=11.6 Hz), 5.30 (1H, D, J=2.8 Hz), 4.95 (1H, d, J=11.3 Hz), 4.89 (1H, d, J=3.5 Hz), 4.8644.67 (9H, m), 4.54–4.39 (9H, m), 4.34 (1H, dd, J=10.4, 2.8 Hz), 4.26–4.06 (9H, m), 3.98–3.45 (23H, m), 3.41 (1H, d, J=10.0 Hz), 3.29–3.20 (5H, m), 0.73 (3H, d, J=6.3 Hz); $^{13}$C-NMR (100 MHz, $CDCl_3$) δ 144.87, 142.49, 139.49, 139.11, 138.87, 138.63, 138.54, 138.37, 138.00, 137.98, 137.97, 137.18, 131.64, 128.74, 128.52, 128.43, 128.33, 128.28, 128.25, 128.21, 128.02, 127.99, 127.97, 127.80, 127074, 127.67, 127.63, 127.61, 127.54, 127.53, 127.50, 127.44, 127.33, 127.31, 127.02, 126.86, 103.39, 102.78, 100.75, 100.09, 99.80, 99.75, 81.42, 80.64, 78.98, 78.86, 77.82, 77.40, 77.26, 76.26, 75.16, 75.09, 75.07, 74.95, 74.69, 74.30, 73.58, 73.17, 73.11, 72.71, 72.67, 72.65, 72.55, 72.36, 72.18, 69.65, 69.53, 68.54, 68.18, 68.08, 67.85, 67.79, 67.21, 54.95, 16.60.

To liquid ammonia (ca 8 mL) under $N_2$ at −78° C. was added metalic sodium (95 mg) and stirred for 2 min. To the blue solution was added a solution of the hexasaccharide glycal above (70 gm, 33.8 mmol) in dry THF(2 mL). After 45 min at 78° C., the reaction was quenched with absolute methanol (4 mL). Most of ammonia was removed with stream of nitrogen (final volume was ca 4 mL) and the reaction diluted with methanol to ca 10 mL. To the solution was added Dowex 50-X8 (890 mg, washed and dried) and stirred for 5 min. The solution was filterate and rinsed with methanol, finally with ammoniacal methanol (5 mL), and the filterate was concentrated in vacuo. The residue and DMAP (2.4 mg) were placed under $N_2$ and suspended in DMF (1.0 mL), THF (1.0 mL) and TEA (1.0 mL), then treated with $Ac_2O$ (0.3 mL). After 20 h (TLC analysis with EtOAc), the reaction was poured into water (40 mL), and extracted with EtOAc (40 mL×2), washed with dil $NaHCO_3$ (30 mL), with water (30 mL), dried ($Na_2SO_4$) and concentrated. Flash chromatography with 80% EtOAc in $CH_2Cl_2$ gave 52.0 mg (93%) of product as white foam.

mp 132–134° C.; $[\alpha]^{23}_D$=+4.7° ($CHCl_3$, c=1.4) ; IR ($CHCl_3$ film) 1742, 1652, 1371, 1227, 1069 $cm^{-1}$; $^1$H-NMR (400 MHz, $CDCl_3$) δ6.68 (1H, d, J=6.8 Hz), 6.42 (1H, d, J=6.0 Hz), 5.58 (1H, d, J=3.2 Hz), 5.47 (1H, d, J=3.4 Hz), 5.40–5.37 (2H, m), 5.29 (1h, dd, J=10.9, 3.1 Hz), 5.25–5.15 (5H, m) 5.06 (1H, dd, J=11.2, 3.3 Hz), 5.02 (1H, d, J=3.6 Hz), 4.99–4.92 (2H, m), 4.84–4.81 (2H, m), 4.67 (1H, d, J=7.8 Hz), 4.56–4.51 (2H, m), 4.45–4.38 (3H,m), 4.29 (1H, dd, J=10.6, 3.4 Hz), 4.22–3.95 (13H, m__, 3.90–3.77 (3H, m), 2.19–1.92 (51H, m), 1.15 (3H, d, J=6.4 Hz).

Peracetyl hexasaccharide glycal above (52 mg) was divided into two portions (22 mg and 30 mg). A solution of hexasaccharide glycal (22.0 mg, 13.4 mmol) in dry $CH_2Cl_2$ (2 mL) under $N_2$ at 0° C., then treated with allyl alcohol (5 mL). The mixture was stirred for 15 h at room temperature. Excess allyl alcohol was removed in vacuo. The other batch (30 mg) was treated similarly. The crude products were combined and chromatographed with 85% EtOAc-$CH_2Cl_2$ to give 35.8 mg (66%) of less polar product and 15.7 mg (29%) of more polar product. A 33.2 mg (19 umol) of the less polar material under $N_2$ was dissolved in absolute MeOH (14 mL) and treated with MeONa solution in methanol (165 uL, 25% by weight). After 6 h, the reaction was neutralized with Dowex 50-X8 (200 mg, washed and dried), filtered and concentrated to give quantitative yield of the title compound 19b.

mp 204–206° (dec); $[\alpha]^{23}_D$=+5.5 (MeOH, c=0.67); IR (MeOH film) 3356 (br), 2923, 1658, 1374, 1071 $cm^{-1}$; $^1$H-NMR (400 MHz, $CD_3OD$) δ 5.99–5.93 (1H, m), 5.24 (1H, d, J=3.8 Hz), 5.18–5.14 (1H, m), 4.93 (1H, d, J=3.9 Hz), 4.56–4.54 (2H, m), 4.42–4.06 (10H, m), 3.99 (1H, s), 3.91–3.47 (26H, m), 3.41–3.37 (1H, m), 3.27 (1H, t, J=8.8 Hz), 2.01 (3H, s), 1.24 (3H, d, J=6.5 Hz); $^{13}$C-NMR (100 MHz, $CD_3OD$, ref=δ49.05) δ 174.55, 135.73, 117.57, 105.48, 105.42, 103.94, 103.26, 102.79, 101.08, 81.21, 80.67, 80.05, 79.20, 78.09, 76.79, 76.56, 76.48, 76.44, 76.41, 75.54, 74.86, 74.68, 73.57, 72.63, 72.50, 71.57, 71.16, 70.64, 70.41, 69.68, 68.16, 62.67, 62.64, 62.57, 61.96, 61.63, 53.11, 23.58, 16.78.

For the purposes of the preparative synthesis of structure 1b a ceramide precursor was attached to the ABC trisaccharide (Scheme 5). Expoxidation of 7b, followed by reaction with the ceramide precursor 17b (as its tributylstannyl ether) promoted by $Zn(OTF)_2$ provided 20b (See FIG. 11). Acetylation and PMB removal proceeded smoothly to furnish 21b which is poised for coupling with a suitable DEF trisaccharide donor.

When trisaccharide 15b was treated with MeOTf in the presence of acceptor 21b, a 4:1 mixture of hexasaccharide isomers was obtained. The major product 22b was obtained (See FIG. 11) in 50% yield.

The ceramide side-chain was elaborated by reduction of the azide functionality using Lindlar's catalyst under an atmosphere $H_2$ in the presence of palmitic anhydride to provide 18b directly. Desilylation was followed by dissolving metal deprotection of the sulfonamide and benzyl groups and MeOH quench to remove the carbonate and acetate groups. Peracetylation of the crude mixture afforded a 78% yield of peracetylated bexasaccharide. Saponification of this material using NaOMe provided the natural product 1b in 96% yield. The coupling constants and chemical shifts of the anomeric protons of 1b matched reported data. In addition, the product was characterized by exact mass, and $_1$H and $^{13}$C NMR.

Synthesis of 20b (See FIG. 11)

The benzylated ceramide precursor (475 mg, 1.14 mmol) was dissolved in 4 mL PhH. Bis(tribuyltin) ether (0.29 mL, 0.34 g, 0.57 mmol) was added and the reaction vessel (equipped with a Dean-Stark trap) was heated to reflux. After 3 h the reaction was allowed to cool and was concentrated under a flow of $N_2$. In a separate flask, the glycal 7b was dissolved in 1 mL anhydrous $CH_2Cl_2$ and the resulting solution was cooled to 0° C. and a solution of 3,3-dimethyldioxirane (2.8 mL, 0.25 mmol, 0.09 M in acetone) was added. After 45 min the solution was concentrated under a flow of $N_2$, then under vacuum. The tin ether was dissolved in 1 mL anhydrous THF and added via cannula to a mixture of $Zn(OTf)_2$ (170 mg, 0.468 mmol) in 1 mL THF at −78° C. (wash 1×0.5 mL THF). The reaction was allowed to warm to room temperature over 12 h and then was quenched with distilled water. The aqueous phase was extracted 3× with EtOAc. The combined organic phases were dried over anhydrous $MgSO_4$. Flash column chromatography (3:1 hexane/EtOAc, 3×16 cm silica gel) afforded 265 mg (66%) of the target compound 20b.

$^1$H NMR ($CDCl_3$) δ 7.43–7.15 (m, 45H), 7.03 (d, J=8.6 Hz, 2H), 6.79 (d, J=8.6 Hz, 2H), 5.76 (dt, J=6.7, 15.4 Hz, 1H), 5.43 (dd, J=8.5, 15.4 Hz, 1H), 5.07 (d, J=3.5 Hz, 1H), 5.05 (d, J=12.0 Hz, 1H), 4.90 (d, J=12.9 Hz, 2H), 4.83–4.77 (m, 3H), 4.69 (d, J=12.0 Hz, 1H), 4.61 (d, J=11.9 Hz, 1H), 4.54–4.45 (m, 3H), 4.42–4.25 (m, 7H), 4.18–4.05 (m, 6H), 4.01–3.91 (m, 4H), 3.83 (dd, J=4.4, 10.6 Hz, 1H), 3.79 (s, 3H), 3.71–3.65 (m, 4H), 3.57–3.32 (m,7H), 3.20 (m, 1H), 2.29 (bs, 1H), 2.11 (bq, J=6.7 Hz, 2H), 1.42–1.29 (m, 22H), 0.91 (t, J=6.6 Hz, 3H); $^{13}$C NMR (CDCl3) δ 158.8, 139.1, 139.0, 138.7, 138.6, 138.34, 138.29, 138.2, 138.1, 130.8, 128.7, 128.55, 128.50, 128.4, 128.33, 128.28, 128.26, 128.12, 128.06, 127.84, 127.76, 127.7, 127.64, 127.60, 127.5, 127.45, 127.36, 125.8, 113.5, 102.7, 100.6, 81.9, 81.5, 79.4, 77.4, 77.0, 76.7, 76.6, 76.4, 75.5, 74.9, 74.7, 74.4, 73.9, 73.3, 73.2, 73.11, 73.06, 72.3, 72.1, 70.0, 69.4, 68.7, 68.1, 67.9, 67.7, 64.2, 55.2, 32.4, 31.9, 29.70, 29.65, 29.5, 29.4, 29.2, 29.0, 22.7, 14.2; IR (thin film) 3447, 3062, 3029, 2923, 2853, 2099, 1612, 1586, 1514, 1496, 1454, 1364 cm$^{-1}$; $[\alpha]^{23}_D$+25.0 (c 0.70).

Synthesis of 21b (See FIG. 11)

The above trisaccharide (256 mg, 0.147 mmol) was dissolved in 2 mL anhydrous CH$_2$Cl$_2$. Triethylamine (0.105 mL, 76 mg, 0.753 mmol), DMAP (2 mg, 0.02 mmol) and acetic anhydride (0.042 mL, 45 mg, 0.445 mmol) were added sequentially. The reaction was stirred for 1 h then quenched with saturated aqueous NaHCO$_3$. The extracts were dried with anhydrous MgSO$_4$, filtered and concentrated. Purification by flash column chromatography (4:1 hexane/EtOAc, 2×16 cm silica gel) afforded 235 mg (90%) of the desired compound.

$^1$H NMR (CDCl$_3$) δ 7.42–7.17 (m, 45H), 7.03 (d, J=8.6 Hz, 2H), 6.81 (d, J=8.6 Hz, 2H), 5.75 (dt, J=6.7, 15.14 Hz, 1H), 5.43 (dd, J=8.6, 15.4 Hz, 1H), 5.07 (d, J=3.4, 1H), 4.99–4.90 (m, 4H), 4.85 (d, J=11.3 Hz, 2H), 4.77 (d, J=11.9 Hz, 1H), 4.76 (d, J=12.4 Hz, 1H), 4.70 (d, J=12.0 Hz, 1H), 4.62 (d, J=11.7 Hz, 1H), 4.57–4.52 (m, 3H), 4.49–4.34 (m, 7H), 4.30 (d, J=11.8 Hz, 1H), 4.25 (d, J=11.8 Hz, 1H), 4.14–4.06 (m, 7H), 4.01–3.95 (m, 2H), 3.91 (dd, J=5.6, 8.6 Hz, 1H), 3.85 (dd, J=4.3, 11.1, Hz, 1H), 3.80 (s, 3H), 3.74 (d, J=9.8 Hz, 1H), 3.69 (dd, 7.7, 9.9 Hz, 1H), 3.63–3.51 (m, 5H), 3.43–3.34 (m, 3H), 3.22 (dd, J=4.6, 8.2 Hz, 1H), 2.12 (dd, J=6.8, 13.6, 2H), 1.87 (s, 3H), 1.43–1.30 (m, 22H), 0.93, (t, J=6.6 Hz, 3H) ; $^{13}$C NMR (CDCl$_3$) δ 169.3, 158.8, 139.1, 139.0, 138.69, 138.65, 138.6, 138.31, 138.26, 138.2, 138.1, 138.0, 130.8, 128.8, 128.6, 128.41, 128.35, 128.30, 128.28, 128.14, 128.0, 127.9, 127.8, 127.64, 127.60, 127.58, 127.51, 127.47, 127.38, 126.0, 113.5, 102.7, 100.8, 1006, 81.5, 79.9, 79.5, 79.4, 79.3, 77.4, 77.1, 76.8, 75.5, 75.3, 74.9, 74.5, 74.2, 73.9, 73.2, 73.1, 73.0, 72.4, 72.2, 72.1, 70.2, 69.4, 68.1, 68.0, 67.9, 67.5, 63.8, 55.2, 32.4, 32.0, 29.72, 29.67, 29.5, 29.4, 29.2, 29.1, 22.7, 20.9, 14.2; IR (thin film) 3028, 2923, 2852, 2098, 1751, 1611, 1513, 1496, 1453, 1365, 1232 cm$^{-1}$; $[\alpha]^{23}_D$+20.3 (c 0.45).

The trisaccharide from above (230 mg, 0.129 mmol) was dissolved in 4 mL CH$_2$Cl$_2$. Distilled water (1 mL) was added and the mixture was cooled to 0° C. DDQ (35 mg, 0.15 mmol) was added and the reaction was stirred for 1 h. The reaction was quenched with saturated aqueous NaHCO$_3$. The aqueous phase was extracted 3× with CH$_2$Cl$_2$. The combined organic phases were washed dried over anhydrous MgSO$_4$. Flash column chromatography (4:1 hexane/EtOAc, 2×16 cm silica) afforded 182 mg (85%) of the target compound 21b.

$^1$H NMR (CDCl$_3$) δ 7.38–7.13 (m, 45H), 5.73 (dt, J=6.7, 15.4 Hz, 1H), 5.41 (dd, J=8.6, 15.4 Hz, 1H), 5.09 (d, J=3.2 Hz, 1H), 4.98 (d, J=12.5 Hz, 1H), 4.95 (d, J=8.0, 9.2 Hz, 1H), 4.87 (d, J=11.2 Hz, 1H), 4.80 (d, J=11.3 Hz, 1H), 4.77 (d, J=10.9 Hz, 1H), 4.70 (d, J=11.4 Hz, 1H), 4.65–4.50 (m, 6H), 4.45–4.42 (m, 3H), 4.38–4.34 (m, 3H), 4.28 (bs, 2H), 4.15 (d, J=11.7 Hz, 1H), 4.11 (d, J=11.8 Hz, 1H), 4.08–4.01 (m, 3H, 3.98–3.94 (m, 3H), 3.88 (dd, J=5.5, 8.5 Hz, 1H), 3.82 (dd, J=4.3, 7.0 Hz, 1H), 3.77 (dd, J=3.1, 10.1 Hz, 1H), 3.70 (d, J=9.8 Hz, 1H), 3.64–3.51 (m, 5H), 3.46 (dd, J=5.4, 9.4, 1H), 3.39 (m, 1H), 3.34–3.30 (m, 2H), 3.21 (dd, J=4.7, 8.4 Hz, 1H), 2.09 (m, 2H), 1.90 (s, 3H), 1.84 (d, J=5.1 Hz, 1H), 1.41–1.27 (m, 22H), 0.90 (t, J=6.5 Hz, 3H); $^{13}$C NMR (CDCl3) δ 169.3, 165.9, 139.3, 138.7, 138.6, 138.5, 138.3, 138.2, 138.1, 138.0, 128.5, 128.4, 128.32, 128.27, 128.25, 128.17, 128.00, 127.94, 127.91, 127.8, 127.75, 127.70, 127.67, 127.61, 127.55, 127.49, 127.45, 127.21, 125.9, 107.8, 102.6, 100.8, 99.4, 81.4, 80.6, 79.3, 77.5, 77.3, 77.0, 76.9, 76.7, 75.5, 75.3,. 75.2, 74.3, 73.2, 73.1, 73.0, 72.9, 72.3, 72.1, 70.1, 70.0, 69.1, 68.1, 68.0, 67.8, 67.4, 63.8, 32.4, 31.9, 29.7, 29.6, 29.5, 29.4, 29.2, 29.1, 22.7, 20.9, 14.1; IR (thin film) 3570, 3087, 3062, 3029, 2924, 2853 2099, 1950, 1873, 1752, 1496, 1453, 1366, 1231 cm$^{-1}$; $[\alpha]^{23}_D$+17.6 (c 1.40).

Synthesis of 22b (See FIG. 11)

Thioglycoside 15b (188 mg, 0.151 mmol) and the acceptor 21b (125 mg, 0.0751 mmol) were azeotropically dried with benzene twice. The mixture was then dissolved in 2.6 mL anhydrous Et$_2$O and 1.3 mL CH$_2$Cl$_2$ and to this solution was added 500 mg of 4 Å mol. sieves. This mixture was stirred for 1 h and then was cooled to 0° C. and MeOTf (0.051 mL, 74 mg, 0.45 mmol) was added. The reaction was stirred at 0° C. for 9 h. Triethylamine (1 mL) was then added and reaction was filtered through a plug of silica and washed with Et$_2$O. The filtrate was washed with saturated aqueous NaHCO$_3$ and dried over anhydrous MgSO$_4$. Purification by preparative HPLC (85:15 hexane/EtOAc) afforded 108 mg (50a) of the target compound 22b. The b/a ratio of the reaction was 4:1.

$^1$H NMR (CDCl$_3$) δ 7.75 (d, J=7.2 Hz, 2H), 7.46–7.05 (m, 63H), 5.75 (dt, J=6.8, 15.2 Hz, 1H0, 5.43 (dd, J=8.6, 15.5 Hz, 1H), 5.13 (m, 2H), 5.09 (d, 3.6 Hz, 1H), 5.05 (d, J=11.6 Hz, 1H), 5.00 (d, J=11.5 Hz, 1H), 4.94–4.86 (m, 5H), 4.83–4.65 (m, 14H), 4.59 (d, 11.7 Hz, 2H), 4.53–4.43 (m, 6H), 4.39–4.31 (ml 4H), 4.23 (d, J=11.9 Hz, 1H), 4.18 (d, J=11.9 Hz, 1H), 4.15–4.08 (m, 2H), 4.05–3.57 (m, 31H), 3.54 (d, J=9.1 Hz, 1H), 3.49–3.45 (m, 2H), 3.38 (m, 1H), 3.31–3.23 (m, 3H), 2.92–2.89 (m, 2H), 2.75 (bt, 6.0 H, H), 2.12 (bq, J=6.9 Hz, 2H), 1.85 (s, 3H), 1.20–1.09 (m, 42H), 0.92 (t, J=6.6 Hz, 3H); $^{13}$C NMR (CDCl3) δ 169.1, 165.9, 155.5, 140.9, 139.2, 139.0, 138.8, 138.64, 138.59, 138.47, 138.43, 138.3, 138.2, 138.10, 138.07, 138.0, 132.1, 129.1, 128.69, 128.65, 128.56, 128.43, 128.40, 128.36, 128.35, 128.26, 128.17, 128.12, 128.08, 127.97, 127.77, 127.66, 127.64, 127.60, 127.54, 127.49, 127.45, 127.41, 127.3, 126.0, 103.0, 102.7, 100.8, 99.7, 99.2, 98.0, 81.2, 80.6, 79.5, 79.2, 79.0, 78.3, 77.7, 76.8, 76.5, 75.5, 75.3, 75.1, 75.03, 74.97, 74.91, 74.87, 74.0, 73.2, 73.10, 73.07, 72.98, 72.93, 72.6, 72.3, 72.1, 72.0, 71.32, 71.25, 70.2, 69.4, 69.32, 69.25, 68.1, 67.9, 67.5, 68.3, 62.1, 62.0, 56.1, 32.4, 31.9, 29.71, 29.68, 29.66, 29.48, 29.38, 29.2, 29.1, 22.7, 20.7, 18.13, 18.11, 18.01, 17.98, 16.9, 14.2, 11.9; IR (thin film) 3344, 3030, 2924, 2864, 2101, 1789, 1754, 1496, 1453, 1366, 1232 cm$^{-1}$.

Synthesis of 18b (See FIG. 11)

The hexasaccharide 22b (66 mg, 0.023 mmol) was dissolved in 1 mL EtOAc. Lindlar's catalyst (66 mg)was added followed by the addition of palmitic anhydride (23 mg, 0.046 mmol). The system was purged under vacuum and then put under 1 atm of $H_2$. After 24 h the reaction was filtered through a plug of silica gel, washed with EtOAc, and concentrated. Purification by preparative HPLC (4:1 hexane/EtOAc) afforded 64 mg (90%) of the desired product 18b.

$^1$-H NMR (CDCl$_3$) δ 7.72 (d, J=7.2 Hz, 2H), 7.42–7.02 (m, 63H), 5.65 (d, J=9.1 Hz, 1H), 5.62 (dt, J=6.6, 15.3 Hz, 1H), 5.31 (dd, J=8.6, 15.3 Hz, 1H), 5.10 (m, 2H), 5.05 (d, J=3.6 Hz, 1H), 5.02 (d, J=11.5 Hz, 1H), 4.96 (d, J=11.4 Hz, 1H), 4.90–4.62 (m, 13H), 4.57–4.38 (m, 8H), 4.32–4.26 (m, 3H), 4.21–4.07 (m, 9H), 4.01–3.41 (m, 31H), 3.30 (m, 1H), 3.23 (m, 3H), 2.20 (m, 4H), 1.82 (s, 3H), 1.52 (bm, 2H), 1.32–1.19 (m, 53H), 1.15–1.08 (m, 42H), 0.88 (t, J=6.8 Hz, 6H); IR (thin film) 3531, 3346, 3063, 3030, 2924, 2854, 1790, 1748, 1674, 1496, 1454, 1365, 1236 cm$^{-1}$; $[\alpha]^{23}_D$ –17.9 (c 0.65).

Synthesis of 1b (See FIG. 11)

The hexasaccharide from above (20 mg, 0.0065 mmol) was dissolved in 0.5 mL THF. A solution of tetrabutylammonium fluoride (1.0 M in THF, 0.050 mL, 0.050 mmol) was added and the reaction was stirred for 2 h. The solution was filtered through a plug of silica, washed with EtOAc and concentrated. The residue was dissolved in 1 mL of anhydrous MeOH and NaOMe (10 mg, 0.19 mmol) was added. The reaction was stirred for 3 h, neutralized with 40 mg of Dowex-50 resin, filtered and concentrated. Purification by flash column chromatography (1.5×4 cm 10–40 u silica gel, 95:5 CH$_2$Cl$_2$/MeOH) afforded 16.5 mg (94%) of the desired compound.

$^1$H NMR (CDCl$_3$) δ 7.78 (d, J=7.6 Hz, 2H), 7.46 (d, J=7.4 Hz, 2H), 7.41–6.97 (m, 61H), 6.02 (d, J=9.1 Hz, 1H), 5.76 (bs, 1H), 5.67 (dt, J=6.6, 15.3 Hz, 1H), 5.37–5.30 (tm, 2H), 5.19 (d, J=2.6 Hz, 1H), 4.96 (d, J=11.3 Hz, 1H), 4.93 (d, J=3.4 Hz, 1H), 4.90–4.83 (m, 3H), 4.78–4.66 (m, 7H), 4.56 (d, J=11.1 Hz, 1H), 4.53 (d, J=10.2 Hz, 1H), 4.47–4.32 (m, 5H), 4.28–4.06 (m, 14H), 4.01–3.13 (m, 36H), 2.73 (bt, 1H), 2.61 (bs, 1H), 2.54 (bs, 1H), (2.05 (m, 4H), 1.50 (m, 2H), 1.38–1.23 (m, 46H), 0.88 (t, J=6.6 Hz, 6H), 0.78 (d, 6.3 Hz, 3H); $^{13}$C NMR (CDCl3) δ 173.4, 142.4, 139.5, 139.0, 138.7, 138.5, 138.33, 138.26, 138.14, 138.09, 137.9, 137.2, 137.1, 131.6, 129.0, 128.8, 128.54, 128.47, 128.37, 128.32, 128.27, 128.22, 128.17, 128.14, 128.05, 127.99, 127.79, 127.73, 127.68, 127.63, 15 127.59, 127.49, 127.46, 127.37, 127.32, 126.98, 126.58, 104.1, 102.83, 102.76, 100.3, 100.2, 82.1, 81.5, 81.2, 79.6, 79.2, 79.0, 78.0, 77.3, 77.0, 76.7, 75.6, 75.3, 75.1, 75.0, 74.8, 74.6, 73.5, 73.4, 73.2, 73.0, 72.7, 72.6, 71.9, 70.1, 69.6, 68.5, 68.2, 68.0, 67.5, 62.4, 20 61.9, 54.8, 52.3, 36.9, 32.3, 31.9, 29.71, 29.67, 29.54, 29.50, 29.43, 29.37, 29.28, 29.20, 25.7, 22.7, 16.7, 14.1; IR (thin film) 3424, 3062, 3023, 2923, 2852, 1641, 1530, 1496, 1453, 1362, 1325 cm$^{-1}$; $[\alpha]^{23}_D$ –3.2 (c 0.83).

A flask was equipped with a dry ice condenser and was charged with 4 mL NH$_3$. Sodium (18 mg, 0.78 mol) was added and to the resulting blue solution was added 29 mg of the above hexasaccharide (0.010 mmol). The reaction was stirred at –78° C. for 45 min. Quench by the addition of MeOH (3 mL). Nitrogen was blown over the solution to evaporate the NH$_3$. The reaction was neutralized with 170 mg of Dowex-50 resin, filtered and concentrated. The resulting residue was dissolved in 1 mL of 4:1 THF/DMF. Triethylamine (0.5 mL) was added followed by the addition of DMAP (3 mg) and acetic anhydride (0.200 mL). After 2 h the reaction was concentrated in vacuo. Purification by flash column (1.5×5 cm 10–40 m silica, 9:1 EtOAc/hexane) afforded 18 mg (78%) of the peracetate. A sample of this hexasaccharide (15 mg, 0.0065 mmol) was dissolved in 0.5 mL of anhydrous MeOH and a NaOMe solution (30% in MeOH, 0.010 mL, 0.05 mmol) was added. The solution was stirred for 3 h, neutralized with 9 mg Dowex-50 resin, filtered and concentrated. The residue was purified by flash column chromatography (1.5×4 cm C-18 reverse phase silica, MeOH) to afford 9.6 mg of the natural product 1. Spectral data agree with those reported by Hakomori, et al.

BIOLOGICAL RESULTS

The MBR1 hexasaccharide has been prepared in two forms, the natural "B" form and the unnatural "A" form as shown below.

The natural structure ("β") is:

Fucα1→GalB1→3GalNAcB1→3Gal
  α1→4GlB1→4GcB1→1Cer

The unnatural structure "α" is:

Fucα1→2GalB1→3GalNAcα1→3Gal
  α1→4GalB1→1Cer

Both have been linked to ceramide to facilitate testing for immunological reactivity with monoclonal antibody (mAb) MBr1.

By Thin Layer Chromatography (TLC) the 2 preparations migrate as similar single bands. Immune TLC (see Ritter, G., et al., Cancer Res. 50, 1403–10 (1990)) demonstrates that both forms react with the MBr1 monoclonal antibody specifically but that the β-form reacts 10 times more strongly (comparable staining is seen with 1/10 the amount of antigen). The high level of reactivity of the β structure with mAb MBr1 was confirmed using flow cytometry inhibition assays. Reactivity of MAb MBr1 with breast cancer cell lines such as MCF-7 was 98% inhibited by 8 μg/ml of the β linkage preparation but was only 6% inhibited by 8 μg of the α-linkage preparation. GD3 ganglioside (negative control) showed no inhibition at all.

Application of the Glycal Assembly Method to the Concise Synthesis of Neoglycoconjugates of the Le$^y$ Carbohydrate Epitope Demonstrated herein is the use of the glycal assembly method to obtain glycals of the Le$^y$ specificity, conjugation to a carrier protein and to a ceramide, and results of immunizations with these conjugates. The conjugation strategy used relies on the protocol of Bernstein and Hall (Bernstein, M. A., and Hall, L. D., Carbohydr. Res., 1980, 78, C1) which calls for reductive coupling of a glycolaldehyde glycoside with the intended carrier, presumably at the ε-amino residues of exposed lysines. The interfacing of the glycal assembly logic with this conjugation strategy led to the paradigm shown in FIG. 1.

Synthesis of a Le$^y$ Epitotope and Conjugation to Protein Carriers

Figure 22A:
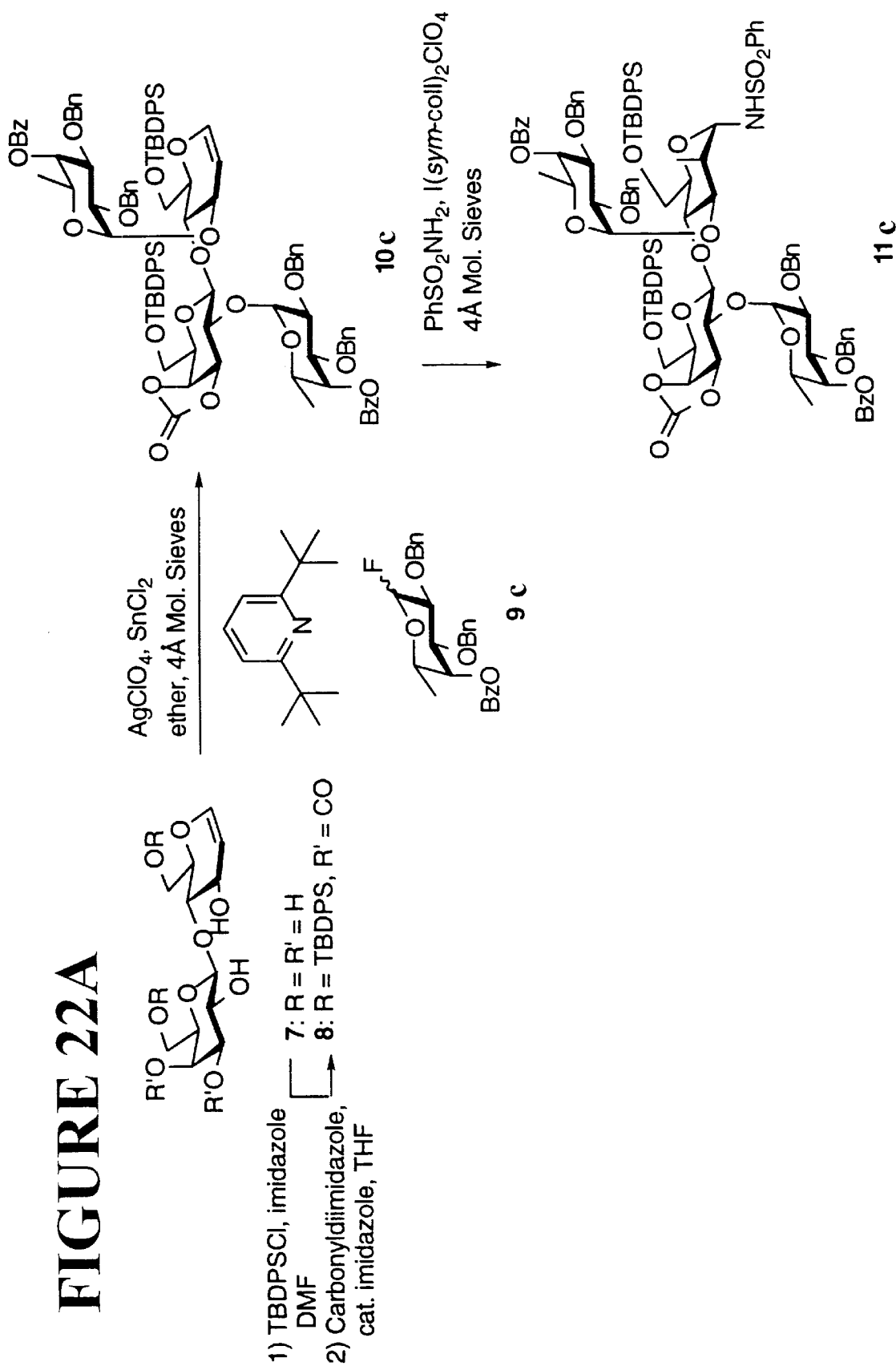
FIG. 22(a) shows the preparation of tetrasaccharide intermediate 11c.

Synthesis of a Le$^y$ pentasaccharide. (For previous syntheses of Lewis Y see: Jacquinet, J. C., and Sinay, P., J. Org. Chem., 1977, 42, 720; Nilsson, S., et al., Glycoconj. J., 1989, 6, 21; Schmidt, R. R., and Topfer, A., Tetrahedron Lett., 1991, 32, 3353; Kinzy, W., and Low, A., Carbohydr. Res., 1993, 245, 193; Hindsgaul, O., et al., Carbohydr. Res., 1982, 109, 109; Windmuller, R., and Schmidt, R. R., Tetrahedron Lett., 1994, 35, 7927.) A pentasaccharide containing the Le$^y$ specificity was prepared as shown in FIGS. 22(a) and (b). In the synthesis of this determinant, the N-acetyllactosamine backbone of the target was exploited. Lactal 7c (Haworth, W. N., et al., J. Chem. Soc., 1930, 2644) was an attractive starting material if a concise way of identifying the C$_3$ and C$_2$-hydroxyls could be effected.

Readily available lactal was silylated at the two primary sites. Following these silylations, the 3' and 4' hydroxyls were engaged as cyclic carbonate, 8c. Accordingly, the pertinent hydroxyl groups were expossed for further transformation. Difucosylation of 8c utilizing fluorosugar 9c (Danishefsky, S. J., et al., *J. Am. Chem. Soc.*, 1992, 114, 8329) as the donor (Mukaiyama, T., et al., *Chem. Lett.*, 1981, 431) provided access to the Le$^y$ series as glycal 10c. The use of a fucosylating agent with a protecting group (4-benzoate) that had the potential to donate into an oxonium intermediate was chosen to ensure a-selectivity. The glycal double bond was activated for azaglycosylation by a previously developed iodosulfonamidation protocol to afford 11c. (Danishefsky, S. J., et al., *J. Am. Chem. Soc.*, 1992, 114, 8331; Griffith, D. A., and Danishefsky, S. J., *J. Am. Chem. Soc.*, 1990, 112, 5811.)

Use of the iodosulfonamide to glycosylate the tin ether of galactal 12c (Danishefsky, S. J., et al., *J. Am. Chem. Soc.*, 1992, 114, 8331) in the presence of silver tetrafluoroborate led to glycal 13c as shown in FIG. 22(*b*). Deprotection followed by peracetylation afforded peracetyl glycal 14c. Reaction of 14c with dimethyldioxirane (Halcomb, R. L., and Danishefsky, S. J., *J. Am. Chem. Soc.*, 1989, 111, 6661) followed by opening of the epoxide with allyl alcohol, followed by deacetylation with catayltic methoxide led to pentasaccharide 15c.

To effect conjugation of the Le$^y$ determinant to a protein carrier, 15c was ozonolyzed in MeOH at −78° C. (See FIG. 22(*c*)). Work-up with dimethylsulfide afforded aldehyde 16c which was reductively attached to its BSA-protein carrier. The reductive amination protocol described by Bernstein and Hall was adapted to the present case. Thus, treatment of 16c with BSA in pH 8 phosphate buffer and excess sodium cyanoborohydride led to conjugate 17c which was purified by exhaustive dialysis. TFA analysis showed the expected sugar composition: 2 parts galactose, 2 parts fucose and 1 part N-acetylglucosamine. (For sugar analysis protocols see: Lloyd, K. O., and Savage, A., *Glycoconj. J.*, 1991, 8, 493; Hardy, M. R., and Townsend, R. R., *Proc. Natl. Acad. Sci.*, 1988, 85, 3289; for protein analysis see: Bradford, M. M., *Anal. Biochem.*, 1976, 72, 248.) Carbohydrate:protein analyses showed the uptake of an average of 15 Le$^y$ moieties per carrier molecule. This conjugate was recognized by an antibody to the Le$^y$ blood group.

For an extended Lewis$^y$ epitope the rollover of iodosulfonamide 11c was attempted with the regiospecifically generated tin ether lactal 18c. Under the usual reaction conditions the best yield of the desired hexasaccharide 19c was 15% as indicated in FIG. 23(*a*).

Figure 23A:
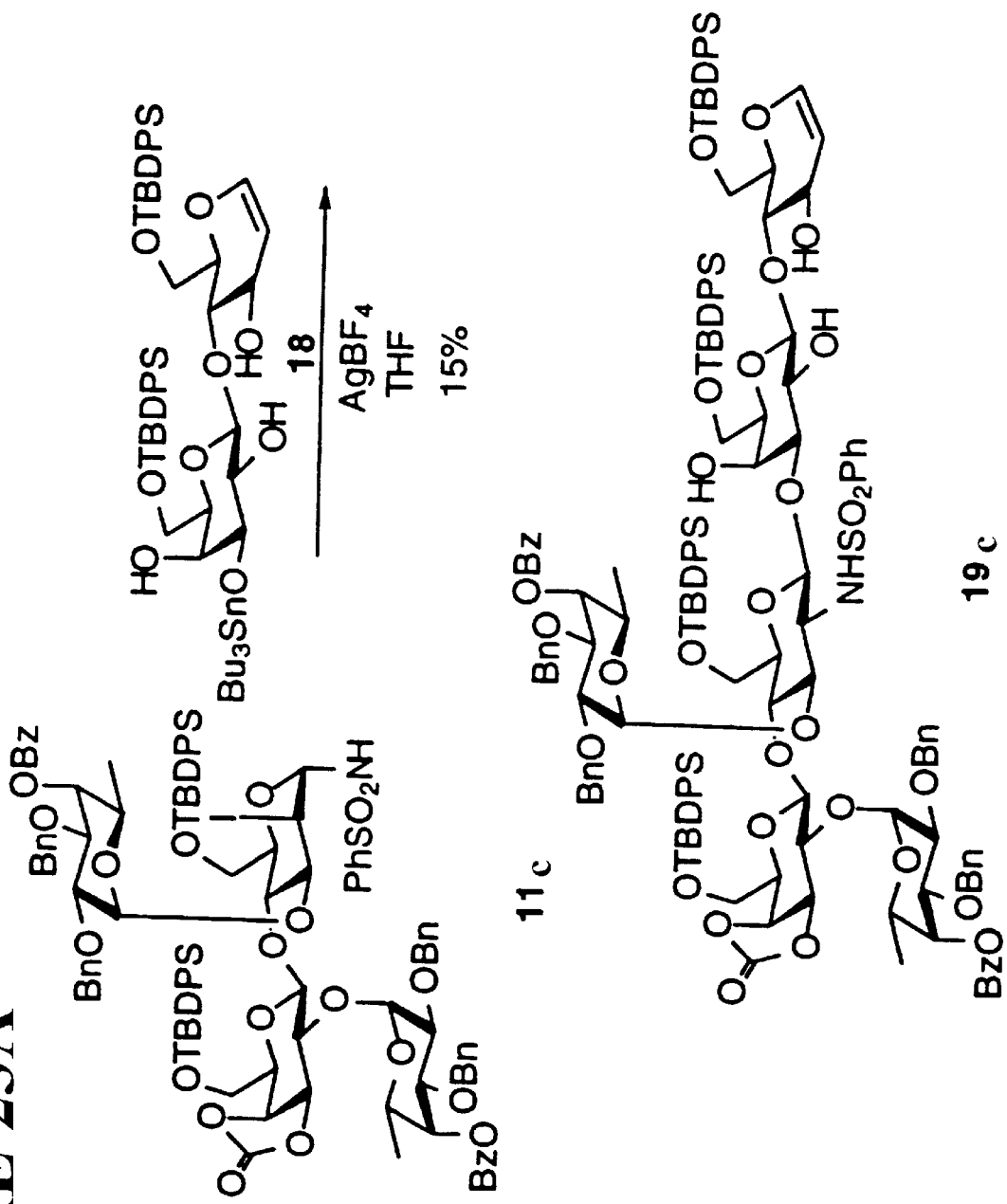
FIG. 23(a) shows the preparation of protected hexasaccharide glycal 19c.
Figure 23B:
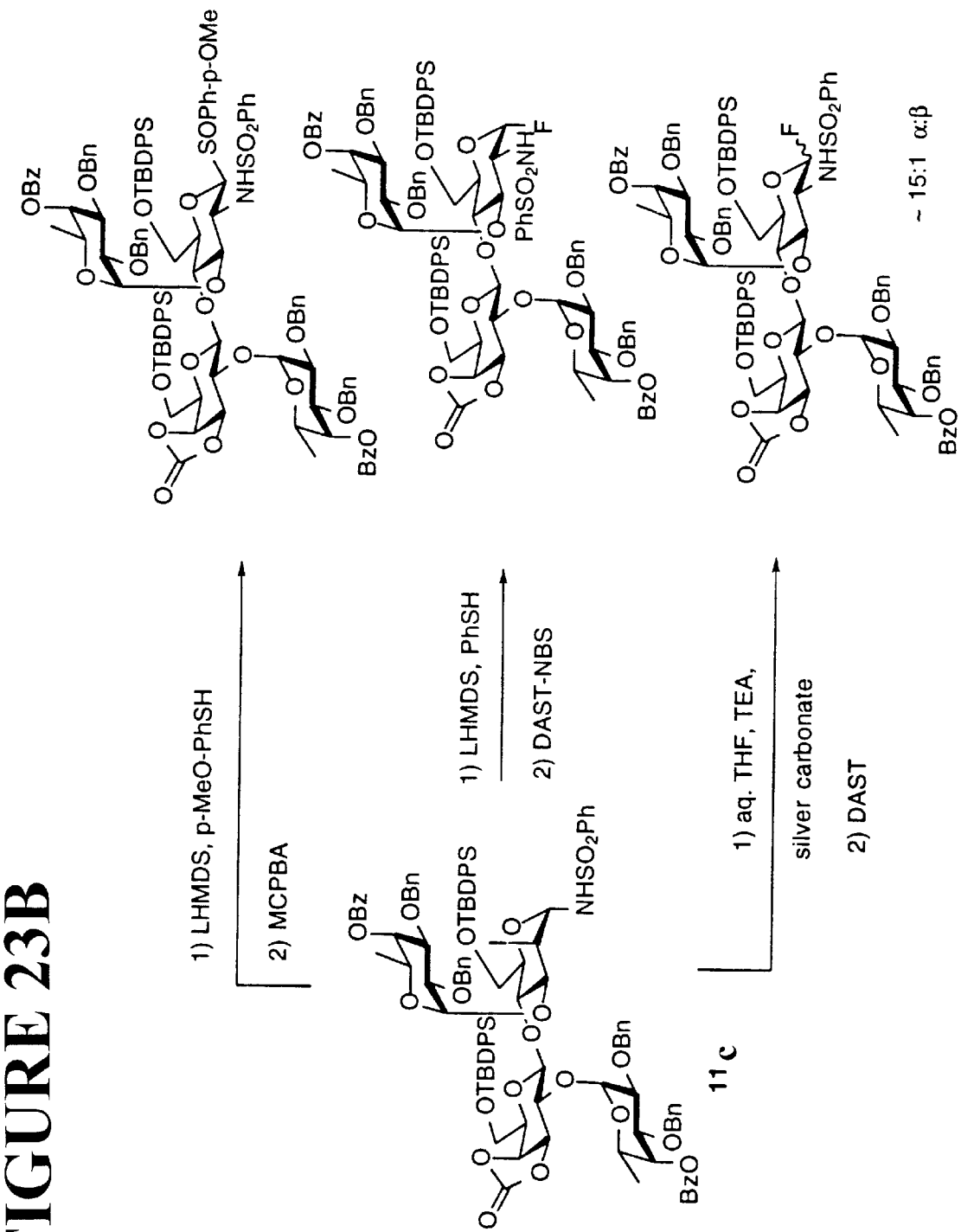
FIG. 23(b) shows three methods of elaborating tetrasaccharide iodosulfonamide 11c.

Similar results were obtained with a variety of other Le$^y$ donors generated from iodosulfonamide 11c (FIG. 23 (*b*)). This led to the hypothesis that the Le$^y$ tetrasaccharide donor may be poor due to the steric demands around the newly forming glycosidic linkage. Only the relatively flattened structure of galactal appears to add to the donor adequately.

Synthesis of a Ceramide-linked Glycoconjugate
(See FIG. 18(*a*))

In the synthesis of the closely related Le$^b$ carbohydrate antigen (Danishefsky, S. J., et al., *J. Am. Chem. Soc.*, 1995, 117, 5701), it was found that simplification of the protecting group scheme was possible by use of the perbenzylated fucosyl fluoride 20c. No erosion of a selectivity in the difucosylation of 21c was evident resulting in a 70% yield of Le$^b$ glycal 22c. When identical conditions were used to generate the Le$^y$ glycal quite the opposite was true as shown in FIG. 18(*a*).

Two major difucosylated products were obtained in a ratio of about 1.8 to 1. Identification of these products required more than direct inspection of the 1-D $^1$H NMR spectra. The tetrasaccharide with the two alpha-linked fucose residues 23c showed one obvious alpha linkage (5.30 ppm, d, J=3.2 Hz). The other alpha link was anomalously upfield (4.62 ppm, d, J=3.7 Hz). The coupling constant was measured by a DQF-COSY (phase-sensitive) experiment. The minor product 24c contained a b-linked fucose at the glucal 3 position. A simple COSY experiment established the existence of an a-linked fucose (5.09 ppm, d, J=3.6 Hz) and a b-linked fucose (4.35 ppm, d, J=7.5 Hz). From the proton assignments in the COSY experiment and with the aid of HMQC and HMBC experiments the b-linked fucose moiety was shown to reside at the glucal 3 position (very strong coupling between C-3 of glucal and H-1 of b-fucose in the HMBC experiment) The chemical yield (80%) for this experiment was exceptionally good despite the lack of stereoselectivity. A similar erosion of selectivity was observed during the study of the monofucosylation of a 6-mono protected glucal in the synthesis of the sialyl Le$^x$ carbohydrate antigen. (Gervay, J., et al., *J. Org. Chem.* 1993, 58, 5465.)

A large body of empirical evidence suggests that α-glycosylations (Lôhn, H. *Carbohydr. Res.* 1985, 139, 105; Kahne, D., et al., *J. Am. Chem. Soc.* 1989, 111, 6881; Rainer, H., et al., *Liebigs Ann. Chem.* 1992, 103; Wessel, H. P., *Tetrahedron Lett.* 1990, 31, 6863) are generally favored in nonpolar solvents. (In fucosyl fluoride 20c, the more hindered hydroxyls tend to favor the alpha linkage.) This suggests it is possible to enhance the selectivity of the reaction by decreasing solvent polarity.

The logical choice was to switch from THF to toluene. Conducting the reaction in toluene as solvent led to no reaction. This was attributed, however, to the insolubility of the tin triflate activator in toluene. The first success in modifying the reaction conditions was the use of a mixed solvent system of 10:1 toluene:THF. The selectivity for the doubly alpha-fucosylated product increased about two-fold with a comparable chemical yield of 83ac. The best ratio of 23c to 24c (>40:1 as determined by HPLC) was obtained with the use of a mixed solvent system of 10:1 toluene-:dichloromethane (DCM) with a modest yield of 50%. Reaction under these conditions was very slow, and presumably suffers from the lack of solubility of the activating tin triflate reagent. Because the isomers were easily separated it was practical to run the glycosylation for scale up with the 10:1 toluene:THF solvent system.

In a survey to find more active Le$^y$ donors in simple model systems, the fluorosugar 25c was found to be a reasonably good donor when activated with zirconcene dichloride (Matsumoto, T., et al., *Tetrahedron Lett.*, 1988, 29, 3567) and silver triflate. 25c was formed by reaction of iodosulfonamide 26c with water/THF/triethylamine in the presence of silver carbonate followed by reaction of the resulting free reducing sugar with DAST as shown below in FIG. 18(*b*).

With the aim of synthesizing a Le$^y$ ceramide conjugate reaction of 25c with azidosphingosine 27c (Schmidt, R. R., and Zimmermann, P., *Tetrahedron Lett.*, 1986, 27, 481) under the mixed metal system gave acceptable yields of the Le$^y$ sphingosine 28c as indicated in FIG. 18(*c*).

The reduction of the azide followed by N-acylation with a palmitic acid side chain proved to be quite challenging. In a model study for the reduction of the azide with subsequent acylation, conditions developed by Corey proved sufficient. (Corey, E. J., et al., *Synthesis*, 1975, 590) Thus, treatment of galactose azidosphingosine 29c in ethyl acetate with Lindlar's catalyst and palmitic anhydride with a balloon of hydrogen led to galactose ceramide 30c in 91% yield after only 6 hours (FIG. 18(d)). As applied to 28c, however, the conditions were less effective. The desired ceramide Le$^y$ conjugate 31c was obtained in only 22% yield (FIG. 19(a)). Two other by-products were formed during the reaction both of which lacked the double bond in the side chain ceramide.

As monitored by TLC, the reduction of the azide moiety in 28c was considerably slower than in the model system. One possible reason for this is that the azide now resides near the bulky branching sugar sector leading to inaccessability to the catalyst surface. Thus, the rate of reduction of the azide may be comparable to the rate of reduction of the double bond. Other conditions to reduce the azide remain to be explored. The conjugate 31c was deblocked as shown in FIG. 19(b); the ceramide linked Le$^y$ conjugate 32c was evaluated in immunological studies.

Figure 19A:
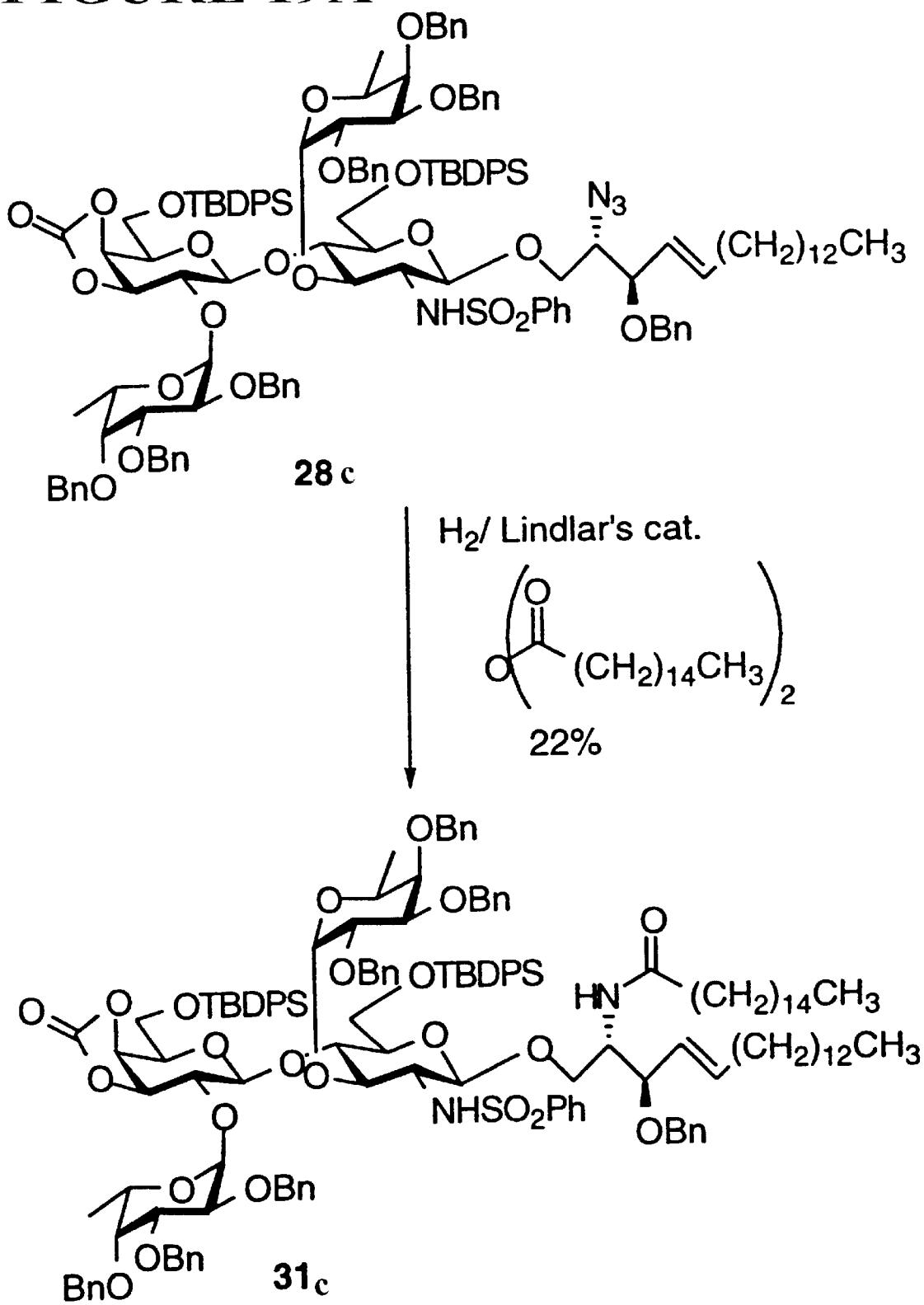
FIG. 19(a) shows a reduction reaction to prepare tetrasaccharide ceramide intermediate 31c.
Figure 19B:
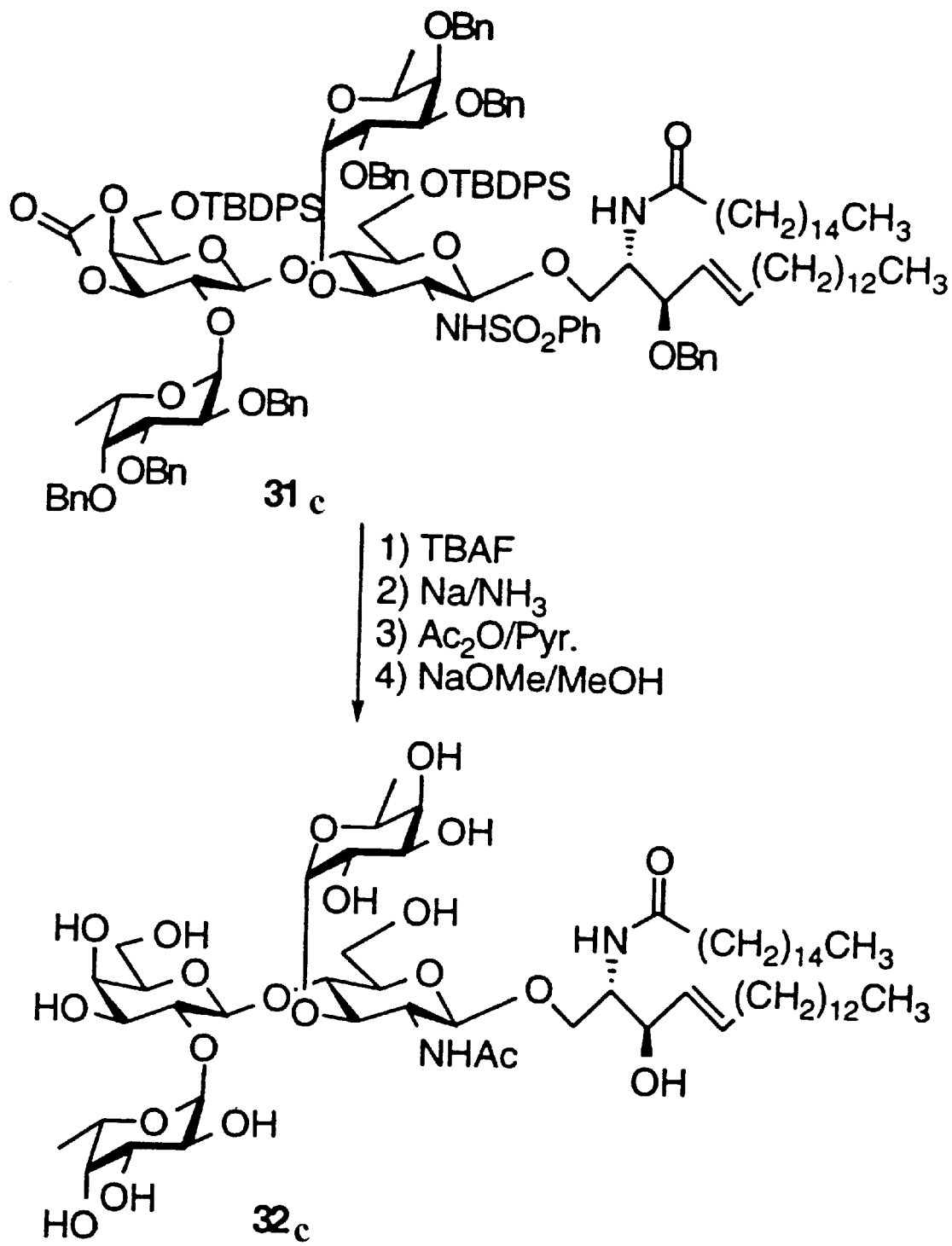
FIG. 19(b) shows a reaction pathway to prepare tetrasaccharide ceramide 32c.
Figures 22B, 22C:
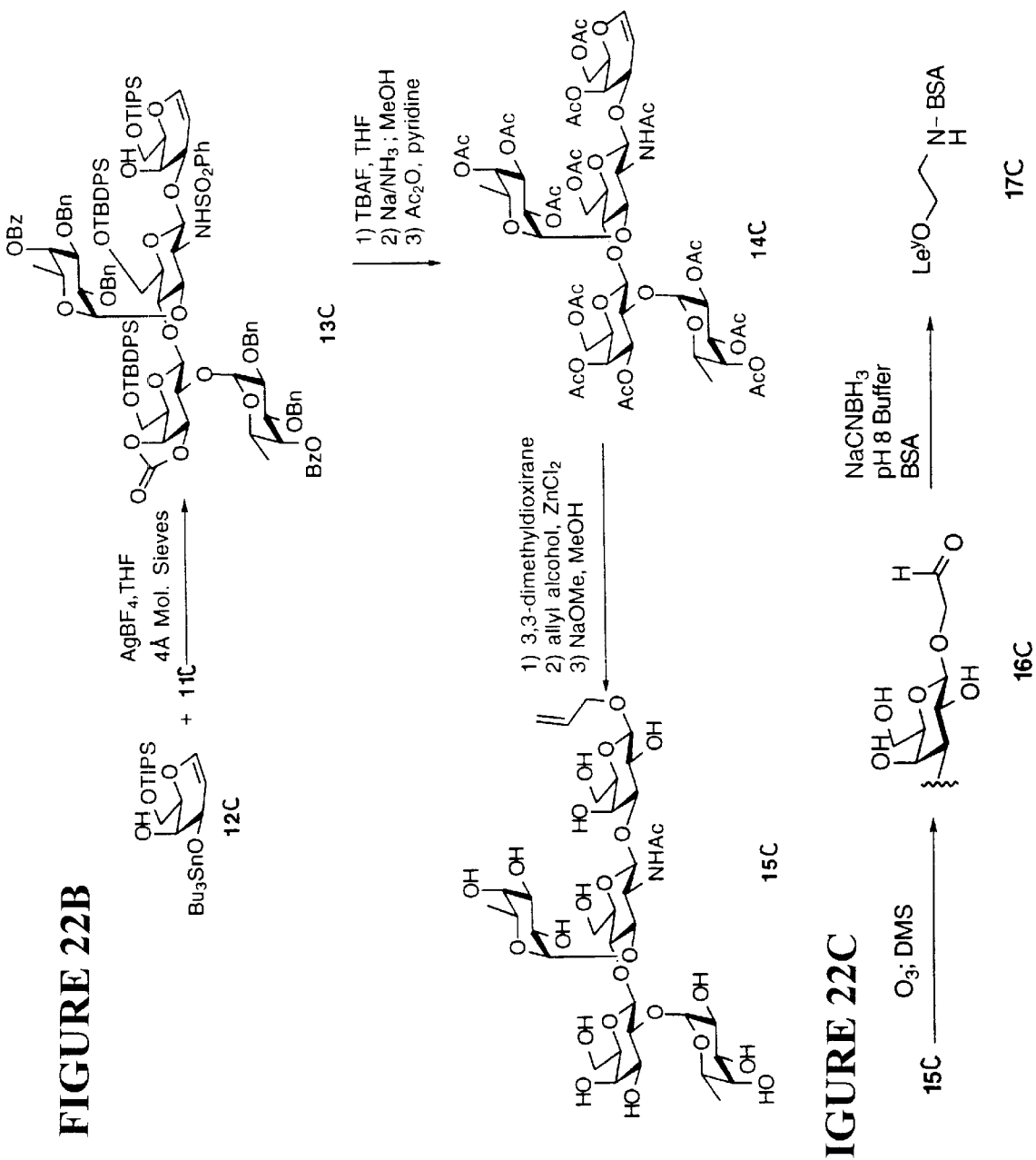
FIG. 22(b) shows the preparation of o-allyl pentasaccharide 15c.
FIG. 22(c) shows the preparation of a Le$^y$-BSA glycoconjugate 17c by reductive amination of petasaccharide aldehyde intermediate 16c.

Results of Immunizations with Le$^y$ Conjugates 17c (FIG. 22(c)) and 32c (FIG. 19(b))

Figure 20A:
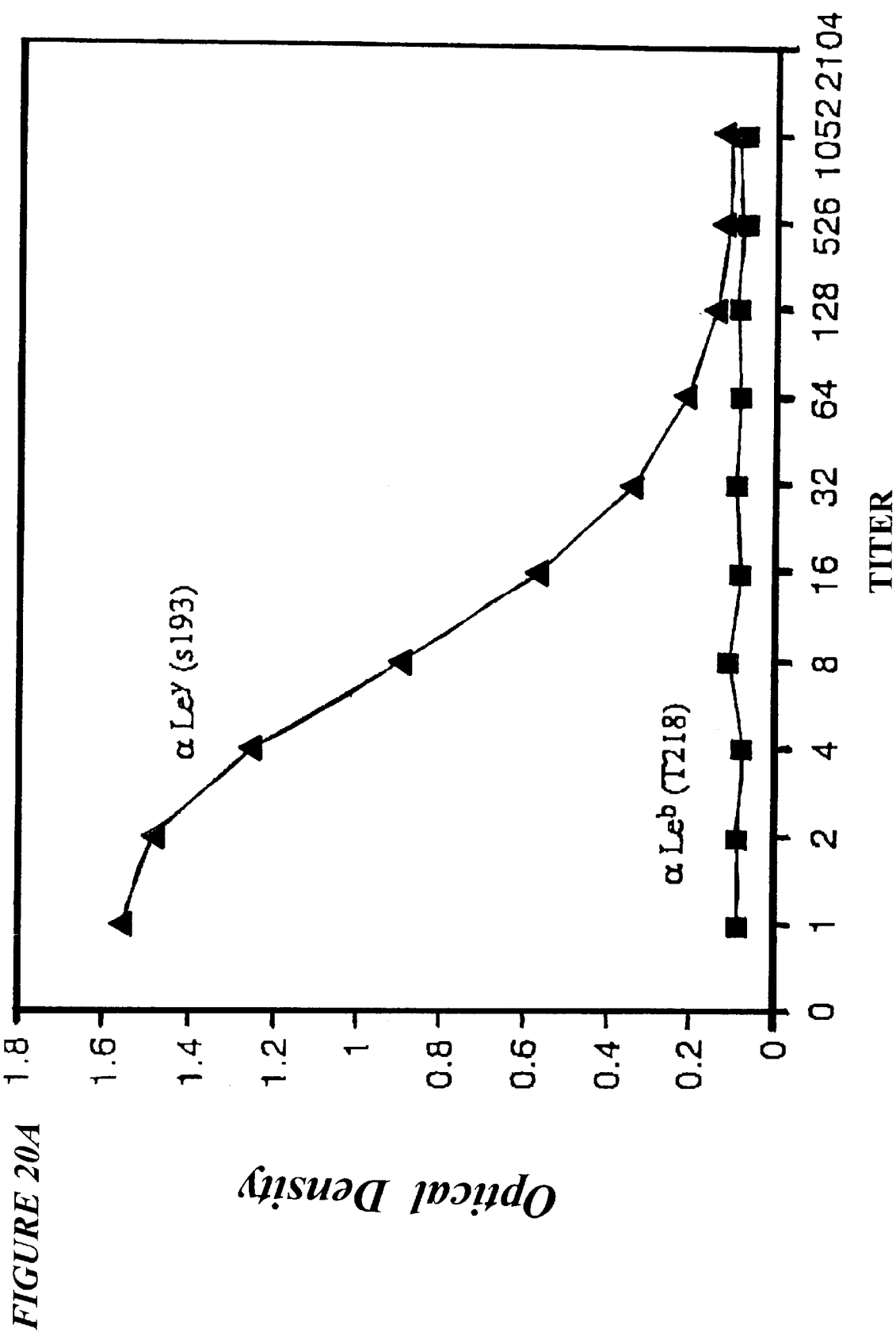
FIG. 20(a) shows the reactivity of compound 17c with αLe$^y$ (s193) and αLe$^b$ (T218) control.

The first experiment to characterize the synthetic antigen entailed testing the reactivity of the synthetic conjugate 17c with known antibodies. This is shown in FIG. 20(a). 17c showed reactivity with aLe$^y$ (s193), an anti-Lewis$^y$ antibody. As a control, 17c was tested against anti-Lewis$^b$ antibody aLe$^b$ (T218). As indicated in the graph, 17c showed no cross reactivity with this antibody.

Figure 20B:
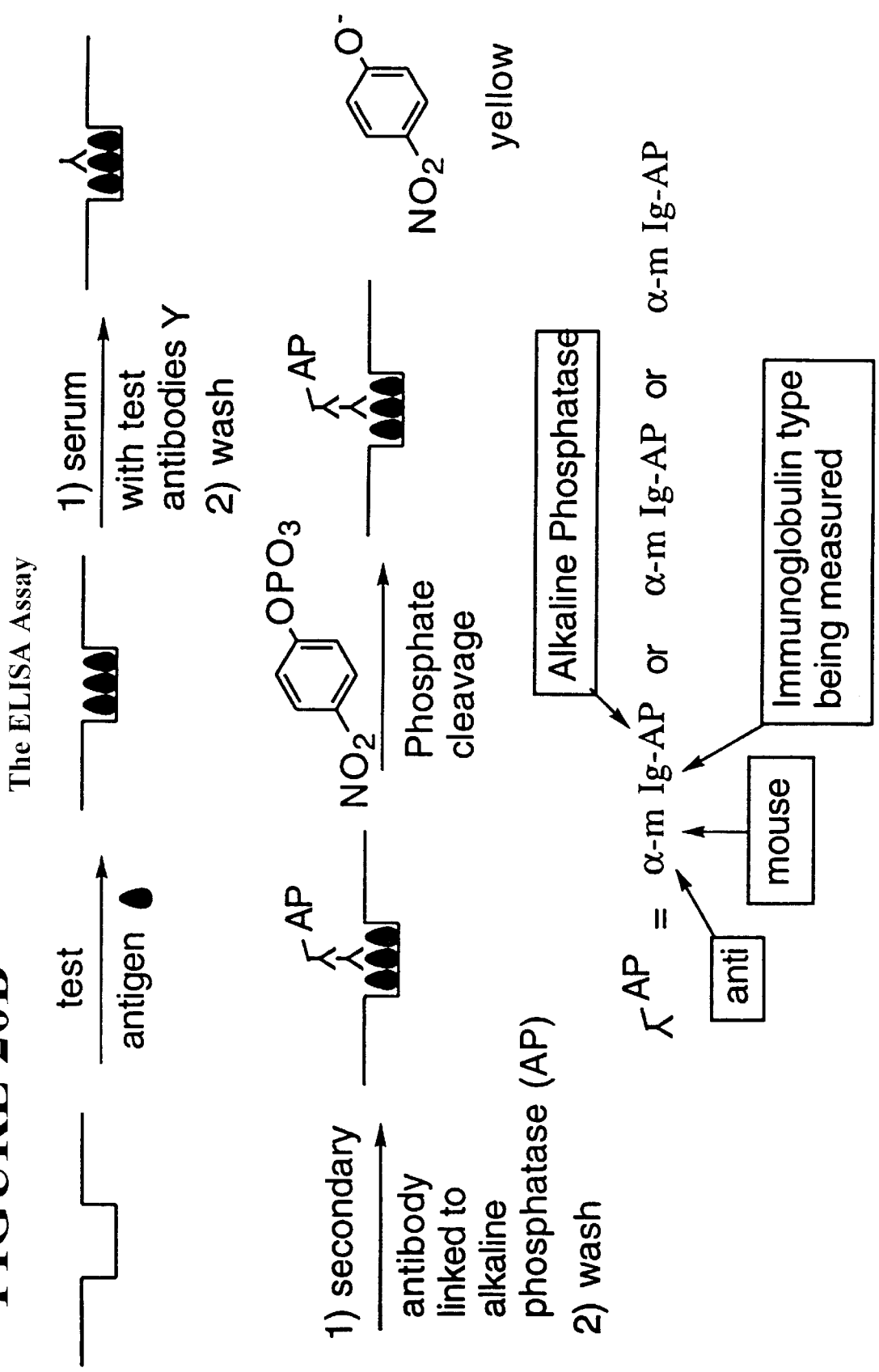
FIG. 20(b) shows the enzyme-linked immunosorbant assay used to measure antibody titer.

The stage was set for immunizations with conjugates 17c and 32c. The immunizations with the BSA conjugate 17c were carried out on two sets of 5 mice and the immunizations with the ceramide conjugate 32c were carried out on one set of 5 mice. An enzyme-linked immunosorbant assay (ELISA) was used to measure antibody titer (FIG. 20(b)). Three different ELISA experiments were performed to measure antibody titer. The first is the measure of total antibody response (aIg), that is the summation of IgM and IgG antibodies, as shown in graphs A, D, G. and J of FIGS. 21(a) and (b). The other two assays measure IgM and IgG antibodies separately as indicated in the graphs. The ELISA assay (see FIG. 20(b)) involves the immobilization of a test antigen in a microtiter well. The serum to be tested for antibodies is placed in the well. Any antibodies in the serum recognizing the test antigen will remain in the well after thorough washing. Next, modified anti-mouse Ig, IgM, or IgG antibodies are placed in the well. These secondary anti-immunoglobulin antibodies have been linked to alkaline phosphatase. After thorough rinsing, the wells are treated with p-nitrophenylphosphate (PNP). The presence of the alkaline phosphatase-linked secondary antibody causes cleavage of the phosphate, yielding the yellow p-nitrophenolate anion, which can be quantified using spectrophotometric techniques.

Figures 21A, 21B, 21C:
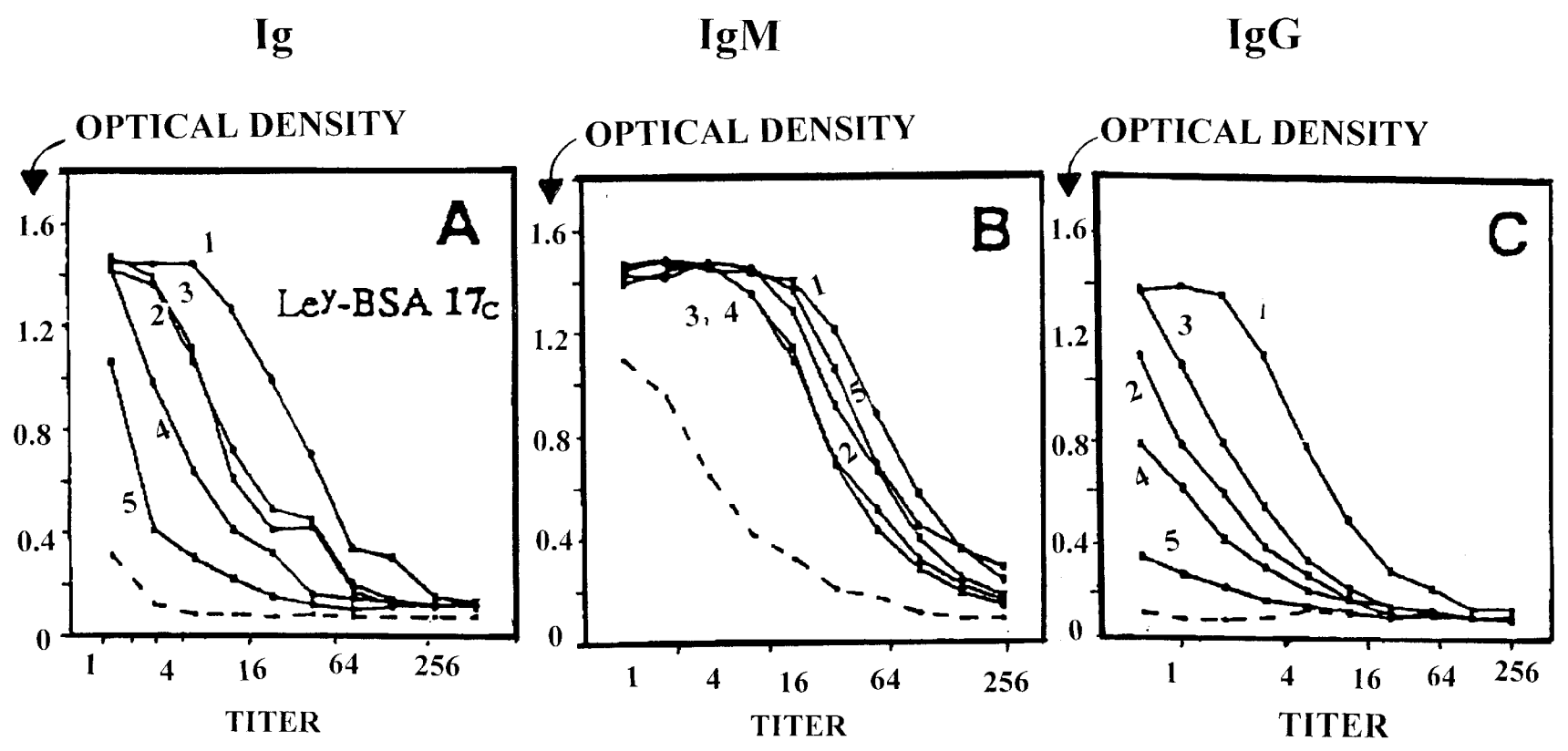
Figure 21D:
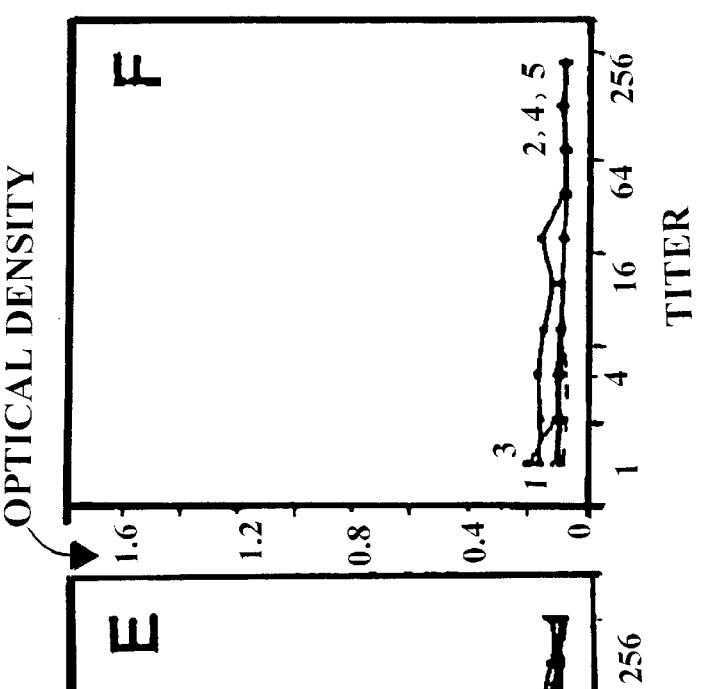
FIG. 21(a–f) shows in panels A, B and C the measured titers of total antibody Ig, IgM and IgG type antibodies, respectively, in five mice immunized with conjugate 17c; in panels D, E and F controls where mice were immunized with BSA carrier alone.
Figure 21E:
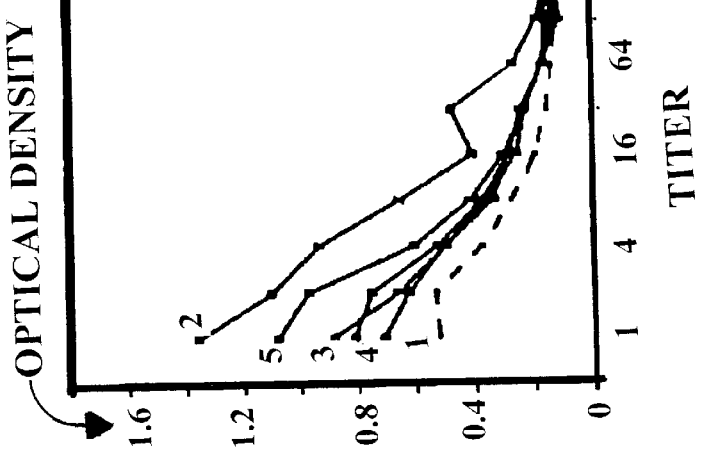
Figure 21F:
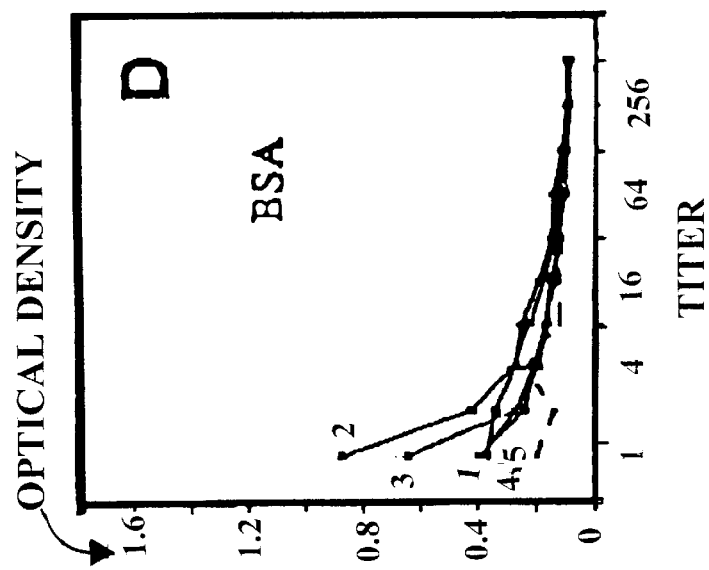
Figures 21J, 21K, 21L:
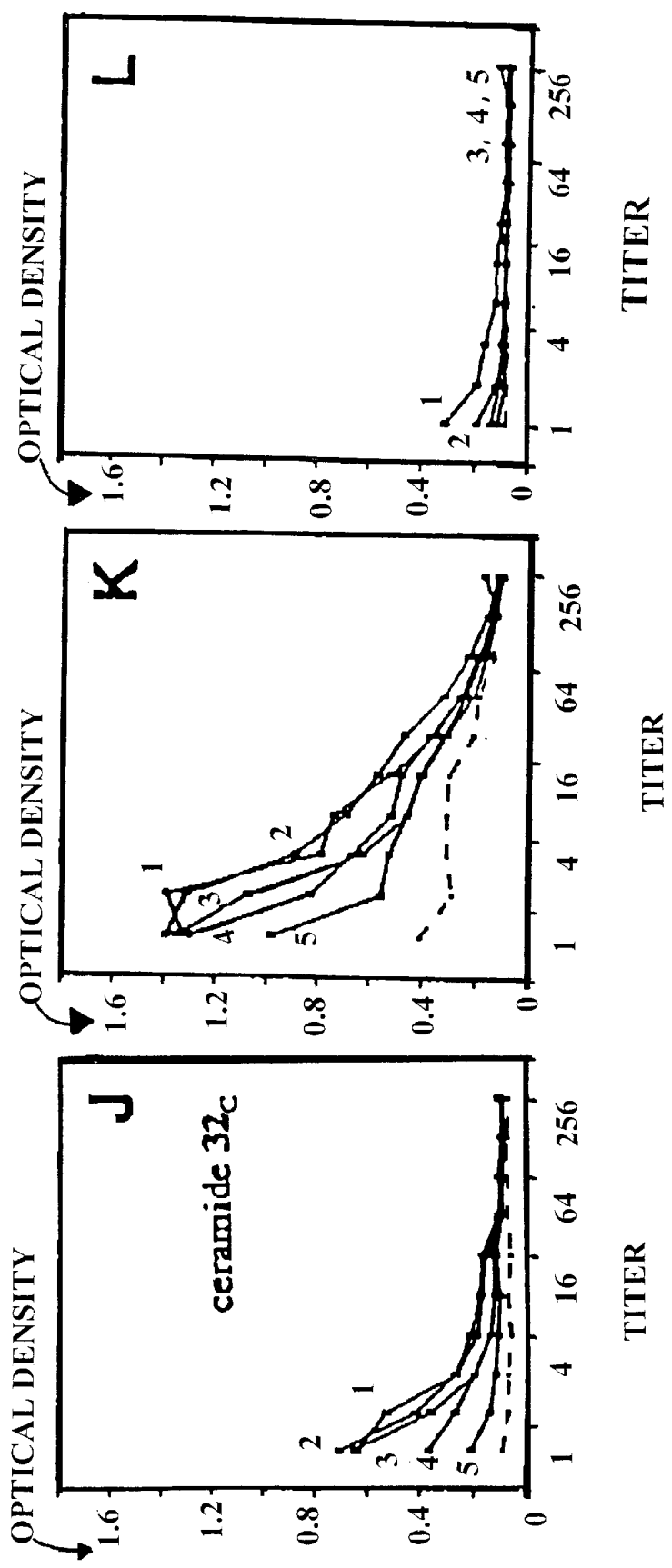

Graphs A, B, and C in FIG. 21(a) show the measured titers of total antibody Ig (A), IgM (B), and IgG (C) type antibodies in five mice immunized with conjugate 17c. The dashed line indicates a control mouse that was not immunized. This serves as the background, since natural antibodies are found in the sera. As seen in these graphs, all mice made antibodies against the immunizing antigen. Remarkably, 4 out of 5 mice produced IgG type antibodies. As discussed previously this is unusual. Graphs D–F represent a control where mice were immunized with the BSA carrier alone. This ensures that the response in A–C is due to the conjugate 17c and not just a response to the protein carrier itself, which is a potential immunogen. As indicated in D–F the response seen in A–C is due to 17c and is not an artifact of the immunogenicity of the carrier.

A more important issue was whether the antibodies to the synthetic antigen were capable of recognizing the Le$^y$ mucin structure. Graphs G–I show the measured titer of antibodies with the Le$^y$ mucin as the test antigen. One mouse showed outstanding response to the immunizing antigen by producing both IgG as well as IgM antibodies. All the mice showed an IgM response (graph H) with the mucin structure.

Results of the immunizations with the ceramide conjugate 32c (graphs J–L) were not as exciting. No mice showed any IgG response. Most mice showed only a weak IgM response. The results of these immunization experiments are encouraging and warrant closer investigation into the factors that result in the potency and specificity of the immune response to synthetically generated carbohydrate-based vaccinations.

EXPERIMENTAL

[(6-O-tert-Butyldiphenylsilyl-3,4-carbonate-b-D-galactopyran osyl)-(1→4)[-1,5-anhydro-6-O-tert-butyldimethylsilyl-2-deoxy-D-arabino-hex-1-enopyranose (8c) (See FIG. 22(a))

To 2.11 g (6.84 mmol) of lactal 7c was added 2.80 g (41 mmol) of imidazole and 25 mL of dry DMF. The solution was cooled to −10° C. and 3.56 mL (13.7 mmol) of tert-butyldiphenylsilyl chloride was added dropwise over 15 minutes. The reaction was allowed to warm gradually to room temperature. After stirring 8 h the reaction was diluted with 200 mL of EtOAc and washed 3 times with 100 mL water and once with saturated brine. The organics were dried over MgSO$_4$, filtered, and concentrated in vacuo. The crude material was run through a plug of silica gel with 50% EtOAc/Hexanes and concentrated to give 4.50 g (84%) of white foam. This was taken up in 125 mL of dry THF and a few crystals of imidazole were added. The solution was cooled to 0° C. and 938 mg (5.79 mmol)of carbonyl diimidazole was added. After 2 hours most of the starting material was consumed as judged by thin layer chromatography. The reaction was concentrated and chromatographed on silica gel (40% EtOAc/Hexanes) to afford 910 mg (20%) of recovered starting material and 2.72 g (58%) of 8c as a white foam: $[a]_D^{23}$=−8.70° (c 1.35, CHCl$_3$); IR (thin film) 3450, 2900, 2830, 1785, 1632, 1415, 1225, 1145, 1100, 810, 730, 695; $^1$H NMR (400 MHz, CDCl$_3$) d 7.76–7.69 (m, 8 H), 7.51–7.43 (m, 12 H), 6.38 (d, 1H, J=5.9 Hz), 4.83 (d, 1H, J=7.2 Hz), 7.75 (dd, 1H, J=2.0, 6.1), 4.72 (d, 1H, J=6.91 Hz), 4.64 (app. t, 1H, J=5.5 Hz), 4.40 (d, 1H), 4.08–3.86 (m, 7H), 3.69–3.68 (br, 2H), 2.80 (d, 1H, J=3.6 Hz), 1.13 (s, 9H), 1.12 (s, 9H); HRMS (FAB) calcd for C$_{45}$H$_{54}$O$_{10}$Si$_2$Na 833.3153, found m/z 833.3157 (M+Na).

[[[(4-O-Benzoyl-2,3-dibenzyl-6-deoxy-a-L-galactopyranosyl)-(1→2)]-(6-O-tert-butyldiphenylsilyl-3,4-carbonate-b-D-galacto pyranosyl)-(1→4)]-(4-0-benzoyl-2,3-dibenzyl-6-deoxy-a-L-galactopyranosyl)-(1→3)]-1,5-anhydro-6-O-tert-butyldiphenylsilyl-2-deoxy-D-arabino-hex-1-enopyranose (10c) (See FIG. 22(a))

To 2.00 g (2.47 mmol) of lactal carbonate 8c was added 4.44 g (9.86 mmol) of fucosyl fluoride 9c. The mixture was azeotroped 5 times with benzene and placed under high vacuum for two hours. Under an argon atmosphere 2.77 mL (12.33 mmol) of di-tert-butyl pyridine and 16 mL of dry ether were added. 2.0 g of freshly activated 4 Å molecular sieves were added and the mixture stirred one hour at room temperature. In an argon glove bag, 2.34 g (12.33 mmol) of stannous chloride (SnCl$_2$) and 2.56 g (12.33 mmol) of silver perchlorate (AgClO$_4$) were added. The flask was equipped with a reflux condensor and the reaction brought to reflux for 72 hours. The reaction was quenched with 5 mL of saturated bicarbonate and filtered through a pad of celite. Diluted with 50 mL ethyl acetate and washed 2 times with saturated bicarbonate, 2 times with sat. copper sulfate and 2 times with sat. brine. The organics were dried over $MgSO_4$ and concentrated. Flash chromatography in 20% ethyl acetate/hexanes afforded 2.10 g (51%) of a white foam 10c: $[a]_D$–78.9° (c 0.555, $CHCl_3$); IR (thin film) 3040, 3000, 2905, 2860, 2830, 1820, 1800, 1710,1635, 1585, 1570, 1480, 1460, 1440, 1415, 1370, 1350, 1300,1260, 1205, 1145, 1100, 950, 735, 695; $^1H$ NMR (400 MHz, $CDCl_3$) d 8.09 (d, J=8.12 Hz, 2H), 8.00 (d, J=8.26 Hz, 2H) 7.66 (m, 4H), 7.59 (d, J=6.74 Hz, 4H), 7.56 (t, J=7.27 Hz, 1H), 7.30–7.50 (m, 22H) 7.16–7.26 (m, 10H) 7.09 (m, 2H), 6.99 (t, J=7.59 Hz, 2H) 6.89 (t, J=7.97 Hz, 1H), 6.43 (d, J=6.08 Hz, 1H), 5.46 (bs, 1H), 5.38 (bs, 1H), 5.35 (d, J=3.42 Hz, 1H), 4.89 (d, J=11.35 Hz, 1H), 4.75–4.80 (m, 4H), 4.72 (d, J=5.88 Hz, 2H), 4.69 (d, J=4.27 Hz, 2H), 4.36–4.55 (m, 5H), 4.28 (q, J=6.51 Hz, 1H), 4.17 (bd, J=5.46 Hz, 1H), 3.90–4.00 (m, 6H), 3.85 (d, J=2.99 Hz, 1H), 3.82 (d, J=2.89 Hz, 1H), 3.56–3.78 (m, 4H), 1.07 (m, 24H); HRMS (FAB) calcd for $C_{99}H_{106}O_{20}Si_2Na$ 1694.6740 found m/z 1694.6787 (M+Na). [[[(4-Benzoyl-2,3-dibenzyl-6-deoxy-a-L-galactopyranosyl)-(1→2)]-(6-O-tert-butyldiphenylsilyl-3,4-carbonate-b-D-galactopyranosyl)-(1→4)]-(4-benzoyl-2,3-dibenzyl-6-deoxy-a-L-galactopyranosyl)-(1→3)]-6O--tert-butyldiphenylsilyl-2-deoxy-2-iodo-a-D-manno-pyranosyl benzenesulfonamide (11c) (See FIG. 22(a)).

To 400 mg (0.239 mmol) of tetrasaccharide glycal 10c (azeotroped 3× with 15 mL benzene) was added 113 mg (0.718 mmol) of benzenesulfonamide and 400 mg of freshly activated 4 Å powdered molecular sieves. This was taken up in 2.7 mL of methylene chloride and cooled to 0° C. Stirred for 30 minutes at 0° C. and then added 392 mg (0.837 mmol) of iodonium di-sym. collidine perchlorate in one portion. Stirred for 30 minutes and then quenched at 0° C. with 3 mL of saturated sodium thiosulfate. The reaction mixture was diluted with EtOAc and filtered through a celite pad into a separatory funnel. Washed once with saturated sodium thiosulfate, once with saturated copper sulfate, and once with saturated brine. The organics were dried over $MgSO_{4,}$ filtered, and concentrated. Purification by silica gel chromatography (32% EtOAc/Hexanes) afforded a white foam 11c: $[a]_D^{23}$=–95.8'° (c 0.58, $CHCl_3$); IR (thin film) 2910, 2835, 1800, 1710, 1440, 1425, 1350, 1260, 1150, 1100, 1040, 695; $^1H$ NMR (400 MHz, $CDCl_3$): d 8.09 (d, 2H, J=7.1 Hz), 8.02 (d, 2H, J=6.99 Hz), 7.75 (d, 2H, J=7.49 Hz), 7.67–7.09 (m, 49H), 5.93 (br s, 1H), 5.61 (br s, 1H), 5.46 (br s, 1H), 5.43 (br s, 1H), 5.06–4.54 (m, 10H), 4.47 (br d, 1H, J=10.3 Hz), 4.36–4.30 (m, 2H), 4.18 (br, 2H), 3.98–3.70 (m, 11H), 3.40–3.28 (br, 2H), 1.10 (s, 9H), 1.05 (s, 9H), 1.02 (d, 3H, J=6.4 Hz), 0.98 (d, 3H, J=6.4 Hz); HRMS (FAB) calcd for $C_{105}H_{112}NO_{22}ISi_2Na$ 1977.5900, found m/z 1977.6037 (M+Na).

[[[(4-Benzoyl-2,3-dibenzyl-6-deoxy-a-L-galactopyranosyl)-(1→2)]-(6-tert-butyldiphenylsilyl-3,4-carbonate-b-D-galactopyranosyl)-(1-4)]-[(4-O-benzoyl-2,3-dibenzyl-6-deoxy-a-L-galactopyranosyl)-(1→3)]-(2-benzenesulfonamido-6-O-tert-butyldiphenylsilyl-2-deoxy-b-D-glucopy ranosyl)-(1→3)]]-1,5-anhydro-2-deoxy-6-O-tri-iso-propylsilyl-D-lyxo-hex-1-enopyranose (13c) (See FIG. 22(b)).

230 mg (0.12mmol) of iodosulfonamide 11c was azeotroped 5 times with dry benzene and placed under high vacuum for two hours. To this was added 2.4 mL of THF solution of 15 eq. of tin ether 12c (generated by azeotropic removal of water overnight with a Dean-Stark trap equipped with freshly activated 4 Å mol. sieves from 561 mg (1.80 mmol) of 6-TIPS-galactal and 673 mL (1.32 mmol) bis (tributyltin) oxide in 80 mL of benzene). To this solution stirring under an argon atmosphere was added 200 mg of freshly activated 4 Å powdered molecular sieves. Stirred one hour at room temperature. Cooled solution to –78° C. and added, via cannula, a solution of 187 mg (0.96 mmol) of silver tetrafluoroborate in 2.4 mL of THF. Warmed to room temperature over 15 hours and quenched the reaction, which had turned bright yellow, with 2 mL. of sat. bicarbonate. The reaction mixture was filtered through a pad of celite into a separatory funnel. The celite pad was washed thoroughly with ethyl acetate. The organics were washed twice with sat. bicarbonate and twice with sat. brine. The organics were dried over $MgSO_4$. Concentration and chromatography in 25% ethyl acetate/hexanes gave 193 mg (75%) as a white foam 13c: $[a]_D$–126.40° (c 0.505, $CHCl_3$); IR (thin film) 3500, 3040, 3000, 2905, 2840, 1820, 1800, 1705, 1635, 1590, 1440, 1410, 1255, 1195, 1100, 1080, 1035, 815, 730, 695; $^1H$ NMR (400 MHz, $CDCl_3$) d 8.09 (app t, 4H), 7.65–7.08 (m, 46H), 6.90 (t, J=7.65 Hz, 3H), 6.76 (d, J=6.91 Hz, 2H), 6.12 (d, J=6.59 Hz, 1H), 5.50 (bs, 1H), 5.45 (bs, 1H), 5.28 (app t, 2H), 4.91–3.03 (m, 36H), 2.82 (br s, 1H) 1.09 (m, 45H); HRMS (FAB) cald for $C_{120}H_{141}NO_{26}SSi N_3a$ 2150.8668 found m/z 2150.8765 (M+Na).

[[[(2,3,4-Tri-O-Acetyl-6-deoxy-a-L-galactopyranosyl)-(1→2)]-(3,4,6-tri-O-acetyl-b-D-galactopyranosyl)-(1→4)]-[(2,3,4-tri-O-acetyl-6-deoxy-a-L-galactopyranosyl)-(1→3)-(2-acetamido-6-O-acetyl-2-deoxy-b-D-glucopyrano-syl)-(1→3)]]-1,5-anhydro-4,6-di-O-acetyl-2-deoxy-D-lyxo-hex-1-enopyranose (14c) (See FIG. 22(b))

480 mg (0.225 mmol) of pentasaccharide glycal 13c was taken up in 200 mL of THF and 52 mL (0.902 mmol) of glacial acetic acid and 1.35 mL of TBAF (1M in THF, 1.35 mmol) were subsequently added at room temperature. After stirring 8 hours 13c was completely consumed and a new product appeared as judged by TLC. The reaction mixture was concentrated and chromatographed in 8% MeOH/$CHCl_3$. The resulting white solid was taken up in THF and added to solution of 15 mL of about 5:1 $NH_3$/THF to which a large excess of solid sodium metal had been added. The dark blue solution was allowed to reflux at –33° C. for 20 minutes. The reaction was quenched with 5 mL of MeOH and stirred overnight. The reaction was partially concentrated and then cooled to 0° C. The reaction mixture was then carefully acidified to pH 8 with Dowex 50-X200 ion exchange resin. The reaction was filtered and concentrated. The crude solids were taken up in 3 mL of pyridine and 3 mL of acetic anhydride and allowed to stir overnight. Purification by silica gel chromatography (30% acetone/benzene) gave 110 mg (37% ) of a white solid 14c: $[a]_D$–121.30° (c 0.635, $CHCl_3$); IR (thin film) 2930, 1735, 1362, 1224, 1060, 1040; $^1H$ NMR (400 MHz, $CDCl_3$) d 6.33 (d, 1H, J=6.3 Hz), 5.70 (d, 1H, J=7.2 Hz), 5.30–5.26 (m, 6H), 5.13 (dd, 1H, J=3.1, 11.0 Hz), 5.05 (dd, 1H, J=3.2, 11.1 Hz), 5.00–4.92 (m, 4H), 4.88 (d, 1H, J=6.6 Hz), 4.79 (dd, 1H, J=3.4, 6.1 Hz), 4.53–4.28 (m, 7H), 4.22–4.08 (m, 4H), 3.83–3.69 (m, 3H), 3.51 (br dd, 1H, J=3.7, 9.5 Hz), 2.17 (s, 3H), 2.14 (br s, 6H), 2.13 (br s, 6H), 2.11 (s, 3H), 2.09 (s, 3H), 2.07 (s, 3H>2.00 (s, 3H), 1.98 (s, 3H), 1.96 (s, 3H), 1.95 (s, 3H), 1.91 (s, 3H), 1.17 (d, 3H, J=6.4 Hz), 1.14 (d, 3H, J=6.5 Hz); HRMS (FAB) cald for $C_{56}H_{77}NO_{34}Na$ 1330.4220 found m/z 1330.4168 (M+Na).

O-Allyl-[[[(6-deoxy-a-L-galactopyranosyl)-(1→2)]-(b-D-galactopyranosyl)-(1→4)]-[(6-deoxy-a-L-galactopyranosyl)-(1→3)]-(2-acetamido-2-deoxy-b-D-glucopyranosyl)-(1→3)]]-b-D-galactopyranose (15c) (See FIG. 22(b))

To 110 mg (84 mmol) of peracetate glycal 14c was added 100 mL of dry methylene chloride. The solution was cooled to 0° C. and 1.44 mL of 3,3-dimethyldioxirane solution (0.07 M in acetone, 100 mmol) was added. Stirring continued for 20 minutes at 0° C. and then the reaction was concentrated in vacuo. The white solid was taken up in 1 mL of allyl alcohol and then cooled to −78° C. 100 mL of $ZnCl_2$ solution was added and the reaction was allowed to warm to room temperature overnight. The reaction was diluted with EtOAc and washed twice with saturated sodium bicarbonate and once with saturated brine. The organics were dried over $MgSO_4$, filtered, and concentrated. Purification by silica gel chromatography (35%; acetone/benzene) gave a white solid which was immediately deacetylated. Added 1 mL of MeOH and then a few drops of 2.5% NaOMe in MeOH (Aldrich 25%, 1mL diluted to 10 mL with MeOH) and stirred overnight. The reaction was cooled to 0° C. and acidified to pH 7 with Dowex 50-X200 ion exchange resin. The reaction was filtered and concentrated. Purification with RP-18 reverse phase silica gel (10% MeOH/$H_2O$) afforded 55 mg (72%) of a white solid 15c: $[a]_D$−72.70 (c .1 MeOH); IR (thin film) 3350, 2940, 2900, 2830, 1650, 1550, 1365, 1300, 1155, 1070. 1030; $^1H$ NMR (400 MHz, $CD_3OD$) d 5.95 (m, 1H), 5.32 (d, J=17.3 Hz, 1H), 5.19–5.14 (m, 2H), 5.04 (d, J=3.8 Hz, 1H), 4.68 (d, J=8.3 Hz, 2H), 4.51 (d, J=5.7 Hz, 1H) 4.36 (dd, 1H, J=5.2, Hz), 4.25 (d, 1H, 7.7 Hz), 4.19–4.10 (m, 2H), 4.04 (d, 1H, J=2.2 Hz), 3.96–3.33 (m, 34H), 1.96 (s, 3H), 1.23 (m, 6H); HRMS (FAB) calcd for $C_{35}H_{56}NO_{24}Na$ 900.3325 found m/z 900.3310 (M+Na).

Synthesis of Le$^y$-BSA Neoglycoconjugate 17c (See FIG. 22(c)): 3.2 mg (3.6 mmol) of allyl glycoside 15c was taken up in 2 mL of MeOH and cooled to −78° C. Ozone was bubbled through the solution until it appeared to be faintly blue (<2 min.). The reaction was stirred for an additional 2–3 minutes and then the excess ozone was purged with a vigorous flow of argon until the blue color dissipated. About 2 mL of dimethyl sulfide was added. The reaction was gradually warmed to room temperature over about 4 hours and then was stirred an additional 4 hours. The reaction was concentrated in vacuo and placed under high vacuum for 1 hour. To the crude aldehyde was added 1 mg (0.015 mmol) of bovine serum albumin (BSA, Sigma Diagnostics Protein Standard) and 200 mL of pH 8 sodium phosphate buffer. 1 mg (14.4 mmol) of sodium cyanoborohydride was then added. The solution was stirred slowly for 3 days after which time it was placed in dialysis tubing (Spectra Por, MWCO 12,400). Exhaustive dialysis against distilled water, followed by lyopholization gave 1.2 mg of a fluffy white cotton 17c. TFA analysis of 17c indicated the Le$^y$ pentasaccharide:protein ratio to be about 15:1. Carbohydrate composition was also determined with a composition of 2 parts L-fucose, 2 parts D-galactose, and 1 part D-glucosamine. Conjugate 17c was recognized by Anti-Le$^y$ (S193).

[[[[(4-O-Benzoyl-2,3-di-O-benzyl-6-deoxy-a-L-galactopyranosyl)-(1→2)]-(6-O-tert-butyldiphenylsilyl-3,4-carbonate-b-D-galactopyranosyl)-(1→4)]-[(4-O-benzoyl-2,3-di-O-benzyl-6-deoxy-a-L-galactopyranosyl)-(1→3)]-(2-benzenesulfonamido-6-O-tert-butyldiphenylsilyl-2-deoxy-b-D-glucopyranosyl)-(1→3)3]-(6-O-tert-butyldiphenylsilyl-b-D-galactopyranosyl)-(1→4)]-1,5-anhydro-6-O-tert-butyldiphenylsilyl-2-deoxy-D-arabino-hex-1-enopyranose (19c) (See FIG. 23(a))

To 110 mg (56 mmol) iodosulfonamide 11c added the tin ether of lactal 18c (formed by azeotroping 704 mg (897 mmol) of disilyllactal with 233 mL (458 mmol) of bistributyltin oxide in 30 mL of benzene) in 1.2 mL of THF. 300 mg of freshly activated 4 Å powdered molecular sieves was added. The reaction mixture was cooled to −78° C. and 88 mg (450 mmol) of silver tetrafluoroborate in 1.2 mL of THF was added to the reaction. The reaction was allowed to warm to room temperature overnight. Stirring continued at room temperature for another 24 hours, during which time the reaction turned a bright yellow-orange color. The starting iodosulfonamide appeared to be consumed by TLC. The reaction was quenched with saturated sodium bicarbonate and filtered through celite. The filtrate was diluted with EtOAc and washed twice with saturated sodium bicarbonate and twice with saturated brine. The organics were dried over $MgSO_4$, filtered and concentrated in vacuo. Purification by silica gel chromatography twice (35% EtOAc/hexanes and then 8% EtOAc/benzene) afforded 17 mg (12%) of hexasaccharide 19c as a white foam: $[a]_D$−44.8° (c .105, $CHCl_3$); IR (thin film) 3450, 2910, 2840, 1800, 1710, 1260, 1150, 1100, 1050, 730, 695; $^1H$ NMR (400 MHz, $CDCl_3$) d 8.14 (d, 2H, J=7.08 Hz), 8.07 (d, 2H, J=6.92 Hz), 7.82 (m, 4H), 7.74 (m, 4H), 7.67 (m, 8H), 7.56–7.37 (m, 30H), 7.32–7.13 (m, 16H), 6.97 (t, 2H, J=7.49 Hz), 6.85 (t, 1H), 6.41 (d, 1H, J=4.19 Hz), 5.52 (d, 1H, J=2.93 Hz), 5.47 (d, 1H, J=2.36 Hz), 5.24 (d, 1H, J=3.58 Hz), 4.90 (d, 1H, J=11.16 Hz), 4.81–4.74 (m, 5H), 4.67–4.48 (m, 7H), 4.37 (m, 2H), 4.27 (m, 2H), 4.10–3.95 (m, 9H), 3.87–3.70 (m, 10H), 3.58–3.40 (m, 5H), 3.11 (broad d, 2H), 2.60 (broad s, 1H), 1.12–1.03 (m, 39 H), 0.87 (d, 3H, 6.41 Hz); LRMS (FAB) cald for $C_{149}H_{167}NO_{31}SSi_4Na$ 2634 found m/z 2634 (M+Na).

Figure 18A:
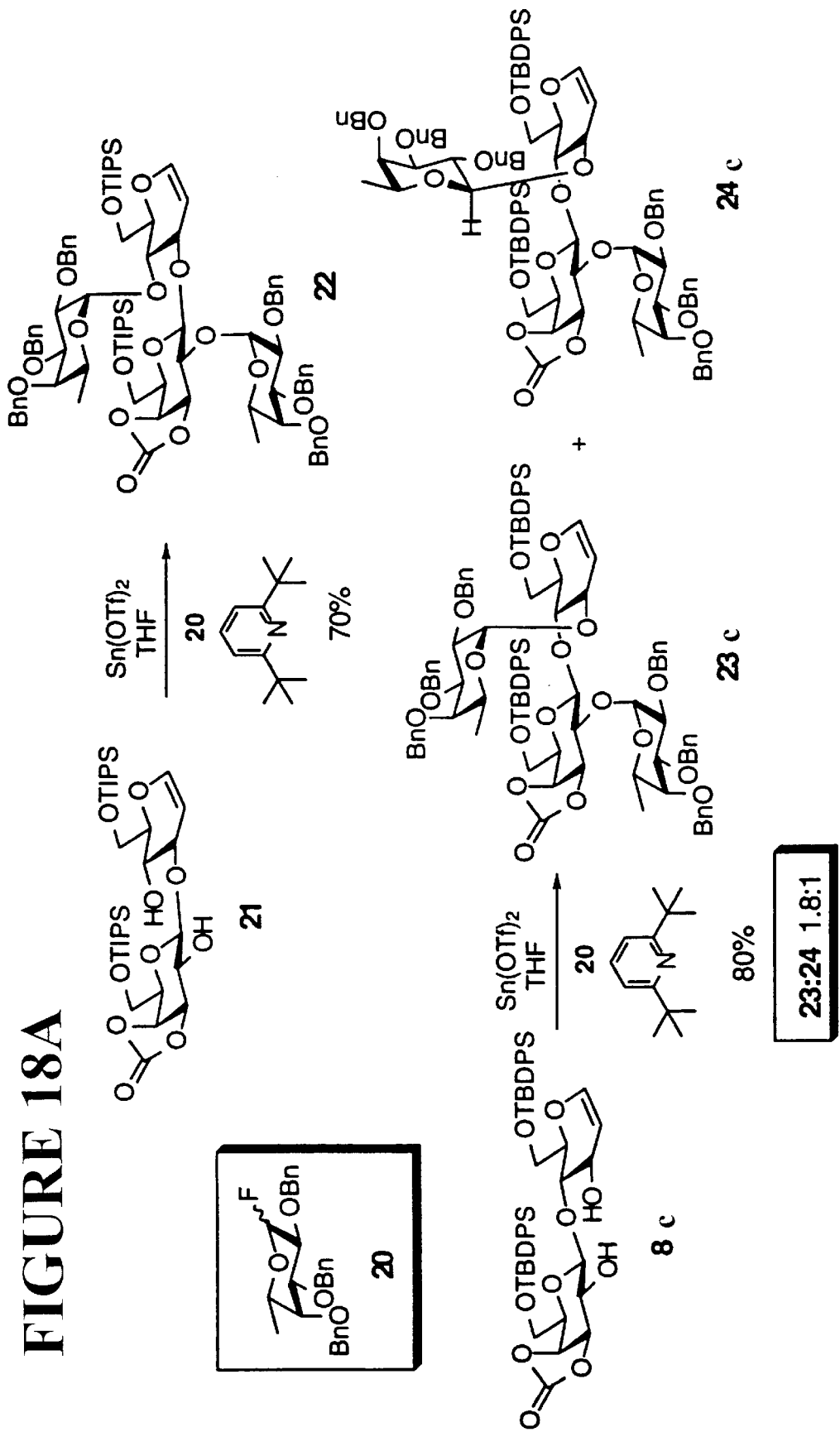
FIG. 18(a) shows the preparation of TIPS- and TBDPS-protected tetrasaccharides 22c, 23c and 24c.
Figure 18B:
FIG. 18(b) shows the preparation of TBDPS-protected tetrasaccharide intermediate 25c.

[[[(2,3,4-Tri-O-benzyl-6-deoxy-a-L-galactopyranosyl)-(1→2)]-(6-O-tert-butyldiphenylsilyl-3,4-carbonate-b-D-galactopyranosyl)-(1→4)]-(2,3,4-tri-O-benzyl-6-deoxy-a-L-galactopyranosyl)-(1→3)]-1,5-anhydro-6-O-tert-butyldiphenylsilyl-2-deoxy-D-arabino-hex-1-enopyranose (Le$^y$-Ceramide) (23c) (See FIG. 18(a))

To 1.43 g (1.76 mmol) of lactal 8c was added 3.07 g (7.04 mmol) of fluorosugar 20c. The two components were azeotroped three times with benzene and then placed under high vacuum overnight. The mixture was taken up in 36 mL of toluene and 3.2 mL (14.08 mmol) of di-tert-butylpyridine was added. 1.00 g of freshly activate 4 Å molecular sieves powder was added and the mixture stirred for 15 minutes. The solution was then cooled to 0° C. In a separate dry flask was added 2.94 g (7.04 mmol) of tin (II) triflate and 3.6 mL of dry THF. The solution of tin triflate was then added via cannula to the cooled reaction mixture. The reaction appeared complete by TLC after 4 hours. The reaction was quenched with saturated sodium bicarbonate solution and then filtered through a pad of celite. The filtrate was washed twice with saturated sodium bicarbonate and twice with saturated brine. The organics were dried over $MgSO_4$, filtered and concentrated in vacuo. Purification by silica gel chromatography (15% EtOAc/hexanes) gave a ~4.9:1 mixture of 23c and 24c which could be separated by HPLC (Waters RCM, 18% EtOAc/hexanes) to give 1.95 g (67%) of 23c as a white foam: $[a]_D^{23}$=−55.5° (c 0.780, $CHCl_3$); IR (thin film): 3050, 3020, 2920, 2850, 1800, 1425, 1350, 1235, 1155, 1105, 1050, 820, 740, 700; $^1H$ NMR (400 MHz, $CDCl_3$): d 7.67 (m, 2H, ArH), 7.62 (m, 4H, ArH), 7.56 (m, 2H, ArH), 7.49 (m, 2H, ArH), 7.46–7.25 (m, 32H, ArH), 7.14 (m, 4H, ArH), 7.01 (m, 4H), 6.35 (d, 1H, J=5.85 Hz, glucal H-1), 5.30 (d, 1H, J=3.22 Hz, a-fucose H-1), 4.98 (d, 1H, J=11.72 Hz, PhCH), 4.86 (d, 1H, J=10.99 Hz, PhCH), 4.82 (d, 1H, J=11.64 Hz, PhCH), 4.79–4.70 (m, 5H, included are PhCH, galactose H-1, H-4), 4.67–4.61 (m, 4H, included are PhCH, glucal H-2, a-fucose' H-1, J=3.76 Hz), 4.56 (d, 1H, J=12.74 Hz, PhCH), 4.55 (d, 1H, J=12.45 Hz, PhCH), 4.49 (m, 2H, PhCH and galactose H-3), 4.35 (m, 2H, glucal H-4 and a-fucose H-5), 4.25 (d, 1H, J=10.62 Hz, PhCH);

4.15–4.07 (m, 4H, included are PhCH, a-fucose H-2, glucal H-3), 3.97–3.87 (m, 5H), 3.82 (t, 1H, J=9.38 Hz), 3.71 (apparent t, 1H, J=7.16 Hz, galactose H-2), 3.66–3.53 (m, 5H), 3.43 (d, 1H, J=1.76 Hz, a-fucose' H-4), 3.36 (d, 1H, J=1.80 Hz, a-fucose' H-4), 1.07 (s, 9H, t-butyl), 1.04 (two buried d, 6H, a-fucose' methyls), 1.01 (s, 9H, t-butyl); LRMS (FAB) calcd for $C_{99}H_{110}O_{18}Si_2K$ 1682, found m/z 1682 (M+K). The minor isomer 24c 480 mg (16%) containing the b-fucose linkage at the glucal center was obtained as a white foam: $^1H$ NMR (400 MHz, $CDCl_3$): d 7.57 (m, 10H, ArH), 7.40–7.06 (m, 39H, ArH), 6.98 (m, 1H, ArH), 6.13 (d, 1H, J=6.22 Hz, glucal H-1), 5.09 (d, 1H, J=3.62 Hz, a-fucose H-1), 4.95 (d, 1H, J=11.72 Hz, PhCH), 4.86 (d, 1H, J=11.92 Hz,PhCH ), 4.86 (m, 1H, buried glucal H-2), 4.81 (d, 1H, J=11.35, PhCH), 4.76 (d, 1H, J=12.08 Hz, PhCH), 4.70 (d, 1H, J=11.43 Hz, PhCH), 4.70 (d, 1H, buried galactose H-1), 4.67–4.44 (m, 8H, galactose H-3, H-4, PhCH), 4.35 (d, 1H, J=11.64 Hz, PhCH), 4.35 (d, 1H, J=7.48 Hz, b-fucose H-1), 4.11–4.00 (m, 5H), 3.95 (q, 1H, J=6.31 Hz, a-fucose H-5), 3.90 (m, 1H), 3.80 (s, 1H), 3.78 (s, 1H), 3.75 (dd, 1H, J=2.71 Hz, J=10.32 Hz, a-fucose H-3), 3.72–3.67 (m, 3H, galactose H-2), 3.53 (dd, 1H, J=7.84 Hz, J=9.46 Hz, b-fucose H-2), 3.49 (d, 1H, J=2.48 Hz, a-fucose H-4), 3.37 (d, 1H, J=2.56 Hz, b-fucose H-4), 3.21 (dd, 1H, J=2.93 Hz, J=9.80 Hz, b-fucose H-3), 3.18 (q, 1H, J=6.60 Hz, b-fucose H-5), 1.05–0.97 (2 s, 18 H, t-butyl, and buried fucose methyls 6H).

[[[(2,3,4-Tri-O-benzyl-6-deoxy-a-L-galactopyranosyl)-(1→2)]-(6-O-tert-butyldiphenylsilyl-3,4-carbonate-b-D-galactopyranosyl)-(1→4)]-(2,3,4-tri-O-benzyl-6-deoxy-a-L-galactopyranosyl)-(1→3)]-6-O-tert-butyldiphenylsilyl-2-deoxy-2-iodo-a-D-manno-pyranosylbenzene sulfonamide (26c)

To 1.95 g (1.19 mmol) of glycal 23c was added 561 mg (3.57 mmol) of benzenesulfonamide and 1.50 g of freshly dried 4 Å powdered molecular sieves. This mixture was taken up in 19 mL of dichloromethane and then cooled to 0° C. The reaction was allowed to stir for 15 minutes and then 1.95 g (4.17 mmol) of iodonium-di-sym-collidine perchlorate was added. The reaction was stirred for 30 minutes and then quenched with saturated sodium thiosulfate solution. The crude mixture was filtered through celite and the filtrate washed once with saturated sodium thiosulfate, once with saturated copper sulfate, and twice with saturated brine solution. The organics were dried over sodium sulfate, filtered and concentrated in vacuo. Purification by silica gel chromatography gave iodosulfonamide 26c as a white foam 2.12 g (93%): $[a]_D^{23}$=–78.3° (c 0.935, $CHCl_3$); IR (thin film) 2920, 2835, 1800, 1450, 1425, 1350, 1150, 1100, 1050, 735, 700; $^1H$ NMR (400MHz, $CDCl_3$): d 7.74–7.53 (m, 6H), 7.45–7.22 (m, 41H), 7.05 (t, 1H, J=7.24 Hz, 6.90 (t, 2H, J=7.61 Hz), 6.07 (d, 1H, J=8.43 Hz), 5.55 (broad s, 1H), 5.01–4.42 (m, 18H), 4.31 (broad s, 1H), 4.02 (dd, 1H, J=3.66 Hz, J=10.17 Hz), 3.96–3.80 (m, 5H), 3.74 (broad d, J=10.26 Hz), 3.66–3.60 (m, 3H), 3.48 (broad s, 1H), 3.41 (broad s, 1H), 3.19 (broad s, 1H), 1.06 (S, 9H), 0.99 (s, 9H), 0.95 (m, 6H);HRMS (FAB) calcd for $C_{105}H_{116}NO_{22}ISi_2Na$ 1948.6290, found m/z 1948.6280 (M+Na).

Figure 18C:
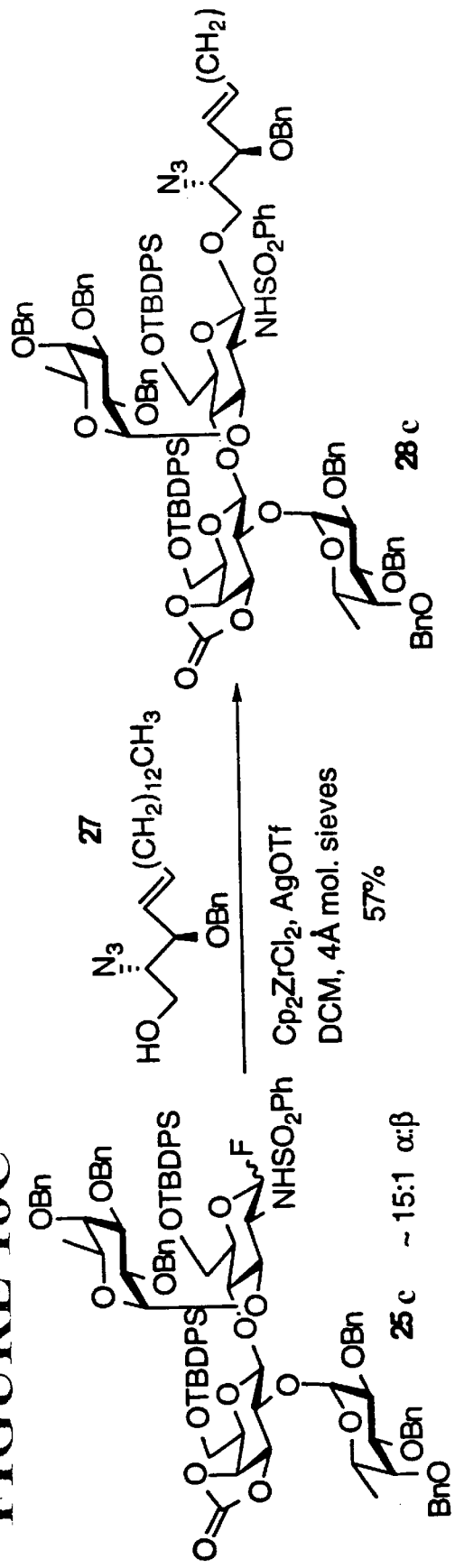
FIG. 18(c) shows the preparation of TBDPS-protected tetrasaccharide ceramide intermediate 28c.
Figure 18D:
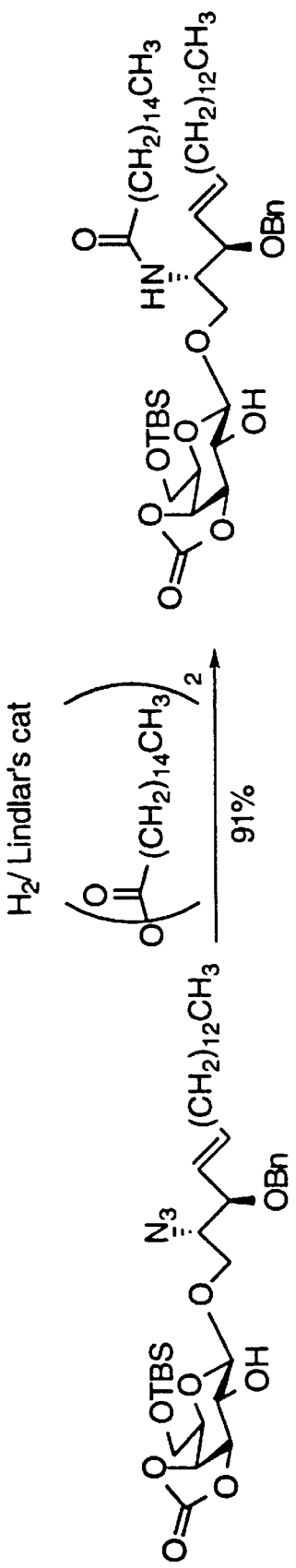
FIG. 18(d) shows a model reduction reaction to prepare tetrasaccharide ceramides.

[[[(2,3,4-Tri-O-benzyl-6-deoxy-a-L-galactopyranosyl)-(1→2)]-(6-O-tert-butyldiphenylsilyl-3,4-carbonate-b-D-galactopyranosyl)-(1→4)]-(2,3,4-tri-O-benzyl-6-deoxy-a-L-galactopyranosyl)-(1→3)]-6-O-tert-butyldiphenylsilyl-2-deoxy-2-benzenesulfonamido-a-D-glucopyranosyl fluoride (25c) (See FIG. 18(c))

To 740 mg (384 mmol) of iodosulfonamide 26c was added 35 mL of 5:2 THF/water. To this solution was added 107 mL (768 mmol) of triethylamine and 106 mg (384 mmol) of silver carbonate. The reaction was stirred for one,hour after which time TLC indicated complete consumption of starting material. The reaction was partitioned between ethyl acetate and brine and the organics were washed twice with saturated brine solution. The organics were dried over sodium sulfate, filtered and concentrated in vacuo. The crude free reducing sugar was azeotroped once with benzene and then taken up in 2 mL of THF. The solution was cooled to –30° C. and 53 mL (403 mmol) of DAST was added. The reaction was warmed to room temperature and stirred for an additional 10 minutes. The reaction was then cooled back down to –30° C. and quenched with 1 mL of MeOH. The reaction was concentrated in vacuo. Purification by column chromatography gave fluorosugar 25c as a white foam 593 mg (85%): $[a]_D^{23}$=–34.1° (c 1.29, $CHCl_3$); IR (thin film): 2920, 1800, 1450, 1160, 1100, 1045, 915, 735, 700; $^1H$ NMR (400 MHz, $CDCl_3$): d 7.78 (d, 2H, J=7.98 Hz), 7.64–6.96 (m, 48H), 6.62 (broad s, 1H), 5.89 (dd, 1H, J=2.11 Hz, J=54.55 Hz, glucose H-1), 4.99 (d, 1H, J=11.44 Hz), 4.94–4.39 (m, 21H), 4.03–3.97 (m, 4H), 3.84–3.77 (m, 6H), 3.69 (m, 7H), 3.59 (m, 2H), 3.49 (m, 5H), 3.39 (m, 1H), 3.29–3.18 (m, 2H), 1.38 (d, 3H, J=6.23 Hz), 1.02 (s, 9H), 0.97 (s, 9H); LRMS (FAB) calcd for $C_{105}H_{116}O_{20}NSFSi_2Na$ 1840.7230, found m/z 1840.7220 (M+Na).

(3R)-O-Benzoyl-(2R)-hexadecanamido-4-octadecenyl-[[[(2,3,4-t ri-O-benzyl-6-deoxy-a-L-galactopyranosyl)-(1→2)]-(6-O-tert-butyldiphenylsilyl-3,4-carbonate-b-D-galactopyranosyl)-(1→4)]-(2,3,4-tri-O-benzyl-6-deoxy-a-L-galactopyranosyl)-(1→3)]-6-O-tert-butyldiphenylsilyl-2-deoxy-2-benzenesulfonamido-b-D-glucopyranose (31c) (See FIGS. 18(c) and 19(a))

To 97 mg (53 mmol) of fluorosugar 25c was added 34 mg (80 mmol) of azidosphingosine 27c. The mixture was azeotroped twice with benzene and then placed under high vacuum for two hours. 100 mg of freshly activated 4 Å powdered molecular sieves were added and then 5 mL of dry dichloromethane. In an argon glove box were added 47 mg (160 mmol) of zirconocene dichloride and then 41 mg (160 mmol) of silver triflate. The reaction was stirred overnight. The reaction was quenched with saturated sodium bicarbonate and filtered through a celite pad. The filtrate was washed twice with saturated sodium bicarbonate and twice with saturated brine solution. The organics were dried over sodium sulfate, filtered and concentrated in vacuo. Purification by silica gel chromatography (15–20% EtOAc/hexanes) gave the labile azide 28c 57 mg (50%) as a white foam: IR (thin film): 2920, 2845, 2100, 1810, 1715, 1450, 1350, 1260, 1150, 1100, 1050, 740, 700; $^1H$ NMR (400 MHz, $CDCl_3$) d 8.04 (d, 2H, J=7.98 Hz), 7.64–7.55 (m, 13H), 7.50–7.10 (m, 40H) , 6.97 (m, 2H), 6.87 (m, 2H), 6.80 (d, 1H, J=3.58 Hz), 5.75 (m, 1H), 5.37 (dd, 1H, J=7.57 Hz, J=15.74 Hz), 5.27 (m, 2H), 5.09 (dd, 1H, J=4.44, J=8.02 Hz), 4.98 (m, 2H), 4.87–4.40 (m, 18H), 4.31 (d, 1H, J=4.03 Hz), 4.29 (d, 1H, J=8.06 Hz), 4.16–4.05 (m, 5H), 3.95 (m, 2H), 3.88 (m, 2H), 3.78 (m, 3H), 3.70–3.53 (m, 6H), 3.46 (broad s, 1H), 3.40 (m, 3H), 3.26 (m, 2H), 2.84 (d, 1H, J=8.87 Hz), 2.69 (dd, 1H, J=2.85 Hz, J=9.52 Hz), 2.57 (m, 1H), 2.04 (m, 2H), 1.21 (broad s, 16H), 1.07 (d, 3H, J=6.79 Hz), 1.01 (m, 24H) HRMS (FAB) calcd for $C_{130}H_{154}O_{23}N_4SSi_2Na$ 2251.0190, found m/z 2251.0197 (M+Na). Azidosphingosine 28c 57 mg (26 mmol) was taken up in 1 mL of ethyl acetate. 100 mg of Lindlar's catalylst and 25 mg (51 mmol) of palmitic anhydride were added. The reaction mixture was degassed and placed under an atmosphere of hydrogen. The reaction appeared complete after 36 hours though there appeared to be extensive decomposition. The reaction mixture was degassed and filtered thru a pad of celite. The filtrate was concentrated in vacuo. The crude material was purified first by gel filtration with LH-20 (lipophilic sephadex, MeOH eluant) and then by silica gel chromatography (15% EtOAc/hexanes) to afford 13.6 mg (22%) of the ceramide linked Lewis$^y$ antigen 31c as a white foam: IR (thin film): 2920, 2855, 1830, 1810, 1720, 1650, 1450, 1430, 1320, 1270, 1165, 1110, 1055, 830, 745, 705; $^1$H NMR (400 MHz, CDCl$_3$): d 7.99 (t, 2H, J=8.24 Hz), 7.74–7.05 (m, H), 6.94 (m, 3H), 6.76 (broad d, 1H, J=12.35 Hz), 6.60 (m, 1H), 5.80 (m, 1H), 5.59 (t, 1H, J=7.89 Hz), 5.41 (dd, 1H, J=7.85 Hz, J=15.42 Hz), 5.24 (m, 1H), 5.18 (m, 1H), 5.00–4.21 (m, 18H), 4.06 (broad d, 1H, J=9.88 Hz), 3.97–3.44 (m, 15H), 3.16 (m, 2H), 2.95 (t, 1H, J=8.43 Hz), 2.08–1.97 (m, 3H), 1.24 (broad s, 54H), 1.00–0.99 (2s, 18H), 0.88 (m, 12H); HRMS (FAB) calcd for $C_{105}H_{116}O_{20}NSFSi_2Na$ 1840.7230, found m/z 1840.7220 (M+Na).

(3R)-Hydroxy-(2R)-hexadecanamido-4-octadecenyl-[[[(6-deoxy-a-L-galactopyranosyl)-(1→2)]-(b-D-galactopyranosyl)-(1→4)]-(6-deoxy-a-L-galactopyranosyl)-(1→3)]-2-deoxy-2-acetamido-b-D-glucopyranose (32c) (See FIG. 19(b))

To 13.6 mg (5.5 mmol) of blocked Lewis$^y$ ceramide was added 100 mL of THF and 20 mL (20 mmol) of TBAF (1M in THF). The reaction was stirred overnight and then concentrated in vacuo. The crude mixture was dissolved in 200 mL of THF and added to a solution of 100 mg of sodium metal in 3 mL of liquid ammonia at −78° C. The blue solution was allowed to stir for 45 minutes at −78° C. and was then quenched carefully with 1 mL of MeOH. The excess ammonia was removed with a rapid stream of argon and then the crude reaction mixture was acidified to a pH of 7 with Dowex 50 X-8 resin. The solution was then filtered and the resin washed with methanol that had been saturated with ammonia. The filtrate was then concentrated in vacuo and the solids dissolved in 200 mL of pyridine and 200 mL of acetic anhydride. The reaction was allowed to proceed for 8 hours at room temperature and was then concentrated in vacuo. Purification by silica chromatography (20% acetone/benzene) gave 2.0 mg of the peracetylated ceramide antigen. The peracetylated product was taken up in 100 mL of dry MeOH and 3 mg of NaOMe was added and the reaction stirred overnight. The reaction was acidified with Dowex 50 X-8 resin to pH 7 and then filtered and concentrated. The product 32c was purified by gel filtration with LH-20 (lipophilic sephadex, MeOH eluant) giving 1.1 mg (17%) of a white solid: HRMS (FAB) calcd for $C_{60}H_{110}O_{21}N_2Na$ 1217.7500, found m/z 1217.7534 (M+Na).

Immunization of Mice with Globo H Antigen

The breast tumor glycolipid associated antigen 2 (See FIG. 24) isolated by Hakomori and co-workers from MCF-7 cells, and termed globe H, constituted a promising possibility for exploration (Kannagi, R., et al., J. Biol. Chem. 1983, 258, 8934; Bremer, G., et al., J. Biol. Chem. 1984 259, 14773). Early studies in this area were facilitated by the immunocharacterization of the antigen by the murine monoclonal antibody Mbr1 (Menard, S., et al., Cancer Res. 1983, 43, 1295). Previously, we had described the total synthesis of the hexacyclic globo H glycal 1 (See FIG. 24) by the method of glycal assembly (See FIG. 24) (Bilodeau, M.T., et al., J. Am. Chem. Soc. 1995 117, 7840; Park, et al., J. Am. Chem. Soc. 1996, 118, 11488). This system was carried forward to reach antigen 2 (See FIG. 24), whose structure assignment was verified by unambiguous spectroscopic corroboration through this synthesis. Furthermore, the synthetic compound 2 (See FIG. 24) did, indeed, bind to the murine monoclonal antibody (mAb) MBr1 and inhibited its binding to MCF-7 cells as measured by flow cytometry (Kim, I. J., et al., J. Org. Chem. 1995, 60, 7716).

We then built upon the logic of our synthesis to prepare congeners of the compound and to use them to map the structural requirements for binding to the mAb MBr1. Thus, allyl glycoside 3 (See FIG. 25), corresponding in its epitope region to 2 (See FIG. 24), was found to bind well (FIG. 25) (Kim, I. J., et al., J. Org. Chem. 1995, 60, 7716). These studies also revealed that for this monoclonal antibody both the fucose appendage (Kim, I. J., et al., J. Org. Chem. 1995, 60, 7716; Shevinsky, L. H., et al., Cell 1982, 30, 697; Andrews, P. W., et al., Int. J. Cancer. 1982, 29, 523; Nunomura, S., et al., Tetrahedron Lett. 1988, 29, 5681; Park, T. K., et al., ibid 1995, 36, 9089) (compound 4 is not bound) and the β-glycoside linkage between the C and D sectors are critical (See FIG. 25). Compound 5 (See FIG. 25) containing an α linkage at this locus is only weakly bound. Both the A ring and the AB sector can be deleted (see compounds 6 and 7, respectively, of FIG. 25). The β linkage of the glycosidic bond between the B and C rings is not of large effect (see compound 8, FIG. 25, which is well recognized).

As previously reported, the double bond at the reducing end of globo H glycal was used as the access point to reach the fully deprotected allyl glycoside 3 (See FIG. 24) (Bilodeau, M. T., et al., J. Am. Chem. Soc. 1995 117, 7840). We proceeded as follows. Ozonolysis of 3 (See FIG. 24) was followed by reductive amination (Bernstein, M. A., et al., Carbohydr. Res. 1980, 78, C1; Lemieux, R. U., Chem. Soc. Rev. 1978, 7, 423; Lemieux, R. U., et al., J. Am. Chem. Soc. 1975, 97, 4076 and references therein) with carrier protein keyhole lympet hemocyanin (KLH) (compound 9 of FIG. 24) and with bovine serum albumin (BSA) (compound 10 of FIG. 24). In the case of the KLH conjugate, we introduced about 150 carbohydrate units per protein (In more recent studies we have been able to load ca. 1000 globo H epitopes per molecule of KLH). Similarly, carbohydrate: protein analyses revealed the presence of 17 carbohydrate units in compound 10 (See FIG. 24). Systems 9 and 10 (of defined carbohydrate structure) were the starting points for immunological investigations (See FIG. 24).

Figure 24:
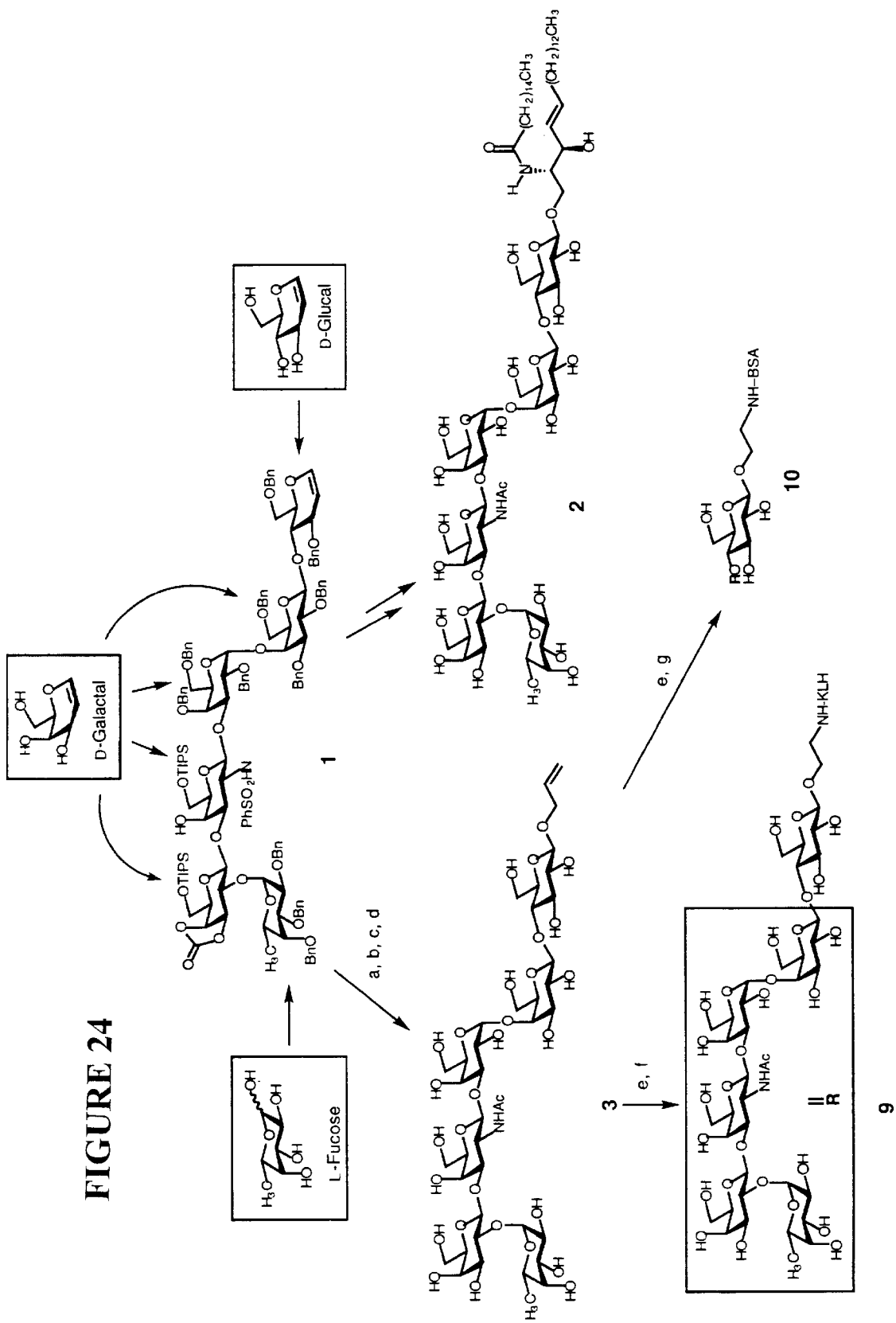
FIG. 24 shows a reaction pathway to Globo-H-KLH and Globo-H-BSA. Reagents: a) TBAF, THF, 94%; b) 1. Na, NH$_3$, THF; 2. Ac$_2$O, Et$_3$N, DMAP, THF, DMF, 85%; c) (i) 3,3-dimethyldioxirane, CH$_2$Cl$_2$, 2. allyl alcohol, 66% (+29% of α-manno isomer); d) NaOMe, MeOH, quantitative; e) O$_3$, then Me$_2$S; f) keyhole limpet hemocyanin (KLH), NaBH$_3$CN, pH 7.2; 2. dialysis; g) 1. bovine serum albumin (BSA), NaBH$_3$CN, pH 7.2, Et$_3$NH$^+$HCO$_3^-$buffer; 2. dialysis. 2: globo H antigen, 3: globo H epitope, Sugar: protein ratios for 9 and 10: 152:1 and 17:1, respectively.

Groups of mice (female CB6F1 mice, Jackson Laboratory, Bar Harbor, Me, USA) were immunized subcutaneously with either construct 9 or 10, which were derived from conjugation of 3 with KLH and BSA, respectively (See FIG. 24). Each vaccination (after weeks 0, 1, 2, 7, 20, and 35) contained 10 μg of the synthetically derived epitope and 10 μg of the immunological adjuvant QS-21. Mice were bled 10 days after the third, fourth, fifth, and sixth vaccinations. Control vaccinations were conducted with phosphate-buffered saline (PBS), and compound 2 (See FIG. 24) with QS-21.

Serological responses were analyzed by several methods. An enzyme-linked immunosorbent assay (ELISA) was used to determine the titer of antibodies against globo H ceramide (compound 2 of FIG. 24), as described previously (Livingston, P.O., et al., Cancer Immunol. Immunother. 1989, 29, 179). Cell surface reactivity of these antibodies was assayed by flow cytometry and immune adherence (IA) assays (Zhang, S., et al., Cancer Immunol. Immunother. 1995, 40, 88; Shiku, H., et al., J. Expt. Med. 1976, 144, 873) on globo H positive MCF-7 cells and as a control, with globo H negative B78.2 melanoma cells. The ability of these sera to mediate complement lysis was assessed by a europium-release complement-dependent cytotoxicity assay against MCF-7 cells (Zhang, S., et al., Cancer Immunol. Immunother. 1995, 40, 88).

Figure 26:
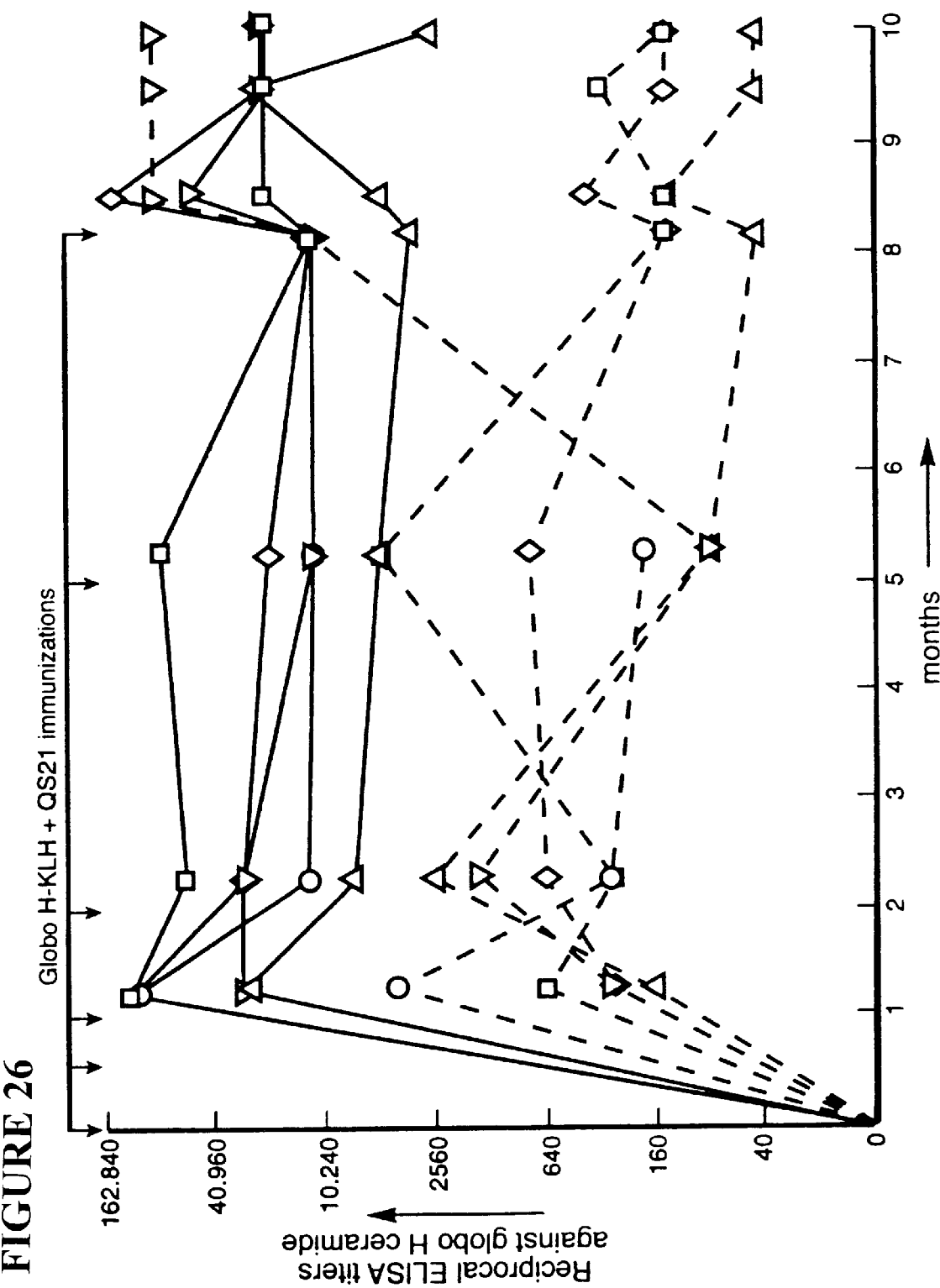
FIG. 26. Time courese of the induction of antibodies in five mice immunized with globo H-KLH conjugate and QS-21. ◇: mouse 1, □: mouse 2, ∆: mouse 3, ○: mouse 4, ∇: mouse 5; solid line: IgM titer, dashed line IgG titer.

The globo H-KLH (system 9 of FIG. 24) vaccine, coadministered with QS-21, induced higher titer IgM and IgG than the globo H-BSA vaccine plus QS-21. The time course of the induction of IgM and IgG antibodies in five mice by the globo H-KLH vaccine is shown in FIG. 26. IgM antibody titers generally remained higher than IgG titers, even after the three booster vaccinations. In general, titers were not higher after the booster immunization than after the initial immunizations. No detectable anti-globo H antibodies were observed with the control vaccines described above.

Figure 27:
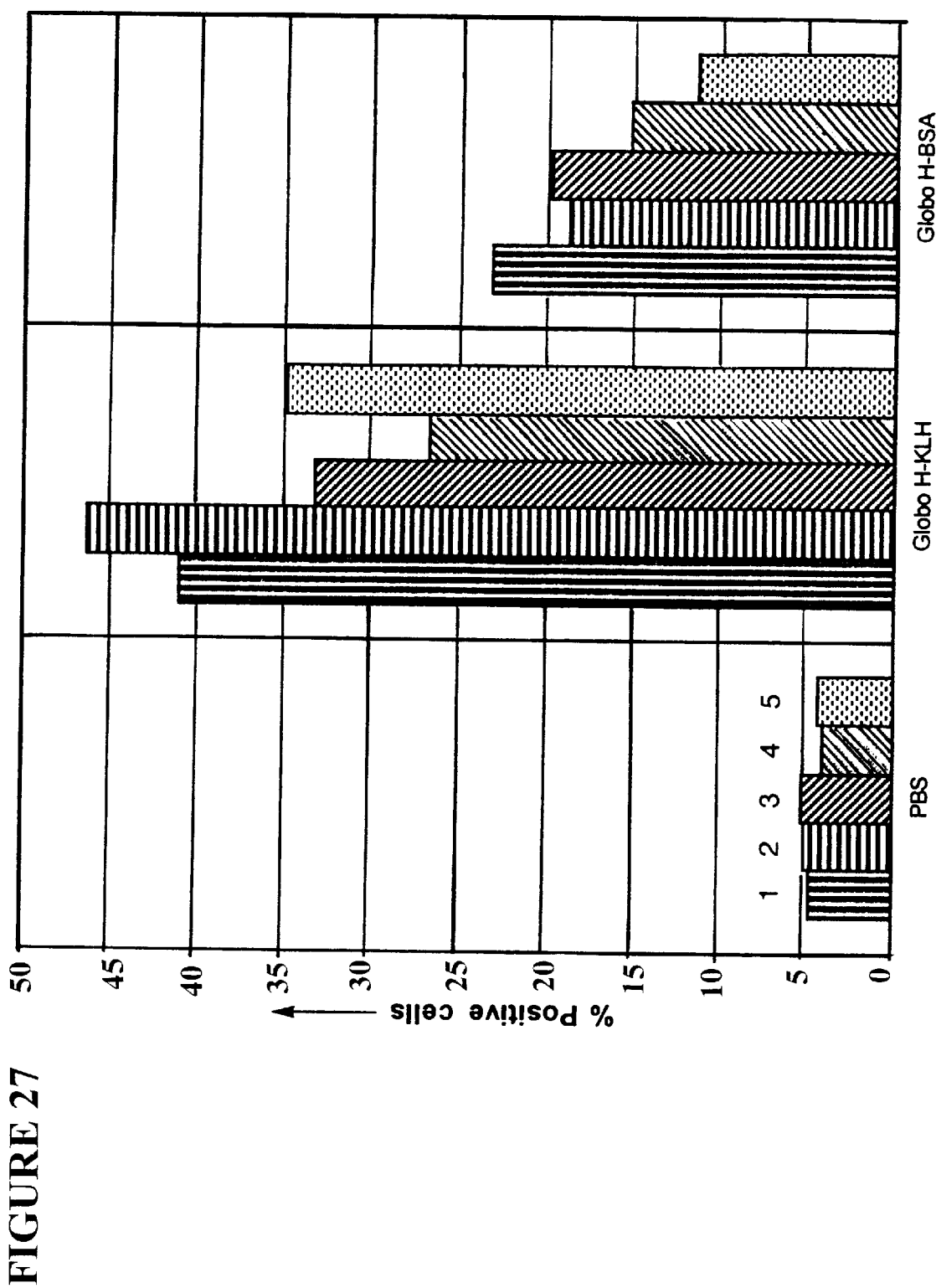
FIG. 27. Reactivity against MCF-7 breast cancer cells of sera from mice immunized with PBS, globo H-KLH and globo H-BSA. 1: mouse 1, 2: mouse 2, 3: mouse 3, 4: mouse 4, 5: mouse 5. Fluorescence-activated cell-sorter (FACS) analysis FIG. 28. Analysis of the specificity of anti-globo H antiserum by inhibition assays. I=inhibition [%]; ELISA reactivity of serum with globo H ceramide with: 2: globo H-ceramide, 3: globo H allyl glycoside, 4: SSEA-3, 5: DC-α, 6: pentasaccharide, 7: tetrasaccharide, 8: CB-β, control: GD-3. SSEA: state-specific embryonic antigen or desfucosylpentasaccharide.

A potentially critical finding was that anti-globo H IgM antibodies showed clear reactivity with MCF-7 breast cancer cells by flow cytometry (FIG. 27) and, in a control experiment, failed to react with globe H-negative B78.2 melanoma cells. Furthermore, antibodies induced by globo H-KLH reacted more strongly than antibodies induced by globo H-BSA. Similarly, cell surface reactivity of the anti-globo H IgM antibody was confirmed by immune adherence methods. This assay revealed that anti-globo H titers increased from 0 to 1/360 after immunization with globo H-KLH (compound 9 of FIG. 24) and to 1/160 after immunization with globo H-BSA (compound 10 of FIG. 24).

These antibodies were also highly effective at inducing complement-mediated cytotoxicity. In background experiments, antisera without complement, or complement without sera as well as complement with sera arising from control vaccines, failed to lyse. As a serum dilution of 1:10 in the presence of human complement, the percentage lysis with antibody induced by globo H-KLH (compound 9 of FIG. 24) conjugate was 48%. Lysis induced by the globo H-BSA vaccine (compound 10 of FIG. 24) was 39%. By way of reference, maximal complement-induced cytotoxicity with monoclonal antibody MBr1 was 72%.

Figure 25:
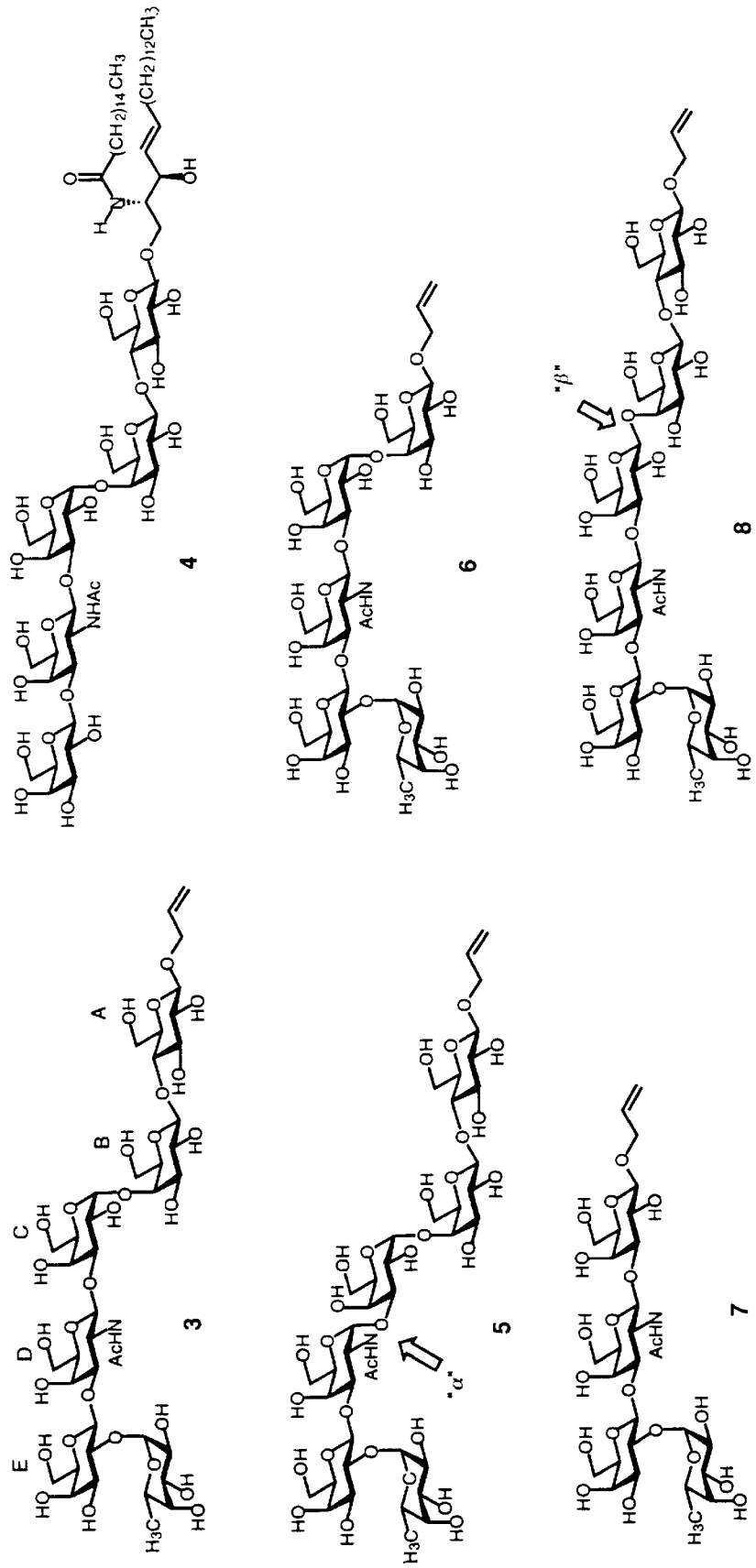
FIG. 25 shows the structure of synthetic globo H epitope and structurally related carbohydrates; 3: globo H epitope, 4: desfucosyl pentasaccharide, 5: isomeric globo H (DC-α), 6: pentasaccharide, 7: tetrasaccharide, 8: isomeric globo H (CB-β).
Figure 28:
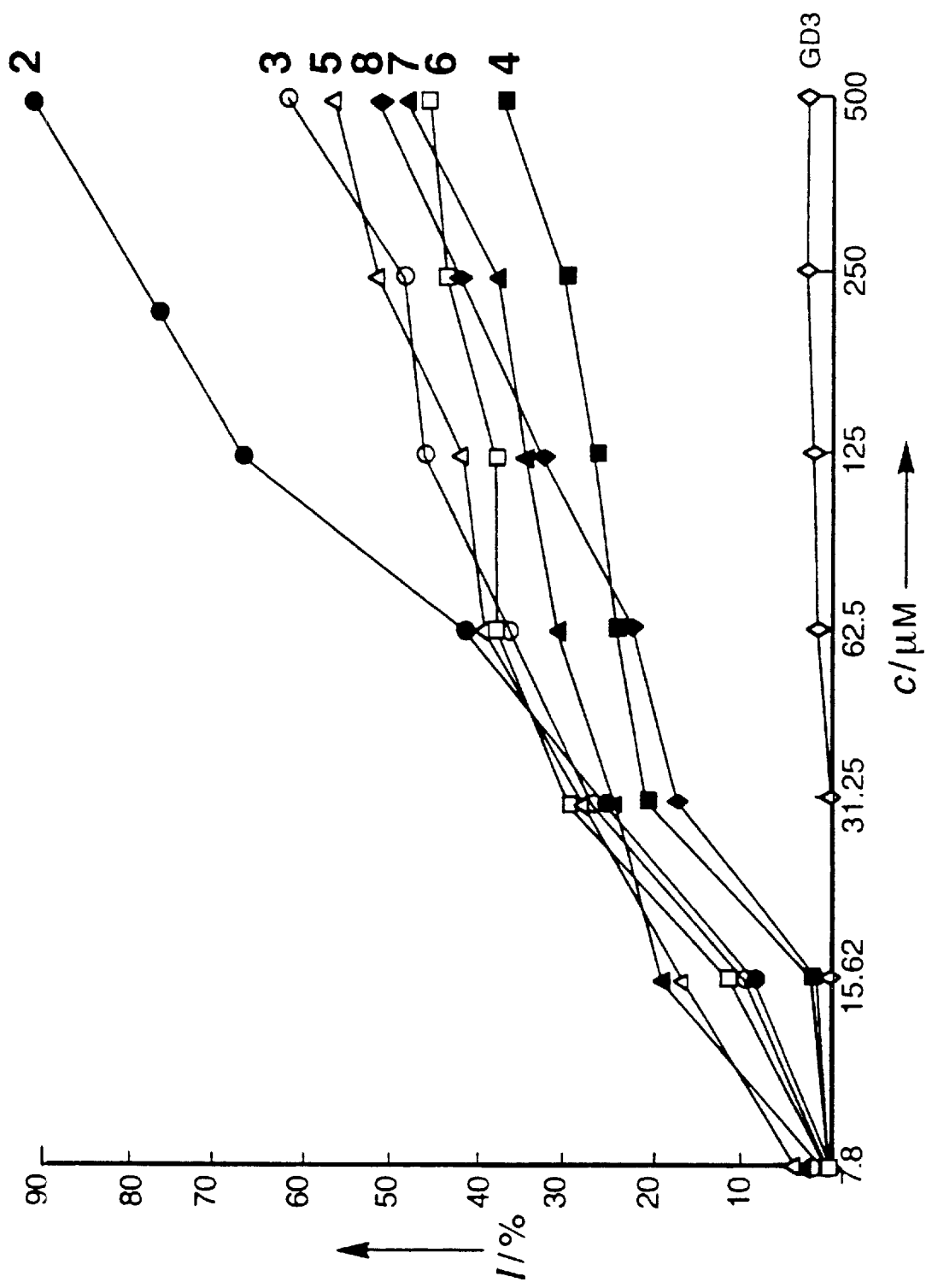

As an indication of specificity, we conducted assays with compounds 2–8 of FIGS. 24 and 25 to determine their ability to inhibit the binding of antisera to the fully synthetic globo H antigen 2 (FIG. 28). Of these probe compounds, only the full globo H hexasaccharide (compound 2) manifested complete inhibition. Partial inhibition resulted from truncated globo H compounds, but not with unrelated compounds such as ganglioside GD3. These findings are consistent with a polyclonal serological response in which different antibodies react with different portions of compound 2.

Figure 29:
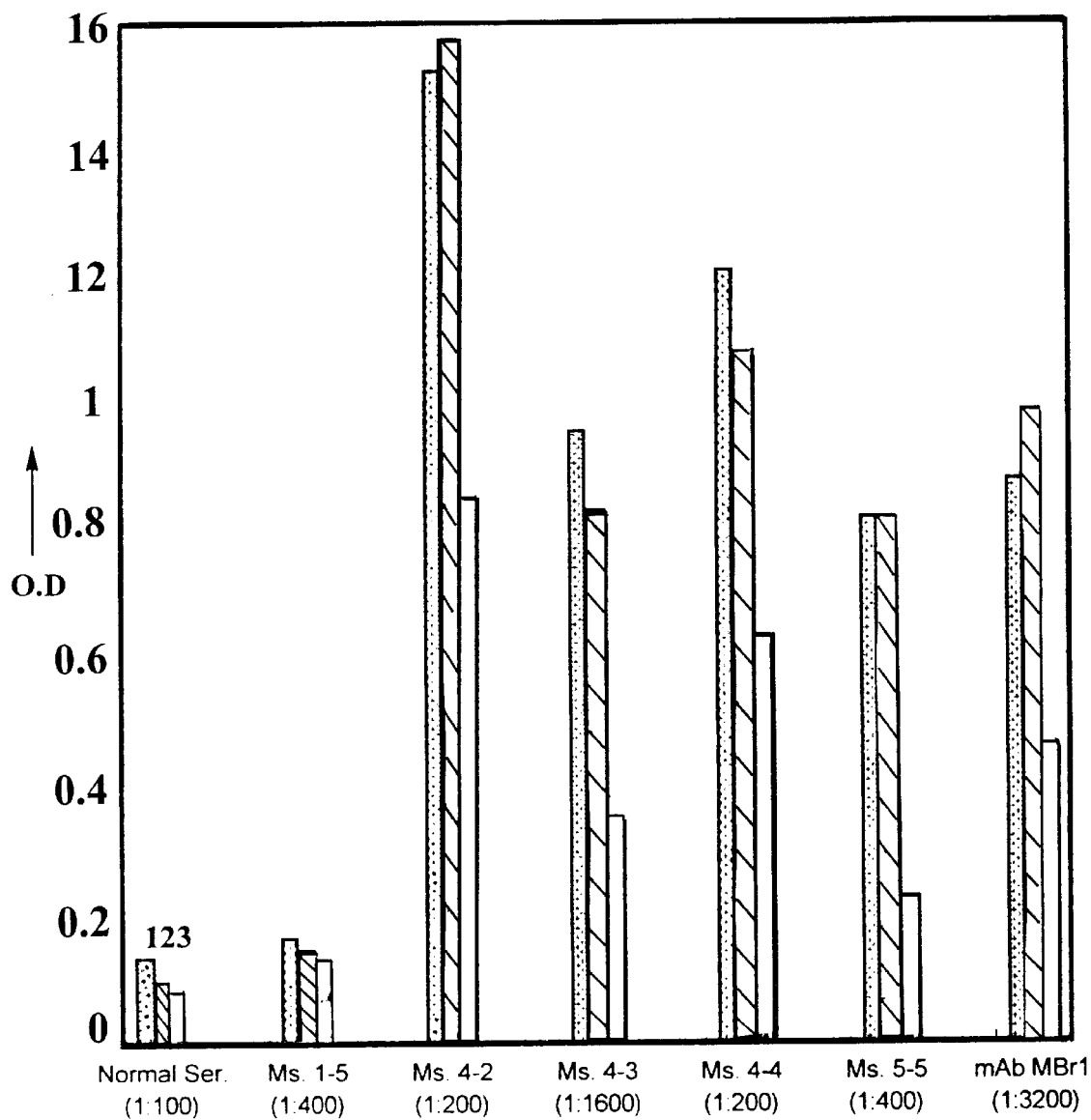
FIG. 29. Absorption analysis of globo H antisera with MCF-7 and B78.2 cells. O.D. (optical density) at 405 nm, 1: no cells, 2: B78.2 (negative control), 3: MCF-7. Ratios given refer to the dilution of serum used for analysis. Ms: mouse serum. Ms. 1-5 vaccinated with PBS; Ms. 4-2, 4-3, and 4-4 vaccinated with globo H-KLH (9); Ms. 5-5 vaccinated with globo H-BSA (10).

Finally, ELISAs were also performed with sera that had been absorbed by incubation with MCF-7 or B78.2 cells. For his assay $5 \times 10^5$ cells were incubated with sera for 1 h and the cells removed by centrifugation. In this experiment more than 50% of the ELISA reactivity against globo H-ceramide was lost following incubation with MCF-7 cells. By contrast, no decrease in the activity was observed following incubation with globo H-negative B78.2 melanoma cells (FIG. 29).

These experiments demonstrate that the response was polycolonal with antibody subpopulations recognizing, in varying degrees, several different globo H epitopes present in probe structures 2–8 (See FIGS. 24 and 25). As with monoclonal antibody MBr1, the fucose terminus of the saccharide was especially important for antibody recognition (see compound 4 of FIG. 28, for the consequence of deletion of the fucose residue). Furthermore, globo H epitopes expressed on the MCF-7 cell surface are readily recognized by the induced antibodies, resulting in complement activation and lysis of globo H-positive tumor cells.

Immunization of Mice with $Le^y$ Oligosaccharide

Figure 30A:
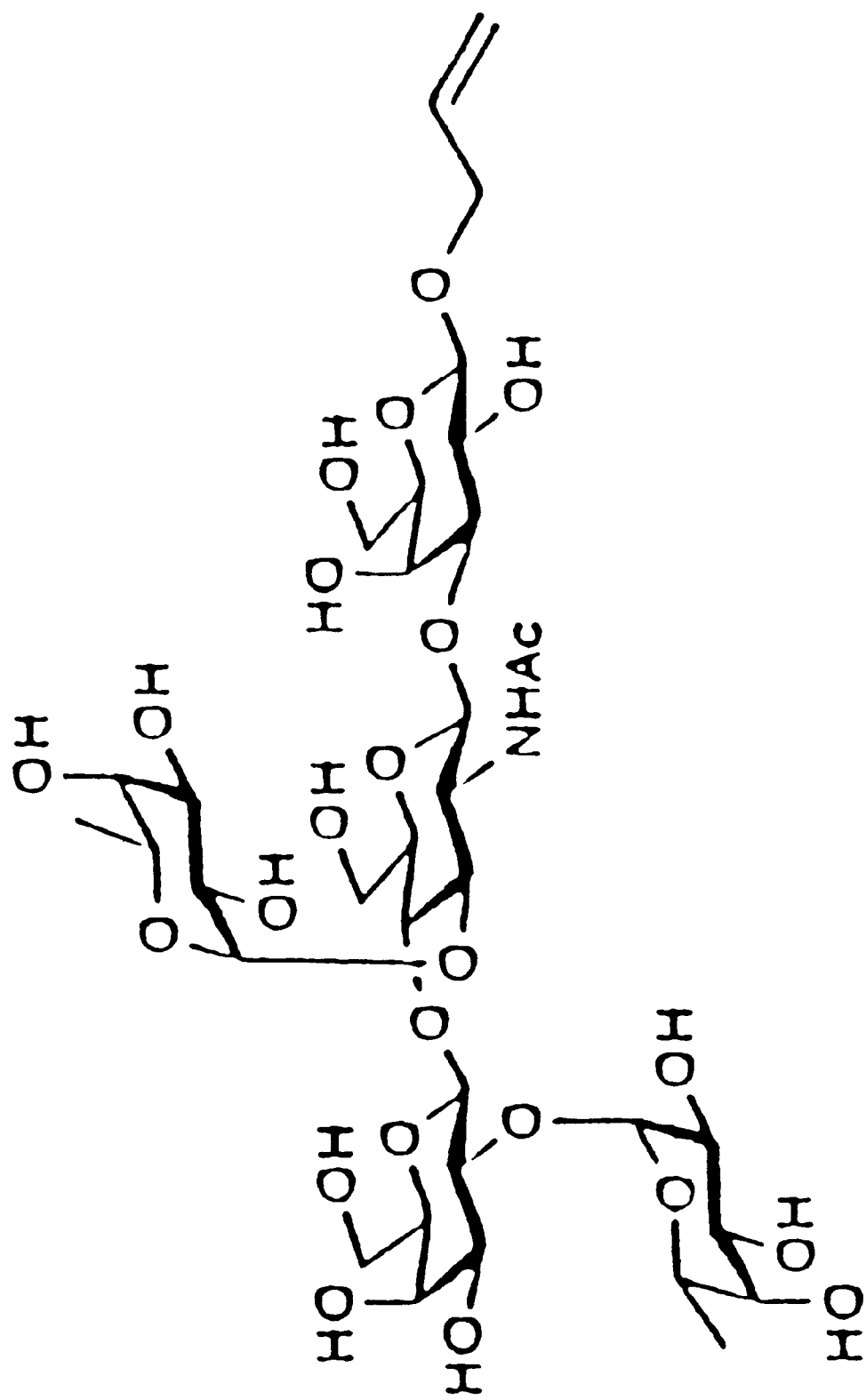
FIG. 30(a–c). Structure of Le$^y$ oligosaccharide and Le$^y$ conjugates used to immunize mice and structures of related blood epitopes.
Figure 31:
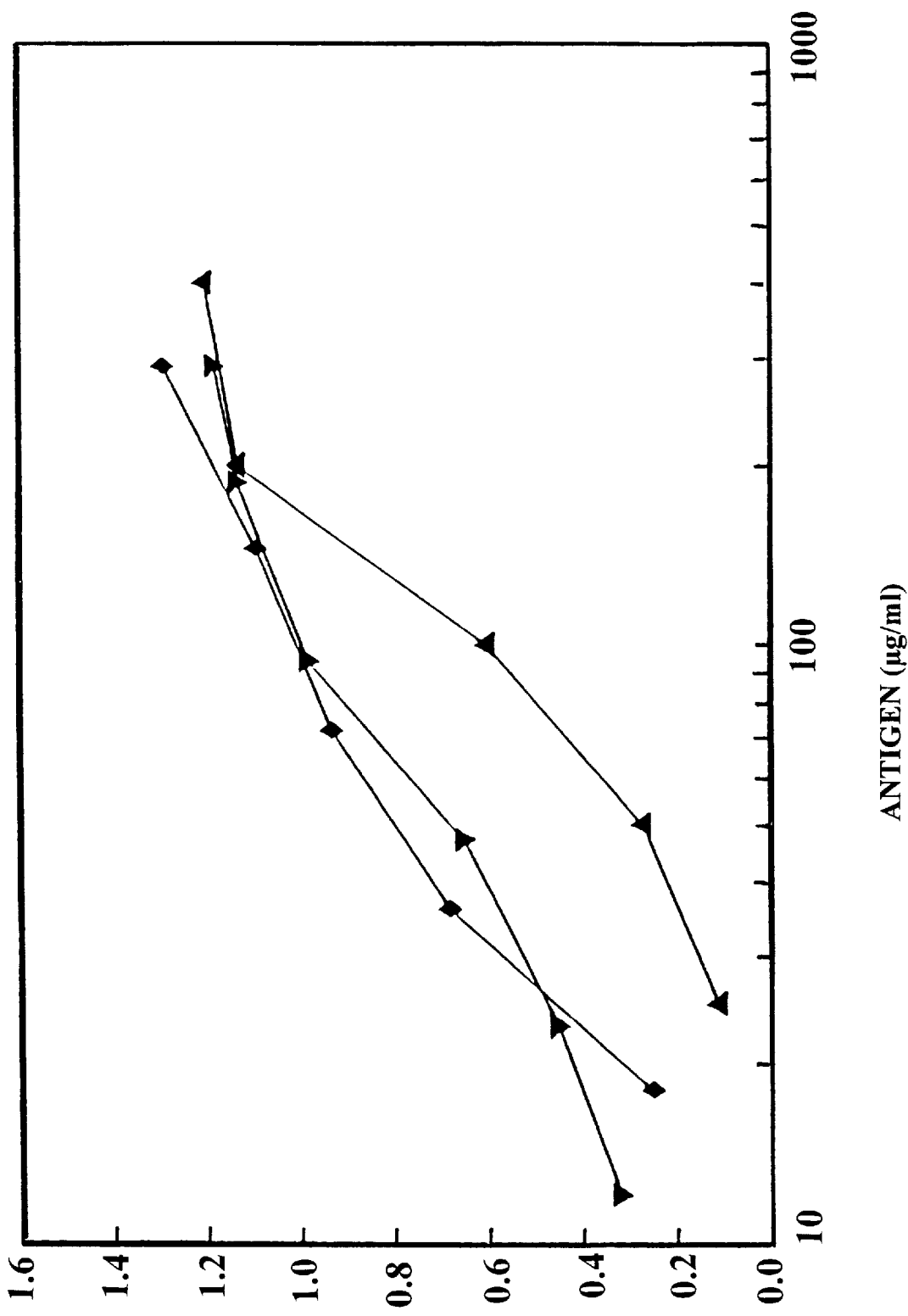
FIG. 31. Reactivity of Le$^y$ conjugates with anti-Le$^y$ antibody (3S193; 0.5 μg/ml) determined by ELISA. ◆: Le$^y$-BSA; ▼: Le$^y$-M$_2$C$_2$H-KLH and ▲: Le$^y$-KLH. Antigen concentration is given in μg carbohydrate in each glycoconjugate/ml.

Materials $Le^y$ pentasaccharide was synthesized as its allyl glycoside (FIG. 30) as described previously (Danishefsky, S. J., et al., J. Am. Chem. Soc. 1995, 117: 5701). The oligosaccharide was coupled directly to bovine serum albumin (BSA) or KLH, after ozonolysis to the corresponding aldehyde, using the reductive amination method (Danishefsky, S. J., et al., J. Am. Chem. Soc. 1995, 117: 5701; Sakamoto, J., et al., Mol Immunol 1984, 21: 1093), with a yield of 7–10% (based on sugar recovery). Conjugates containing 30 $Le^y$ residues/mole BSA and 287 $Le^y$ residues/mole KLH were prepared. These ratios were determined by analyzing the sugar content by HPAEC after acid hydrolysis as described (Hakomori, S-I., Cancer Res. 1996 56: 5309; Lloyd, KO 1966 Biochemistry 5: 1489) and the protein content by the method of Lowry, et al. (Lowry, Ohio, J. Biol. Chem. 1951 193: 265). $Le^y$ oligosaccharide was also coupled to KLH using a recently devised procedure (Ragupathi, G., et al., Glycocon J. In Press )in which the oligosaccharide is first coupled to 4-(N-maleidomethyl cyclohexane-1-carboxyhydrazide ($M_2C_2H$; Pierce Chemical Co., Rockford, Ill.) and the product in turn was coupled to 2-iminothiolane (Trout's reagent; Pierce Chemical Co.) derivatized KLH. The resulting conjugate was isolated in 39% yield (based on sugar recovery) and contained 540 moles $Le^y$/mole KLH. The conjugates were also evaluated by ELISA for their reactivity with an anti-$Le^y$ monoclonal antibody (FIG. 31).

Ovarian cyst mucins carrying $Le^y$ and $Le^b$ and $Le^a$ and $Le^x$ and blood group epitopes have been described (Lloyd, KO, et al., Biochemistry 1966, 5: 1489). $Le^y$-ceramide was synthesized as described for globo H ceramide in ref. 2. Monoclonal antibody 3S193, directed to the $Le^y$ structure was derived by Kitamura et al. (Proc. Natl. Acad. Sci. 1994 91: 12957) and mAb R24, directed to GD3 ganglioside on melanoma cells, was derived by Dippold, et al. (Proc. Natl. Acad. Sci. USA 1980 77: 6114).

Immunization of Mice

Groups of 5 mice (BALB/c, female) were immunized subcutaneously in 2 sites with $Le^y$-KLH (10 μg carbohydrate), $Le^y$-BSA (16 μg carbohydrate), $Le^y$-$M_2C_2$H-KLH (15 μg carbohydrate) together with QS21 adjuvant (Aquila, Worcester, Mass.). The mice were reimmunized with the same antigen sample and adjuvant at 1, 2 and 3 weeks and bled 7–10 days after the final immunization.

Serological Assays

Reactivity of the antisera with glycolipid and glycoprotein antigens was assayed by ELISA as described previously (Sakamoto, J., et al., Mol Immunol 1984, 21: 1093). Briefly, antigen was coated on to the wells of 60 well microtiter plates by allowing a water solution (glycoproteins) or ethanol solution (glycolipids) to evaporate at 37° C. After blocking with 2% BSA-PBS, diluted antiserum (10 μl) was added and allowed to incubate for 1 hr at room temperature. Excess antibody was removed and the plate washed three time's with 0.5% BSA-PBS. Antigen-antibody complexes were then detected with one of three alkaline phosphatase conjugated anti-lg reagents: (i) rabbit anti-mouse whole lg (Sigman Chemical Co., St. Louis, Mo.), (ii) rabbit anti-mouse lgG specific (Zymed, S. San Francisco, Calif.) and (iii) rabbit anti-mouse lgM specific (Southern Biotechnology Associates, Birmingham, Ala.). After washing the plate, p-nitrophenylphosphate was added and allowed to react for 15 min and 60 min before reading in a plate reader at 405 nm.

Reactivity of the antisera with tumor cells was tested using a Mixed Hemagglutination Assay (MHA) (Real, FX, et al., Manual of Clinical Immunology. 3rd. Ed. Washington, DC Amer. Soc Microbiol. 1986, pages 798–802) and an Immune Adherence (IA) assay (Shiku, H., et al., *J. Exp. Med.* 1976, 144: 873). Briefly, cells are cultured in MEM-10% FCS in the wells of 60-well microtiter plates for 1–2 days. After washing the cell layer briefly in PBS –0.5% BSA, serially diluted antisera are added to the wells and incubated at room temperature for 1 hr. Excess antiserum is then removed and the plates are washed 3 times in PBS –0.5% BSA. For the MHA assay, indicator cells consisting of a 2% suspension human O erythrocytes coated with anti-mouse lg were added and after 1 hr at room temperature non-bound erythrocytes are removed by gentle washing. The percentage of tumor cells with red cell rosettes was estimated visually under a microscope. For the IA method (Shiku, H., et al., *J. Exp. Med.* 1976, 144: 873), O erythrocytes and guinea pig complement (1:60 dilution) are added at the final step and after washing, red rosettes are observed under a microscope.

Cytotoxic tests for antibody-dependent, complement-mediated lysis was carried out with human complement as described previously (Kitamura, K., et al. (*Proc. Natl. Acad. Sci. USA* 1994 91: 12957).

Results and Discussion

Following immunization of groups of 5 mice with three different $Le^y$ conjugates, antisera were tested by ELISA against four different antigens: (i) a synthetic glycoconjugate (either $Le^y$-BSA or $Le^y$-KLH); (ii) a synthetic glycolipid ($Le^y$-ceramide); (iii) an ovarian cyst muchin expressing $Le^y$ and $Le^b$ blood group specificities and (iv) an ovaria cyst mucin expressing $Le^x$ and $Le^a$ blood group specificities. In order to determine the immunoglobulin class of the antibody response three different second antibodies were used in the assays: (i) anti-mouse lg (whole molecule); (ii) anti-mouse lgG (heavy chain specific) and (iii) anti-mouse lgM (heavy chain specific).

Figure 32:
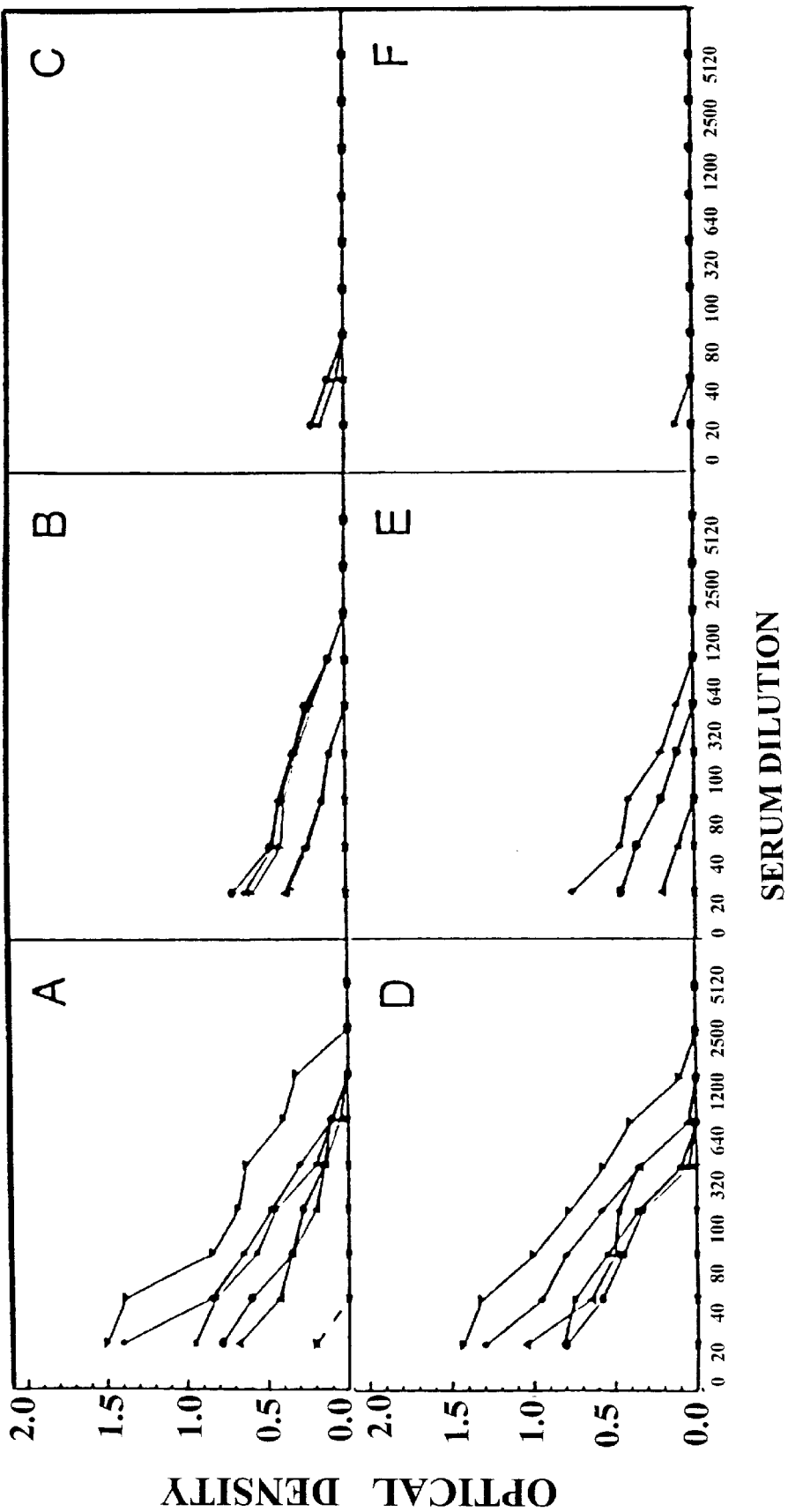
FIG. 32A–32I. Assay of reactivity of antisera from mice immunized with Le$^y$-KLH, Le$^y$-M$_2$C$_2$H-KLH and Le$^y$-BSA tested by ELISA on Le$^y$-ceramide. A, B, C: antimouse Ig (whole molecule) second antibody; D, E, F, anti-mouse IgG (heavy chain specific) and G, H, I: anti-mouse IgM (heavy chain specific). ▲: mouse 1; ▼: mouse 2; ■: mouse 3; ◆: mouse 4; ●: mouse 5; 561 : normal mouse serum.
Figure 33:
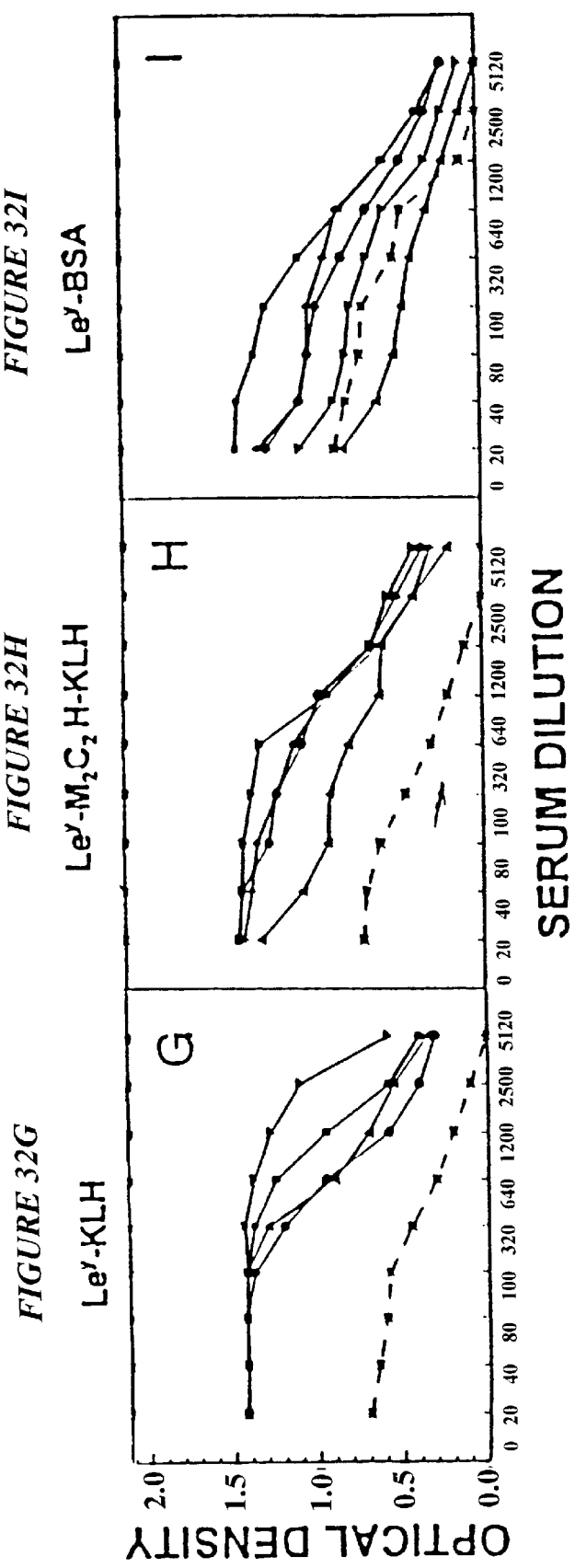
FIG. 33. Summary of reactivity of antisera of mice immunized with Le$^y$-KLH or Le$^y$-BSA conjugates tested on various glycoconjugates.

The antibody responses were tested after four immunizations which are usually sufficient to obtain a maximal response with conjugate antigens (Ragupathi, G., et al., *Angew Chem. Int. Ed. Engl.* 1997, 36: 125). The results against one of the test antigens ($Le^y$-ceramide) are shown in detail in FIG. 32 and the results with all the test antigens are summarized in Table 1 of FIG. 33. Immunization of the mice for a fifth time did not significantly change these results. Although there was some variation between individual mice, the results enabled us to reach the following conclusions: (i) of the three immunogens tested, $Le^y$-KLH gave the most consistently positive responses; $Le^y$-BSA gave the poorest responses and the KLH conjugate with a linker ($Le^y$-$M_2C_2H$-KLH) gave intermediate responses, (ii) IgG responses, as well as IgM responses, were obtained, particularly using $Le^y$-KLH as the immunogen, (iii) IgM antibody responses were higher in titer than the IgG responses, and (iv) even though the mice were immunized with synthetic conjugates, antibody responses to naturally-occurring forms of $Le^y$ ($Le^y$-expressing mucin and $Le^y$-ceramide), were found. We also observed that a portion of the IgM response (but not the IgG response) was cross-reactive with $Le^x$ blood group antigen; this result can probably be explained by the fact that the $Le^x$ structure is contained within the $Le^y$ structure (FIG. 30C).

Figure 34:
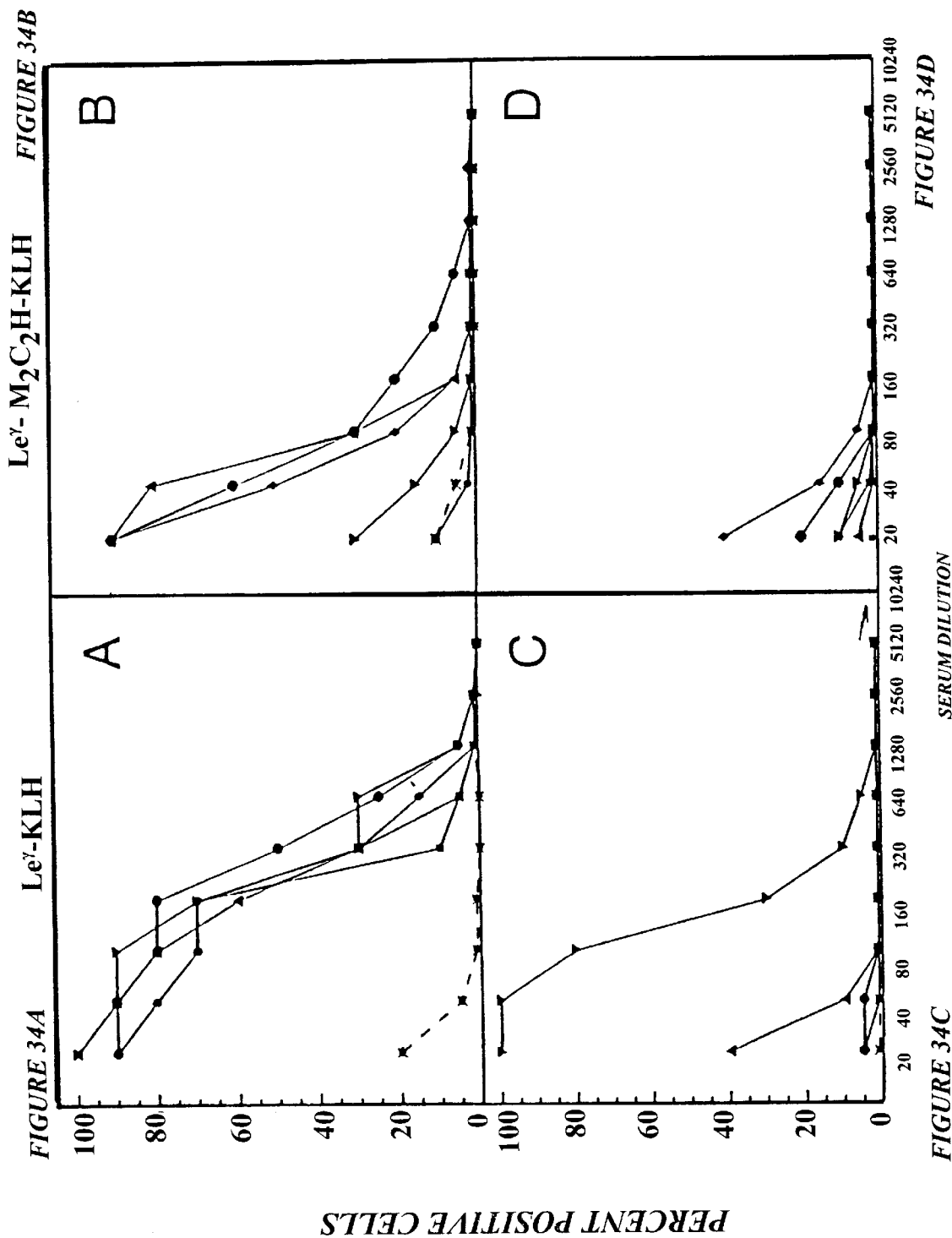
FIGS. 34A–34D. Tumor cell surface reactivity of antisera from mice immunized with Le$^y$-KLH, and Le$^y$-M$_2$C$_2$H tested with MHA assay. A and B: MCF-7 Le$^y$-positive breast cancer cells; C and D: SK-MEL-28 Le$^y$-negative melanoma cell line. The symbols used are the same as in FIG. 31. An anti-Le$^y$ monoclonal antibody (3S193) reacted with MCF-7 cells but did not react with SK-MEL-28 cells. These two cell lines are Le$^a$ and Le$^b$ negative. SK-MEL-28 is Le$^x$ negative but MCF-7 is slightly positive.

The antisera were also tested for their reactivity with $Le^y$-expressing tumor cells. As shown in FIG. 34A, all the antisera from $Le^y$-KLH immunized mice were strongly reactive with a $Le^y$-expressing cell line (MCF-7) as measured with a mixed hemagglutination assay (MHA) that detects all classes of lg. The antisera from $Le^y$-$M_2C_2H$-KLH immunized mice were also reactive with MCF-7 cells, although only three mice gave strong responses (FIG. 34B). The antisera from both sets of mice were generally poorly reactive with the $Le^y$-negative cell line SK-MEL-28, although one of the $Le^y$-KLH immunized mice was strongly reactive (FIG. 34C); the reason for this reactivity is not clear but it probably represents a cross-reaction with an unknown antigen present on SK-MEL-28 cells. The antisera were also tested with an IA (immune adherence) assay which detects complement-binding antibodies (mainly IgM). All the mice immunized with KLH conjugates produced MCF-7-cell reactive IgM antibodies detected by this assay (data not shown). In this case, the difference between $Le^y$-KLH and $Le^y$-$M_2C_2H$-KLH immunized mice was less obvious than with the MHA assay. Again only minimal reactivity was observed with SK-MEL-28 cells, in the presence of human complement (Table 2 of FIG. 35).

In summary, these studies show that mice immunized with a synthetic $Le^y$-KLH conjugate, together with the immunological adjuvant QS21, produced high titers of both IgG and IgM antibodies capable of reacting with epitopes carried on $Le^y$ glycolipids and mucins and with tumor cells expressing $Le^y$. Another conjugate, $Le^y$-$M_2C_2H$-KLH, produced by a novel procedure, was also capable of inducing antibody response, although at lower levels. Thus even though conjugation through $M_2C_2H$ was more efficient in terms of the yield and degree of coupling, the product, in this instance, was not as immunogenic as the standard $Le^y$-KLH conjugate. $Le^y$-BSA was less immunogenic than either of the two KLH conjugates. In a related study we recently showed that a synthetic globo H hexasaccharide-KLH, together with QS21, also was also an effective vaccine for producing IgM and IgG antibodies in mice (Ragupathi, G., et al., *Cancer Immunol Immunother* 1996, 43: 152). The approach of using protein conjugates to improve the immunogenicity of low molecules weight, haptenic, molecules have been well known since the early work of Lansteiner (Specificity of serological reactions. CC Thomas, Springfield, Ill. 1936) on aormatic hapens and of Avery and Goebel (*J. Exp. Med.* 1931, 54: 437) on carbohydrate-protein conjugates. Polysaccharide-protein conjugates have been explored extensively as vaccines for the prevention and treatment of various bacterial infections (Schneerson, R., et al., 1987, *Towards Better Carbohydrate Vaccines*, Wiley, N.Y., p307). It should be noted, however, that not all carbohydrate-protein conjugates are capable of inducing an antibody response that reacts with naturally-occurring forms of the carbohydrate hapten (Kitamura, K., et al., *Proc. Natl. Acad. Sci. USA* 1994, 91: 12957; Ritter, G., et al., *Int. J. Cancer* 1991 48: 379). Coupling to KLH, as we show in this and previous studies (Helling, F., et al., 1994 *Cancer Res.* 54: 197; Helling, F., et al., 1995, *Cancer Res.* 55: 2783; Ragupathi, G., et al.,*Angew Chem Int Ed Engl* 1997 36: 125) is a particularly effective way of inducing such a response. Moreover, this type of conjugate yields IgG as well as IgM responses; again this is not invariably the case with carbohydrate antigens (Livingston, P.O., et al., *Proc. Natl. Acad. Sci. USA* 1987, 84, 2911). The use of the immunological adjuvant QS21 (a saponin derivative from the bark of the *Quillaja saponaria* Molina tree) may also be an important parameter in inducing optimal responses. In this study, we did not examine other adjuvants as in the past we have shown the superiority of QS21 over other adjuvants (Livingston, P.O., et al., 1991 *Vaccine Res.* 1: 99). Another rationale for using QS21 as an adjuvant is that it is nontoxic and has been used safely and successfully in humans (Livingston, P.O., et al., 1994 Vaccine 12: 1275). On the basis of these studies we are planning a phase I trial of Le$^y$-KLH plus QS21, in patients with ovarian and prostate cancer. Initially, we will be testing the safety of the vaccine and any antibodies that may be produced in response to the vaccine. This is of particular concern since Le$^y$ is expressed on a number of normal epithelial and their secretions (Kitamura, K., et al., Proc. Natl. Acad. Sci. USA 1994, 91: 12957). On the other hand, normal expression is confined mainly to the apical layer of secretory ducts and thus may not be accessible to the immune system. Consistently an immunogenic vaccines to other tumor-associated carbohydrate antigens that also show normal expression, e.g. G$_{ms}$ or sialyl Tn, did not show any serious adverse reactions when tested in humans (Livingston, P.O., et al., 1994 Vaccine 12: 1275; MacLean, GD, et al., 1993 Cancer Immunol immunother 36: 215).

Clinical Trial Data from Globo H-KLH Vaccine

Twenty patients have been accrued to IRB protocol 96-55, a dose-escalating trial vaccinating patients with Globo H-KLH with the immune adjuvant QS21.

Nineteen of 20 patients completed the vaccine program receiving 5 vaccines over 24 weeks. Minimal adverse effects were noted and included redness and swelling at the injection site and occasional arthralgias or low-grade fever as high as 38° C. One patient experienced an adverse event at the beginning of the trial which was fatal. Formal review suggested that this patient died of overwhelming sepsis and not from a reaction to any of the constituents of the vaccine.

To date, of the remaining 19 patients who have received the 5 immunizations, 7 have been taken off-study for significant radiographic progression of disease in either lymph nodes or bone. These patients were treated with conventional hormonal therapy.

Figure 36A:
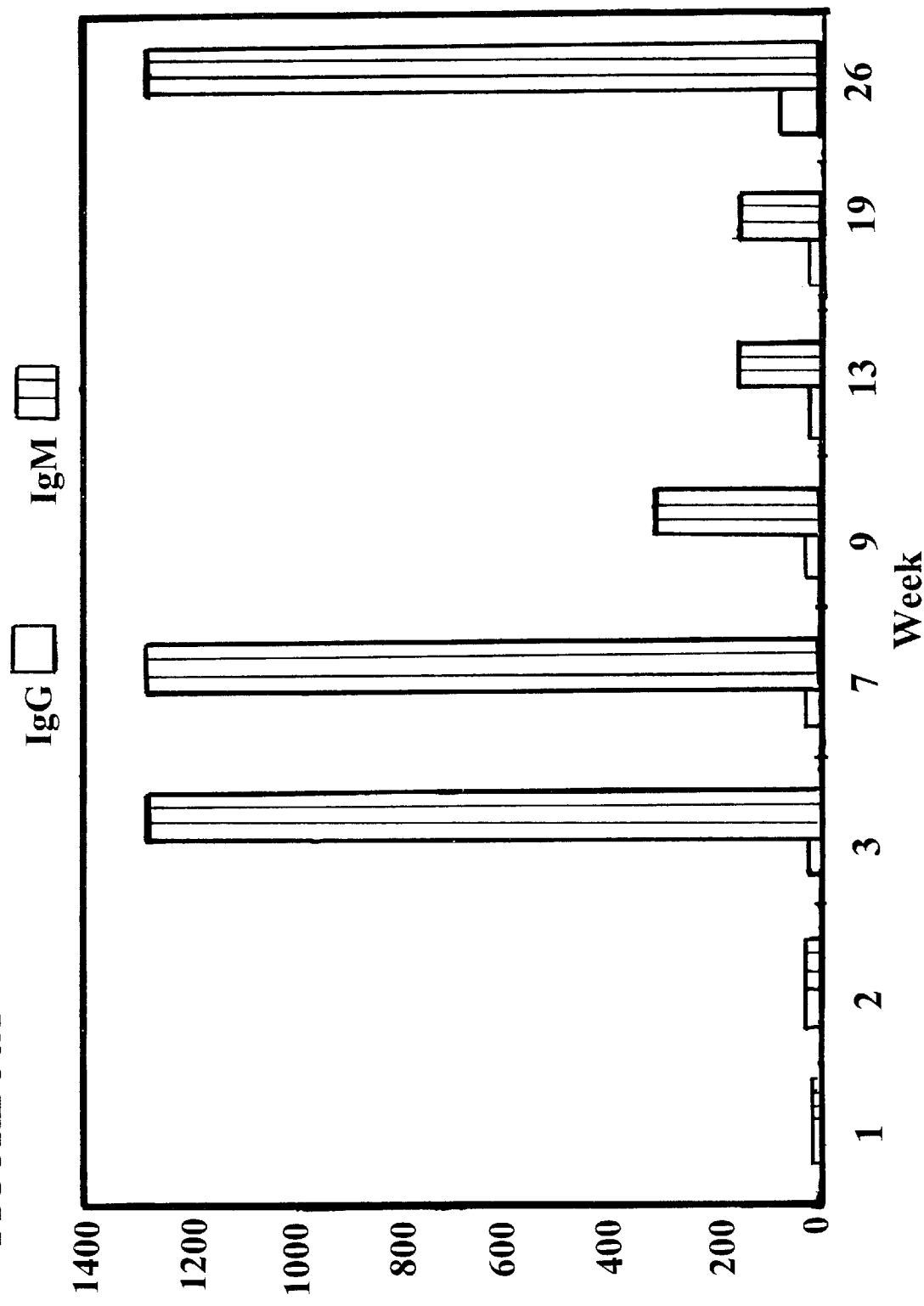
FIGS. 36A and 36B. Results from Globo H vaccine study with titers ranging from 1:40 to greater than 1:1280.
Figure 36B:
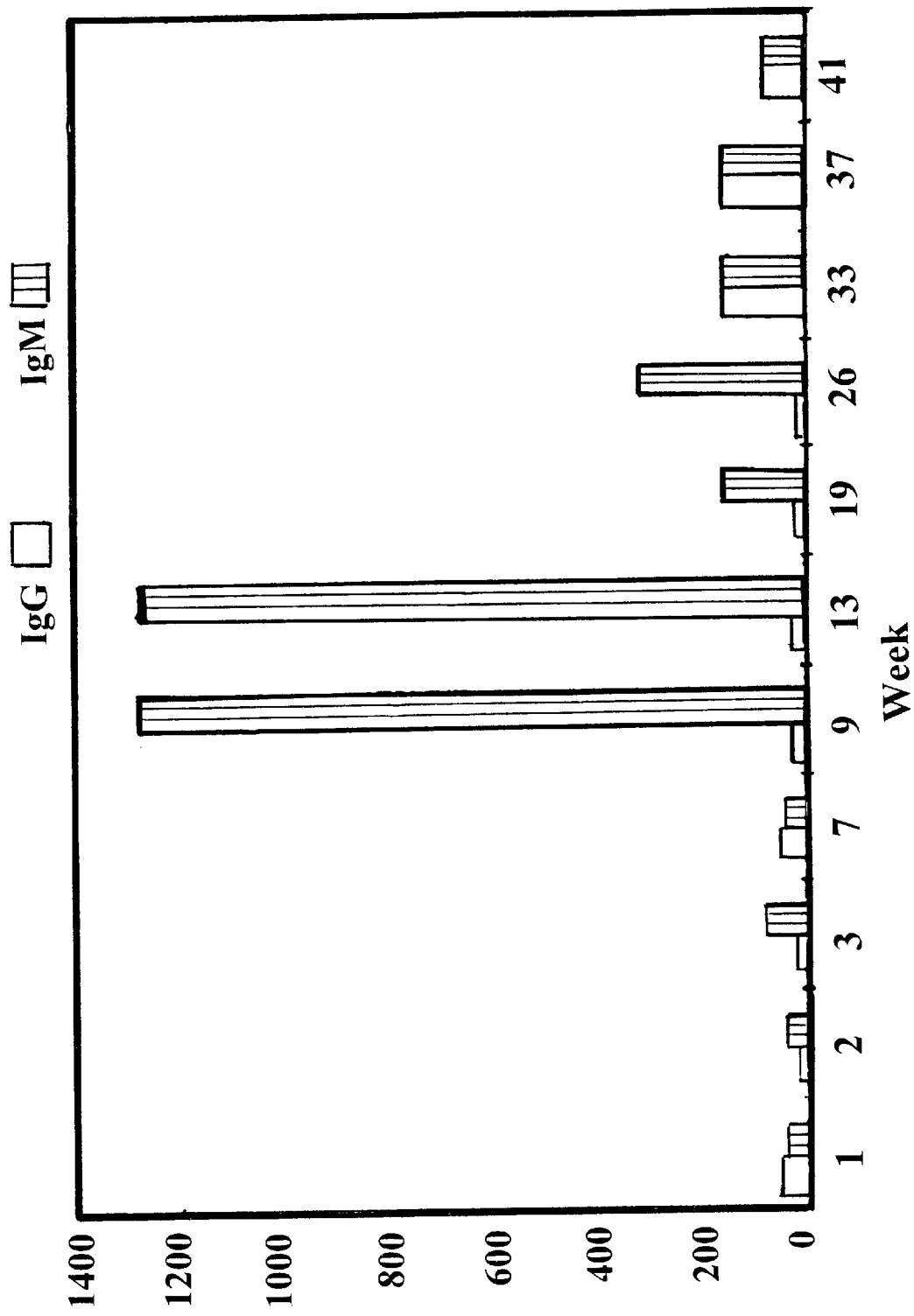

Immunologically, all patients generated predominantly IgM and IgG antibody responses with titers varying from 1:40 to >1:1280, (FIGS. 36A, 36B). Specificity of the antibody response for the Globo H antigen was confirmed by thin layer chromatography and immunoabsorption studies. These titers have remained elevated for greater than 12 months. Of the 8 patients remaining on-study, all have continued to have active antibody responses and no radiographic evidence of disease since their initiation on trial. These patients are candidates for a booster immunization when the IgM and IgG titers decline by >50% by week 50.

Figure 37A:
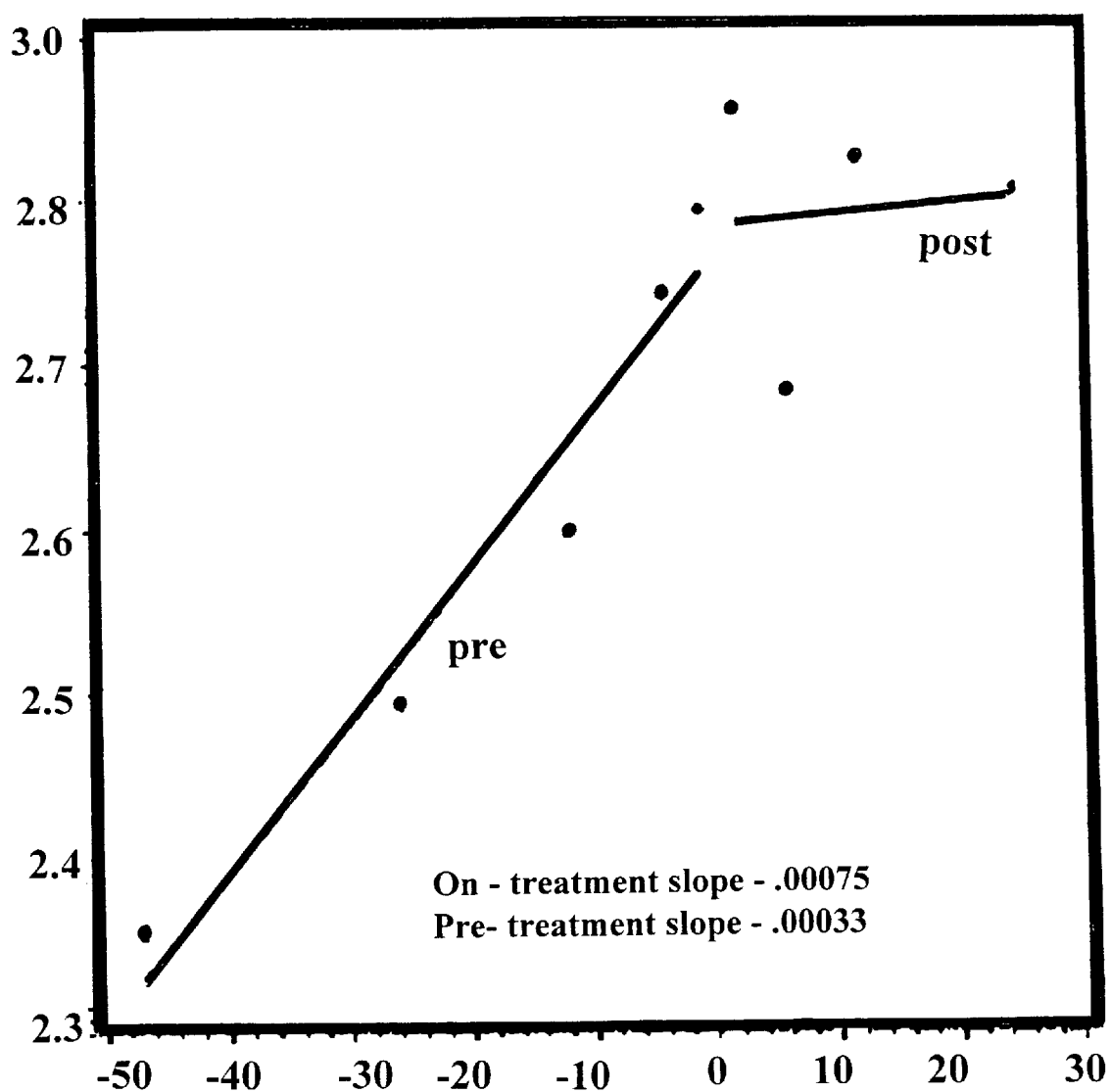
FIGS. 37A and 37B. Results from Globo H vaccine study indicate that treatment may be successful in slowing the slopes of PSA rise in patients.
Figure 37B:
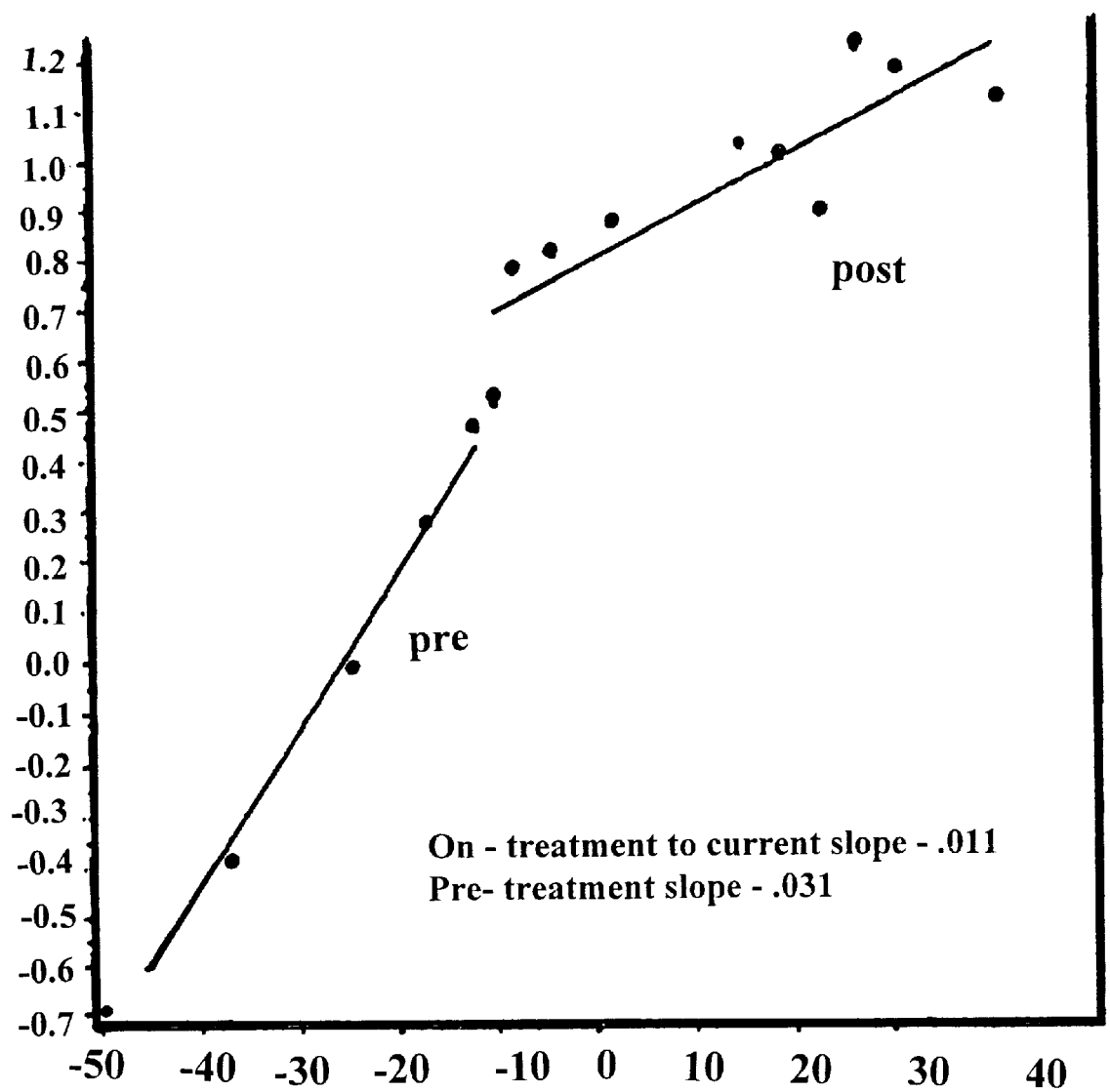
Figure 38A:
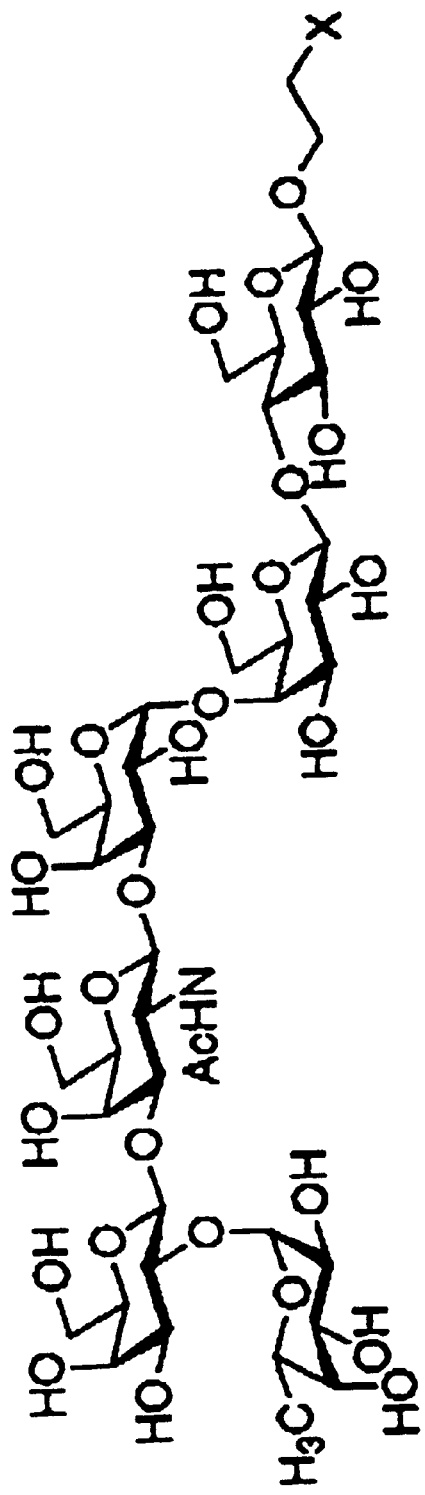
FIG. 38(a–c). Synthetic scheme for attaching a lipid to Globo-H.

There has also been a suggestion of a biological effect of this treatment in slowing the slopes of PSA rise in several patients, (FIGS. 37A, 37B). While it is too early to determine whether this change in slope will ultimately effect the time to progression of disease remains to be seen and therefore larger controlled trials are needed to analyze this observation.

In the context of the present invention the preferred dosage range for the vaccine is 30 to 100 µg with a most preferred dosage of 30 µg. In the clinical trial outlined above vaccinations were administered at week 1, 2, 3, 7 and 19 with a booster shot administered in week 50 or when titers decline by 50%. While a preferred number of vaccinations would be 5 this number can be lower than 5 or up to 8 vaccinations. The first 5 vaccines are preferably administered within a 24 week period, however this period may be increased or decreased depending on various factors.

The following is an alternative procedure for attaching KLH to Globo-H.

Results of Globo H KLH+QS-21 in Prostate Cancer Clinical Trial

The trial was designed to determine the safety of the vaccine, and to evaluate the effect of vaccine dose on the antibody and T cell response against Globo H and Globo H expressing cell lines. The primary endpoints are the ability to generate high titer antibodies to Globo H; and the secondary endpoints: 1) post-therapy changes in PSA, and, if present, changes in radionuclide bone scans, and/or measurable disease, and 2) clearance of tumor cells from the peripheral blood using a PCR based assay. Entry requires histologic confirmation of disease, and evidence of disease progression based on 1) biochemical parameters or 2) radiographic changes. The entry PSA requirements are summarized:

| Extent of disease | Minimum No. of determinations | Interval | Minimal value prior to entry (ng/ml) | Percentage increase in range of values |
|---|---|---|---|---|
| PSA Only: Post-prostatectomy | 3 | ≧2 weeks | 1.0 | 50% |
| PSA Only: Post-radiation | 3 | ≧2 weeks | 2.0 | 50% |
| Androgen independent | 3 | ≧2 weeks | 10 | 25% |

Patients were enrolled in sequential groups of 5 patients and received the following µg amounts of Globo H-KLH per vaccination.

DOSE LEVELS

| Group | No. of Patients | Dose (µg Globo H-KLH per vaccination) |
|---|---|---|
| 1 | 5 | 10 |
| 2 | 5 | 30 |
| 3 | 5 | 100 |
| 4 | 5 | 3 |

RESULTS TO DATE

Patients treated at the first three dose levels had similar antibody titers. As such, dose level four was a deescalation to 3 µg of the Globo-H. Accrual has been completed. The initial rise in antibody titer is slightly delayed relative to previous antigens. There have been no significant toxicities to normal tissues on which Globo-H is expressed, as precautions were taken to monitor patients carefully for toxicities the kidney, gut and pancreas. It is too early to assess the effects on PSA levels, a secondary endpoint, and samples have been stored so that specificity of the antibody response can be assessed.

ADVERSE EVENTS

Toxicities Encountered on the First Three Dose Levels

| TYPE | 0 | 1 | 2 | 3 | 4 | 5 | TOTAL |
|---|---|---|---|---|---|---|---|
| CHILLS | 14 | 0 | 1 | 0 | 0 | 0 | 15 |
| FAINT | 14 | 1 | 0 | 0 | 0 | 0 | 15 |
| FATIGUE | 14 | 1 | 0 | 0 | 0 | 0 | 15 |

-continued

| TYPE | 0 | 1 | 2 | 3 | 4 | 5 | TOTAL |
|---|---|---|---|---|---|---|---|
| LOCAL REACTION | 3 | 12 | 0 | 0 | 0 | 0 | 15 |
| MUSCLE ACHES | 13 | 2 | 0 | 0 | 0 | 0 | 15 |
| PAIN at INJECTION SITE | 5 | 10 | 0 | 0 | 0 | 0 | 15 |
| PRURITIS | 14 | 1 | 0 | 0 | 0 | 0 | 15 |
| STOMACH ACHES | 14 | 1 | 0 | 0 | 0 | 0 | 15 |
| FEVER | 13 | 1 | 2 | 0 | 0 | 0 | 15 |
| NAUSEA | 14 | 0 | 1 | 0 | 0 | 0 | 15 |
| HEADACHE | 13 | 1 | 1 | 0 | 0 | 0 | 15 |
| DEATH | 14 | 0 | 0 | 0 | 0 | 1 | 15 |

One adverse drug report was filed for an episode of grade 5, death. This mortality was unrelated to the study treatment.

In summary, the aim of this trial is to determine the optimal dose for the Globo-H-KLH+QS-21 vaccine for phase II investigations. The antibody response at dose levels 1, 2 and 3 were equivalent, hence we are exploring the lower dose of the vaccine as level IV. Pending the specificity of the antibody response, we will consider including this vaccine as one of the components of the polyvalent vaccines that will begin testing in 1998.

Conjugation of Globo-H-aldehyde Through $M_2C_2H$ to Thiolated KLH

Preparation of Globo-H-$M_2C_2H$

Two mg of Globo-H-aldehyde was dissolved in 1 ml of 0.1M sodium acetate buffer pH 5.5, and 4 mg of $M_2C_2H$ in 100 μl of dimethyl sulfoxide (DMSO) was added. The reaction mixture was incubated at room temperature for 15 minutes with gentle stirring. At the end of 15 min, 2 mg of solid sodium cyanoborohydride was added and the incubation continued at room temperature for 2 hours. Unreacted $M_2C_2H$ was removed in a Sephadex G10 column equilibrated previously with 0.1 M sodium phosphate buffer pH 6.0 containing 5mM EDTA and eluted with the same buffer. The fractions positive for Globo-H by TLC with orcinol were combined.

Addition of Sulfhydryl Groups to KLH

2-Iminothiolane (2mg) dissolved in thiolation buffer (50 mM triethanolamine, 0.15 M NaCl, 5 mM EDTA, pH 8.0) was added to 4 mg of KLH and incubated with stirring at room temperature for 2 hours. Unreacted 2-iminothiolane was removed by a Sephadex G15 column equilibrated previously with 0.1M sodium phosphate buffer pH 7.2 containing 5 mM EDTA and eluted with the same buffer. Fractions positive for KLH with BioRad protein assay dye reagent were combined. A small portion was used to estimate sulfhydryl groups in the thiolated KLH using Ellman's reagents and cysteine as standard as described earlier. The KLH was estimated by a dye method using BioRad dye reagent according to the manufacturer's instructions.

Conjugation of Globo-H-$M_2C_2H$ Thiolated KLH

The Globo-H-$M_2C_2H$ product and thiolated KLH were mixed and adjusted to pH 7.2 with 0.1M sodium phosphate buffer pH 8.0. The reaction mixture was incubated at room temperature overnight. The content of the Globo-H-$M_2C_2H$-KLH reaction vial was transferred to a Centriprep concentrator 30 (Amicon: molecular cut-off 30,000 Daltons) and unreacted Globo-H-$M_2C_2H$ was removed completely with multiple washes. The conjugate was checked by HPTLC for the absence of unreacted Globo-H as mentioned above. The epitope ratios of two batches of conjugate were determined by estimating protein content by BioRad dye binding protein assay and carbohydrate by a HPAEC-PAD assay. The epitope ratio of hepta-KLH and hepta-$M_2$-KLH was 112/1 and 197/1 respectively. The epitope ratio of Globo-H-KLH and Globo-H-$M_2$-KLH was 141/1 and 492/1 respectively.

What is claimed is:

1. A synthetic compound having the structure:

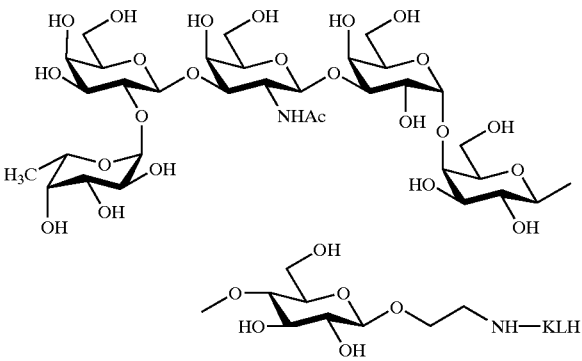

2. A pharmaceutical composition comprising an amount of the compound of claim 1 effective to induce antibodies capable of specifically binding with tumor cells and a pharmaceutically acceptable carrier.

3. A vaccine comprising an amount of the compound of claim 1 effective to prevent the recurrence of cancer in a subject.

4. The vaccine of claim 3 which further comprises an immunological adjuvant.

5. The vaccine of claim 4 wherein the immunological adjuvant is bacteria or liposomes.

6. The vaccine of claim 4, wherein the immunological adjuvant is QS21.

7. A composition comprising an amount of the compound of claim 1 effective to induce in a subject antibodies capable of specifically binding with tumor cells.

8. The composition of claim 7, wherein the tumor cells are selected from the group consisting of epithelial, colon, ovarian, lung, breast and prostate tumor cells.

9. The composition of claim 7 which further comprises an immunological adjuvant.

10. The composition of claim 9, wherein the immunological adjuvant is bacteria or liposomes.

11. The composition of claim 9, wherein the immunological adjuvant is QS21.

* * * * *